(12) United States Patent
Schneiderman

(10) Patent No.: US 10,143,780 B2
(45) Date of Patent: Dec. 4, 2018

(54) METHODS AND COMPOSITIONS RELATING TO LEPTIN ANTAGONISTS

(71) Applicant: Jacob Schneiderman, Kiryat Ono (IL)

(72) Inventor: Jacob Schneiderman, Kiryat Ono (IL)

( * ) Notice: Subject to any disclaimer, the term of this patent is extended or adjusted under 35 U.S.C. 154(b) by 63 days.

(21) Appl. No.: 15/000,062

(22) Filed: Jan. 19, 2016

(65) Prior Publication Data
US 2016/0263292 A1 Sep. 15, 2016

Related U.S. Application Data

(63) Continuation-in-part of application No. PCT/IL2015/050866, filed on Aug. 27, 2015, which is a continuation of application No. 14/730,282, filed on Jun. 4, 2015.

(60) Provisional application No. 62/210,966, filed on Feb. 26, 2015, provisional application No. 62/188,676, filed on Jul. 5, 2015.

(51) Int. Cl.

| | |
|---|---|
| *A61K 38/22* | (2006.01) |
| *A61K 38/00* | (2006.01) |
| *A61K 38/10* | (2006.01) |
| *A61F 13/00* | (2006.01) |
| *A61F 2/00* | (2006.01) |
| *A61L 31/16* | (2006.01) |
| *A61L 27/54* | (2006.01) |
| *A61L 27/58* | (2006.01) |
| *A61L 27/22* | (2006.01) |
| *A61L 31/14* | (2006.01) |
| *A61L 31/06* | (2006.01) |
| *A61L 31/04* | (2006.01) |
| *A61L 31/08* | (2006.01) |
| *A61L 27/18* | (2006.01) |
| *A61K 9/00* | (2006.01) |
| *A61K 9/70* | (2006.01) |
| *A61K 47/34* | (2017.01) |
| *A61K 9/06* | (2006.01) |

(52) U.S. Cl.
CPC .......... *A61L 31/16* (2013.01); *A61K 38/2264* (2013.01); *A61L 27/18* (2013.01); *A61L 27/227* (2013.01); *A61L 27/54* (2013.01); *A61L 27/58* (2013.01); *A61L 31/047* (2013.01); *A61L 31/06* (2013.01); *A61L 31/08* (2013.01); *A61L 31/148* (2013.01); *A61K 9/0019* (2013.01); *A61K 9/06* (2013.01); *A61K 9/7007* (2013.01); *A61K 47/34* (2013.01); *A61L 2300/43* (2013.01); *A61L 2430/20* (2013.01)

(58) Field of Classification Search
None
See application file for complete search history.

(56) References Cited

U.S. PATENT DOCUMENTS

| | | | |
|---|---|---|---|
| 6,451,346 B1 | 9/2002 | Shah et al. | |
| 6,955,685 B2 * | 10/2005 | Escamilla | A61B 17/12022 606/200 |
| 7,307,142 B2 * | 12/2007 | Gertler | A61K 47/60 435/69.1 |
| 7,807,154 B2 * | 10/2010 | Strasburger | C07K 16/2869 424/130.1 |
| 8,969,292 B2 * | 3/2015 | Gertler | A61K 38/22 514/21.2 |
| 2002/0090388 A1 | 7/2002 | Humes et al. | |
| 2005/0187607 A1 | 8/2005 | Akhtar et al. | |
| 2006/0229715 A1 | 10/2006 | Istephanous et al. | |
| 2007/0129790 A1 * | 6/2007 | Peng | A61L 24/0015 623/1.42 |
| 2009/0274739 A1 | 11/2009 | Marks et al. | |
| 2013/0084322 A1 * | 4/2013 | Wu | A61L 27/46 424/426 |
| 2014/0336750 A1 | 11/2014 | Mazer et al. | |

FOREIGN PATENT DOCUMENTS

| | | |
|---|---|---|
| WO | 2007/120897 A2 | 10/2007 |
| WO | 2011163669 A2 | 12/2011 |

OTHER PUBLICATIONS

Tao et al. 2013. Art. Thromb Vasc Biol. 33:311-320.*
Purdham, et al. 2008. Am. J. Physio. Heart Circ Physiol. 295:H441-H446.*
Gundogdu et al. 2007. Int J. Angiol. 16:31-32.*
Bowie et al, 1990, Science 247:1306-1310.*
Wells, 1990, Biochemistry 29:8509-8517.*
Ngo et al., 1994, The Protein Folding Problem and Tertiary Structure Prediction, Merz et al., eds, Birkhauser, Boston, pp. 433-506.*
Wang et al 2001. J. Biol Chem. 276:49213-49220.*
Local Application of Leptin Antagonist Attenuates Angiotensin II-Induced Ascending Aortic Aneurysm and Cardiac Remodeling J Am Heart Assoc. 2016:5:e003474 doi:10.1161/JAHA.116.003474.
Animal Experimentation Protocol submitted to the Harvard Medical Area (HMA) Standing Committee on Animals, 2013.
Amendment Approval Notice received from the HMA Standing Committee on Animals, 2014.

* cited by examiner

*Primary Examiner* — Shulamith H Shafer
(74) *Attorney, Agent, or Firm* — Soroker Agmon Nordman

(57) ABSTRACT

Devices, methods and compositions for treating cardiovascular disorders are configured for sustained-release of leptin antagonist into a blood vessel in order to downregulate an expression or activity of leptin in a cardiovascular tissue that is affected by a disorder.

28 Claims, 28 Drawing Sheets
Specification includes a Sequence Listing.

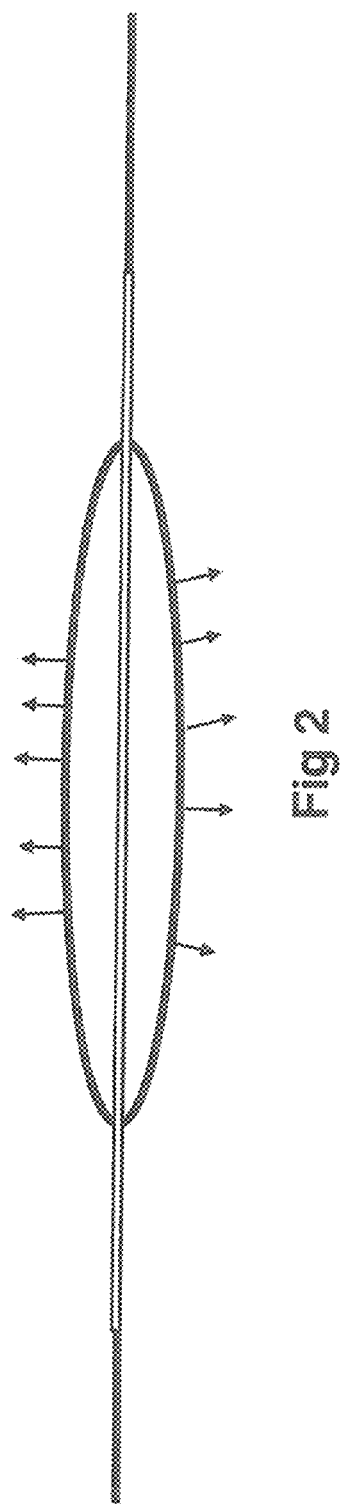

Leptin & Leptin Receptor in Human Normal Aortic Valve

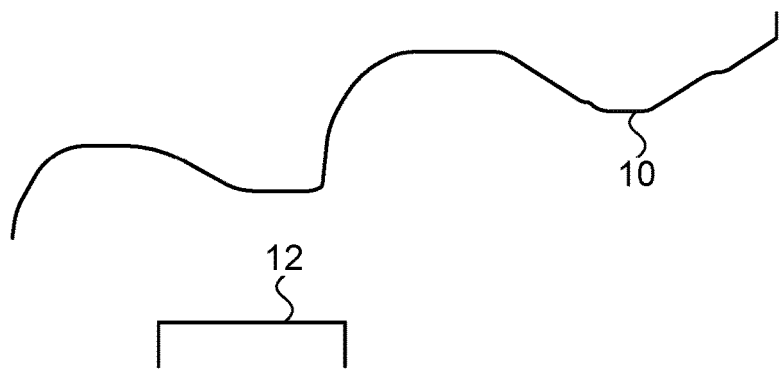
Figure 27
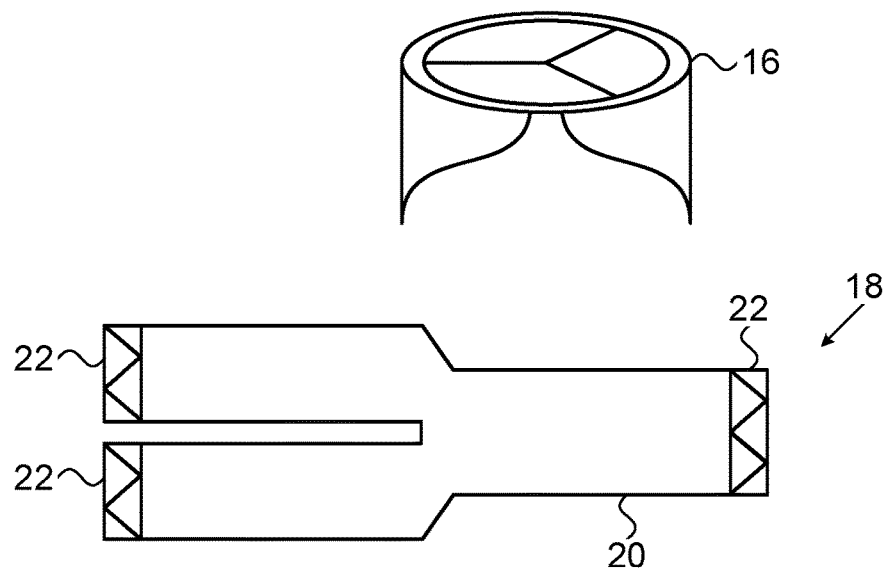
Figure 28

SEQUENCE LISTING

<160> NUMBER OF SEQ ID NOS: 72

<210> SEQ ID NO 1
<211> LENGTH: 167
<212> TYPE: PRT
<213> ORGANISM: Homo sapiens

<400> SEQUENCE: 1

Met His Trp Gly Thr Leu Cys Gly Phe Leu Trp Leu Trp Pro Tyr Leu
1               5                   10                  15

Phe Tyr Val Gln Ala Val Pro Ile Gln Lys Val Gln Asp Asp Thr Lys
            20                  25                  30

```
Thr Leu Ile Lys Thr Ile Val Thr Arg Ile Asn Asp Ile Ser His Thr
             35                  40                  45

Gln Ser Val Ser Ser Lys Gln Lys Val Thr Gly Leu Asp Phe Ile Pro
         50                  55                  60

Gly Leu His Pro Ile Leu Thr Leu Ser Lys Met Asp Gln Thr Leu Ala
 65                  70                  75                  80

Val Tyr Gln Gln Ile Leu Thr Ser Met Pro Ser Arg Asn Val Ile Gln
                 85                  90                  95

Ile Ser Asn Asp Leu Glu Asn Leu Arg Asp Leu Leu His Val Leu Ala
            100                 105                 110

Phe Ser Lys Ser Cys His Leu Pro Trp Ala Ser Gly Leu Glu Thr Leu
            115                 120                 125

Asp Ser Leu Gly Gly Val Leu Glu Ala Ser Gly Tyr Ser Thr Glu Val
        130                 135                 140

Val Ala Leu Ser Arg Leu Gln Gly Ser Leu Gln Asp Met Leu Trp Gln
145                 150                 155                 160

Leu Asp Leu Ser Pro Gly Cys
                165

<210> SEQ ID NO 2
<211> LENGTH: 3444
<212> TYPE: DNA
<213> ORGANISM: Homo sapiens

<400> SEQUENCE: 2
gtaggaatcg cagcgccagc ggttgcaagg cccaagaagc ccatcctggg aaggaaaatg      60
cattggggaa ccctgtgcgg attcttgtgg ctttggccct atcttttcta tgtccaagct     120
gtgcccatcc aaaagtccaa agatgacacc aaaaccctca tcaagacaat tgtcaccagg     180
atcaatgaca tttcacacac gcagtcagtc tcctccaaac agaaagtcac cggtttggac     240
ttcattcctg gctccaccc catcctgacc ttatccaaga tggaccagac actggcagtc     300
taccaacaga tcctcaccag tatgccttcc agaaacgtga tccaaatatc caacgacctg     360
gagaacctcc gggatcttct tcacgtgctg gccttctcta gagctgcca cttgccctgg     420 gccagtggcc tggagacctt ggacagcctg ggggtgtcc tggaagcttc aggctactcc     480
acagaggtgg tggccctgag caggctgcag gggtctctgc aggacatgct gtggcagctg     540
gacctcagcc ctgggtgctg aggccttgaa ggtcactctt cctgcaagga ctacgttaag     600
ggaaggaact ctggcttcca ggtatctcca ggattgaaga gcattgcatg acacccctt      660 atccaggact ctgtcaattt ccctgactcc tctaagccac tcttccaaag cataagacc      720 ctaagcctcc ttttgcttga aaccaaagat atatacacag gatcctattc tcaccaggaa     780
gggggtccac ccagcaaaga gtgggctgca tctgggattc ccaccaaggt cttcagccat     840
caacaagagt tgtcttgtcc cctcttgacc catctccccc tcactgaatg cctcaatgtg     900 accagggtg atttcagaga gggcagaggg gtaggcagag cctttggatg accagaacaa     960
ggttccctct gagaattcca aggagttcca tgaagaccac atccacacac gcaggaactc    1020
ccagcaacac aagctggaag cacatgttta tttattctgc attttattct ggatggattt    1080
gaagcaaagc accagcttct ccaggctctt tgggtcagc cagggccagg gtctccctg      1140 gagtgcagtt ccaatcccca tagatgggtc tggctgagct gaacccattt tgagtgactc    1200
gagggttggg ttcatctgag caagagctgg caaaggtggc tctccagtta gttctctcgt    1260
aactggtttc atttctactg tgactgatgt tacatcacag tgtttgcaat ggtgttgccc    1320
```

```
tgagtggatc tccaaggacc aggttatttt aaaaagattt gttttgtcaa gtgtcatatg   1380
taggtgtctg cacccagggg tggggaatgt tgggcagaa gggagaagga tctagaatgt    1440
gttttctgaa taacatttgt gtggtgggtt ctttggaagg agtgagatca ttttcttatc   1500
ttctgcaatt gcttaggatg tttttcatga aaatagctct ttcagggggg ttgtgaggcc   1560
tggccaggca ccccctggag agaagtttct ggccctggct gaccccaaag agcctggaga   1620
agctgatgct ttgcttcaaa tccatccaga ataaaacgca aagggctgaa agccatttgt   1680
tggggcagtg gtaagctctg ctttctccg actgctaggg agtggtcttt cctatcatgg    1740
agtgacggtc ccacactggt gactgcgatc ttcagagcag gggtccttgg tgtgaccctc   1800
tgaatggtcc agggttgatc acactctggg tttattacat ggcagtgttc ctatttgggg   1860
cttgcatgcc aaattgtagt tcttgtctga ttggctcacc caagcaaggc caaaattacc   1920
aaaaatcttg gggggttttt actccagtgg tgaagaaaac tcctttagca ggtggtcctg   1980
agacctgaca agcactgcta ggcgagtgcc aggactcccc aggccaggcc accaggatgg   2040
cccttcccac tggaggtcac attcaggaag atgaaagagg aggtttgggg tctgccacca   2100
tcctgctgct gtgtttttgc tatcacacag tgggtggtgg atctgtccaa ggaaacttga   2160
atcaaagcag ttaactttaa gactgagcac ctgcttcatg ctcagccctg actggtgcta   2220
taggctggag aagctcaccc aataaacatt aagattgagg cctgccctca gggatcttgc   2280
attcccagtg gtcaaaccgc actcacccat gtgccaaggt gggtattta ccacagcagc    2340 tgaacagcca aatgcatggt gcagttgaca gcaggtggga aatggtatga gctgaggggg   2400
gccgtgccca ggggcccaca gggaaccctg cttgcacttt gtaacatgtt tacttttcag   2460
ggcatcttag cttctattat agccacatcc ctttgaaaca agataactga gaatttaaaa   2520
ataagaaaat acataagacc ataacagcca acaggtggca ggaccaggac tatagcccag   2580
gtcctctgat acccagagca ttacgtgagc caggtaatga gggactggaa ccagggagac   2640
cgagcgcttt ctggaaaaga ggagtttcga ggtagagttt gaaggaggtg agggatgtga   2700
attgcctgca gagagaagcc tgttttgttg aaggtttgg tgtgtggaga tgcagaggta    2760
aaagtgtgag cagtgagtta cagcgagagg cagagaaaga agagacagga gggcaagggc   2820
catgctgaag ggaccttgaa gggtaaagaa gtttgatatt aaaggagtta agagtagcaa   2880
gttctagaga agaggctggt gctgtggcca gggtgagagc tgctctggaa aatgtgaccc   2940
agatcctcac aaccacctaa tcaggctgag gtgtcttaag ccttttgctc acaaaacctg   3000
gcacaatggc taattcccag agtgtgaaac ttcctaagta taaatggttg tctgttttg    3060 taacttaaaa aaaaaaaaaa aagtttggcc gggtgcggtg gctcacgcct gtaatcccag   3120
cactttggga ggccaaggtg gggggatcac aaggtcacta gatggcgagc atcctggcca   3180
acatggtgaa accccgtctc tactaaaaac acaaaagtta gctgagcgtg gtggcgggcg   3240
cctgtagtcc cagccactcg ggaggctgag acaggagaat cgcttaaacc tgggaggcgg   3300
agagtacagt gagccaagat cgcgccactg cactccggcc tgatgacaga gcgagattcc   3360
gtcttaaaaa aaaaaaaaaa aaagtttgtt tttaaaaaaa tctaaataaa ataactttgc   3420
cccctgcaaa aaaaaaaaaa aaaa                                         3444
```

<210> SEQ ID NO 3
<211> LENGTH: 146
<212> TYPE: PRT
<213> ORGANISM: Artificial Sequence
<220> FEATURE:
<223> OTHER INFORMATION: synthetic

<400> SEQUENCE: 3

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Ala Ala Phe Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 4
<211> LENGTH: 146
<212> TYPE: PRT
<213> ORGANISM: Artificial Sequence
<220> FEATURE:
<223> OTHER INFORMATION: synthetic

<400> SEQUENCE: 4

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Leu Asp Ala Ala Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 5
<211> LENGTH: 146
<212> TYPE: PRT
<213> ORGANISM: Artificial Sequence
<220> FEATURE:

<223> OTHER INFORMATION: synthetic

<400> SEQUENCE: 5

```
Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Ala Ala Phe Ile Pro Gly Leu His Pro Leu
        35                  40                  45

Leu Ser Leu Ser Lys Met Asp Gln Thr Leu Ala Ile Tyr Gln Gln Ile
    50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145
```

<210> SEQ ID NO 6
<211> LENGTH: 146
<212> TYPE: PRT
<213> ORGANISM: Artificial Sequence
<220> FEATURE:
<223> OTHER INFORMATION: synthetic

<400> SEQUENCE: 6

```
Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Leu Asp Ala Ala Pro Gly Leu His Pro Leu
        35                  40                  45

Leu Ser Leu Ser Lys Met Asp Gln Thr Leu Ala Ile Tyr Gln Gln Ile
    50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145
```

<210> SEQ ID NO 7
<211> LENGTH: 146
<212> TYPE: PRT
<213> ORGANISM: Artificial Sequence
<220> FEATURE:
<223> OTHER INFORMATION: synthetic

<400> SEQUENCE: 7

Val Pro Ile Gln Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Lys Val Thr Gly Ala Ala Ile Pro Gly Leu His Pro Ile
        35                  40                  45

Leu Thr Leu Ser Lys Met Asp Gln Thr Leu Ala Val Tyr Gln Gln Ile
    50                  55                  60

Leu Thr Ser Met Pro Ser Arg Asn Val Ile Arg Ile Ser Asn Asp Leu
65                  70                  75                  80

Glu Asn Leu Arg Asp Leu Leu His Val Leu Ala Phe Ser Lys Ser Cys
                85                  90                  95

His Leu Pro Trp Ala Ser Gly Leu Glu Thr Leu Asp Ser Leu Gly Gly
            100                 105                 110

Val Leu Glu Ala Ser Gly Tyr Ser Thr Glu Val Val Ala Leu Ser Arg
        115                 120                 125

Leu Gln Gly Ser Leu Gln Asp Met Leu Trp Gln Leu Asp Leu Ser Pro
    130                 135                 140

Gly Cys
145

<210> SEQ ID NO 8
<211> LENGTH: 146
<212> TYPE: PRT
<213> ORGANISM: Artificial Sequence
<220> FEATURE:
<223> OTHER INFORMATION: synthetic

<400> SEQUENCE: 8

Val Ser Ile Arg Lys Val Gln Asp Asp Thr Lys Thr Leu Ile Lys Thr
1               5                   10                  15

Ile Val Thr Arg Ile Asn Asp Ile Ser His Thr Gln Ser Val Ser Ser
            20                  25                  30

Lys Gln Arg Val Thr Gly Ala Ala Ile Pro Gly Leu His Pro Leu
        35                  40                  45

Leu Ser Leu Ser Lys Met Asp Gln Thr Leu Ala Ile Tyr Gln Gln Ile
    50                  55                  60

Leu Ala Ser Leu Pro Ser Arg Asn Val Ile Gln Ile Ser Asn Asp Leu
65                  70                  75                  80

Glu Asn Leu Arg Asp Leu Leu His Leu Leu Ala Ala Ser Lys Ser Cys
                85                  90                  95

Pro Leu Pro Gln Val Arg Ala Leu Glu Ser Leu Glu Ser Leu Gly Val
            100                 105                 110

Val Leu Glu Ala Ser Leu Tyr Ser Thr Glu Val Val Ala Leu Ser Arg
        115                 120                 125

Leu Gln Gly Ser Leu Gln Asp Met Leu Arg Gln Leu Asp Leu Ser Pro
    130                 135                 140

Gly Cys
145

<210> SEQ ID NO 9
<211> LENGTH: 146
<212> TYPE: PRT

<213> ORGANISM: Artificial Sequence
<220> FEATURE:
<223> OTHER INFORMATION: synthetic

<400> SEQUENCE: 9

```
Val Pro Ile Gln Lys Val Gln Asp Asp Thr Lys Thr Leu Ile Lys Thr
1               5                   10                  15
Ile Val Thr Arg Ile Asn Asp Ile Ser His Thr Gln Ser Val Ser Ser
            20                  25                  30
Lys Gln Lys Val Thr Gly Ala Ala Ala Pro Gly Leu His Pro Ile
        35                  40                  45
Leu Thr Leu Ser Lys Met Asp Gln Thr Leu Ala Val Tyr Gln Gln Ile
    50                  55                  60
Leu Thr Ser Met Pro Ser Arg Asn Val Ile Arg Ile Ser Asn Asp Leu
65                  70                  75                  80
Glu Asn Leu Arg Asp Leu Leu His Val Leu Ala Phe Ser Lys Ser Cys
                85                  90                  95
His Leu Pro Trp Ala Ser Gly Leu Glu Thr Leu Asp Ser Leu Gly Gly
            100                 105                 110
Val Leu Glu Ala Ser Gly Tyr Ser Thr Glu Val Val Ala Leu Ser Arg
        115                 120                 125
Leu Gln Gly Ser Leu Gln Asp Met Leu Trp Gln Leu Asp Leu Ser Pro
    130                 135                 140
Gly Cys
145
```

<210> SEQ ID NO 10
<211> LENGTH: 146
<212> TYPE: PRT
<213> ORGANISM: Artificial Sequence
<220> FEATURE:
<223> OTHER INFORMATION: synthetic

<400> SEQUENCE: 10

```
Val Ser Ile Arg Lys Val Gln Asp Asp Thr Lys Thr Leu Ile Lys Thr
1               5                   10                  15
Ile Val Thr Arg Ile Asn Asp Ile Ser His Thr Gln Ser Val Ser Ser
            20                  25                  30
Lys Gln Arg Val Thr Gly Ala Ala Ala Pro Gly Leu His Pro Leu
        35                  40                  45
Leu Ser Leu Ser Lys Met Asp Gln Thr Leu Ala Ile Tyr Gln Gln Ile
    50                  55                  60
Leu Ala Ser Leu Pro Ser Arg Asn Val Ile Gln Ile Ser Asn Asp Leu
65                  70                  75                  80
Glu Asn Leu Arg Asp Leu Leu His Leu Leu Ala Ala Ser Lys Ser Cys
                85                  90                  95
Pro Leu Pro Gln Val Arg Ala Leu Glu Ser Leu Glu Ser Leu Gly Val
            100                 105                 110
Val Leu Glu Ala Ser Leu Tyr Ser Thr Glu Val Val Ala Leu Ser Arg
        115                 120                 125
Leu Gln Gly Ser Leu Gln Asp Met Leu Arg Gln Leu Asp Leu Ser Pro
    130                 135                 140
Gly Cys
145
```

<210> SEQ ID NO 11
<211> LENGTH: 438

<212> TYPE: DNA
<213> ORGANISM: Artificial Sequence
<220> FEATURE:
<223> OTHER INFORMATION: synthetic

<400> SEQUENCE: 11

```
gtgcccatcc aaaaagtcca agatgacacc aaaaccctca tcaagacaat tgtcaccagg    60
atcaatgaca tttcacacac gcagtcagtc tcctccaaac agaaagtcac tggtgcggct   120
ttcattcctg ggctccaccc catcctgacc ttatccaaga tggaccagac actggcagtc   180
taccaacaga tcctcaccag tatgccttcc agaaacgtga tccgaatatc caacgacctg   240
gagaacctcc gggatcttct tcacgtgctg gccttctcta agagctgcca cttgccctgg   300
gccagtggcc tggagacctt ggacagcctg gggggtgtcc tggaagcttc aggctactcc   360
acagaggtgg tggccctgag caggctgcag gggtctctgc aggacatgct gtggcagctg   420
gacctcagcc ctgggtgc                                                 438
```

<210> SEQ ID NO 12
<211> LENGTH: 438
<212> TYPE: DNA
<213> ORGANISM: Artificial Sequence
<220> FEATURE:
<223> OTHER INFORMATION: synthetic

<400> SEQUENCE: 12

```
gtgcccatcc aaaaagtcca agatgacacc aaaaccctca tcaagacaat tgtcaccagg    60
atcaatgaca tttcacacac gcagtcagtc tcctccaaac agaaagtcac tggtttggac   120
gccgctcctg ggctccaccc catcctgacc ttatccaaga tggaccagac actggcagtc   180
taccaacaga tcctcaccag tatgccttcc agaaacgtga tccgaatatc caacgacctg   240
gagaacctcc gggatcttct tcacgtgctg gccttctcta agagctgcca cttgccctgg   300
gccagtggcc tggagacctt ggacagcctg gggggtgtcc tggaagcttc aggctactcc   360
acagaggtgg tggccctgag caggctgcag gggtctctgc aggacatgct gtggcagctg   420
gacctcagcc ctgggtgc                                                 438
```

<210> SEQ ID NO 13
<211> LENGTH: 438
<212> TYPE: DNA
<213> ORGANISM: Artificial Sequence
<220> FEATURE:
<223> OTHER INFORMATION: synthetic

<400> SEQUENCE: 13

```
gtgtcgatcc gcaaggtcca ggatgacacc aaaaccctca tcaagacgat tgtcaccagg    60
atcaatgaca tctcacacac gcagtccgtc tcctccaaac agagggtcac cggtgctgct   120
ttcatccctg ggctccaccc tctcctgagt ttgtccaaga tggaccagac attggcaatc   180
taccaacaga tcctcgccag tctgccttcc agaaatgtga tccaaatatc taatgacctg   240
gagaacctcc gggaccttct ccacctgctg gccgcctcca agagctgccc cttgccgcag   300
gtcagggccc tagagagctt ggagagcctg ggcgtcgtcc tggaagcctc cctctactcc   360
accgaggtgg tggccctgag ccggctacag gggtctctac aggacatgtt gcggcagctg   420
gacctgagtc ccggctgc                                                 438
```

<210> SEQ ID NO 14
<211> LENGTH: 438
<212> TYPE: DNA

<213> ORGANISM: Artificial Sequence
<220> FEATURE:
<223> OTHER INFORMATION: synthetic

<400> SEQUENCE: 14

```
gtgtcgatcc gcaaggtcca ggatgacacc aaaaccctca tcaagacgat tgtcaccagg      60
atcaatgaca tctcacacac gcagtccgtc tcctccaaac agagggtcac cggtttggac     120
gctgctcctg ggctccaccc tctcctgagt ttgtccaaga tggaccagac attggcaatc     180
taccaacaga tcctcgccag tctgccttcc agaaatgtga tccaaatatc taatgacctg     240
gagaacctcc gggaccttct ccacctgctg gccgcctcca gagctgccc  cttgccgcag     300
gtcagggccc tagagagctt ggagagcctg ggcgtcgtcc tggaagcctc cctctactcc     360
accgaggtgg tggccctgag ccggctacag gggtctctac aggacatgtt gcggcagctg     420
gacctgagtc ccggctgc                                                   438
```

<210> SEQ ID NO 15
<211> LENGTH: 438
<212> TYPE: DNA
<213> ORGANISM: Artificial Sequence
<220> FEATURE:
<223> OTHER INFORMATION: synthetic

<400> SEQUENCE: 15

```
gtgcccatcc aaaaagtcca agatgacacc aaaaccctca tcaagacaat tgtcaccagg      60
atcaatgaca tttcacacac gcagtcagtc tcctccaaac agaaagtcac tggtgcggct     120
gccattcctg ggctccaccc catcctgacc ttatccaaga tggaccagac actggcagtc     180
taccaacaga tcctcaccag tatgccttcc agaaacgtga tccgaatatc caacgacctg     240
gagaacctcc gggatcttct tcacgtgctg gccttctcta gagctgcca  cttgccctgg     300
gccagtggcc tggagacctt ggacagcctg ggggggtgtcc tggaagcttc aggctactcc     360
acagaggtgg tggccctgag caggctgcag gggtctctgc aggacatgct gtggcagctg     420
gacctcagcc ctgggtgc                                                   438
```

<210> SEQ ID NO 16
<211> LENGTH: 438
<212> TYPE: DNA
<213> ORGANISM: Artificial Sequence
<220> FEATURE:
<223> OTHER INFORMATION: synthetic

<400> SEQUENCE: 16

```
gtgtcgatcc gcaaggtcca ggatgacacc aaaaccctca tcaagacgat tgtcaccagg      60
atcaatgaca tctcacacac gcagtccgtc tcctccaaac agagggtcac cggtgctgca     120
gctatccctg ggctccaccc tctcctgagt ttgtccaaga tggaccagac attggcaatc     180
taccaacaga tcctcgccag tctgccttcc agaaatgtga tccaaatatc taatgacctg     240
gagaacctcc gggaccttct ccacctgctg gccgcctcca gagctgccc  cttgccgcag     300
gtcagggccc tagagagctt ggagagcctg ggcgtcgtcc tggaagcctc cctctactcc     360
accgaggtgg tggccctgag ccggctacag gggtctctac aggacatgtt gcggcagctg     420
gacctgagtc ccggctgc                                                   438
```

<210> SEQ ID NO 17
<211> LENGTH: 438
<212> TYPE: DNA
<213> ORGANISM: Artificial Sequence

```
<220> FEATURE:
<223> OTHER INFORMATION: synthetic

<400> SEQUENCE: 17
gtgcccatcc aaaaagtcca agatgacacc aaaaccctca tcaagacaat tgtcaccagg      60
atcaatgaca tttcacacac gcagtcagtc tcctccaaac agaaagtcac tggtgcggct     120
gccgctcctg ggctccaccc catcctgacc ttatccaaga tggaccagac actggcagtc     180
taccaacaga tcctcaccag tatgccttcc agaaacgtga tccgaatatc aacgacctg     240 gagaacctcc gggatcttct tcacgtgctg gccttctcta agagctgcca cttgccctgg     300
gccagtggcc tggagacctt ggacagcctg ggggtgtcc tggaagcttc aggctactcc      360
acagaggtgg tggccctgag caggctgcag gggtctctgc aggacatgct gtggcagctg     420
gacctcagcc ctgggtgc                                                   438

<210> SEQ ID NO 18
<211> LENGTH: 438
<212> TYPE: DNA
<213> ORGANISM: Artificial Sequence
<220> FEATURE:
<223> OTHER INFORMATION: synthetic

<400> SEQUENCE: 18
gtgtcgatcc gcaaggtcca ggatgacacc aaaaccctca tcaagacgat tgtcaccagg     60
atcaatgaca tctcacacac gcagtccgtc tcctccaaac agagggtcac cggtgctgct    120
gctgctcctg ggctccaccc tctcctgagt ttgtccaaga tggaccagac attggcaatc    180
taccaacaga tcctcgccag tctgccttcc agaaatgtga tccaaatatc taatgacctg    240
gagaacctcc gggaccttct ccacctgctg gccgcctcca agagctgccc cttgccgcag    300
gtcagggccc tagagagctt ggagagcctg ggcgtcgtcc tggaagcctc cctctactcc    360
accgaggtgg tggccctgag ccggctacag gggtctctac aggacatgtt gcggcagctg    420
gacctgagtc ccggctgc                                                  438

<210> SEQ ID NO 19
<211> LENGTH: 41
<212> TYPE: DNA
<213> ORGANISM: Artificial Sequence
<220> FEATURE:
<223> OTHER INFORMATION: synthetic

<400> SEQUENCE: 19
ccaaacagaa agtcactggt gcggctttca ttcctgggct c                         41

<210> SEQ ID NO 20
<211> LENGTH: 41
<212> TYPE: DNA
<213> ORGANISM: Artificial Sequence
<220> FEATURE:
<223> OTHER INFORMATION: synthetic

<400> SEQUENCE: 20
gagcccagga atgaaagccg caccagtgac tttctgtttg g                         41

<210> SEQ ID NO 21
<211> LENGTH: 45
<212> TYPE: DNA
<213> ORGANISM: Artificial Sequence
<220> FEATURE:
<223> OTHER INFORMATION: synthetic
```

<400> SEQUENCE: 21
ccaaacagaa agtcactggt ttggacgccg ctcctgggct ccacc            45

<210> SEQ ID NO 22
<211> LENGTH: 45
<212> TYPE: DNA
<213> ORGANISM: Artificial Sequence
<220> FEATURE:
<223> OTHER INFORMATION: synthetic

<400> SEQUENCE: 22
ggtggagccc aggagcggcg tccaaaccag tgactttctg tttgg            45

<210> SEQ ID NO 23
<211> LENGTH: 41
<212> TYPE: DNA
<213> ORGANISM: Artificial Sequence
<220> FEATURE:
<223> OTHER INFORMATION: synthetic

<400> SEQUENCE: 23
ccaaacagaa agtcactggt gcggccgcca ttcctgggct c                41

<210> SEQ ID NO 24
<211> LENGTH: 41
<212> TYPE: DNA
<213> ORGANISM: Artificial Sequence
<220> FEATURE:
<223> OTHER INFORMATION: synthetic

<400> SEQUENCE: 24
gagcccagga atggcggccg caccagtgac tttctgtttg g                41

<210> SEQ ID NO 25
<211> LENGTH: 45
<212> TYPE: DNA
<213> ORGANISM: Artificial Sequence
<220> FEATURE:
<223> OTHER INFORMATION: synthetic

<400> SEQUENCE: 25
ccaaacagaa agtcactggt gcggccgccg ctcctgggct ccacc            45

<210> SEQ ID NO 26
<211> LENGTH: 45
<212> TYPE: DNA
<213> ORGANISM: Artificial Sequence
<220> FEATURE:
<223> OTHER INFORMATION: synthetic

<400> SEQUENCE: 26
ggtggagccc aggagcggcg gccgcaccag tgactttctg tttgg            45

<210> SEQ ID NO 27
<211> LENGTH: 41
<212> TYPE: DNA
<213> ORGANISM: Artificial Sequence
<220> FEATURE:
<223> OTHER INFORMATION: synthetic

<400> SEQUENCE: 27
cagagggtca ccggtgctgc tttcatccct gggctccacc c                41

<210> SEQ ID NO 28
<211> LENGTH: 41

<212> TYPE: DNA
<213> ORGANISM: Artificial Sequence
<220> FEATURE:
<223> OTHER INFORMATION: synthetic

<400> SEQUENCE: 28
gggtggagcc cagggatgaa agcagcaccg gtgaccctct g                 41

<210> SEQ ID NO 29
<211> LENGTH: 44
<212> TYPE: DNA
<213> ORGANISM: Artificial Sequence
<220> FEATURE:
<223> OTHER INFORMATION: synthetic

<400> SEQUENCE: 29
cctccaaaca gagggtcacc ggtttggacg ctgctcctgg gctc              44

<210> SEQ ID NO 30
<211> LENGTH: 44
<212> TYPE: DNA
<213> ORGANISM: Artificial Sequence
<220> FEATURE:
<223> OTHER INFORMATION: synthetic

<400> SEQUENCE: 30
gagcccagga gcagcgtcca aaccggtgac cctctgtttg gagg              44

<210> SEQ ID NO 31
<211> LENGTH: 46
<212> TYPE: DNA
<213> ORGANISM: Artificial Sequence
<220> FEATURE:
<223> OTHER INFORMATION: synthetic

<400> SEQUENCE: 31
tccaaacaga gggtcaccgg tgctgcagct atccctgggc tccacc            46

<210> SEQ ID NO 32
<211> LENGTH: 46
<212> TYPE: DNA
<213> ORGANISM: Artificial Sequence
<220> FEATURE:
<223> OTHER INFORMATION: synthetic

<400> SEQUENCE: 32
gggtggagcc cagggatagc tgcagcaccg gtgaccctct gtttgg            46

<210> SEQ ID NO 33
<211> LENGTH: 40
<212> TYPE: DNA
<213> ORGANISM: Artificial Sequence
<220> FEATURE:
<223> OTHER INFORMATION: synthetic

<400> SEQUENCE: 33
cagagggtca ccggtgctgc tgctgctccc gggctccacc                   40

<210> SEQ ID NO 34
<211> LENGTH: 41
<212> TYPE: DNA
<213> ORGANISM: Artificial Sequence
<220> FEATURE:
<223> OTHER INFORMATION: synthetic

<400> SEQUENCE: 34
gggtggagcc cgggagcagc agcagcaccg gtgaccctct g    41

<210> SEQ ID NO 35
<211> LENGTH: 4
<212> TYPE: PRT
<213> ORGANISM: Artificial Sequence
<220> FEATURE:
<223> OTHER INFORMATION: synthetic

<400> SEQUENCE: 35

Leu Asp Phe Ile
1

<210> SEQ ID NO 36
<211> LENGTH: 147
<212> TYPE: PRT
<213> ORGANISM: Artificial Sequence
<220> FEATURE:
<223> OTHER INFORMATION: synthetic

<400> SEQUENCE: 36

Ala Val Pro Ile Gln Lys Val Gln Asp Asp Thr Lys Thr Leu Ile Lys
1               5                   10                  15

Thr Ile Val Thr Arg Ile Asn Leu Ile Ser His Thr Gln Ser Val Ser
            20                  25                  30

Ser Lys Gln Lys Val Thr Gly Ala Ala Ile Pro Gly Leu His Pro
        35                  40                  45

Ile Leu Thr Leu Ser Lys Met Asp Gln Thr Leu Ala Val Tyr Gln Gln
 50                  55                  60

Ile Leu Thr Ser Met Pro Ser Gln Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145

<210> SEQ ID NO 37
<211> LENGTH: 147
<212> TYPE: PRT
<213> ORGANISM: Homo sapiens

<400> SEQUENCE: 37

Ala Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
            20                  25                  30

Ser Lys Gln Lys Val Thr Gly Leu Asp Phe Ile Pro Gly Leu His Pro
        35                  40                  45

Ile Leu Thr Leu Ser Lys Met Asp Gln Thr Leu Ala Val Tyr Gln Gln
 50                  55                  60

Ile Leu Thr Ser Met Pro Ser Gln Asn Val Ile Gln Ile Ser Asn Asp
65                  70                  75                  80

Leu Glu Asn Leu Arg Asp Leu Leu His Val Leu Ala Phe Ser Lys Ser

```
                    85                  90                  95
Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
        115                 120                 125

Arg Leu Gln Gly Ser Leu Gln Asp Met Leu Trp Gln Leu Asp Leu Ser
    130                 135                 140

Pro Gly Cys
145

<210> SEQ ID NO 38
<211> LENGTH: 147
<212> TYPE: PRT
<213> ORGANISM: Artificial Sequence
<220> FEATURE:
<223> OTHER INFORMATION: synthetic

<400> SEQUENCE: 38

Ala Val Pro Ile Gln Lys Val Gln Asp Asp Thr Lys Thr Leu Ile Lys
1               5                   10                  15

Thr Leu Val Thr Arg Ile Asn Leu Ile Ser His Thr Gln Ser Val Ser
            20                  25                  30

Ala Lys Gln Arg Val Thr Gly Ala Ala Ala Ile Pro Gly Leu His Pro
        35                  40                  45

Ile Leu Ser Leu Ser Lys Met Asp Gln Thr Leu Ala Val Tyr Gln Gln
    50                  55                  60

Val Leu Thr Ser Leu Pro Ser Gln Asn Val Leu Gln Ile Ala Asn Asp
65                  70                  75                  80

Leu Glu Asn Leu Arg Asp Leu Leu His Leu Leu Ala Phe Ser Lys Ser
                85                  90                  95

Cys Ser Leu Pro Gln Thr Ser Gly Leu Gln Lys Pro Glu Ser Leu Asp
            100                 105                 110

Gly Val Leu Glu Ala Ser Leu Tyr Ser Thr Glu Val Val Ala Leu Ser
        115                 120                 125

Arg Leu Gln Gly Ser Leu Gln Asp Ile Leu Gln Gln Val Asp Leu Ser
    130                 135                 140

Pro Gly Cys
145

<210> SEQ ID NO 39
<211> LENGTH: 464
<212> TYPE: DNA
<213> ORGANISM: Artificial Sequence
<220> FEATURE:
<223> OTHER INFORMATION: synthetic

<400> SEQUENCE: 39
ccatggctgt tccgatccag aaagttcagg atgacaccaa accctgatc aaaaccatcg      60 ttacccgtat taatctgatc tctcataccc agtctgtttc tgctaagcag cgtgttaccg    120
gcgcggctgc aatcccgggc ctgcatccga tcctgtctct gtctaaaatg accagaccc     180 tggctgttta tcagcaggtt ctgacctctc tgccgtctca gaacgttctg cagatcgcta    240
acgacctgga aaacctgcgt gacctgctgc atctgctggc tttctctaaa tcttgctctc    300
tgccgcagac tctggcctg cagaaaccgg aatctctgga cggcgttctg gaggcttctc    360
tgtattctac cgaagttgtt gctctgtctc gtctgcaggg ctctctgcag gacatcctgc    420
agcagttgga cgtttctccg gaatgctgat gaaagcttgg atcc                    464
```

<210> SEQ ID NO 40
<211> LENGTH: 438
<212> TYPE: DNA
<213> ORGANISM: Artificial Sequence
<220> FEATURE:
<223> OTHER INFORMATION: synthetic

<400> SEQUENCE: 40

```
gtgcccatcc aaaaagtcca agatgacacc aaaaccctca tcaagacaat tgtcaccagg      60
atcaatgaca tttcacacac gcagtcagtc tcctccaaac agaaagtcac tggtgcggct     120
ttcattcctg ggctccaccc catcctgacc ttatccaaga tggaccagac actggcagtc     180
taccaacaga tcctcaccag tatgccttcc agaaacgtga tccgaatatc caacgacctg     240
gagaacctcc gggatcttct tcacgtgctg gccttctcta agagctgcca cttgccctgg     300
gccagtggcc tggagacctt ggacagcctg gggggtgtcc tggaagcttc aggctactcc     360
acagaggtgg tggccctgag caggctgcag gggtctctgc aggacatgct gtggcagctg     420
gacctcagcc ctgggtgc                                                   438
```

<210> SEQ ID NO 41
<211> LENGTH: 438
<212> TYPE: DNA
<213> ORGANISM: Artificial Sequence
<220> FEATURE:
<223> OTHER INFORMATION: synthetic

<400> SEQUENCE: 41

```
gtgcccatcc aaaaagtcca agatgacacc aaaaccctca tcaagacaat tgtcaccagg      60
atcaatgaca tttcacacac gcagtcagtc tcctccaaac agaaagtcac tggtttggac     120
gccgctcctg ggctccaccc catcctgacc ttatccaaga tggaccagac actggcagtc     180
taccaacaga tcctcaccag tatgccttcc agaaacgtga tccgaatatc caacgacctg     240
gagaacctcc gggatcttct tcacgtgctg gccttctcta agagctgcca cttgccctgg     300
gccagtggcc tggagacctt ggacagcctg gggggtgtcc tggaagcttc aggctactcc     360
acagaggtgg tggccctgag caggctgcag gggtctctgc aggacatgct gtggcagctg     420
gacctcagcc ctgggtgc                                                   438
```

<210> SEQ ID NO 42
<211> LENGTH: 438
<212> TYPE: DNA
<213> ORGANISM: Artificial Sequence
<220> FEATURE:
<223> OTHER INFORMATION: synthetic

<400> SEQUENCE: 42

```
gtgtcgatcc gcaaggtcca ggatgacacc aaaaccctca tcaagacgat tgtcaccagg      60
atcaatgaca tctcacacac gcagtccgtc tcctccaaac agagggtcac cggtgctgct     120
ttcatccctg ggctccaccc tctcctgagt ttgtccaaga tggaccagac attggcaatc     180
taccaacaga tcctcgccag tctgccttcc agaaatgtga tccaaatatc taatgacctg     240
gagaacctcc gggaccttct ccacctgctg gccgcctcca agagctgccc cttgccgcag     300
gtcagggccc tagagagctt ggagagcctg ggcgtcgtcc tggaagcctc cctctactcc     360
accgaggtgg tggccctgag ccggctacag gggtctctac aggacatgtt gcggcagctg     420
gacctgagtc ccggctgc                                                   438
```

<210> SEQ ID NO 43
<211> LENGTH: 438
<212> TYPE: DNA
<213> ORGANISM: Artificial Sequence
<220> FEATURE:
<223> OTHER INFORMATION: synthetic

<400> SEQUENCE: 43

```
gtgtcgatcc gcaaggtcca ggatgacacc aaaaccctca tcaagacgat tgtcaccagg      60
atcaatgaca tctcacacac gcagtccgtc tcctccaaac agagggtcac cggtttggac     120
gctgctcctg ggctccaccc tctcctgagt ttgtccaaga tggaccagac attggcaatc     180
taccaacaga tcctcgccag tctgccttcc agaaatgtga tccaaatatc taatgacctg     240
gagaaccctcc gggaccttct ccacctgctg gccgcctcca gagctgccc  cttgccgcag    300
gtcagggccc tagagagctt ggagagcctg ggcgtcgtcc tggaagcctc cctctactcc     360
accgaggtgg tggccctgag ccggctacag gggtctctac aggacatgtt gcggcagctg     420
gacctgagtc ccggctgc                                                    438
```

<210> SEQ ID NO 44
<211> LENGTH: 438
<212> TYPE: DNA
<213> ORGANISM: Artificial Sequence
<220> FEATURE:
<223> OTHER INFORMATION: synthetic

<400> SEQUENCE: 44

```
gtgcccatcc aaaagtcca agatgacacc aaaaccctca tcaagacaat tgtcaccagg       60
atcaatgaca tttcacacac gcagtcagtc tcctccaaac agaaagtcac tggtgcggct     120
gccattcctg ggctccaccc catcctgacc ttatccaaga tggaccagac actggcagtc     180
taccaacaga tcctcaccag tatgccttcc agaaacgtga tccgaatatc caacgacctg     240
gagaaccctc gggatcttct tcacgtgctg gccttctcta agagctgcca cttgccctgg     300
gccagtggcc tggagacctt ggacagcctg ggggggtgtcc tggaagcttc aggctactcc    360
acagaggtgg tggccctgag caggctgcag gggtctctgc aggacatgct gtggcagctg     420
gacctcagcc ctgggtgc                                                    438
```

<210> SEQ ID NO 45
<211> LENGTH: 438
<212> TYPE: DNA
<213> ORGANISM: Artificial Sequence
<220> FEATURE:
<223> OTHER INFORMATION: synthetic

<400> SEQUENCE: 45

```
gtgtcgatcc gcaaggtcca ggatgacacc aaaaccctca tcaagacgat tgtcaccagg      60
atcaatgaca tctcacacac gcagtccgtc tcctccaaac agagggtcac cggtgctgca     120
gctatccctg ggctccaccc tctcctgagt ttgtccaaga tggaccagac attggcaatc     180
taccaacaga tcctcgccag tctgccttcc agaaatgtga tccaaatatc taatgacctg     240
gagaaccctc gggaccttct ccacctgctg gccgcctcca gagctgccc  cttgccgcag    300
gtcagggccc tagagagctt ggagagcctg ggcgtcgtcc tggaagcctc cctctactcc     360
accgaggtgg tggccctgag ccggctacag gggtctctac aggacatgtt gcggcagctg     420
gacctgagtc ccggctgc                                                    438
```

<210> SEQ ID NO 46
<211> LENGTH: 438
<212> TYPE: DNA
<213> ORGANISM: Artificial Sequence
<220> FEATURE:
<223> OTHER INFORMATION: synthetic

<400> SEQUENCE: 46

```
gtgcccatcc aaaaagtcca agatgacacc aaaccctca tcaagacaat tgtcaccagg      60
atcaatgaca tttcacacac gcagtcagtc tcctccaaac agaaagtcac tggtgcggct    120
gccgctcctg ggctccaccc catcctgacc ttatccaaga tggaccagac actggcagtc    180
taccaacaga tcctcaccag tatgccttcc agaaacgtga tccgaatatc aacgacctg     240
gagaacctcc gggatcttct tcacgtgctg gccttctcta agagctgcca cttgccctgg    300
gccagtggcc tggagacctt ggacagcctg ggggtgtcc tggaagcttc aggctactcc     360
acagaggtgg tggccctgag caggctgcag gggtctctgc aggacatgct gtggcagctg    420
gacctcagcc ctgggtgc                                                   438
```

<210> SEQ ID NO 47
<211> LENGTH: 438
<212> TYPE: DNA
<213> ORGANISM: Artificial Sequence
<220> FEATURE:
<223> OTHER INFORMATION: synthetic

<400> SEQUENCE: 47

```
gtgtcgatcc gcaaggtcca ggatgacacc aaaccctca tcaagacgat tgtcaccagg      60
atcaatgaca tctcacacac gcagtccgtc tcctccaaac agagggtcac cggtgctgct    120
gctgctcctg ggctccaccc tctcctgagt ttgtccaaga tggaccagac attggcaatc    180
taccaacaga tcctcgccag tctgccttcc agaaatgtga tccaaatatc taatgacctg    240
gagaacctcc gggaccttct ccacctgctg gccgcctcca agagctgccc cttgccgcag    300
gtcagggccc tagagagctt ggagagcctg ggcgtcgtcc tggaagcctc cctctactcc    360
accgaggtgg tggccctgag ccggctacag gggtctctac aggacatgtt gcggcagctg    420
gacctgagtc ccggctgc                                                   438
```

<210> SEQ ID NO 48
<211> LENGTH: 167
<212> TYPE: PRT
<213> ORGANISM: Rattus norvegicus

<400> SEQUENCE: 48

```
Met Cys Trp Arg Pro Leu Cys Arg Phe Leu Trp Leu Trp Ser Tyr Leu
  1               5                  10                  15

Ser Tyr Val Gln Ala Val Pro Ile His Lys Val Gln Asp Asp Thr Lys
             20                  25                  30

Thr Leu Ile Lys Thr Ile Val Thr Arg Ile Asn Asp Ile Ser His Thr
         35                  40                  45

Gln Ser Val Ser Ala Arg Gln Arg Val Thr Gly Leu Asp Phe Ile Pro
     50                  55                  60

Gly Leu His Pro Ile Leu Ser Leu Ser Lys Met Asp Gln Thr Leu Ala
 65                  70                  75                  80

Val Tyr Gln Gln Ile Leu Thr Ser Leu Pro Ser Gln Asn Val Leu Gln
             85                  90                  95

Ile Ala His Asp Leu Glu Asn Leu Arg Asp Leu Leu His Leu Leu Ala
            100                 105                 110
```

```
Phe Ser Lys Ser Cys Ser Leu Pro Gln Thr Arg Gly Leu Gln Lys Pro
        115                 120                 125

Glu Ser Leu Asp Gly Val Leu Glu Ala Ser Leu Tyr Ser Thr Glu Val
130                 135                 140

Val Ala Leu Ser Arg Leu Gln Gly Ser Leu Gln Asp Ile Leu Gln Gln
145                 150                 155                 160

Leu Asp Leu Ser Pro Glu Cys
                165

<210> SEQ ID NO 49
<211> LENGTH: 576
<212> TYPE: DNA
<213> ORGANISM: Mus musculus

<400> SEQUENCE: 49
gtgggacagc gagctaatac ccagaactga gttgtgtcct gctaagtcct ctgccacgta    60
cccacgggat gaagaacctt tcatttcccc tccttttcct tttcttcctt gtccctgaac   120
tgctgggctc cagcatgcca ctgtgtccca tcgatgaagc catcgacaag aagatcaaac   180
aagacttcaa ctccctgttt ccaaatgcaa taaagaacat tggcttaaat tgctggacag   240
tctcctccag agggaagttg gcctcctgcc cagaaggcac agcagtcttg agctgctcct   300
gtggctctgc ctgtggctcg tgggacattc gtgaagaaaa agtgtgtcac tgccagtgtg   360
caaggataga ctggacagca gcccgctgct gtaagctgca ggtcgcttcc tgatgtcggg   420
gaagtgagcg tggtttccag cacagccacc cgttcctgta gctccagaga tgtctgatgt   480
cctccggtct ctacaggcac ctgcactcac gtgcgcgaat ccacacacaa gcacacatac   540
ttaaaaataa aacaaaacag gctggaaaaa aaaaaa                             576

<210> SEQ ID NO 50
<211> LENGTH: 114
<212> TYPE: PRT
<213> ORGANISM: Mus musculus

<400> SEQUENCE: 50

Met Lys Asn Leu Ser Phe Pro Leu Leu Phe Leu Phe Phe Leu Val Pro
1               5                   10                  15

Glu Leu Leu Gly Ser Ser Met Pro Leu Cys Pro Ile Asp Glu Ala Ile
            20                  25                  30

Asp Lys Lys Ile Lys Gln Asp Phe Asn Ser Leu Phe Pro Asn Ala Ile
        35                  40                  45

Lys Asn Ile Gly Leu Asn Cys Trp Thr Val Ser Ser Arg Gly Lys Leu
    50                  55                  60

Ala Ser Cys Pro Glu Gly Thr Ala Val Leu Ser Cys Ser Cys Gly Ser
65                  70                  75                  80

Ala Cys Gly Ser Trp Asp Ile Arg Gly Gly Lys Val Cys His Cys Gln
                85                  90                  95

Cys Ala Arg Ile Asp Trp Thr Ala Ala Arg Cys Cys Lys Leu Gln Val
            100                 105                 110

Ala Ser

<210> SEQ ID NO 51
<211> LENGTH: 479
<212> TYPE: DNA
<213> ORGANISM: Homo sapiens
<220> FEATURE:
<221> NAME/KEY: misc_feature
```

<222> LOCATION: (140)..(140)
<223> OTHER INFORMATION: n is a, c, g, or t

<400> SEQUENCE: 51

```
gtgtgccgga tttggttagc tgagcccacc gagaggcgcc tgcaggatga aagctctctg      60
tctcctcctc ctccctgtcc tggggctgtt ggtgtctagc aagaccctgt gctccatgga     120
agaagccatc aatgagaggn tccaggaggt cgccggctcc ctaatattta gggcaataag     180
cagcattggc ctggagtgcc agagcgtcac ctccaggggg gacctggcta cttgccccg      240
aggcttcgcc gtcaccggct gcacttgtgg ctccgcctgt ggctcgtggg atgtgcgcgc     300
cgagaccaca tgtcactgcc agtgcgcggg catggactgg accggagcgc gctgctgtcg     360
tgtgcagccc tgaggtcgcg cgcagcgcgt gcacagcgcg ggcggaggcg gctccaggtc     420
cggaggggtt gcggggagc tggaaataaa cctggagatg atgatgatga tgatgatgg      479
```

<210> SEQ ID NO 52
<211> LENGTH: 107
<212> TYPE: PRT
<213> ORGANISM: Homo sapiens

<400> SEQUENCE: 52

```
Met Lys Ala Leu Cys Leu Leu Leu Val Leu Gly Leu Leu Val Ser
1               5                  10                  15

Ser Lys Thr Leu Cys Ser Met Glu Glu Ala Ile Asn Glu Arg Ile Gln
            20                  25                  30

Glu Val Ala Gly Ser Leu Ile Phe Arg Ala Ile Ser Ser Ile Gly Leu
        35                  40                  45

Glu Cys Gln Ser Val Thr Ser Arg Gly Asp Leu Ala Thr Cys Pro Arg
    50                  55                  60

Gly Phe Ala Val Thr Gly Ser Thr Cys Gly Ser Ala Cys Gly Ser Trp
65                  70                  75                  80

Asp Val Arg Ala Glu Thr Thr Cys His Cys Gln Cys Ala Gly Met Asp
                85                  90                  95

Trp Thr Gly Ala Arg Cys Cys Arg Val Gln Pro
            100                 105
```

<210> SEQ ID NO 53
<211> LENGTH: 4420
<212> TYPE: DNA
<213> ORGANISM: Homo sapiens

<400> SEQUENCE: 53

```
aacctagcca acatggtgaa actccttctc tactaaaaat acaaaaatta gccaggtatg      60
gtggcgagcg cctgtagtcc cagctacgtg ggaggctgag gcaggagaat cgcttgaacc     120
caggaggcag aggcttgcgg tgagccgaga ttgcaccact gcactccagc ctgggcaaca     180
gagcgagacc ctgtctcaaa aaaaaaaaac ttggtttcgt gtggtgtatc ttcgcttgtt     240
tctgtgtgat ctgtgattgt ccttctgtcg tttcttggtt ttctcttatt ctcggcgtgt     300
tatgttgcgc tgtgcttcgt ttggttctac tgtttctgt ttccttcttt ctcgttttg      360
tcagtcgtct tgtctgtctc cgcagcgcgc ttgtcactct ggtcgcgttg cctgtacgtc     420
attcgtcgtt ctgcctgctc gttatcgttc tcgcatgatt gttttcctcc gggatcgcat     480
ggctgctccc cttcttgtat gtcttcttgt ctcctgggct cgtcttctcc cgcttcttcg     540
tttgtctttc attctctctt ttcattcctc tttcttcac aattacattt cctctccgac     600
agtgagtcga ttgtctagtg tcaggggaag ggaagggaag aaacgaaacc ctgggggga     660
```

-continued

```
tctaggagca gacaagtccc ctgctctgtg ttttcataat ctagtatcca ggaagggta      720 agcaccctgc gtgtatctgg ttgtaactaa ctactcacaa ctgcacttgc ctgtgtgaaa      780
acgtgagctt gtgatgatgc gtgacgtcag gtaggcgtcc ctgactctcc gtaacccaac      840
tttgcctgtg ccttgggat tcctccttgc aggtaggaag tgaggggtac aggttccagc      900
tctgggctga gacatgattc agggttccac cctgacctgg ggctcctgga gtcttggggc      960
cctggagggt cccgtccact gcccagactg acccaggtcc tcgatgaagc tcattatga     1020 ggactggggg aaaaggaccc agccacttcc tggggaggtc ggagacccca gggtgagcgt     1080
caaggtagcc tcaaagatga gacgtcacct cttgaaggca gccatgagcc ttgggtgggg     1140
acgtcactag aggaagttca ggccctattt tcggaggaag cagttggaga ccccatagga     1200
ggaagggcga tggggcagta gaaagtcgcg gtgtccccgc ccctccagc agctacgcgc     1260 cccactctct tggagacgct agatcagtcc ctccgggcct actaaagaaa ccacgcaggg     1320
ctcagatccg ctccatcatc atcatcatca tcatcatcat catctccagg tttatttcca     1380
gctcccccgc aaccctccg gacctggagc cgcctccgcc cgcgctgtgc acgcgctgcg     1440
cgcgacctca gggctgcaca cgacagcagc gcgctccggt ccagtccatg cccgcgcact     1500
ggcagtgaca tgtggtctcg gcgcgcacat cccacgagcc acaggcggag ccacaagtgc     1560
agccggtgac ggcgaagcct gcagcccgga acacaggagc gtggactctg agctgggagg     1620
ctgagggtgg gagcgggagg ggggtgggga gcgcggaggg gggttggggg ggcggggtg     1680 gggacgggga cggctggagg ctccaaccac tgaatgggca ctggaggcag ggagtgaggg     1740
tggacaccag tgtccagatg gtgggcggag aaggctggga gtcaggacca agatcctagg     1800
ggagtagagg ctggacacgg ggaacgtggc ggggagggg cattcccagg ggacttggaa     1860
cagaaatggg cgcctggaca acagtctcct gcactcacct cggggggcaag tagccaggtc     1920 cccctggag gtgacgctct ggcactccag gccaatgctg cttattgccc taaatactgg     1980
ggggcaggag gaaaggagac aggggagct gtgagaccaa acgtccctc ccccatcctc     2040 ccctagccct gttggtttgg agctaggtcc ctgtgggcat aggagctcac tggcctccag     2100
gaccctgtct tgagttgggt gttttggagt aagggaaggt ttggagtgag agcggggatt     2160
gggtttggag ccgtggataa ggtggggaca gtcggagggg ttgggagtgg agttggggtt     2220
gaatttatga tctggttgga tttgaggatg agatttggtg agcgctgggg ctgggttgga     2280
gtcaggtctg tgccagggat cagtgaggtc tctgagaccc ttggggagct tgcccaagtg     2340 ggggtcctc acttagggag ccggcgacct cctggatcct ctcattgatg gcttcttcca     2400
tggagcacag ggtcttgcta gacaccaaca gccccaggac agggaggagg aggagacaga     2460
gagctttcat cctgcaggcg ctgaaagagg gaaccaagag acccacagct ggatcagccc     2520
tgccctgtgg ggaagatccg gcccatggag ggagtaggat ctgcccctgg acctggaccc     2580
ctgtcccccc atgtggggga cagggatgga ggctcagcct tgaccccagc ctcccgctg     2640 gtgccatggc aagcgcagga gcagctgtca cttaccctct cggtgggctc agctaaccaa     2700
atccggcaca cgaattcctg caccgcagct ctttctttga ggcctcttgg ggtggggctt     2760
cctggcttgg ctaataagtc cctgggcccc caaccctccg gtcccacatc cggggccaag     2820
aggaagcccc tgagcagaca gtaagggctg gaggaggaag ggagccttcc cacttccaac     2880
agggcctccg tcttcatgtc cagagactgg tcaggaggtg gtccccagg gataatgcca     2940 ggggctgtgg tctgaggaac aggtagacaa gcagagtttt gcatgcaagg gtggctgatg     3000
```

```
caaacatgac aaaattaatg cctcttgcta ggcatggtgc ggacaagcac ttgtagtccc    3060
agctactaag gaggctgacg tgagagaatt gcttgagccc gggagttcga agctacagtg    3120
acttatgatc acagcactgc actccagtct gggcaacaga gcaagaccac ttctctaaaa    3180
tagtaataat aattatgtct ctgggtgaga atgacatacc acattcatac ccaaatgccc    3240
atgagcaata gaactggtaa ataaaatcat ggtttatggc cggtggctca cgcctgtaat    3300
cccagcactt tgggaggcca aggcgggcgg atcacttgag gtcaggagct gagaccaac     3360
ctggccaaca tgatgaaacc ctgtctccat tagacataca aaaattaact gggcgtggtg    3420
gcgtgtgcct gtaatcccag ctacttggga ggctgaggtg ggagaatcac ttgaacccgg    3480
gatgtggagg ttgcagtgca ctgagatcgt gcccctgcac tccatcctgg atgactagct    3540
tgggcaccat agcaagactc catctcaaaa agaagaaaga aaaatcatgg tttattccat    3600
caatggcatc acctgcaaca gaagttggaa agccattgct catgggccaa ggtccagctc    3660
atgtttcttc ttggaccacc catgagcttg gaatggttat acattttat ttgttctttg     3720
tttccagtac aacgggcctt tttgtggtaa aatacatata acatcaaact taccattata    3780
acttactttt ttctgttttt gagacggaat cttgctctgt cgcccaggct ggagtgcagt    3840
ggcgcgatct cggctcacta caagctccgc ctcctgggtt cacgccattc tcctgcttca    3900
gcctcccaag tagctgggac tacaggcgcc tgccaccacg cccagctaat ttttgtatt     3960
tttttttttt tagtagagat ggagtttcac cgtgttagcc aggatggtct cgatcccctg    4020
accttgtgat ctgcccgcct tggcctccca aagtgctggg attacaggcg tgaaccaccg    4080
tgcccggcct tttttttttt tttttgaga cggggtcttg ctatgttgcc caagctagtg     4140
tcagactcct ggcttcaagt aatcctccca ccttggactc cccagtagct gaagctacag    4200
gtatgcacca tcttgttcca ttttaaccat tgcttttgtt tgtttctttg tttcagagtc    4260
tcactcagtt gctcaggctg gagtacagtg gctcaatctt ggctcactgc aacctccacc    4320
tcctgggttc aagcaattct cctgcctcag cctcccgagt agctgggatt acaggcgtgc    4380
accaccatgc ccggctaatt ttttgtattt ttagtagaga                          4420
```

`<210>` SEQ ID NO 54
`<211>` LENGTH: 4420
`<212>` TYPE: DNA
`<213>` ORGANISM: Homo sapiens

`<400>` SEQUENCE: 54

```
tctctactaa aaatacaaaa aattagccgg gcatggtggt gcacgcctgt aatcccagct      60
actcgggagg ctgaggcagg agaattgctt gaacccagga ggtggaggtt gcagtgagcc     120
aagattgagc cactgtactc cagcctgagc aactgagtga gactctgaaa caaagaaaca    180
aacaaaagca atggttaaaa tggaacaaga tggtgcatac ctgtagcttc agctactggg    240
gagtccaagg tgggaggatt acttgaagcc aggagtctga cactagcttg gcaacatag     300
caagaccccg tctcaaaaaa aaaaaaaaaa aggccgggca cggtggttca cgcctgtaat    360
cccagcactt tgggaggcca aggcgggcag atcacaaggt caggggatcg agaccatcct    420
ggctaacacg gtgaaactcc atctctacta aaaaaaaaaa aatacaaaaa attagctggg    480
cgtggtggca ggcgcctgta gtcccagcta cttgggaggc tgaagcagga gatggcgtg    540
aacccaggag gcggagcttg tagtgagccg agatcgcgcc actgcactcc agcctgggcg    600
acagagcaag attccgtctc aaaaacagaa aaaagtaagt tataatggta agttgtatgt    660
tatatgtatt ttaccacaaa aaggcccgtt gtactggaaa caaagaacaa ataaaaatgt    720
```

```
ataaccattc caagctcatg ggtggtccaa gaagaaacat gagctggacc ttggcccatg    780
agcaatggct ttccaacttc tgttgcaggt gatgccattg atggaataaa ccatgatttt    840
tctttcttct ttttgagatg gagtcttgct atggtgccca agctagtcat ccaggatgga    900
gtgcaggggc acgatctcag tgcactgcaa cctccacatc ccgggttcaa gtgattctcc    960
cacctcagcc tcccaagtag ctgggattac aggcacacgc caccacgccc agttaatttt   1020
tgtatgtcta atgagacag ggtttcatca tgttggccag gttggtctca agctcctgac   1080
ctcaagtgat ccgcccgcct tggcctccca aagtgctggg attacaggcg tgagccaccg   1140
gccataaacc atgattttat ttaccagttc tattgctcat gggcatttgg gtatgaatgt   1200
ggtatgtcat tctcacccag agacataatt attattacta ttttagagaa gtggtcttgc   1260
tctgttgccc agactggagt gcagtgctgt gatcataagt cactgtagct tcgaactccc   1320
gggctcaagc aattctctca cgtcagcctc cttagtagct gggactacaa gtgcttgtcc   1380
gcaccatgcc tagcaagagg cattaatttt gtcatgtttg catcagccac ccttgcatgc   1440
aaaactctgc ttgtctacct gttcctcaga ccacagcccc tggcattatc cctggggcac   1500
cacctcctga ccagtctctg gacatgaaga cggaggccct gttggaagtg gaaggctcc   1560 cttcctcctc cagcccttac tgtctgctca ggggcttcct cttggccccg gatgtgggac   1620
cggagggttg ggggcccagg gacttattag ccaagccagg aagccccacc caagaggcc   1680 tcaaagaaag agctgcggtg caggaattcg tgtgccggat ttggttagct gagcccaccg   1740
agagggtaag tgacagctgc tcctgcgctt gccatggcac cagcggggag gctgggtca   1800 aggctgagcc tccatccctg tcccccacat ggggggacag gggtccaggt ccaggggcag   1860
atcctactcc ctccatgggc cggatcttcc ccacagggca gggctgatcc agctgtgggt   1920
ctcttggttc cctctttcag cgcctgcagg atgaaagctc tctgtctcct cctcctccct   1980
gtcctggggc tgttggtgtc tagcaagacc ctgtgctcca tggaagaagc catcaatgag   2040
aggatccagg aggtcgccgg ctccctaagt gaggaccccc cacttgggca agctccccaa   2100
gggtctcaga gacctcactg atccctggca cagacctgac tccaacccag ccccagcgct   2160
caccaaatct catcctcaaa tccaaccaga tcataaattc aaccccaact ccactcccaa   2220
cccctccgac tgtccccacc ttatccacgg ctccaaaccc aatccccgct ctcactccaa   2280
accttccctt actccaaaac acccaactca agacagggtc ctggaggcca gtgagctcct   2340
atgcccacag ggacctagct ccaaaccaac agggctaggg gaggatgggg gagggaccgt   2400
ttggtctcac agctccccct gtctcctttc ctcctgcccc ccagtattta gggcaataag   2460
cagcattggc ctggagtgcc agagcgtcac ctccaggggg gacctggcta cttgcccccg   2520
aggtgagtgc aggagactgt tgtccaggcg cccatttctg ttccaagtcc cctgggaatg   2580 cccctccc gccacgttcc ccgtgtccag cctctactcc cctaggatct tggtcctgac   2640
tcccagcctt ctccgcccac catctggaca ctggtgtcca ccctcactcc ctgcctccag   2700
tgcccattca gtggttggag cctccagccg tccccgtccc caccccgcc ccccaaccc   2760 ccctccgcgc tccccacccc cctccgctc ccacctcag cctccagct cagagtccac   2820 gctcctgtgt tccgggctgc aggcttcgcc gtcaccggct gcacttgtgg ctccgcctgt   2880
ggctcgtggg atgtgcgcgc cgagaccaca tgtcactgcc agtgcgcggg catggactgg   2940
accggagcgc gctgctgtcg tgtgcagccc tgaggtcgcg cgcagcgcgt gcacagcgcg   3000
ggcggaggcg gctccaggtc cggagggtt gcggggagc tggaaataaa cctggagatg   3060
```

| | | |
|---|---|---|
| atgatgatga tgatgatgat gatgatggag cggatctgag ccctgcgtgg tttctttagt | 3120 |
| aggcccggag ggactgatct agcgtctcca agagagtggg gcgcgtagct gctggagggg | 3180 |
| gcggggacac cgcgactttc tactgcccca tcgcccttcc tcctatgggg tctccaactg | 3240 |
| cttcctccga aaatagggcc tgaacttcct ctagtgacgt ccccacccaa ggctcatggc | 3300 |
| tgccttcaag aggtgacgtc tcatctttga ggctaccttg acgctcaccc tggggtctcc | 3360 |
| gacctcccca ggaagtggct gggtcctttt cccccagtcc tcataatgag gcttcatcga | 3420 |
| ggacctgggt cagtctgggc agtggacggg accctccagg gccccaagac tccaggagcc | 3480 |
| ccaggtcagg gtggaaccct gaatcatgtc tcagcccaga gctggaacct gtacccctca | 3540 |
| cttcctacct gcaaggagga atccccaagg cacaggcaaa gttgggttac ggagagtcag | 3600 |
| ggacgcctac ctgacgtcac gcatcatcac aagctcacgt tttcacacag gcaagtgcag | 3660 |
| ttgtgagtag ttagttacaa ccagatacac gcagggtgct taccccttcc tggatactag | 3720 |
| attatgaaaa cacagagcag gggacttgtc tgctcctaga tcccccccag ggtttcgttt | 3780 |
| cttcccttcc cttcccctga cactagacaa tcgactcact gtcggagagg aaatgtaatt | 3840 |
| gtgaaagaaa gaggaatgaa aagagagaat gaaagacaaa cgaagaagcg ggagaagacg | 3900 |
| agcccaggag acaagaagac atacaagaag gggagcagcc atgcgatccc ggaggaaaac | 3960 |
| aatcatgcga gaacgataac gagcaggcag aacgacgaat gacgtacagg caacgcgacc | 4020 |
| agagtgacaa gcgcgctgcg gagacagaca agacgactga caaaaacgag aaagaaggaa | 4080 |
| acagaaaaca gtagaaccaa acgaagcaca gcgcaacata acacgccgag aataagagaa | 4140 |
| aaccaagaaa cgacagaagg acaatcacag atcacacaga aacaagcgaa gatacaccac | 4200 |
| acgaaaccaa gttttttttt tttgagacag gtctcgctc tgttgcccag gctggagtgc | 4260 |
| agtggtgcaa tctcggctca ccgcaagcct ctgcctcctg ggttcaagcg attctcctgc | 4320 |
| ctcagcctcc cacgtagctg ggactacagg cgctcgccac catacctggc taattttttgt | 4380 |
| attttttagta gagaaggagt ttcaccatgt tggctaggtt | 4420 |

```
<210> SEQ ID NO 55
<211> LENGTH: 114
<212> TYPE: PRT
<213> ORGANISM: Artificial Sequence
<220> FEATURE:
<223> OTHER INFORMATION: consensus resistin sequence mouse/human
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (5)..(7)
<223> OTHER INFORMATION: Xaa can be any naturally occurring amino acid
<220> FEATURE:
<221> NAME/KEY: misc_feature
<222> LOCATION: (10)..(13)
<223> OTHER INFORMATION: Xaa can be any naturally occurring amino acid
<220> FEATURE:
<221> NAME/KEY: misc_feature
<222> LOCATION: (15)..(17)
<223> OTHER INFORMATION: Xaa can be any naturally occurring amino acid
<220> FEATURE:
<221> NAME/KEY: misc_feature
<222> LOCATION: (20)..(20)
<223> OTHER INFORMATION: Xaa can be any naturally occurring amino acid
<220> FEATURE:
<221> NAME/KEY: misc_feature
<222> LOCATION: (23)..(24)
<223> OTHER INFORMATION: Xaa can be any naturally occurring amino acid
<220> FEATURE:
<221> NAME/KEY: misc_feature
```

```
<222> LOCATION: (27)..(29)
<223> OTHER INFORMATION: Xaa can be any naturally occurring amino acid
<220> FEATURE:
<221> NAME/KEY: misc_feature
<222> LOCATION: (33)..(35)
<223> OTHER INFORMATION: Xaa can be any naturally occurring amino acid
<220> FEATURE:
<221> NAME/KEY: misc_feature
<222> LOCATION: (37)..(41)
<223> OTHER INFORMATION: Xaa can be any naturally occurring amino acid
<220> FEATURE:
<221> NAME/KEY: misc_feature
<222> LOCATION: (44)..(46)
<223> OTHER INFORMATION: Xaa can be any naturally occurring amino acid
<220> FEATURE:
<221> NAME/KEY: misc_feature
<222> LOCATION: (49)..(50)
<223> OTHER INFORMATION: Xaa can be any naturally occurring amino acid
<220> FEATURE:
<221> NAME/KEY: misc_feature
<222> LOCATION: (54)..(54)
<223> OTHER INFORMATION: Xaa can be any naturally occurring amino acid
<220> FEATURE:
<221> NAME/KEY: misc_feature
<222> LOCATION: (56)..(57)
<223> OTHER INFORMATION: Xaa can be any naturally occurring amino acid
<220> FEATURE:
<221> NAME/KEY: misc_feature
<222> LOCATION: (59)..(59)
<223> OTHER INFORMATION: Xaa can be any naturally occurring amino acid
<220> FEATURE:
<221> NAME/KEY: misc_feature
<222> LOCATION: (63)..(63)
<223> OTHER INFORMATION: Xaa can be any naturally occurring amino acid
<220> FEATURE:
<221> NAME/KEY: misc_feature
<222> LOCATION: (66)..(66)
<223> OTHER INFORMATION: Xaa can be any naturally occurring amino acid
<220> FEATURE:
<221> NAME/KEY: misc_feature
<222> LOCATION: (69)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (77)..(77)
<223> OTHER INFORMATION: Xaa can be any naturally occurring amino acid
<220> FEATURE:
<221> NAME/KEY: misc_feature
<222> LOCATION: (87)..(87)
<223> OTHER INFORMATION: Xaa can be any naturally occurring amino acid
<220> FEATURE:
<221> NAME/KEY: misc_feature
<222> LOCATION: (89)..(89)
<223> OTHER INFORMATION: Xaa can be any naturally occurring amino acid
<220> FEATURE:
<221> NAME/KEY: misc_feature
<222> LOCATION: (91)..(92)
<223> OTHER INFORMATION: Xaa can be any naturally occurring amino acid
<220> FEATURE:
<221> NAME/KEY: misc_feature
<222> LOCATION: (99)..(100)
<223> OTHER INFORMATION: Xaa can be any naturally occurring amino acid
<220> FEATURE:
<221> NAME/KEY: misc_feature
<222> LOCATION: (104)..(104)
<223> OTHER INFORMATION: Xaa can be any naturally occurring amino acid
<220> FEATURE:
<221> NAME/KEY: misc_feature
<222> LOCATION: (109)..(110)
<223> OTHER INFORMATION: Xaa can be any naturally occurring amino acid
<220> FEATURE:
```

<221> NAME/KEY: misc_feature
<222> LOCATION: (112)..(114)
<223> OTHER INFORMATION: Xaa can be any naturally occurring amino acid

<400> SEQUENCE: 55

```
Met Lys Xaa Leu Xaa Xaa Xaa Leu Leu Xaa Xaa Xaa Xaa Leu Xaa Xaa
1               5                   10                  15

Xaa Leu Leu Xaa Ser Ser Xaa Xaa Leu Cys Xaa Xaa Xaa Glu Ala Ile
            20                  25                  30

Xaa Xaa Xaa Ile Xaa Xaa Xaa Xaa Ser Leu Xaa Xaa Xaa Ala Ile
        35                  40                  45

Xaa Xaa Ile Gly Leu Xaa Cys Xaa Xaa Val Xaa Ser Arg Gly Xaa Leu
    50                  55                  60

Ala Xaa Cys Pro Xaa Gly Xaa Ala Val Xaa Xaa Cys Xaa Cys Gly Ser
65                  70                  75                  80

Ala Cys Gly Ser Trp Asp Xaa Arg Xaa Glu Xaa Xaa Cys His Cys Gln
                85                  90                  95

Cys Ala Xaa Xaa Asp Trp Thr Xaa Ala Arg Cys Cys Xaa Xaa Gln Xaa
            100                 105                 110

Xaa Xaa
```

<210> SEQ ID NO 56
<211> LENGTH: 5446
<212> TYPE: DNA
<213> ORGANISM: Artificial Sequence
<220> FEATURE:
<223> OTHER INFORMATION: Plasmid

<400> SEQUENCE: 56

```
gacggatcgg gagatctccc gatccctat ggtcgactct cagtacaatc tgctctgatg      60
ccgcatagtt aagccagtat ctgctccctg cttgtgtgtt ggaggtcgct gagtagtgcg    120
cgagcaaaat ttaagctaca acaaggcaag gcttgaccga caattgcatg aagaatctgc    180
ttaggggtag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggac tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gcttggtacc    900
gagctcggat ccactagtaa cggccgccag tgtgctggaa ttctgcagat atccatcaca    960
ctggcggccg ctcgagcatg catctagagg gccctattct atagtgtcac ctaaatgcta   1020
gagctcgctg atcagcctcg actgtgcctt ctagttgcca gccatctgtt gtttgcccct   1080
cccccgtgcc ttccttgacc ctggaaggtg ccactcccac tgtcctttcc taataaaatg   1140
aggaaattgc atcgcattgt ctgagtaggt gtcattctat tctggggggt ggggtggggc   1200
```

| | |
|---|---|
| aggacagcaa gggggaggat tgggaagaca atagcaggca tgctggggat gcggtgggct | 1260 |
| ctatggcttc tgaggcggaa agaaccagct ggggctctag ggggtatccc cacgcgccct | 1320 |
| gtagcggcgc attaagcgcg gcgggtgtgg tggttacgcg cagcgtgacc gctacacttg | 1380 |
| ccagcgccct agcgcccgct cctttcgctt tcttcccttc ctttctcgcc acgttcgccg | 1440 |
| gctttccccg tcaagctcta atcggggca tccctttagg gttccgattt agtgctttac | 1500 |
| ggcacctcga ccccaaaaaa cttgattagg gtgatggttc acgtagtggg ccatcgccct | 1560 |
| gatagacggt ttttcgccct tgacgttgg agtccacgtt ctttaatagt ggactcttgt | 1620 |
| tccaaactgg aacaacactc aaccctatct cggtctattc ttttgattta taagggattt | 1680 |
| tggggatttc ggcctattgg ttaaaaatg agctgattta acaaaatttt aacgcgaatt | 1740 |
| aattctgtgg aatgtgtgtc agttaggggtg tggaaagtcc ccaggctccc caggcaggca | 1800 |
| gaagtatgca aagcatgcat ctcaattagt cagcaaccag gtgtggaaag tccccaggct | 1860 |
| ccccagcagg cagaagtatg caaagcatgc atctcaatta gtcagcaacc atagtcccgc | 1920 |
| ccctaactcc gcccatcccg ccctaactc cgcccagttc cgcccattct ccgccccatg | 1980 |
| gctgactaat ttttttatt tatgcagagg ccgaggccgc ctctgcctct gagctattcc | 2040 |
| agaagtagtg aggaggcttt tttggaggcc taggcttttg caaaaagctc ccgggagctt | 2100 |
| gtatatccat tttcggatct gatcaagaga caggatgagg atcgtttcgc atgattgaac | 2160 |
| aagatggatt gcacgcaggt tctccggccg cttgggtgga gaggctattc ggctatgact | 2220 |
| gggcacaaca gacaatcggc tgctctgatg ccgccgtgtt ccggctgtca gcgcaggggc | 2280 |
| gcccggttct ttttgtcaag accgacctgt ccggtgccct gaatgaactg caggacgagg | 2340 |
| cagcgcggct atcgtggctg gccacgacgg gcgttccttg cgcagctgtg ctcgacgttg | 2400 |
| tcactgaagc gggaagggac tggctgctat tgggcgaagt gccggggcag gatctcctgt | 2460 |
| catctcacct tgctcctgcc gagaaagtat ccatcatggc tgatgcaatg cggcggctgc | 2520 |
| atacgcttga tccggctacc tgcccattcg accaccaagc gaaacatcgc atcgagcgag | 2580 |
| cacgtactcg gatggaagcc ggtcttgtcg atcaggatga tctggacgaa gagcatcagg | 2640 |
| ggctcgcgcc agccgaactg ttcgccaggc tcaaggcgcg catgcccgac ggcgaggatc | 2700 |
| tcgtcgtgac ccatggcgat gcctgcttgc cgaatatcat ggtggaaaat ggccgctttt | 2760 |
| ctggattcat cgactgtggc cggctgggtg tggcggaccg ctatcaggac atagcgttgg | 2820 |
| ctacccgtga tattgctgaa gagcttggcg gcgaatgggc tgaccgcttc ctcgtgcttt | 2880 |
| acggtatcgc cgctcccgat tcgcagcgca tcgccttcta tcgccttctt gacgagttct | 2940 |
| tctgagcggg actctggggt tcgaaatgac cgaccaagcg acgcccaacc tgccatcacg | 3000 |
| agatttcgat tccaccgccg ccttctatga aggttgggc ttcggaatcg ttttccggga | 3060 |
| cgccggctgg atgatcctcc agcgcgggga tctcatgctg gagttcttcg cccacccaa | 3120 |
| cttgtttatt gcagcttata atggttacaa ataaagcaat agcatcacaa atttcacaaa | 3180 |
| taaagcattt ttttcactgc attctagttg tggtttgtcc aaactcatca atgtatctta | 3240 |
| tcatgtctgt ataccgtcga cctctagcta gagcttggcg taatcatggt catagctgtt | 3300 |
| tcctgtgtga aattgttatc cgctcacaat tccacacaac atacgagccg aagcataaa | 3360 |
| gtgtaaagcc tggggtgcct aatgagtgag ctaactcaca ttaattgcgt tgcgctcact | 3420 |
| gcccgctttc cagtcgggaa acctgtcgtg ccagctgcat taatgaatcg gccaacgcgc | 3480 |
| ggggagaggc ggtttgcgta ttgggcgctc ttccgcttcc tcgctcactg actcgctgcg | 3540 |
| ctcggtcgtt cggctgcggc gagcggtatc agctcactca aaggcggtaa tacggttatc | 3600 |

```
cacagaatca ggggataacg caggaaagaa catgtgagca aaaggccagc aaaaggccag    3660
gaaccgtaaa aaggccgcgt tgctggcgtt tttccatagg ctccgccccc ctgacgagca    3720
tcacaaaaat cgacgctcaa gtcagaggtg gcgaaacccg acaggactat aaagatacca    3780
ggcgtttccc cctggaagct ccctcgtgcg ctctcctgtt ccgaccctgc cgcttaccgg    3840
atacctgtcc gcctttctcc cttcgggaag cgtggcgctt tctcaatgct cacgctgtag    3900
gtatctcagt tcggtgtagg tcgttcgctc caagctgggc tgtgtgcacg aaccccccgt    3960
tcagcccgac cgctgcgcct tatccggtaa ctatcgtctt gagtccaacc cggtaagaca    4020
cgacttatcg ccactggcag cagccactgg taacaggatt agcagagcga ggtatgtagg    4080
cggtgctaca gagttcttga agtggtggcc taactacggc tacactagaa ggacagtatt    4140
tggtatctgc gctctgctga agccagttac cttcggaaaa agagttggta gctcttgatc    4200
cggcaaacaa accaccgctg gtagcggtgg tttttttgtt tgcaagcagc agattacgcg    4260
cagaaaaaaa ggatctcaag aagatccttt gatcttttct acggggtctg acgctcagtg    4320
gaacgaaaac tcacgttaag ggattttggt catgagatta tcaaaaagga tcttcaccta    4380 gatccttttaa aattaaaaat gaagttttaa atcaatctaa agtatatatg agtaaacttg    4440
gtctgacagt taccaatgct taatcagtga ggcacctatc tcagcgatct gtctatttcg    4500
ttcatccata gttgcctgac tccccgtcgt gtagataact acgatacggg agggcttacc    4560
atctggcccc agtgctgcaa tgataccgcg agacccacgc tcaccggctc cagatttatc    4620
agcaataaac cagccagccg gaagggccga gcgcagaagt ggtcctgcaa ctttatccgc    4680
ctccatccag tctattaatt gttgccggga agctagagta agtagttcgc cagttaatag    4740
tttgcgcaac gttgttgcca ttgctacagg catcgtggtg tcacgctcgt cgtttggtat    4800
ggcttcattc agctccggtt cccaacgatc aaggcgagtt acatgatccc ccatgttgtg    4860
caaaaaagcg gttagctcct tcggtcctcc gatcgttgtc agaagtaagt tggccgcagt    4920
gttatcactc atggttatgg cagcactgca taattctctt actgtcatgc catccgtaag    4980
atgcttttct gtgactggtg agtactcaac caagtcattc tgagaatagt gtatgcggcg    5040
accgagttgc tcttgcccgg cgtcaatacg ggataatacc gcgccacata gcagaacttt    5100
aaaagtgctc atcattggaa aacgttcttc ggggcgaaaa ctctcaagga tcttaccgct    5160
gttgagatcc agttcgatgt aacccactcg tgcacccaac tgatcttcag catcttttac    5220
tttcaccagc gtttctgggt gagcaaaaac aggaaggcaa aatgccgcaa aaaagggaat    5280
aagggcgaca cggaaatgtt gaatactcat actcttcctt tttcaatatt attgaagcat    5340
ttatcagggt tattgtctca tgagcggata catatttgaa tgtatttaga aaataaaca    5400 aatagggggtt ccgcgcacat ttccccgaaa agtgccacct gacgtc              5446
```

<210> SEQ ID NO 57
<211> LENGTH: 5428
<212> TYPE: DNA
<213> ORGANISM: Artificial Sequence
<220> FEATURE:
<223> OTHER INFORMATION: plasmid

<400> SEQUENCE: 57

```
gacggatcgg gagatctccc gatcccctat ggtgcactct cagtacaatc tgctctgatg      60
ccgcatagtt aagccagtat ctgctccctg cttgtgtgtt ggaggtcgct gagtagtgcg     120
cgagcaaaat ttaagctaca acaaggcaag gcttgaccga caattgcatg aagaatctgc     180
```

```
ttagggttag gcgttttgcg ctgcttcgcg atgtacgggc cagatatacg cgttgacatt    240
gattattgac tagttattaa tagtaatcaa ttacggggtc attagttcat agcccatata    300
tggagttccg cgttacataa cttacggtaa atggcccgcc tggctgaccg cccaacgacc    360
cccgcccatt gacgtcaata atgacgtatg ttcccatagt aacgccaata gggactttcc    420
attgacgtca atgggtggag tatttacggt aaactgccca cttggcagta catcaagtgt    480
atcatatgcc aagtacgccc cctattgacg tcaatgacgg taaatggccc gcctggcatt    540
atgcccagta catgacctta tgggactttc ctacttggca gtacatctac gtattagtca    600
tcgctattac catggtgatg cggttttggc agtacatcaa tgggcgtgga tagcggtttg    660
actcacgggg atttccaagt ctccacccca ttgacgtcaa tgggagtttg ttttggcacc    720
aaaatcaacg ggactttcca aaatgtcgta acaactccgc cccattgacg caaatgggcg    780
gtaggcgtgt acggtgggag gtctatataa gcagagctct ctggctaact agagaaccca    840
ctgcttactg gcttatcgaa attaatacga ctcactatag ggagacccaa gctggctagc    900
gtttaaactt aagcttggta ccgagctcgg atccactagt ccagtgtggt ggaattctgc    960
agatatccag cacagtggcg gccgctcgag tctagagggc ccgtttaaac ccgctgatca   1020
gcctcgactg tgccttctag ttgccagcca tctgttgttt gcccctcccc cgtgccttcc   1080
ttgaccctgg aaggtgccac tcccactgtc ctttcctaat aaaatgagga aattgcatcg   1140
cattgtctga gtaggtgtca ttctattctg ggggtgggg tggggcagga cagcaagggg   1200
gaggattggg aagacaatag caggcatgct ggggatgcgg tgggctctat ggcttctgag   1260
gcggaaagaa ccagctgggg ctctaggggg tatccccacg cgccctgtag cggcgcatta   1320
agcgcggcgg gtgtggtggt tacgcgcagc gtgaccgcta cacttgccag cgccctagcg   1380
cccgctcctt tcgctttctt cccttccttt ctcgccacgt tcgccggctt tccccgtcaa   1440
gctctaaatc gggggctccc tttagggttc cgatttagtg ctttacggca cctcgacccc   1500
aaaaaacttg attagggtga tggttcacgt agtgggccat cgccctgata gacggttttt   1560
cgccctttga cgttggagtc acgttctttt aatagtggac tcttgttcca aactggaaca   1620
acactcaacc ctatctcggt ctattctttt gatttataag gattttgcc gatttcggcc   1680 tattggttaa aaatgagct gatttaacaa aaatttaacg cgaattaatt ctgtggaatg   1740
tgtgtcagtt agggtgtgga agtccccag gctccccagc aggcagaagt atgcaaagca   1800
tgcatctcaa ttagtcagca accaggtgtg gaaagtcccc aggctcccca gcaggcagaa   1860
gtatgcaaag catgcatctc aattagtcag caaccatagt cccgccccta actccgccca   1920
tcccgcccct aactccgccc agttccgccc attctccgcc ccatggctga ctaatttttt   1980
ttatttatgc agaggccgag gccgcctctg cctctgagct attccagaag tagtgaggag   2040
gcttttttgg aggcctaggc ttttgcaaaa agctcccggg agcttgtata tccattttcg   2100
gatctgatca agacagga tgaggatcgt ttcgcatgat tgaacaagat ggattgcacg   2160
caggttctcc ggccgcttgg gtggagaggc tattcggcta tgactgggca acagacaa   2220 tcggctgctc tgatgccgcc gtgttccggc tgtcagcgca ggggcgcccg gttcttttg   2280 tcaagaccga cctgtccggt gccctgaatg aactgcagga cgaggcagcg cggctatcgt   2340
ggctggccac gacgggcgtt ccttgcgcag ctgtgctcga cgttgtcact gaagcgggaa   2400
gggactggct gctattgggc gaagtgccgg ggcaggatct cctgtcatct caccttgctc   2460
ctgccgagaa agtatccatc atggctgatg caatgcggcg gctgcatacg cttgatccgg   2520
ctacctgccc attcgaccac caagcgaaac atcgcatcga gcgagcacgt actcggatgg   2580
```

```
aagccggtct tgtcgatcag gatgatctgg acgaagagca tcaggggctc gcgccagccg    2640
aactgttcgc caggctcaag gcgcgcatgc ccgacggcga ggatctcgtc gtgacccatg    2700
gcgatgcctg cttgccgaat atcatggtgg aaaatggccg cttttctgga ttcatcgact    2760
gtggccggct gggtgtggcg gaccgctatc aggacatagc gttggctacc cgtgatattg    2820
ctgaagagct tggcggcgaa tgggctgacc gcttcctcgt gctttacggt atcgccgctc    2880
ccgattcgca gcgcatcgcc ttctatcgcc ttcttgacga gttcttctga gcgggactct    2940
ggggttcgaa atgaccgacc aagcgacgcc caacctgcca tcacgagatt tcgattccac    3000
cgccgccttc tatgaaaggt tgggcttcgg aatcgttttc cgggacgccg gctggatgat    3060
cctccagcgc ggggatctca tgctggagtt cttcgcccac cccaacttgt ttattgcagc    3120
ttataatggt tacaaataaa gcaatagcat cacaaatttc acaaataaag catttttttc    3180
actgcattct agttgtggtt tgtccaaact catcaatgta tcttatcatg tctgtatacc    3240
gtcgacctct agctagagct tggcgtaatc atggtcatag ctgtttcctg tgtgaaattg    3300
ttatccgctc acaattccac acaacatacg agccggaagc ataaagtgta aagcctgggg    3360
tgcctaatga gtgagctaac tcacattaat tgcgttgcgc tcactgcccg ctttccagtc    3420
gggaaacctg tcgtgccagc tgcattaatg aatcggccaa cgcgcgggga gaggcggttt    3480
gcgtattggg cgctcttccg cttcctcgct cactgactcg ctgcgctcgg tcgttcggct    3540
gcggcgagcg gtatcagctc actcaaaggc ggtaatacgg ttatccacag aatcagggga    3600
taacgcagga aagaacatgt gagcaaaagg ccagcaaaag gccaggaacc gtaaaaaggc    3660
cgcgttgctg gcgttttcc ataggctccg ccccctgac gagcatcaca aaaatcgacg    3720
ctcaagtcag aggtggcgaa acccgacagg actataaaga taccaggcgt ttccccctgg    3780
aagctccctc gtgcgctctc ctgttccgac cctgccgctt accggatacc tgtccgcctt    3840
tctcccttcg ggaagcgtgg cgctttctca tagctcacgc tgtaggtatc tcagttcggt    3900
gtaggtcgtt cgctccaagc tgggctgtgt gcacgaaccc cccgttcagc ccgaccgctg    3960
cgccttatcc ggtaactatc gtcttgagtc caacccggta agacacgact tatcgccact    4020
ggcagcagcc actggtaaca ggattagcag agcgaggtat gtaggcggtg ctacagagtt    4080
cttgaagtgg tggcctaact acggctacac tagaagaaca gtatttggta tctgcgctct    4140
gctgaagcca gttaccttcg gaaaaagagt tggtagctct tgatccggca acaaaccac    4200 cgctggtagc ggttttttg tttgcaagca gcagattacg cgcagaaaaa aaggatctca    4260
agaagatcct ttgatctttt ctacggggtc tgacgctcag tggaacgaaa actcacgtta    4320
agggattttg gtcatgagat tatcaaaaag gatcttcacc tagatccttt taaattaaaa    4380
atgaagtttt aaatcaatct aaagtatata tgagtaaact tggtctgaca gttaccaatg    4440
cttaatcagt gaggcaccta tctcagcgat ctgtctattt cgttcatcca tagttgcctg    4500
actccccgtc gtgtagataa ctacgatacg ggagggctta ccatctggcc ccagtgctgc    4560
aatgataccg cgagacccac gctcaccggc tccagattta tcagcaataa accagccagc    4620
cggaagggcc gagcgcagaa gtggtcctgc aactttatcc gcctccatcc agtctattaa    4680
ttgttgccgg gaagctagag taagtagttc gccagttaat agtttgcgca acgttgttgc    4740
cattgctaca ggcatcgtgg tgtcacgctc gtcgtttggt atggcttcat tcagctccgg    4800
ttcccaacga tcaaggcgag ttacatgatc ccccatgttg tgcaaaaaag cggttagctc    4860
cttcggtcct ccgatcgttg tcagaagtaa gttggccgca gtgttatcac tcatggttat    4920
```

| | |
|---|---:|
| ggcagcactg cataattctc ttactgtcat gccatccgta agatgctttt ctgtgactgg | 4980 |
| tgagtactca accaagtcat tctgagaata gtgtatgcgg cgaccgagtt gctcttgccc | 5040 |
| ggcgtcaata cgggataata ccgcgccaca tagcagaact ttaaaagtgc tcatcattgg | 5100 |
| aaaacgttct cgggggcgaa aactctcaag gatcttaccg ctgttgagat ccagttcgat | 5160 |
| gtaacccact cgtgcaccca actgatcttc agcatctttt actttcacca gcgtttctgg | 5220 |
| gtgagcaaaa acaggaaggc aaaatgccgc aaaaaaggga ataagggcga cacgaaatg | 5280 |
| ttgaatactc atactcttcc ttttcaata ttattgaagc atttatcagg gttattgtct | 5340 |
| catgagcgga tacatatttg aatgtattta gaaaaataaa caaatagggg ttccgcgcac | 5400 |
| atttccccga aaagtgccac ctgacgtc | 5428 |

<210> SEQ ID NO 58
<211> LENGTH: 5427
<212> TYPE: DNA
<213> ORGANISM: Artificial Sequence
<220> FEATURE:
<223> OTHER INFORMATION: plasmid

<400> SEQUENCE: 58

| | |
|---|---:|
| gacggatcgg gagatctccc gatccctat ggtgcactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag cttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggag tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta caactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| gtttaaacgg gccctctaga ctcgagcggc cgccactgtg ctggatatct gcagaattcc | 960 |
| accacactgg actagtggat ccgagctcgg taccaagctt aagtttaaac cgctgatcag | 1020 |
| cctcgactgt gccttctagt tgccagccat ctgttgtttg cccctccccc gtgccttcct | 1080 |
| tgaccctgga aggtgccact cccactgtcc tttcctaata aaatgaggaa attgcatcgc | 1140 |
| attgtctgag taggtgtcat tctattctgg ggggtggggt ggggcaggac agcaagggg | 1200 |
| aggattggga agacaatagc aggcatgctg gggatgcggt gggctctatg gcttctgagg | 1260 |
| cggaaagaac cagctggggc tctagggggt atccccacgc gccctgtagc ggcgcattaa | 1320 |
| gcgcggcggg tgtggtggtt acgcgcagcg tgaccgctac acttgccagc gccctagcgc | 1380 |
| ccgctccttt cgctttcttc ccttcctttc tcgccacgtt cgccggcttt ccccgtcaag | 1440 |
| ctctaaatcg ggggctccct ttagggttcc gatttagtgc tttacggcac ctcgacccca | 1500 |
| aaaaacttga ttagggtgat ggttcacgta gtgggccatc gccctgatag acggtttttc | 1560 |

```
gcccttttgac gttggagtcc acgttcttta atagtggact cttgttccaa actggaacaa    1620
cactcaaccc tatctcggtc tattcttttg atttataagg gattttgccg atttcggcct    1680
attggttaaa aaatgagctg atttaacaaa aatttaacgc gaattaattc tgtggaatgt    1740
gtgtcagtta gggtgtggaa agtccccagg ctccccagca ggcagaagta tgcaaagcat    1800
gcatctcaat tagtcagcaa ccaggtgtgg aaagtcccca ggctcccag caggcagaag    1860 tatgcaaagc atgcatctca attagtcagc aaccatagtc ccgcccctaa ctccgcccat    1920 cccgcccta actccgccca gttccgccca ttctccgccc catggctgac taatttttt    1980 tatttatgca gaggccgagg ccgcctctgc ctctgagcta ttccagaagt agtgaggagg    2040
cttttttgga ggcctaggct tttgcaaaaa gctcccggga gcttgtatat ccattttcgg    2100
atctgatcaa gagacaggat gaggatcgtt tcgcatgatt gaacaagatg gattgcacgc    2160
aggttctccg ccgcttgggt ggagaggct attcggctat gactgggcac aacagacaat    2220
cggctgctct gatgccgccg tgttccggct gtcagcgcag gggcgcccgg ttcttttgt    2280 caagaccgac ctgtccggtg ccctgaatga actgcaggac gaggcagcgc ggctatcgtg    2340
gctggccacg acgggcgttc cttgcgcagc tgtgctcgac gttgtcactg aagcgggaag    2400
ggactggctg ctattgggcg aagtgccggg gcaggatctc ctgtcatctc accttgctcc    2460
tgccgagaaa gtatccatca tggctgatgc aatgcggcgg ctgcatacgc ttgatccggc    2520
tacctgccca ttcgaccacc aagcgaaaca tcgcatcgag cgagcacgta ctcggatgga    2580
agccggtctt gtcgatcagg atgatctgga cgaagagcat caggggctcg cgccagccga    2640
actgttcgcc aggctcaagg cgcgcatgcc cgacggcgag gatctcgtcg tgacccatgg    2700
cgatgcctgc ttgccgaata tcatggtgga aaatggccgc ttttctggat tcatcgactg    2760
tggccggctg ggtgtggcgg accgctatca ggacatagcg ttggctaccc gtgatattgc    2820
tgaagagctt ggcggcgaat gggctgaccg cttcctcgtg ctttacggta tcgccgctcc    2880
cgattcgcag cgcatcgcct tctatcgcct tcttgacgag ttcttctgag cgggactctg    2940
gggttcgaaa tgaccgacca agcgacgccc aacctgccat cacgagattt cgattccacc    3000
gccgccttct atgaaaggtt gggcttcgga atcgttttcc gggacgccgg ctggatgatc    3060
ctccagcgcg ggatctcat gctggagttc ttcgcccacc ccaacttgtt tattgcagct    3120
tataatggtt acaaataaag caatagcatc acaaatttca caaataaagc atttttttca    3180
ctgcattcta gttgtggttt gtccaaactc atcaatgtat cttatcatgt ctgtataccg    3240
tcgacctcta gctagagctt ggcgtaatca tggtcatagc tgtttcctgt gtgaaattgt    3300
tatccgctca caattccaca acatacga gccggaagca taaagtgtaa agcctggggt    3360
gcctaatgag tgagctaact cacattaatt gcgttgcgct cactgcccgc tttccagtcg    3420
ggaaacctgt cgtgccagct gcattaatga atcggccaac gcgcggggag aggcggtttg    3480
cgtattgggc gctcttccgc ttcctcgctc actgactcgc tgcgctcggt cgttcggctg    3540
cggcgagcgg tatcagctca ctcaaaggcg gtaatacggt tatccacaga atcaggggat    3600
aacgcaggaa agaacatgtg agcaaaaggc cagcaaaagg ccaggaaccg taaaaaggcc    3660
gcgttgctgg cgttttccta taggctccgc cccctgacg agcatcacaa aaatcgacgc    3720
tcaagtcaga ggtggcgaaa cccgacagga ctataaagat accaggcgtt tccccctgga    3780
agctccctcg tgcgctctcc tgttccgacc ctgccgctta ccggatacct gtccgccttt    3840
ctcccttcgg gaagcgtggc gctttctcat agctcacgct gtaggtatct cagttcggtg    3900
```

```
taggtcgttc gctccaagct gggctgtgtg cacgaacccc ccgttcagcc cgaccgctgc    3960
gccttatccg gtaactatcg tcttgagtcc aacccggtaa gacacgactt atcgccactg    4020
gcagcagcca ctggtaacag gattagcaga gcgaggtatg taggcggtgc tacagagttc    4080
ttgaagtggt ggcctaacta cggctacact agaagaacag tatttggtat ctgcgctctg    4140
ctgaagccag ttaccttcgg aaaaagagtt ggtagctctt gatccggcaa acaaaccacc    4200
gctggtagcg gtttttttgt ttgcaagcag cagattacgc gcagaaaaaa aggatctcaa    4260
gaagatcctt tgatcttttc tacggggtct gacgctcagt ggaacgaaaa ctcacgttaa    4320
gggattttgg tcatgagatt atcaaaaagg atcttcacct agatcctttt aaattaaaaa    4380
tgaagtttta aatcaatcta agtatatat gagtaaactt ggtctgacag ttaccaatgc     4440
ttaatcagtg aggcacctat ctcagcgatc tgtctatttc gttcatccat agttgcctga    4500
ctccccgtcg tgtagataac tacgatacgg gagggcttac catctggccc cagtgctgca    4560
atgataccgc gagacccacg ctcaccggct ccagatttat cagcaataaa ccagccagcc    4620
ggaagggccg agcgcagaag tggtcctgca actttatccg cctccatcca gtctattaat    4680
tgttgccggg aagctagagt aagtagttcg ccagttaata gtttgcgcaa cgttgttgcc    4740
attgctacag gcatcgtggt gtcacgctcg tcgtttggta tggcttcatt cagctccggt    4800
tcccaacgat caaggcgagt tacatgatcc cccatgttgt gcaaaaaagc ggttagctcc    4860
ttcggtcctc cgatcgttgt cagaagtaag ttggccgcag tgttatcact catggttatg    4920
gcagcactgc ataattctct tactgtcatg ccatccgtaa gatgcttttc tgtgactggt    4980
gagtactcaa ccaagtcatt ctgagaatag tgtatgcggc gaccgagttg ctcttgcccg    5040
gcgtcaatac gggataatac cgcgccacat agcagaactt taaaagtgct catcattgga    5100
aaacgttctt cggggcgaaa actctcaagg atcttaccgc tgttgagatc cagttcgatg    5160
taacccactc gtgcacccaa ctgatcttca gcatctttta ctttcaccag cgtttctggg    5220
tgagcaaaaa caggaaggca aaatgccgca aaaaagggaa taagggcgac acggaaatgt    5280
tgaatactca tactcttcct ttttcaatat tattgaagca tttatcaggg ttattgtctc    5340
atgagcggat acatatttga atgtatttag aaaaataaac aataggggt tccgcgcaca    5400
tttccccgaa aagtgccacc tgacgtc                                        5427
```

<210> SEQ ID NO 59
<211> LENGTH: 4818
<212> TYPE: DNA
<213> ORGANISM: Artificial Sequence
<220> FEATURE:
<223> OTHER INFORMATION: plasmid

<400> SEQUENCE: 59

```
ggtaccgagc tcttacgcgt gctagcccgg gctcgagatc tgcgatctaa gtaagcttgg      60
cattccggta ctgttggtaa agccaccatg aagacgcca aaaacataaa gaaaggcccg     120
gcgccattct atccgctgga agatggaacc gctggagagc aactgcataa ggctatgaag    180
agatacgccc tggttcctgg aacaattgct tttacagatg cacatatcga ggtggacatc    240
acttacgctg agtacttcga aatgtccgtt cggttggcag aagctatgaa acgatatggg    300
ctgaatacaa atcacagaat cgtcgtatgc agtgaaaact ctcttcaatt ctttatgccg    360
gtgttgggcg cgttatttat cggagttgca gttgcgcccg cgaacgacat ttataatgaa    420
cgtgaattgc tcaacagtat gggcatttcg cagcctaccg tggtgttcgt ttccaaaaag    480
gggttgcaaa aaattttgaa cgtgcaaaaa aagctcccaa tcatccaaaa aattattatc    540
```

-continued

| | |
|---|---|
| atggattcta aaacggatta ccagggattt cagtcgatgt acacgttcgt cacatctcat | 600 |
| ctacctcccg gttttaatga atacgatttt gtgccagagt ccttcgatag ggacaagaca | 660 |
| attgcactga tcatgaactc ctctggatct actggtctgc ctaaaggtgt cgctctgcct | 720 |
| catagaactg cctgcgtgag attctcgcat gccagagatc ctattttggg caatcaaatc | 780 |
| attccggata ctgcgatttt aagtgttgtt ccattccatc acggttttgg aatgtttact | 840 |
| acactcggat atttgatatg tggatttcga gtcgtcttaa tgtatagatt tgaagaagag | 900 |
| ctgtttctga ggagccttca ggattacaag attcaaagtg cgctgctggt gccaacccta | 960 |
| ttctccttct tcgccaaaag cactctgatt gacaaatacg atttatctaa tttacacgaa | 1020 |
| attgcttctg gtggcgctcc cctctctaag gaagtcgggg aagcggttgc caagaggttc | 1080 |
| catctgccag gtatcaggca aggatatggg ctcactgaga ctacatcagc tattctgatt | 1140 |
| acacccgagg gggatgataa accgggcgcg gtcggtaaag ttgttccatt ttttgaagcg | 1200 |
| aaggttgtgg atctggatac cgggaaaacg ctgggcgtta atcaaagagg cgaactgtgt | 1260 |
| gtgagaggtc ctatgattat gtccggttat gtaaacaatc cggaagcgac caacgccttg | 1320 |
| attgacaagg atggatggct acattctgga gacatagctt actgggacga agacgaacac | 1380 |
| ttcttcatcg ttgaccgcct gaagtctctg attaagtaca aaggctatca ggtggctccc | 1440 |
| gctgaattgg aatccatctt gctccaacac cccaacatct cgacgcagg tgtcgcaggt | 1500 |
| cttcccgacg atgacgccgg tgaacttccc gccgccgttg ttgttttgga gcacggaaag | 1560 |
| acgatgacgg aaaagagat cgtggattac gtcgccagtc aagtaacaac cgcgaaaaag | 1620 |
| ttgcgcggag gagttgtgtt tgtggacgaa gtaccgaaag gtcttaccgg aaaactcgac | 1680 |
| gcaagaaaaa tcagagagat cctcataaag gccaagaagg gcggaaagat cgccgtgtaa | 1740 |
| ttctagagtc ggggcggccg gccgcttcga gcagacatga taagatacat tgatgagttt | 1800 |
| ggacaaacca caactagaat gcagtgaaaa aaatgcttta tttgtgaaat ttgtgatgct | 1860 |
| attgctttat ttgtaaccat tataagctgc aataaacaag ttaacaacaa caattgcatt | 1920 |
| cattttatgt ttcaggttca gggggaggtg tgggaggttt tttaaagcaa gtaaaacctc | 1980 |
| tacaaatgtg gtaaaatcga taaggatccg tcgaccgatg cccttgagag ccttcaaccc | 2040 |
| agtcagctcc ttccggtggg cgcggggcat gactatcgtc gccgcactta tgactgtctt | 2100 |
| ctttatcatg caactcgtag gacaggtgcc ggcagcgctc ttccgcttcc tcgctcactg | 2160 |
| actcgctgcg ctcggtcgtt cggctgcggc gagcggtatc agctcactca aaggcggtaa | 2220 |
| tacggttatc cacagaatca ggggataacg caggaaagaa catgtgagca aaaggccagc | 2280 |
| aaaaggccag gaaccgtaaa aaggccgcgt tgctggcgtt tttccatagg ctccgccccc | 2340 |
| ctgacgagca tcacaaaaat cgacgctcaa gtcagaggtg gcgaaacccg acaggactat | 2400 |
| aaagatacca ggcgtttccc cctggaagct ccctcgtgcg ctctcctgtt ccgaccctgc | 2460 |
| cgcttaccgg atacctgtcc gcctttctcc cttcgggaag cgtggcgctt tctcaatgct | 2520 |
| cacgctgtag gtatctcagt tcggtgtagg tcgttcgctc caagctgggc tgtgtgcacg | 2580 |
| aaccccccgt tcagcccgac cgctgcgcct tatccggtaa ctatcgtctt gagtccaacc | 2640 |
| cggtaagaca cgacttatcg ccactggcag cagccactgg taacaggatt agcagagcga | 2700 |
| ggtatgtagg cggtgctaca gagttcttga agtggtggcc taactacggc tacactagaa | 2760 |
| ggacagtatt tggtatctgc gctctgctga agccagttac cttcggaaaa agagttggta | 2820 |
| gctcttgatc cggcaaacaa accaccgctg gtagcggtgg tttttttgtt tgcaagcagc | 2880 |

```
agattacgcg cagaaaaaaa ggatctcaag aagatccttt gatcttttct acggggtctg    2940
acgctcagtg gaacgaaaac tcacgttaag ggattttggt catgagatta tcaaaaagga    3000
tcttcaccta gatcctttta aattaaaaat gaagttttaa atcaatctaa agtatatatg    3060
agtaaacttg gtctgacagt taccaatgct taatcagtga ggcacctatc tcagcgatct    3120
gtctatttcg ttcatccata gttgcctgac tccccgtcgt gtagataact acgatacggg    3180
agggcttacc atctggcccc agtgctgcaa tgataccgcg agacccacgc tcaccggctc    3240
cagatttatc agcaataaac cagccagccg aagggccga gcgcagaagt ggtcctgcaa    3300
ctttatccgc ctccatccag tctattaatt gttgccggga agctagagta agtagttcgc    3360
cagttaatag tttgcgcaac gttgttgcca ttgctacagg catcgtggtg tcacgctcgt    3420
cgtttggtat ggcttcattc agctccggtt cccaacgatc aaggcgagtt acatgatccc    3480
ccatgttgtg caaaaaagcg gttagctcct tcggtcctcc gatcgttgtc agaagtaagt    3540
tggccgcagt gttatcactc atggttatgg cagcactgca taattctctt actgtcatgc    3600
catccgtaag atgcttttct gtgactgtg agtactcaac caagtcattc tgagaatagt    3660
gtatgcggcg accgagttgc tcttgcccgg cgtcaatacg ggataatacc gcgccacata    3720
gcagaacttt aaaagtgctc atcattggaa aacgttcttc ggggcgaaaa ctctcaagga    3780
tcttaccgct gttgagatcc agttcgatgt aacccactcg tgcacccaac tgatcttcag    3840
catcttttac tttcaccagc gtttctgggt gagcaaaaac aggaaggcaa aatgccgcaa    3900
aaaagggaat aagggcgaca cggaaatgtt gaatactcat actcttcctt tttcaatatt    3960
attgaagcat ttatcagggt tattgtctca tgagcggata catatttgaa tgtatttaga    4020
aaaataaaca aataggggtt ccgcgcacat ttccccgaaa agtgccacct gacgcgccct    4080
gtagcggcgc attaagcgcg gcgggtgtgg tggttacgcg cagcgtgacc gctacacttg    4140
ccagcgccct agcgcccgct cctttcgctt tcttcccttc ctttctcgcc acgttcgccg    4200
gctttccccg tcaagctcta aatcgggggc tccctttagg gttccgattt agtgctttac    4260
ggcacctcga ccccaaaaaa cttgattagg gtgatggttc acgtagtggg ccatcgccct    4320
gatagacggt ttttcgccct ttgacgttgg agtccacgtt ctttaatagt ggactcttgt    4380
tccaaactgg aacaacactc aaccctatct cggtctattc ttttgattta agggatttt    4440 tgccgatttc ggcctattgg ttaaaaaatg agctgattta caaaaatttt aacgcgaatt    4500
ttaacaaaat attaacgttt acaatttccc attcgccatt caggctgcgc aactgttggg    4560
aagggcgatc ggtgcgggcc tcttcgctat tacgccagcc caagctacca tgataagtaa    4620
gtaatattaa ggtacgggag gtacttggag cggccgcaat aaaatatctt tattttcatt    4680
acatctgtgt gttggttttt tgtgtgaatc gatagtacta acatacgctc tccatcaaaa    4740
caaaacgaaa caaaacaaac tagcaaaata ggctgtcccc agtgcaagtg caggtgccag    4800
aacatttctc tatcgata                                                 4818

<210> SEQ ID NO 60
<211> LENGTH: 3451
<212> TYPE: DNA
<213> ORGANISM: Artificial Sequence
<220> FEATURE:
<223> OTHER INFORMATION: plasmid

<400> SEQUENCE: 60
ggatccgctg tggaatgtgt gtcagttagg gtgtggaaag tccccaggct ccccagcagg      60
cagaagtatg caaagcatgc atctcaatta gtcagcaacc aggtgtggaa agtccccagg     120
```

```
ctccccagca ggcagaagta tgcaaagcat gcatctcaat tagtcagcaa ccatagtccc    180 gccectaact ccgcccatcc cgcccctaac tccgcccagt tccgcccatt ctccgcccca    240
tggctgacta attttttta tttatgcaga ggccgaggcc gcctcggcct ctgagctatt     300
ccagaagtag tgaggaggct ttttggagg cctaggcttt tgcaaaaagc ttattaaccc     360
tcactaaagg gagtactagt accggtacct cgagaattcg aacgcgtgat cagctgttct    420
atagtgtcac ctaaatagct tcgaggtcga cctcgaaact tgtttattgc agcttataat    480
ggttacaaat aaagcaatag catcacaaat ttcacaaata aagcattttt ttcactgcat    540
tctagttgtg gtttgtccaa actcatcaat gtatcttatc atgtctggat ccctcggaga    600
tctgggccca tgcggccgcg gatcgatgct cactcaaagg cggtaatacg gttatccaca    660
gaatcagggg ataacgcagg aaagaacatg tgagcaaaag gccagcaaaa ggccaggaac    720
cgtaaaaagg ccgcgttgct ggcgtttttc cataggctcc gcccccctga cgagcatcac    780
aaaaatcgac gctcaagtca gaggtggcga acccgacag gactataaag ataccaggcg    840 ttttccctg gaagctccct cgtgcgctct cctgttccga ccctgccgct taccggatac    900
ctgtccgcct ttctcccttc gggaagcgtg gcgctttctc aatgctcacg ctgtaggtat    960
ctcagttcgg tgtaggtcgt tcgctccaag ctgggctgtg tgcacgaacc cccgttcag   1020 cccgaccgct gcgccttatc cggtaactat cgtcttgagt ccaacccggt aagacacgac   1080
ttatcgccac tggcagcagc cactggtaac aggattagca gagcgaggta tgtaggcggt   1140
gctacagagt tcttgaagtg gtggcctaac tacggctaca ctagaaggac agtatttggt   1200
atctgcgctc tgctgaagcc agttaccttc ggaaaaagag ttggtagctc ttgatccggc   1260
aaacaaacca ccgctggtag cggtggtttt tttgtttgca agcagcagat tacgcgcaga   1320 aaaaaggat ctcaagaaga tcctttgatc ttttctacgg ggtctgacgc tcagtggaac   1380
gaaaactcac gttaagggat tttggtcatg acattaacct ataaaaatag gcgtatcacg   1440
aggccctttc gtctcgcgcg tttcggtgat gacggtgaaa acctctgaca catgcagctc   1500
ccggagacgg tcacagcttg tctgtaagcg gatgccggga gcagacaagc ccgtcagggc   1560
gcgtcagcgg gtgttggcgg gtgtcggggc tggcttaact atgcggcatc agagcagatt   1620
gtactgagag tgcaccatat gcggtgtgaa ataccgcaca gatgcgtaag gagaaaatac   1680
cgcatcaggc gacgcgccct gtagcggcgc attaagcgcg gcgggtgtgg tggttacgcg   1740
cagcgtgacc gctacacttg ccagcgccct agcgcccgct cctttcgctt tcttcccttc   1800 cttttctcgcc acgttcgccg gctttccccg tcaagctcta aatcggggc tccctttagg   1860 gttccgattt agagctttac ggcacctcga ccgcaaaaaa cttgatttgg gtgatggttc   1920
acgtagtggg ccatcgccct gatagacggt ttttcgccct ttgacgttgg agtccacgtt   1980
ctttaatagt ggactcttgt tccaaactgg aacaacactc aaccctatct cggtctattc   2040
ttttgattta aagggatttt tgccgatttc ggcctattgg ttaaaaaatg agctgattta   2100
acaaatattt aacgcgaatt ttaacaaaat attaacgttt acaatttcca ttcgccattc   2160
aggctgcaac tagatctaga gtccgttaca taacttacgg taaatggccc gcctggctga   2220
ccgcccaacg acccccgccc attgacgtca ataatgacgt atgttcccat agtaacgcca   2280
atagggactt tccattgacg tcaatgggtg gagtatttac ggtaaactgc ccacttggca   2340
gtacatcaag tgtatcatat gccaagtacg ccccctattg acgtcaatga cggtaaatgg   2400
cccgcctggc attatgccca gtacatgacc ttatgggact ttcctacttg gcagtacatc   2460
```

| | |
|---|---|
| tacgtattag tcatcgctat taccatggtg atgcggtttt ggcagtacat caatgggcgt | 2520 |
| ggatagcggt ttgactcacg gggatttcca agtctccacc ccattgacgt caatgggagt | 2580 |
| ttgttttggc accaaaatca acgggacttt ccaaaatgtc gtaacaactc cgccccattg | 2640 |
| acgcaaatgg gcggtaggcg tgtacggtgg gaggtctata taagcagagc tcgtttagtg | 2700 |
| aaccgtcaga tcgcctggag acgccatcca cgctgttttg acctccatag aagacaccgg | 2760 |
| gaccgatcca gcctccgcgg ccgggaacgg tgcattggaa cggacctgca gcacgtgttg | 2820 |
| acaattaatc atcggcatag tatatcggca tagtataata cgactcacta taggagggcc | 2880 |
| accatggcca agttgaccag tgccgttccg gtgctcaccg cgcgcgacgt cgccggagcg | 2940 |
| gtcgagttct ggaccgaccg gctcgggttc tcccgggact cgtggagga cgacttcgcc | 3000 |
| ggtgtggtcc gggacgacgt gaccctgttc atcagcgcgg tccaggacca ggtggtgccg | 3060 |
| gacaacaccc tggcctgggt gtgggtgcgc ggcctggacg agctgtacgc cgagtggtcg | 3120 |
| gaggtcgtgt ccacgaactt ccgggacgcc tccgggccgg ccatgaccga gatcggcgag | 3180 |
| cagccgtggg ggcgggagtt cgccctgcgc gacccggccg caactgcgt gcacttcgtg | 3240 |
| gccgaggagc aggactgacc gacgccgacc aacaccgccg gtccgacggc ggcccacggg | 3300 |
| tcccaggggg gtcgacctcg aaacttgttt attgcagctt ataatggtta caaataaagc | 3360 |
| aatagcatca caatttcac aaataaagca ttttttcac tgcattctag ttgtggtttg | 3420 |
| tccaaactca tcaatgtatc ttatcatgtc t | 3451 |

<210> SEQ ID NO 61
<211> LENGTH: 5163
<212> TYPE: DNA
<213> ORGANISM: Artificial Sequence
<220> FEATURE:
<223> OTHER INFORMATION: plasmid

<400> SEQUENCE: 61

| | |
|---|---|
| gacggatcgg gagatctccc gatccctat ggtcgactct cagtacaatc tgctctgatg | 60 |
| ccgcatagtt aagccagtat ctgctccctg cttgtgtgtt ggaggtcgct gagtagtgcg | 120 |
| cgagcaaaat ttaagctaca acaaggcaag gcttgaccga caattgcatg aagaatctgc | 180 |
| ttagggttag gcgttttgcg ctgcttcgcg atgtacgggc cagatatacg cgttgacatt | 240 |
| gattattgac tagttattaa tagtaatcaa ttacggggtc attagttcat agcccatata | 300 |
| tggagttccg cgttacataa cttacggtaa atggcccgcc tggctgaccg cccaacgacc | 360 |
| cccgcccatt gacgtcaata atgacgtatg ttcccatagt aacgccaata gggactttcc | 420 |
| attgacgtca atgggtggac tatttacggt aaactgccca cttggcagta catcaagtgt | 480 |
| atcatatgcc aagtacgccc cctattgacg tcaatgacgg taaatggccc gcctggcatt | 540 |
| atgcccagta catgacctta tgggactttc ctacttggca gtacatctac gtattagtca | 600 |
| tcgctattac catggtgatg cggttttggc agtacatcaa tgggcgtgga tagcggtttg | 660 |
| actcacgggg atttccaagt ctccacccca ttgacgtcaa tgggagtttg ttttggcacc | 720 |
| aaaatcaacg ggactttcca aaatgtcgta acaactccgc cccattgacg caaatgggcg | 780 |
| gtaggcgtgt acggtgggag gtctatataa gcagagctct ctggctaact agagaaccca | 840 |
| ctgcttactg gcttatcgaa attaatacga ctcactatag ggagacccaa gctggctagc | 900 |
| caccatggag acagacacac tcctgctatg ggtactgctg ctctgggttc aggttccac | 960 |
| tggtgacgcg gccagccgg ccaggcgcgc gcgccgtacg aagcttggta ccgagctcgg | 1020 |
| atccactcca gtgtggtgga attctgcaga tatccagcac agtggcggcc gctcgaggag | 1080 |

```
ggcccgaaca aaaactcatc tcagaagagg atctgaatag cgccgtcgac catcatcatc   1140
atcatcattg agtttaaacc cgctgatcag cctcgactgt gccttctagt tgccagccat   1200
ctgttgtttg cccctccccc gtgccttcct tgaccctgga aggtgccact cccactgtcc   1260
tttcctaata aaatgaggaa attgcatcgc attgtctgag taggtgtcat tctattctgg   1320
ggggtggggt ggggcaggac agcaagggg aggattggga agacaatagc aggcatgctg    1380
gggatgcggt gggctctatg gcttctgagg cggaaagaac cagctgggc tctagggggt    1440 atccccacgc gccctgtagc ggcgcattaa gcgcggcggg tgtggtggtt acgcgcagcg   1500
tgaccgctac acttgccagc gccctagcgc ccgctccttt cgctttcttc ccttcctttc   1560
tcgccacgtt cgccggcttt ccccgtcaag ctctaaatcg ggcatccct ttagggttcc    1620 gatttagtgc tttacggcac ctcgacccca aaaaacttga ttagggtgat ggttcacgta   1680
gtgggccatc gccctgatag acggtttttc gccctttgac gttggagtcc acgttcttta   1740
atagtggact cttgttccaa actgaacaa cactcaaccc tatctcggtc tattcttttg    1800
atttataagg gattttgggg atttcggcct attggttaaa aaatgagctg atttaacaaa   1860
aatttaacgc gaattaattc tgtggaatgt gtgtcagtta gggtgtggaa agtccccagg   1920
ctccccagca ggcagaagta tgcaaagcat gcatctcaat tagtcagcaa ccaggtgtgg   1980
aaagtcccca ggctccccag caggcagaag tatgcaaagc atgcatctca attagtcagc   2040
aaccatagtc ccgcccctaa ctccgcccat cccgccccta actccgccca gttccgccca   2100
ttctccgccc catggctgac taattttttt tatttatgca gaggccgagg ccgcctctgc   2160
ctctgagcta ttccagaagt agtgaggagg cttttttgga ggcctaggct tttgcaaaaa   2220
gctcccggga gcttgtatat ccattttcgg atctgatcag cacgtgttga caattaatca   2280
tcggcatagt atatcggcat agtataatac gacaaggtga ggaactaaac catggccaag   2340
ttgaccagtg ccgttccggt gctcaccgcg cgcgacgtcg ccggagcggt cgagttctgg   2400
accgaccggc tcgggttctc ccgggacttc gtggaggacg acttcgccgg tgtggtccgg   2460
gacgacgtga ccctgttcat cagcgcggtc caggaccagg tggtgccgga caacaccctg   2520
gcctgggtgt gggtgcgcgg cctggacgag ctgtacgccg agtggtcgga ggtcgtgtcc   2580
acgaacttcc gggacgcctc cgggccggcc atgaccgaga tcggcgagca gccgtggggg   2640
cgggagttcg ccctgcgcga cccggccggc aactgcgtgc acttcgtggc cgaggagcag   2700
gactgacacg tgctacgaga tttcgattcc accgccgcct tctatgaaag gttgggcttc   2760
ggaatcgttt tccgggacgc cggctggatg atcctccagc gcggggatct catgctggag   2820
ttcttcgccc accccaactt gtttattgca gcttataatg gttacaaata aagcaatagc   2880
atcacaaatt tcacaaataa agcatttttt tcactgcatt ctagttgtgg tttgtccaaa   2940
ctcatcaatg tatcttatca tgtctgtata ccgtcgacct ctagctagag cttggcgtaa   3000
tcatggtcat agctgtttcc tgtgtgaaat tgttatccgc tcacaattcc acacaacata   3060
cgagccggaa gcataaagtg taaagcctgg ggtgcctaat gagtgagcta actcacatta   3120
attgcgttgc gctcactgcc cgctttccag tcgggaaacc tgtcgtgcca gctgcattaa   3180
tgaatcggcc aacgcgcggg gagaggcggt ttgcgtattg ggcgctcttc cgcttcctcg   3240
ctcactgact cgctgcgctc ggtcgttcgg ctgcggcgag cggtatcagc tcactcaaag   3300
gcggtaatac ggttatccac agaatcaggg gataacgcag gaaagaacat gtgagcaaaa   3360
ggccagcaaa aggccaggaa ccgtaaaaag gccgcgttgc tggcgttttt ccataggctc   3420
```

```
cgccccctg acgagcatca caaaaatcga cgctcaagtc agaggtggcg aaacccgaca    3480
ggactataaa gataccaggc gtttccccct ggaagctccc tcgtgcgctc tcctgttccg    3540
accctgccgc ttaccggata cctgtccgcc tttctccctt cgggaagcgt ggcgctttct    3600
caatgctcac gctgtaggta tctcagttcg gtgtaggtcg ttcgctccaa gctgggctgt    3660
gtgcacgaac ccccgttca gcccgaccgc tgcgccttat ccggtaacta tcgtcttgag    3720
tccaacccgg taagacacga cttatcgcca ctggcagcag ccactggtaa caggattagc    3780
agagcgaggt atgtaggcgg tgctacagag ttcttgaagt ggtggcctaa ctacggctac    3840
actagaagga cagtatttgg tatctgcgct ctgctgaagc cagttacctt cggaaaaaga    3900
gttggtagct cttgatccgg caaacaaacc accgctggta gcggtggttt ttttgtttgc    3960
aagcagcaga ttacgcgcag aaaaaaagga tctcaagaag atcctttgat cttttctacg    4020
gggtctgacg ctcagtggaa cgaaaactca cgttaaggga ttttggtcat gagattatca    4080
aaaaggatct tcacctagat ccttttaaat taaaaatgaa gttttaaatc aatctaaagt    4140
atatatgagt aaacttggtc tgacagttac caatgcttaa tcagtgaggc acctatctca    4200
gcgatctgtc tatttcgttc atccatagtt gcctgactcc ccgtcgtgta gataactacg    4260
atacgggagg gcttaccatc tggccccagt gctgcaatga taccgcgaga cccacgctca    4320
ccggctccag atttatcagc aataaaccag ccagccggaa gggccgagcg cagaagtggt    4380
cctgcaactt tatccgcctc catccagtct attaattgtt gccgggaagc tagagtaagt    4440
agttcgccag ttaatagttt gcgcaacgtt gttgccattg ctacaggcat cgtggtgtca    4500
cgctcgtcgt ttggtatggc ttcattcagc tccggttccc aacgatcaag gcgagttaca    4560
tgatccccca tgttgtgcaa aaaagcggtt agctccttcg gtcctccgat cgttgtcaga    4620
agtaagttgg ccgcagtgtt atcactcatg gttatggcag cactgcataa ttctcttact    4680
gtcatgccat ccgtaagatg cttttctgtg actggtgagt actcaaccaa gtcattctga    4740
gaatagtgta tgcggcgacc gagttgctct tgcccggcgt caatacggga taataccgcg    4800
ccacatagca gaactttaaa agtgctcatc attggaaaac gttcttcggg gcgaaaactc    4860
tcaaggatct taccgctgtt gagatccagt tcgatgtaac ccactcgtgc acccaactga    4920
tcttcagcat cttttacttt caccagcgtt tctgggtgag caaaaacagg aaggcaaaat    4980
gccgcaaaaa agggaataag ggcgacacgg aaatgttgaa tactcatact cttcctttt     5040
caatattatt gaagcattta tcagggttat tgtctcatga gcggatacat atttgaatgt    5100
atttagaaaa ataaacaaat aggggttccg cgcacatttc cccgaaaagt gccacctgac    5160
gtc                                                                 5163
```

<210> SEQ ID NO 62
<211> LENGTH: 5325
<212> TYPE: DNA
<213> ORGANISM: Artificial Sequence
<220> FEATURE:
<223> OTHER INFORMATION: plasmid

<400> SEQUENCE: 62

```
gcgcgcgttg acattgatta ttgactagtt attaatagta atcaattacg gggtcattag     60
ttcatagccc atatatggag ttccgcgtta cataacttac ggtaaatggc ccgcctggct    120
gaccgcccaa cgacccccgc ccattgacgt caataatgac gtatgttccc atagtaacgc    180
caatagggac tttccattga cgtcaatggg tggactattt acggtaaact gcccacttgg    240
cagtacatca agtgtatcat atgccaagta cgccccctat tgacgtcaat gacggtaaat    300
```

```
ggcccgcctg gcattatgcc cagtacatga ccttatggga ctttcctact tggcagtaca    360
tctacgtatt agtcatcgct attaccatgg tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta taagcaga gctctctggc     600
taactagaga acccactgct tactggctta tcgaaattaa tacgactcac tataggaga    660
cccaagcttg gtaccgagct cggatccact agtaacggcc gccagtgtgc tggaattcgg    720
cttggggata tccaccatgg agacagacac actcctgcta tgggtactgc tgctctgggt    780
tccaggttcc actggtgact atccatatga tgttccagat tatgctgggg cccagccggc    840
cagatctccc gggatccgcg gctgcaggtc gacgaacaaa aactcatctc agaagaggat    900
ctgaatgctg tgggccagga cacgcaggag gtcatcgtgg tgccacactc cttgcccttt    960
aaggtggtgg tgatctcagc catcctggcc ctggtggtgc tcaccatcat ctcccttatc   1020
atcctcatca tgctttggca gaagaagcca cgttaggcgg ccgctcgaga tcagcctcga   1080
ctgtgccttc tagttgccag ccatctgttg tttgcccctc cccgtgcctt ccttgaccc    1140
tggaaggtgc cactcccact gtcctttcct aataaaatga ggaaattgca tcgcattgtc   1200
tgagtaggtg tcattctatt ctggggggtg ggtggggca ggacagcaag ggggaggatt    1260
gggaagacaa tagcaggcat gctggggatg cggtgggctc tatggcttct gaggcggaaa   1320
gaaccagtgg cggtaatacg gttatccaca gaatcagggg ataacgcagg aaagaacatg   1380
tgagcaaaag gccagcaaaa ggccaggaac cgtaaaaagg ccgcgttgct ggcgtttttc   1440
cataggctcc gccccctga cgagcatcac aaaaatcgac gctcaagtca gaggtggcga    1500
aacccgacag gactataaag ataccaggcg tttccccctg gaagctccct cgtgcgctct   1560
cctgttccga ccctgccgct taccggatac ctgtccgcct ttctcccttc gggaagcgtg   1620
gcgctttctc atagctcacg ctgtaggtat ctcagttcgg tgtaggtcgt tcgctccaag   1680
ctgggctgtg tgcacgaacc ccccgttcag cccgaccgct gcgccttatc cggtaactat   1740
cgtcttgagt ccaacccggt aagacacgac ttatcgccac tggcagcagc cactggtaac   1800
aggattagca gagcgaggta tgtaggcggt gctacagagt tcttgaagtg gtggcctaac   1860
tacggctaca ctagaaggac agtatttggt atctgcgctc tgctgaagcc agttaccttc   1920
ggaaaaagag ttggtagctc ttgatccggc aaacaaacca ccgctggtag cggtggtttt   1980
tttgtttgca agcagcagat tacgcgcaga aaaaaaggat ctcaagaaga tcctttgatc   2040
ttttctacgg ggtctgacgc tcagtggaac gaaaactcac gttaagggat tttggtcatg   2100
agattatcaa aaaggatctt cacctagatc cttttaaatt aaaaatgaag ttttaaatca   2160
atctaaagta tatatgagta aacttggtct gacagttacc aatgcttaat cagtgaggca   2160
atctaaagta tatatgagta aacttgaggct atggcagggc ctgccgcccc gacgttggct   2220
gcgagccctg gccttcacc cgaacttggg gggtggggtg gggaaaagga agaaacgcgg   2280
gcgtattggc cccaatgggg tctcggtggg gtatcgacag agtgccagcc ctgggaccga   2340
accccgcgtt tatgaacaaa cgacccaaca ccgtgcgttt tattctgtct ttttattgcc   2400
gtcatagcgc gggttccttc cggtattgtc tccttccgtg tttcagttag cctcccccta   2460
gggtgggcga agaactccag catgagatcc ccgcgctgga ggatcatcca gccggcgtcc   2520
cggaaaacga ttccgaagcc caacctttca tagaaggcgg cggtggaatc gaaatctcgt   2580
gatggcaggt tgggcgtcgc ttggtcggtc atttcgaacc ccagagtccc gctcagaaga   2640
```

```
actcgtcaag aaggcgatag aaggcgatgc gctgcgaatc gggagcggcg ataccgtaaa    2700
gcacgaggaa gcggtcagcc cattcgccgc caagctcttc agcaatatca cgggtagcca    2760
acgctatgtc ctgatagcgg tccgccacac ccagccggcc acagtcgatg aatccagaaa    2820
agcggccatt ttccaccatg atattcggca agcaggcatc gccatgggtc acgacgagat    2880
cctcgccgtc gggcatgctc gccttgagcc tggcgaacag ttcggctggc gcgagcccct    2940
gatgctcttg atcatcctga tcgacaagac cggcttccat ccgagtacgt gctcgctcga    3000
tgcgatgttt cgcttggtgg tcgaatgggc aggtagccgg atcaagcgta tgcagccgcc    3060
gcattgcatc agccatgatg gatactttct cggcaggagc aaggtgagat gacaggagat    3120
cctgccccgg cacttcgccc aatagcagcc agtcccttcc cgcttcagtg acaacgtcga    3180
gcacagctgc gcaaggaacg cccgtcgtgg ccagccacga tagccgcgct gcctcgtctt    3240
gcagttcatt cagggcaccg gacaggtcgg tcttgacaaa aagaaccggg cgcccctgcg    3300
ctgacagccg gaacacggcg gcatcagagc agccgattgt ctgttgtgcc cagtcatagc    3360
cgaatagcct ctccacccaa gcggccgag aacctgcgtg caatccatct tgttcaatca    3420
tgcgaaacga tcctcatcct gtctcttgat cgatctttgc aaaagcctag gcctccaaaa    3480
aagcctcctc actacttctg gaatagctca gaggccgagg aggcggcctc ggcctctgca    3540
taaataaaaa aaattagtca gccatggggc ggagaatggg cggaactggg cggagttagg    3600
ggcgggatgg gcggagttag gggcgggact atggttgctg actaattgag atgcatgctt    3660
tgcatacttc tgcctgctgg ggagcctggg gactttccac acctggttgc tgactaattg    3720
agatgcatgc tttgcatact tctgcctgct ggggagcctg ggactttcc acaccctaac    3780
tgacacacat tccacagctg gttctttccg cctcaggact cttccttttt caataaatca    3840
atctaaagta tatatgagta aacttggtct gacagttacc aatgcttaat cagtgaggca    3900
cctatctcag cgatctgtct atttcgttca tccatagttg cctgactccc cgtcgtgtag    3960
ataactacga tacgggaggg cttaccatct ggccccagtg ctgcaatgat accgcgagac    4020
ccacgctcac cggctccaga tttatcagca ataaaccagc cagccggaag ggccgagcgc    4080
agaagtggtc ctgcaacttt atccgcctcc atccagtcta ttaattgttg ccgggaagct    4140
agagtaagta gttcgccagt taatagtttg cgcaacgttg ttgccattgc tacaggcatc    4200
gtggtgtcac gctcgtcgtt tggtatggct tcattcagct ccggttccca acgatcaagg    4260
cgagttacat gatcccccat gttgtgcaaa aaagcggtta gctccttcgg tcctccgatc    4320
gttgtcagaa gtaagttggc cgcagtgtta tcactcatgg ttatggcagc actgcataat    4380
tctcttactg tcatgccatc cgtaagatgc ttttctgtga ctggtgagta ctcaaccaag    4440
tcattctgag aatagtgtat gcggcgaccg agttgctctt gcccggcgtc aatacgggat    4500
aataccgcgc cacatagcag aactttaaaa gtgctcatca ttggaaaacg ttcttcgggg    4560
cgaaaactct caaggatctt accgctgttg agatccagtt cgatgtaacc cactcgtgca    4620
cccaactgat cttcagcatc ttttactttc accagcgttt ctgggtgagc aaaaacagga    4680
aggcaaaatg ccgcaaaaaa gggaataagg gcgacacgga aatgttgaat actcatactc    4740
ttcctttttc aatattattg aagcatttat cagggttatt gtctcatgag cggatacata    4800
tttgaatgta tttagaaaaa taaacaaata ggggttccgc gcacatttcc ccgaaaagtg    4860
ccacctgacg cgccctgtag cggcgcatta agcgcggcgg gtgtggtggt tacgcgcagc    4920
gtgaccgcta cacttgccag cgccctagcg cccgctcctt tcgctttctt cccttccttt    4980
ctcgccacgt tcgccggctt tccccgtcaa gctctaaatc gggggctccc tttagggttc    5040
```

```
cgatttagtg ctttacggca cctcgacccc aaaaaacttg attagggtga tggttcacgt    5100
agtgggccat cgccctgata gacggttttt cgcccttttga cgttggagtc cacgttcttt    5160
aatagtggac tcttgttcca aactggaaca acactcaacc ctatctcggt ctattctttt    5220
gatttataag ggattttgcc gatttcggcc tattggttaa aaaatgagct gatttaacaa    5280
aaatttaacg cgaattttaa caaaatatta acgcttacaa tttac                   5325
```

<210> SEQ ID NO 63
<211> LENGTH: 5452
<212> TYPE: DNA
<213> ORGANISM: Artificial Sequence
<220> FEATURE:
<223> OTHER INFORMATION: plasmid

<400> SEQUENCE: 63

```
gtaccgaatt caagcttcgt gaggctccgg tgcccgtcag tgggcagagc gcacatcgcc     60
cacagtcccc gagaagttgg ggggaggggt cggcaattga accggtgcct agagaaggtg    120
gcgcggggta aactgggaaa gtgatgtcgt gtactggctc cgccttttc ccgagggtgg    180 gggagaaccg tatataagtg cagtagtcgc cgtgaacgtt cttttttcgca acgggtttgc    240 cgccagaaca caggtaagtg ccgtgtgtgg ttcccgcggg cctggcctct ttacgggtta    300
tggcccttgc gtgccttgaa ttacttccac ctggctccag tacgtgattc ttgatcccga    360
gctggagcca ggggcgggcc ttgcgcttta ggagccccct cgcctcgtgc ttgagttgag    420
gcctggcctg ggcgctgggg ccgccgcgtg cgaatctggt ggcaccttcg cgcctgtctc    480
gctgctttcg ataagtctct agccatttaa aattttgat gacctgctgc gacgcttttt    540
ttctggcaag atagtcttgt aaatgcgggc caggatctgc acactggtat ttcggttttt    600
gggcccgcgg ccggcgacgg ggcccgtgcg tcccagcgca catgttcggc gaggcggggc    660
ctgcgagcgc ggccaccgag aatcggacgg gggtagtctc aagctggccg gcctgctctg    720
gtgcctggcc tcgcgccgcc gtgtatcgcc ccgccctggg cggcaaggct ggcccggtcg    780
gcaccagttg cgtgagcgga agatggccgc ttcccggcc ctgctccagg ggctcaaaa    840 tggaggacgc ggcgctcggg agagcggcg ggtgagtcac ccacacaaag gaaaagggcc    900
tttccgtcct cagccgtcgc ttcatgtgac tccacggagt accgggcgcc gtccaggcac    960
ctcgattagt tctggagctt ttggagtacg tcgtctttag gttgggggga ggggttttat   1020
gcgatggagt ttccccacac tgagtgggtg gagactgaag ttaggccagc ttggcacttg   1080
atgtaattct ccttggaatt tggcctttt gagtttggat cttggttcat tctcaagcct   1140
cagacagtgg ttcaaagttt ttttcttcca tttcaggtgt cgtgaacacg tggccaccat   1200
ggcccaggtg cagctgcagg tcgacctcga gatcaaacgg gcggccgcag aacaaaaact   1260
catctcagaa gaggatctga atggggccgc atagtctaga agctcgctga tcagcctcga   1320
ctgtgccttc tagttgccag ccatctgttg tttgcccctc cccgtgcct tccttgaccc   1380 tggaaggtgc cactcccact gtcctttcct aataaaatga ggaaattgca tcgcattgtc   1440
tgagtaggtg tcattctatt ctggggggtg ggtggggca ggacagcaag ggggaggatt   1500
gggaagacaa tagcaggcat gctggggatg cccgggctc tatggcttct gaggcggaaa   1560
gaaccagctg gggctctagg gggtatcccc acgcgccctg tagcggcgca ttaagcgcgg   1620
cgggtgtggt ggttacgcgc agcgtgaccg ctacacttgc cagcgcccta gcgcccgctc   1680
ctttcgcttt cttccctccc tttctcgcca cgttcgccgg ctttccccgt caagctctaa   1740
```

```
atcgggcat cccctttaggg ttccgattta gtgctttacg gcacctcgac cccaaaaaac    1800
ttgattaggg tgatggttca cgtagtgggc catcgccctg atagacggtt tttcgccctt    1860
tgacgttgga gtccacgttc tttaatagtg gactcttgtt ccaaactgga acaacactca    1920
accctatctc ggtctattct tttgatttat aagggatttt ggggatttcg gcctattggt    1980
taaaaatga gctgatttaa caaaaattta acgcgaatta attctgtgga atgtgtgtca    2040
gttagggtgt ggaaagtccc caggctcccc aggcaggcag aagtatgcaa agcatgcatc    2100
tcaattagtc agcaaccagg tgtggaaagt ccccaggctc ccagcaggc agaagtatgc    2160
aaagcatgca tctcaattag tcagcaacca tagtcccgcc cctaactccg cccatcccgc    2220
ccctaactcc gcccagttcc gcccattctc cgcccctagg ctgactaatt ttttttattt    2280
atgcagaggc cgaggccgcc tctgcctctg agctattcca gaagtagtga ggaggctttt    2340
ttggaggcct aggcttttgc aaaaagctcc cgggaggtcc acaatgattg aacaagatgg    2400
attgcacgca ggttctccgg ccgcttgggt ggagaggcta ttcggctatg actgggcaca    2460
acagacaatc ggctgctctg atgccgccgt gttccggctg tcagcgcagg ggcgcccggt    2520
tcttttttgtc aagaccgacc tgtccggtgc cctgaatgaa ctccaggacg aggcagcgcg    2580
gctatcgtgg ctggccacga cgggcgttcc ttgcgcagct gtgctcgacg ttgtcactga    2640
agcgggaagg gactggctgc tattgggcga agtgccgggg caggatctcc tgtcatctca    2700
ccttgctcct gccgagaaag tatccatcat ggctgatgca atgcggcggc tgcatacgct    2760
tgatccggct acctgcccat tcgaccacca agcgaaacat cgcatcgagc gagcacgtac    2820
tcggatggaa gccggtcttg tcgatcagga tgatctggac gaagagcatc aggggctcgc    2880
gccagccgaa ctgttcgcca ggctcaaggc gcgtatgccc gacggcgagg atctcgtcgt    2940
gactcatggc gatgcctgct tgccgaatat catggtggaa aatggccgct tttctggatt    3000
catcgactgt ggccggctgg gtgtggcgga ccgctatcag gacatagcgt tggctacccg    3060
tgatattgct gaagagcttg gcggcgaatg ggctgaccgc ttcctcgtgc tttacggtat    3120
cgccgctccc gattcgcagc gcatcgcctt ctatcgcctt cttgacgagt tcttctgagc    3180
gggactctgg ggttcgaaat gaccgaccaa gcgacgccca acctgccatc acgagatttc    3240
gattccaccg ccgccttcta tgaaaggttg gccttcggaa tcgttttccg gacgccggc    3300
tggatgatcc tccagcgcgg ggatctcatg ctggagttct cgcccaccc caacttgttt    3360
attgcagctt ataatggtta caaataaagc aatagcatca caaatttcac aaataaagca    3420
ttttttttcac tgcattctag ttgtggtttg tccaaactca tcaatgtatc ttatcatgtc    3480
tgtataccgg atctttccgc ttcctcgctc actgactcgc tgcgctcggt cgttcggctg    3540
cggcgagcgg tatcagctca ctcaaaggcg gtaatacggt tatccacaga atcagggat    3600
aacgcaggaa agaacatgtg agcaaaaggc cagcaaaagg ccaggaaccg taaaaaggcc    3660
gcgttgctgg cgttttttcca taggctccgc cccccctgacg agcatcacaa aaatcgacgc    3720
tcaagtcaga ggtggcgaaa cccgacagga ctataaagat accaggcgtt tccccctgga    3780
agctccctcg tgcgctctcc tgttccgacc ctgccgctta ccggatacct gtccgccttt    3840
ctcccttcgg gaagcgtggc gctttctcaa tgctcacgct gtaggtatct cagttcggtg    3900
taggtcgttc gctccaagct gggctgtgtg cacgaacccc ccgttcagcc cgaccgctgc    3960
gccttatccg gtaactatcg tcttgagtcc aacccggtaa gacacgactt atcgccactg    4020
gcagcagcca ctggtaacag gattagcaga gcgaggtatg taggcggtgc tacagagttc    4080
ttgaagtggt ggcctaacta cggctacact agaaggacag tatttggtat ctgcgctctg    4140
```

```
ctgaagccag ttaccttcgg aaaaagagtt ggtagctctt gatccggcaa acaaaccacc    4200
gctggtagcg gtggtttttt tgtttgcaag cagcagatta cgcgcagaaa aaaggatct     4260 caagaagatc ctttgatctt ttctacgggg tctgacgctc agtggaacga aaactcacgt    4320
taagggattt tggtcatgag attatcaaaa aggatcttca cctagatcct tttaaattaa    4380
aaatgaagtt ttaaatcaat ctaaagtata tatgagtaaa cttggtctga cagttaccaa    4440
tgcttaatca gtgaggcacc tatctcagcg atctgtctat ttcgttcatc catagttgcc    4500
tgactccccg tcgtgtagat aactacgata cgggagggct taccatctgg ccccagtgct    4560
gcaatgatac cgcgagaccc acgctcaccg gctccagatt tatcagcaat aaaccagcca    4620
gccggaaggg ccgagcgcag aagtggtcct gcaactttat ccgcctccat ccagtctatt    4680
aattgttgcc gggaagctag agtaagtagt tcgccagtta atagtttgcg caacgttgtt    4740
gccattgcta caggcatcgt ggtgtcacgc tcgtcgtttg gtatggcttc attcagctcc    4800
ggttcccaac gatcaaggcg agttacatga tcccccatgt tgtgcaaaaa agcggttagc    4860
tccttcggtc ctccgatcgt tgtcagaagt aagttggccg cagtgttatc actcatggtt    4920
atggcagcac tgcataattc tcttactgtc atgccatccg taagatgctt ttctgtgact    4980
ggtgagtact caaccaagtc attctgagaa tagtgtatgc ggcgaccgag ttgctcttgc    5040
ccggcgtcaa tacgggataa taccgcgcca catagcagaa ctttaaaagt gctcatcatt    5100
ggaaaacgtt cttcggggcg aaaactctca aggatcttac cgctgttgag atccagttcg    5160
atgtaaccca ctcgtgcacc caactgatct tcagcatctt ttactttcac cagcgtttct    5220
gggtgagcaa aaacaggaag gcaaaatgcc gcaaaaaagg gaataagggc gacacggaaa    5280
tgttgaatac tcatactctt cctttttcaa tattattgaa gcatttatca gggttattgt    5340
ctcatgagcg gatacatatt tgaatgtatt tagaaaaata aacaaatagg ggttccgcgc    5400
acatttcccc gaaaagtgcc acctgacgtc agatcgacgg atcgggagat cg            5452
```

<210> SEQ ID NO 64
<211> LENGTH: 4883
<212> TYPE: DNA
<213> ORGANISM: Artificial Sequence
<220> FEATURE:
<223> OTHER INFORMATION: plasmid

<400> SEQUENCE: 64

```
gtaccgaatt cacattgatt attgagtagt tattaatagt aatcaattac ggggtcatta     60
gttcatagcc catatatgga gttccgcgtt acataactta cggtaaatgg cccgcctggc    120
tgaccgccca acgaccccccg cccattgacg tcaataatga cgtatgttcc catagtaacg    180 ccaatagggac ctttccattg acgtcaatgg gtggagtatt tacggtaaac tgcccacttg    240
gcagtacatc aagtgtatca tatgccaagt acgccccta ttgacgtcaa tgacggtaaa    300
tggcccgcct ggcattatgc ccagtacatg accttatggg actttcctac ttggcagtac    360
atctacggtt agtcatcgct attaccatag tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta taagcagagc tttctggc     600 taactagaga acccgtggcc accatggccc aggtgcagct gcaggtcgac ctcgagatca    660
aacgggcggc cgcagaacaa aaactcatct cagaagagga tctgaatggg gccgcatagt    720
```

```
ctagaagctc gctgatcagc ctcgactgtg ccttctagtt gccagccatc tgttgtttgc    780
ccctcccccg tgccttcctt gaccctggaa ggtgccactc ccactgtcct ttcctaataa    840
aatgaggaaa ttgcatcgca ttgtctgagt aggtgtcatt ctattctggg gggtggggtg    900
gggcaggaca gcaaggggga ggattgggaa gacaatagca ggcatgctgg ggatggcccg    960
ggctctatgg cttctgaggc ggaaagaacc agctggggct ctaggggta tccccacgcg   1020 ccctgtagcg gcgcattaag cgcggcgggt gtggtggtta cgcgcagcgt gaccgctaca   1080
cttgccagcg ccctagcgcc cgctccttc gctttcttcc cttcctttct cgccacgttc    1140
gccggctttc cccgtcaagc tctaaatcgg gggctcccctt tagggttccg atttagtgct   1200
ttacggcacc tctcccccaa aaacttgat taggtgatg gttcacgtag tgggccatcg     1260
ccctgataga cggttttcg ccctttgacg ttggagtcca cgttctttaa tagtggactc    1320
ttgttccaaa ctggaacaac actcaaccct atctcggtct attctttga tttataaggg    1380 attttgccga tttcggccta ttggttaaaa aatgagctga tttaacaaaa atttaacgcg   1440
aattaattct gtgaatgtg tgtcagttag ggtgtggaaa gtccccaggc tccccagcag    1500
gcagaagtat gcaaagcatg catctcaatt agtcagcaac caggtgtgga aagtccccag   1560
gctccccagc aggcagaagt atgcaaagca tgcatctcaa ttagtcagca accatagtcc    1620
cgcccctaac ccgcccatc ccgccctaa ctccgcccag ttccgcccat tctccgcccc    1680
taggctgact aatttttttt atttatgcag aggccgaggc cgcctctgcc tctgagctat    1740
tccagaagta gtgaggaggc ttttttggag gcctaggctt ttgcaaaaag ctcccccccc    1800
gggaggtcca caatggttga acaagatgga ttgcacgcag gttctccggc cgcttgggtg    1860
gagaggctat tcggctatga ctgggcacaa cagacaatcg gctgctctga tgccgccgtg   1920
ttccggctgt cagcgcaggg gcgcccggtt cttttttgtca agaccgacct gtccggtgcc    1980
ctgaatgaac tccaggacga ggcagcgcgg ctatcgtggc tggccacgac gggcgttcct    2040
tgcgcagctg tgctcgacgt tgtcactgaa gcgggaaggg actggctgct attgggcgaa   2100
gtgccggggc aggatctcct gtcatctcac cttgctcctg ccgagaaagt atccatcatg   2160
gctgatgcaa tgcggcggct gcatacgctt gatccggcta cctgcccatt cgaccaccaa   2220
gcgaaacatc gcatcgagcg agcacgtact cggatggaag ccggtcttgt cgatcaggat   2280
gatctggacg aagagcatca ggggctcgcg ccagccgaac tgttcgccag gctcaaggcg   2340
cgtatgcccg acggcgagga tctcgtcgtg actcatggcg atgcctgctt gccgaatatc   2400
atggtggaaa atggccgctt ttctggattc atcgactgtg gccggctggg tgtggcggac   2460
cgctatcagg acatagcgtt ggctacccgt gatattgctg aagagcttgg cggcgaatgg   2520
gctgaccgct tcctcgtgct ttacggtatc gccgctcccg attcgcagcg catcgccttc   2580
tatcgccttc ttgacgagtt cttctgagcg ggactctggg gttcgaaatg accgaccaag   2640
cgacgcccaa cctgccatca cgagatttcg attccaccgc cgccttctat gaaaggttgg   2700
gcttcggaat cgttttccgg gacgccggct ggatgatcct ccagcgcggg gatctcatgc   2760
tggagttctt cgcccacccc aacttgttta ttgcagctta taatggttac aaataaagca   2820
atagcatcac aaatttcaca aataaagcat ttttttcact gcattctagt tgtggtttgt   2880
ccaaactcat caatgtatct tatcatgtct gtataccgtc gatctttccg cttcctcgct   2940
cactgactcg ctgcgctcgg tcgttcggct gcggcgagcg gtatcagctc actcaaaggc   3000
ggtaatacgg ttatccacag aatcagggga taacgcagga aagaacatgt gagcaaaagg   3060
ccagcaaaag gccaggaacc gtaaaaaggc cgcgttgctg gcgtttttcc ataggctccg   3120
```

```
cccccctgac gagcatcaca aaaatcgacg ctcaagtcag aggtggcgaa acccgacagg    3180
actataaaga taccaggcgt ttcccctgg  aagctccctc gtgcgctctc ctgttccgac   3240
cctgccgctt accggatacc tgtccgcctt tctcccttcg ggaagcgtgg cgctttctca   3300
tagctcacgc tgtaggtatc tcagttcggt gtaggtcgtt cgctccaagc tgggctgtat   3360
gcacgaaccc cccgttcagc ccgaccgctg cgccttatcc ggtaactatc gtcttgagtc   3420
caacccggta agacacgact tatcgccact ggcagcagcc actggtaaca ggattagcag   3480
agcgaggtat gtaggcggtg ctacagagtt cttgaagtgg tggcctaact acggctacac   3540
tagaagaaca gtatttggta tctgcgctct gctgaagcca gttaccttcg gaaaaagagt   3600
tggtagctct tgatccggca aacaaaccac cgctggtagc ggtggttttt ttgtttgcaa   3660
gcagcagatt acgcgcagaa aaaaggatc  tcaagaagat cctttgatct tttctacggg   3720
gtctgacgct cagtggaacg aaaactcacg ttaagggatt ttggtcatga gattatcaaa   3780
aaggatcttc acctagatcc ttttaaatta aaaatgaagt tttaaatcaa tctaaagtat   3840
atatgagtaa acttggtctg acagttacca atgcttaatc agtgaggcac ctatctcagc   3900
gatctgtcta tttcgttcat ccatagttgc ctgactcccc gtcgtgtaga taactacgat   3960
acgggagggc ttaccatctg gccccagtgc tgcaatgata ccgcgagacc cacgctcacc   4020
ggctccagat ttatcagcaa taaaccagcc agccggaagg gccgagcgca gaagtggtcc   4080
tgcaacttta tccgcctcca tccagtctat taattgttgc cgggaagcta gagtaagtag   4140
ttcgccagtt aatagtttgc gcaacgttgt tgccattgct acaggcatcg tggtgtcacg   4200
ctcgtcgttt ggtatggctt cattcagctc cggttcccaa cgatcaaggc gagttacatg   4260 atccccatg  ttgtgcaaaa aagcggttag ctccttcggt cctccgatcg ttgtcagaag   4320
taagttggcc gcagtgttat cactcatggt tatggcagca ctgcataatt ctcttactgt   4380
catgccatcc gtaagatgct tttctgtgac tggtgagtac tcaaccaagt cattctgaga   4440
atagtgtatg cggcgaccga gttgctcttg cccggcgtca tacgggata ataccgcgcc    4500 acatagcaga actttaaaag tgctcatcat tggaaaacgt tcttcgggc gaaaactctc     4560 aaggatctta ccgctgttga tccagttc gatgtaaccc actcgggcac ccaactgatc     4620
ttcagcatct tttactttca ccagcgtttc tgggtgagca aaaacaggaa ggcaaaatgc   4680
cgcaaaaaag ggaataaggg cgacacgaaa atgttgaata ctcatactct tcctttttca   4740
atattattga agcatttatc agggttattg tctcatgagc ggatacatat ttgaatgtat   4800
ttagaaaaat aaacaaatag gggttccgcg cacatttccc cgaaaagtgc cacctgacgt   4860
cagatcgacg gatcgggaga tcg                                          4883
```

<210> SEQ ID NO 65
<211> LENGTH: 5060
<212> TYPE: DNA
<213> ORGANISM: Artificial Sequence
<220> FEATURE:
<223> OTHER INFORMATION: plasmid

<400> SEQUENCE: 65

```
gcgcgcgttg acattgatta ttgactagtt attaatagta atcaattacg ggtcattag     60 ttcatagccc atatatggag ttccgcgtta cataacttac ggtaaatggc ccgcctggct   120
gaccgcccaa cgaccccgc  ccattgacgt caataatgac gtatgttccc atagtaacgc   180
caatagggac tttccattga cgtcaatggg tggactattt acggtaaact gcccacttgg   240
```

```
cagtacatca agtgtatcat atgccaagta cgccccctat tgacgtcaat gacggtaaat    300
ggcccgcctg gcattatgcc cagtacatga ccttatggga ctttcctact tggcagtaca    360
tctacgtatt agtcatcgct attaccatgg tgatgcggtt ttggcagtac atcaatgggc    420
gtggatagcg gtttgactca cggggatttc caagtctcca ccccattgac gtcaatggga    480
gtttgttttg gcaccaaaat caacgggact ttccaaaatg tcgtaacaac tccgccccat    540
tgacgcaaat gggcggtagg cgtgtacggt gggaggtcta tataagcaga gctctctggc    600
taactagaga acccactgct tactggctta tcgaaattaa tacgactcac tatagggaga    660
cccaagctgg ctagcgttta aacttaagct tggtaccgag ctcggatcca ctagtccagt    720
gtggtggaat tcggcttaag ccgaattctg cagatatcca gcacagtggc ggccgctcga    780
gtctagaggg cccgtttaaa cccgctgatc agcctcgact gtgccttcta gttgccagcc    840
atctgttgtt tgcccctccc ccgtgccttc cttgaccctg gaaggtgcca ctcccactgt    900
cctttcctaa taaaatgagg aaattgcatc gcattgtctg agtaggtgtc attctattct    960 gggggtggg gtggggcagg acagcaaggg ggaggattgg gaagacaata gcaggcatgc   1020
tggggatgcg gtgggctcta tggcttctga ggcggaaaga accagtggcg gtaatacggt   1080
tatccacaga atcaggggat aacgcaggaa agaacatgtg agcaaaaggc cagcaaaagg   1140
ccaggaaccg taaaaaggcc gcgttgctgg cgttttccca taggctccgc cccctgacg   1200 agcatcacaa aaatcgacgc tcaagtcaga ggtggcgaaa cccgacagga ctataaagat   1260
accaggcgtt ccccctggaa gctccctcg tgcgctctcc tgttccgacc ctgccgctta   1320
ccggatacct gtccgccttt ctcccttcgg aagcgtggc gctttctcat agctcacgct   1380
gtaggtatct cagttcggtg taggtcgttc gctccaagct gggctgtgtg cacgaaccc   1440 ccgttcagcc cgaccgctgc gccttatccg gtaactatcg tcttgagtcc aacccggtaa   1500
gacacgactt atcgccactg gcagcagcca ctggtaacag gattagcaga gcgaggtatg   1560
taggcggtgc tacagagttc ttgaagtggt ggcctaacta cggctacact agaaggacag   1620
tatttggtat ctgcgctctg ctgaagccag ttaccttcgg aaaaagagtt ggtagctctt   1680
gatccggcaa acaaaccacc gctggtagcg gtggtttttt tgtttgcaag cagcagatta   1740
cgcgcagaaa aaaaggatct caagaagatc ctttgatctt ttctacgggg tctgacgctc   1800
agtggaacga aaactcacgt taagggattt tggtcatgag attatcaaaa aggatcttca   1860
cctagatcct tttaaattaa aaatgaagtt ttaaatcaat ctaaagtata tatgagtaac   1920
ctgaggctat gcagggcct gccgccccga cgttggctgc gagccctggg ccttcacccg   1980
aacttggggg gtggggtggg gaaaaggaag aaacgcgggc gtattggccc caatggggtc   2040 tcggtgggggt atcgacagag tgccagccct gggaccgaac cccgcgttta tgaacaaacg   2100
acccaacacc gtgcgtttta ttctgtcttt ttattgccgt catagcgcgg gttccttccg   2160
gtattgtctc cttccgtgtt tcagttagcc tcccctagg gtgggcgaag aactccagca   2220
tgagatcccc gcgctggagg atcatccagc cggcgtcccg gaaaacgatt ccgaagccca   2280
acctttcata gaaggcggcg gtggaatcga atctcgtga tggcaggttg ggcgtcgctt   2340
ggtcggtcat ttcgaacccc agagtccgc tcagaagaac tcgtcaagaa ggcgatagaa   2400
ggcgatgcgc tgcgaatcgg gagcggcgat accgtaaagc acgaggaagc ggtcagccca   2460
ttcgccgcca agctcttcag caatatcacg ggtagccaac gctatgtcct gatagcggtc   2520
cgccacaccc agccggccac agtcgatgaa tccagaaaag cggccatttt ccaccatgat   2580
attcggcaag caggcatcgc catgggtcac gacgagatcc tcgccgtcgg gcatgctcgc   2640
```

```
cttgagcctg gcgaacagtt cggctggcgc gagcccctga tgctcttgat catcctgatc    2700
gacaagaccg gcttccatcc gagtacgtgc tcgctcgatg cgatgtttcg cttggtggtc    2760
gaatgggcag gtagccggat caagcgtatg cagccgccgc attgcatcag ccatgatgga    2820
tactttctcg gcaggagcaa ggtgagatga caggagatcc tgccccggca cttcgcccaa    2880
tagcagccag tcccttcccg cttcagtgac aacgtcgagc acagctgcgc aaggaacgcc    2940
cgtcgtggcc agccacgata gccgcgctgc ctcgtcttgc agttcattca gggcaccgga    3000
caggtcggtc ttgacaaaaa gaaccgggcg ccctgcgct gacagccgga acacggcggc     3060
atcagagcag ccgattgtct gttgtgccca gtcatagccg aatagcctct ccacccaagc    3120
ggccggagaa cctgcgtgca atccatcttg ttcaatcatg cgaaacgatc ctcatcctgt    3180
ctcttgatcg atctttgcaa aagcctaggc ctccaaaaaa gcctcctcac tacttctgga    3240
atagctcaga ggccgaggcg gcctcggcct ctgcataaat aaaaaaaatt agtcagccat    3300
ggggcggaga atgggcggaa ctgggcggag ttaggggcgg gatgggcgga gttaggggcg    3360
ggactatggt tgctgactaa ttgagatgca tgctttgcat acttctgcct gctggggagc    3420
ctggggactt ccacacctg gttgctgact aattgagatg catgctttgc atacttctgc     3480
ctgctgggga gcctggggac tttccacacc ctaactgaca cacattccac agctggttct    3540
ttccgcctca ggactcttcc tttttcaata aatcaatcta aagtatatat gagtaaactt    3600
ggtctgacag ttaccaatgc ttaatcagtg aggcacctat ctcagcgatc tgtctatttc    3660
gttcatccat agttgcctga ctccccgtcg tgtagataac tacgatacgg gagggcttac    3720
catctggccc cagtgctgca atgataccgc gagacccacg ctcaccggct ccagatttat    3780
cagcaataaa ccagccagcc ggaagggccg agcgcagaag tggtcctgca actttatccg    3840
cctccatcca gtctattaat tgttgccggg aagctagagt aagtagttcg ccagttaata    3900
gtttgcgcaa cgttgttgcc attgctacag gcatcgtggt gtcacgctcg tcgtttggta    3960
tggcttcatt cagctccggt tcccaacgat caaggcgagt tacatgatcc cccatgttgt    4020
gcaaaaaagc ggttagctcc ttcggtcctc cgatcgttgt cagaagtaag ttggccgcag    4080
tgttatcact catggttatg gcagcactgc ataattctct tactgtcatg ccatccgtaa    4140
gatgcttttc tgtgactggt gagtactcaa ccaagtcatt ctgagaatag tgtatgcggc    4200
gaccgagttg ctcttgcccg gcgtcaatac gggataatac cgcgccacat agcagaactt    4260
taaaagtgct catcattgga aaacgttctt cggggcgaaa actctcaagg atcttaccgc    4320
tgttgagatc cagttcgatg taacccactc gtgcacccaa ctgatcttca gcatctttta    4380
ctttcaccag cgtttctggg tgagcaaaaa caggaaggca aaatgccgca aaaaagggaa    4440
taagggcgac acggaaatgt tgaatactca tactcttcct ttttcaatat tattgaagca    4500
tttatcaggg ttattgtctc atgagcggat acatatttga atgtatttag aaaaataaac    4560
aaataggggt tccgcgcaca tttccccgaa aagtgccacc tgacgcgccc tgtagcggcg    4620
cattaagcgc ggcgggtgtg gtggttacgc gcagcgtgac cgctacactt gccagcgccc    4680
tagcgcccgc tcctttcgct ttcttccctt cctttctcgc cacgttcgcc ggctttcccc    4740
gtcaagctct aaatcggggg ctccctttag ggttccgatt tagtgcttta cggcacctcg    4800
accccaaaaa acttgattag ggtgatggtt cacgtagtgg gccatcgccc tgatagacgg    4860
tttttcgccc tttgacgttg gagtccacgt tctttaatag tggactcttg ttccaaactg    4920
gaacaacact caaccctatc tcggtctatt cttttgattt ataagggatt ttgccgattt    4980
```

```
cggcctattg gttaaaaaat gagctgattt aacaaaaatt taacgcgaat tttaacaaaa    5040
tattaacgct tacaatttac                                                5060

<210> SEQ ID NO 66
<211> LENGTH: 13905
<212> TYPE: DNA
<213> ORGANISM: Artificial Sequence
<220> FEATURE:
<223> OTHER INFORMATION: plasmid

<400> SEQUENCE: 66
atggctgcgt gagacacacg tagcctacca gtttcttact gctctactct gcaaagcaag      60
agattaataa cccatcatgg attctgtgta cgtggacata gacgctgaca gcgccttttt     120
gaaggccctg caacgtgcgt accccatgtt tgaggtggaa cctaggcagg tcacatcgaa     180
tgaccatgct aatgctagag cgttctcgca tctagccata aaactaatag agcaggaaat     240
tgatcccgac tcaaccatcc tggatatagg tagtgcgcca gcaaggagga tgatgtcgga     300
caggaagtac cactgcgttt gcccgatgcg cagcgcagaa gatcccgaga gactcgctaa     360
ttatgcgaga aagctcgcat ctgccgcagg aaaagtcctg gacagaaaca tttctggaaa     420
gatcggggac ttacaagcgg tgatggccgt gccagacacg gagacgccaa cattttgctt     480
acacacagat gtctcatgta gacagagagc agacgtcgcg atataccaag acgtctatgc     540
tgtacacgca cccacgtcgc tataccacca ggcgattaaa ggagtccgag tggcgtactg     600
ggtagggttc gacacaaccc cgttcatgta caacgctatg cgggtgcctc acccctcata     660
ctcgacaaat tgggcggatg agcaggtact gaaggctaag aacataggat tatgttcaac     720
agacctgacg gaaggtagac gaggcaaatt gtctatcatg agagggaaaa agctaaaacc     780
gtgcgaccgt gtgctgttct cagtagggtc aacgctttac ccggaaagcc gcacgctact     840
taagagctgg cacctaccat cggtgttcca tctaaagggc aagcttagct tcacatgccg     900
ctgtgacaca gtggtttcgt gtgagggcta cgtcgttaag agaataacga tgagcccagg     960
cctttatgga aaaaccatag ggtatgcggt aacccaccac gcagacggat tcttgatgtg    1020
caagactacc gacacggttg acggcgaaag agtgtcattc tcggtgtgca cgtacgtgcc    1080
ggcgaccatt tgtgatcaaa tgaccggcat ccttgctaca gaagtcacgc cggaggatgc    1140
acagaagctg ttggtggggc tgaaccagag gatagtggtt aacggcagaa cgcaacggaa    1200
cacgaacacc atgaagaact acctacttcc cgtggtcgcc caggccttca gtaagtgggc    1260
aaaggagtgc cggaaggaca tggaagatga gaagcttctg ggggtcagag aaagaacact    1320
aacctgctgc tgtctatggg catttaagaa gcagaaaaca cacacggtct acaagaggcc    1380
tgatacccag tcaatccaga aggttcaggc cgaatttgac agctttgtag taccgggcct    1440
gtggtcgtcc gggttgtcaa tcccgttgag gactagaatc aagtggttgt tacgcaaggt    1500
gccgaaaaca gacctgatcc catacagcgg gaatgcccaa gaagcccagg atgcagaaaa    1560
agaagcagag gaagaacgag aagcagaact gactcatgag gctctaccac ccctacaggc    1620
agcacaggaa gatgtccagg tcgaaatcga cgtggaacag cttgaggata gagctggtgc    1680
tggaataata gagactccga gaggcgctat caaagttact gcccaactaa cagaccacgt    1740 cgtggggag tacctggtac tttccccgca gactgtacta cgcagccaga gctcagcct     1800 gatccacgct ttagcggagc aagtgaagac gtgtacgcac agcggacgag cagggaggta    1860
tgcggtcgaa gcgtacgatg gccgagtcct agtgccctca ggctatgcaa tttcgcctga    1920
agacttccag agtctaagcg aaagcgcaac gatggtgtac aacgaaagag agttcgtaaa    1980
```

```
cagaaagtta caccacattg cgatgcacgg accagccctg aacactgacg aagagtcgta   2040
tgagctggtg agggcagaga ggacagaaca cgagtacgtc tacgacgtgg accagagaag   2100
atgctgtaag aaggaagaag ctgcaggact ggtactggtg ggcgacttga ctaatccgcc   2160
ctaccacgaa ttcgcatacg aagggctaaa aattcgcccc gcctgccat acaaaattgc    2220 agtcatagga gtcttcgggg taccaggatc tggcaagtca gccattatca agaacctagt   2280
taccaggcaa gacctggtga ctagcggaaa gaaagaaaac tgccaagaaa tcagcaccga   2340
cgtgatgaga cagagaggtc tagagatatc tgcacgtacg gtagattcgc tgctcttgaa   2400
tggatgcaac agaccagtcg acgtgttgta cgtagacgag gcgtttgcgt gccactctgg   2460
aacgttactt gctttgatcg ccttggtgag accaagacag aaagttgtac tttgtggtga   2520
cccgaagcag tgcggcttct tcaatatgat gcagatgaaa gtcaactaca atcataacat   2580
ctgcacccaa gtgtaccaca aaagtatctc caggcggtgt acactgcctg tgactgccat   2640
tgtgtcatcg ttgcattacg aaggcaaaat gcgcactacg aatgagtaca acatgccgat   2700
tgtagtggac actacaggct caacgaaacc tgaccctgga gacctcgtgt aacgtgctt    2760 cagagggtgg gttaaacaac tgcaaattga ctatcgtgga cacgaggtca tgacagcagc   2820
cgcatcccaa gggttaacta gaaaggagt ttacgcagtt aggcaaaaag ttaacgaaaa    2880
cccactctat gcatcaacat cagagcacgt caacgtactc ctaacgcgta cggaaggtaa   2940
actggtatgg aagacactct ctggtgaccc gtggataaag acgctgcaga acccaccgaa   3000
aggaaacttc aaagcaacta ttaaggagtg ggaggtggag cacgcatcga taatggcggg   3060
catctgcagt caccaagtga cctttgacac attccaaaac aaagccaacg tttgctgggc   3120
taagagcttg gtccctatcc tcgaaacagc ggggataaaa ctaaatgata ggcagtggtc   3180
ccagataatt caagccttca agaagacaa agcatactca cccgaagtag ccctgaatga    3240
aatatgcacg cgcatgtatg gggtggatct agacagtggg ctattctcta aaccgttggt   3300
atctgtgtat tacgcggata accattggga taataggccg ggaggaaaga tgttcggatt   3360 caacccctgag gcagcgtcca ttctagaaag aaagtaccca tttacaaaag gaaagtggaa   3420
catcaacaag cagatctgcg tgactaccag gaggatagaa gacttcaacc ctaccaccaa   3480
cattataccg gtcaacagga gactaccaca ctcattagtg gccgaacacc gcccagtaaa   3540
aggggaaaga atggaatggc tggttaacaa gataaacgga caccacgtac tcctggttag   3600
cggctataac cttgcactgc ctactaagag agtcacctgg gtagcgccac taggtgtccg   3660
cggagcggac tatacataca acctagagct gggtctacca gcaacacttg gtaggtatga   3720
cctagtggtc ataaacatcc acaccctttt tcgcatacac cattccaac agtgcgtaga    3780 tcacgcaatg aaactgcaaa tgctaggggg tgactcactg agactgctca accgggtgg    3840 ctctctattg atcagagcat acggttacgc agatagaacc agtgaacgag tcatctgcgt   3900
actgggacgc aagtttagat cgtctagagc attgaaacca ccatgtgtca ccagtaatac   3960
tgagatgttt ttcctatttta gcaattttga caatggcaga aggaattta caacgcatgt    4020 catgaacaat caactgaatg cagccttttgt aggacaggcc acccgagcag gatgtgcacc   4080
atcgtaccgg gtaaaacgca tggacatcgc gaagaacgat gaagagtgcg tggttaacgc   4140
cgccaaccct cgcgggttac caggtgacgg tgtttgcaag gcagtatata aaaagtggcc   4200
ggagtccttt aaaaacagtg caacaccagt aggaaccgca aaaacagtta tgtgcggtac   4260
gtatccagta atccacgccg taggaccaaa cttctcaaat tattcggagt ctgaagggga   4320
```

```
ccgggaattg gcggctgcct atcgagaagt cgcaaaggaa gtaactagac tgggagtaaa    4380
tagcgtagct atacctctcc tctccacagg tgtatactca ggagggaaag acaggctaac    4440
ccagtcactg aaccacctct ttacagccat ggactcgacg gatgcagacg tggtcatcta    4500
ctgccgagac aaggaatggg agaagaaaat atctgaggcc atacagatgc ggacccaagt    4560
ggagctgctg gatgagcaca tctccataga ctgcgatgtc attcgcgtgc accctgacag    4620
tagcttggca ggcagaaaag gatacagcac cacggaaggc gcactgtatt catatctaga    4680
agggacacgt tttcaccaga cggcagtgga tatggcagag atatacacta tgtggccaaa    4740
gcaaacagag gccaatgagc aagtctgcct atatgccctg ggggaaagta ttgaatcaat    4800
caggcagaaa tgcccggtgg atgatgcaga cgcatcatct cccccgaaaa ctgtcccgtg    4860
tctttgccgg tatgccatga ctcctgaacg cgtcacccga cttcgcatga accatgtcac    4920
aaatataatt gtgtgttctt catttcccct tccaaagtac aagatagaag gagtgcaaaa    4980
agtcaaatgc tccaaggtaa tgttattcga tcacaatgtg ccatcgcgcg taagtccaag    5040
ggaatacaga tcttcccagg agtctgtaca ggaagtgagt acgacaacgt cattgacgca    5100
tagccagttt gatctaagcg ccgatggcga gacactgcct gtcccgtcag acctggatgc    5160
tgacgcccca gccctagaac cggccctaga cgacggggcg gtacatacat taccaaccat    5220
aatcggaaac cttgcggccg tgtctgactg ggtaatgagc accgtacctg tcgcgccgcc    5280
tagaagaagg agagggagaa acctgactgt gacatgtgac gagagagaag ggaatataac    5340
acccatggct agcgtccgat tctttagagc agagctgtgt ccggccgtac aagaaacagc    5400
ggagacgcgt gacacagcta tttcccttca ggcaccgcca agtaccacca tggaactgag    5460
ccatccaccg atctccttcg gagcaccaag cgagacgttc cccatcacat ttgggactt     5520
cgacgaagga gaaatcgaaa gcttgtcttc tgagctacta actttcggag acttcctacc    5580
cggtgaagtg gatgatctga cagatagcga ctggtccacg tgcccagaca cggacgacga    5640
gttatgacta gacagggcag gtgggtatat attctcgtcg gacactggtc caggccattt    5700
acaacagaag tcggtacgcc agtcagtgct gccggtaaac accctggagg aagtccacga    5760
ggagaagtgt taccccccta agctggatga attaaaggag caactactac ttaagaaact    5820
ccaggagagt gcgtccatgg ccaatagaag caggtatcag tcacgcaaag tggaaaatat    5880
gaaagcaaca atcatccaga gactaaagag aggctgtaaa ctgtatttaa tggcagagac    5940
cccgaaagtc ccgacttatc ggaccatata cccggcgcct gtgtactcgc ctccgatcaa    6000
tgtccgattg tccaacccg agtccgcagt ggcagcatgt aatgagttct agctagaaaa    6060
ctacccaact gttcatcat accaaatcac cgacgagtat gatgcatatc tagacatggt    6120
ggacgggtcg gagagttgct tggaccgagc gacattcaat ccgtcaaaac ttaggagcta    6180
cccgaaacaa catgcttatc acgcgccttc tatcagaagc gctgtacctt ccccattcca    6240
gaacacacta cagaatgtac tggcagcagc cacgaaaagg aactcaacg tcacacagat    6300
gagggaatta cccactttgg actcagcagt attcaacgtg gagtgttta aaaaattcgc    6360
atgtaaccga gaatactggg aagaatttgc agccagccct atcaggataa caactgagaa    6420
tctaacaacc tatgtcacta aactaaaggg gccaaaagca gcagcgctgt ttgcaaaaac    6480
ccataatctg ctgccactgc aggatgtacc aatggatagg ttcacagtag atatgaaaag    6540
ggatgtgaag gtaactcctg gtacaaagca tacagaggaa agacctaagg tgcaggttat    6600
acaggcggct gaacccttgg caacagcgta cctatgtgga attcacagag aactggttag    6660
gagattgaac gccgtcctcc tacccaatgt gcatacacta tttgacatgt ctgccgagga    6720
```

-continued

```
cttcgatgcc attatagccg cacacttcaa gccaggagac gctgttttag aaacggacat    6780
agcctccttt gataagagcc aagatgattc acttgcgctt accgccttaa tgctgttaga    6840
agatttggga gtggatcact ccctgttgga cttgatagag gctgctttcg gagagatttc    6900
cagctgtcat ctgccgacag gtacgcgctt caagttcggc gctatgatga aatccggtat    6960
gttcctaact ctgttcgtca acacgttgtt aaatatcacc atcgctagcc gggtgttgga    7020
agatcgtctg acaaaatccg catgcgcggc cttcatcggc gacgcaacaa taatacatgg    7080
tgtcgtctcc gatgaattga tggcagccag atgcgctact tggatgaaca tggaagtgaa    7140
gatcatagat gcagttgtat cccagaaagc tccttacttt tgtggagggt ttatactgca    7200
tgatactgtg acaggaacag cttgcagagt ggcggacccg ctaaaaaggt tatttaaatt    7260
gggcaaaccg ttagcggcag gtgacgaaca agatgaagac agaagacggg cgctggctga    7320
tgaagtaatc agatggcaac gaacagggct aatagatgag ctggagaaag cggtgtactc    7380
taggtacgaa gtgcagggta tatcagttgc ggtaatgtcc atggccacct ttgcaagctc    7440
cagatccaac ttcgagaagc tcagaggacc cgtcataact ttgtacggcg gtcctaaata    7500
ggtacgcact acagctacct attttgcaga agccgacagc aggtacctaa ataccaatca    7560
gccataatgg agtttatccc aacccaaact ttctacaata ggaggtacca gcctcgacct    7620
tggactccgc gccctactat ccaagttatc agacccagac cgcgtccgca aaggaaagcc    7680
gggcaacttg cccagctgat ctcagcagtt aataaactga caatgcgcgc ggtacctcaa    7740
cagaagccgc gcaagaatcg gaagaataag aagcaaaagc aaaagcagca ggcgccacga    7800
aacaacatga atcaaaagaa gcagcccccct aaaagaaac cggctcaaaa gaaaaagaag    7860
ccgggccgta gagagagaat gtgcatgaaa atcgaaaatg attgcatctt cgaagtcaag    7920
catgaaggta aggtaacagg ttacgcgtgc ttggtagggg acaaagtaat gaagccagca    7980
cacgtaaagg ggaccatcga taatgcggac ctggccaaat tggccttcaa gcggtcatct    8040
aagtacgacc ttgaatgcgc gcagataccc gtgcacatga agtccgacgc ttcgaagttc    8100
acccatgaga aaccggaggg gtactacaac tggcaccacg gagcagtaca gtactcagga    8160
ggccggttca ccatccctac aggtgcgggc aaaccagggg acagcggtag accgatcttc    8220
gacaacaagg ggcgcgtggt ggccatagtt ttaggaggag ctaatgaagg agcccgtaca    8280
gccctctcgg tggtgacctg gaacaaagac atcgtcacga aaatcacccc tgaggggcc    8340
gaagagtgga gtcttgccat tccagttatg tgcctgctgg caaataccac gttccctgc    8400
tcccagccc cttgcacacc ctgctgctac gaaaaagagc cggagaaaac cctgcgcatg    8460
ctagaagaca acgtcatgag ccccgggtac tatcagctgc tacaagcatc cttaacatgt    8520
tctccccgcc gccagcgacg cagtattaag gacaacttca atgtctataa agccataaga    8580
ccgtacctag ctcactgtcc cgactgtgga gaagggcact cgtgccatag tcccgtagcg    8640
ctagaacgca tcagaaacga agcgacagac gggacgctga aaatccaggt ttccttgcaa    8700
atcggaataa agacggatga tagccatgat tggaccaagc tgcgttacat ggacaatcat    8760
atgccagcag acgcagagag ggccaggcta tttgtaagaa cgtcagcacc gtgcacgatt    8820
actgaacaa tgggacactt catcctggcc cgatgtccga aggagaaaac tctgacggtg    8880
ggattcactg acggtaggaa gatcagtcac tcatgtacgc acccatttca ccacgaccct    8940
cctgtgatag gccgggaaaa atttcattcc gaccgcagc acggtagaga actaccttgc    9000
agcacgtacg cgcagagcac cgctgcaact gccgaggaga tagaggtaca tatgcccca    9060
```

```
gacaccccag atcgcacatt gatgtcacaa cagtccggta atgtaaagat cacagtcaat    9120
agtcagacgg tgcggtacaa gtgtaattgc ggtgactcaa atgaaggact aaccactaca    9180
gacaaagtga ttaataactg caaggttgat caatgccatg ccgcggtcac caatcacaaa    9240
aaatggcagt ataattcccc tctggtcccg cgtaatgctg aactcgggga ccgaaaagga    9300
aaagttcaca ttccgtttcc tctggcaaat gtgacatgca gggtgcctaa ggcaaggaac    9360
cccaccgtga cgtacggaaa aaaccaagtc atcatgctgc tgtatcctga ccacccaacg    9420
ctcctgtcct accggaatat gggagaagaa ccaaactatc aagaagagtg ggtgacgcat    9480
aagaaggaga tcaggttaac cgtgccgact gaagggctcg aggtcacgtg gggcaacaac    9540
gagccgtaca agtattggcc gcagttatcc acaaacggta cagcccacgg ccacccgcat    9600
gagataattt tgtattatta tgagctgtac cctactatga ctgtggtagt tgtgtcagtg    9660
gcctcgttcg tactcctgtc gatggtgggt gtggcagtgg ggatgtgcat gtgtgcacga    9720
cgcagatgca ttacaccgta cgaactgaca ccaggagcta ccgtcccttt cctgcttagc    9780
ctaatatgct gcattagaac agctaaagcg gccacatacc aagaggctgc ggtatacctg    9840
tggaacgagc agcagccttt gttttggctg caagccctta ttccgctggc agccctgatt    9900
gtcctatgca actgtctgag actcttacca tgcttttgta aaacgttgac ttttttagcc    9960
gtaatgagcg tcggtgccca cactgtgagc gcgtacgaac acgtaacagt gatcccgaac   10020
acggtgggag taccgtataa gactctagtc aacagaccgg gctacagccc catggtactg   10080
gagatggagc ttctgtcagt cactttggag ccaacgctat cgcttgatta catcacgtgc   10140
gagtataaaa ccgtcatccc gtctccgtac gtgaaatgct gcggtacagc agagtgcaag   10200
gacaagagcc tacctgatta cagctgtaag gtcttcaccg gcgtctaccc attcatgtgg   10260
ggcggcgcct actgcttctg cgacactgaa aatacgcaat tgagcgaagc acatgtggag   10320
aagtccgaat catgcaaaac agaatttgca tcagcatata gggctcatac cgcatccgca   10380
tcagctaagc tccgcgtcct ttaccaagga aataatgtta ctgtatctgc ttatgcaaac   10440
ggcgatcatg ccgtcacagt taaggacgct aaattcattg tggggccaat gtcttcagcc   10500
tggacacctt ttgacaataa aatcgtggtg tacaaaggcg acgtctacaa catggactac   10560
ccgcccttcg gcgcaggaag accaggacaa tttggcgaca tccaaagtcg cacgcctgag   10620
agcgaagacg tctatgctaa cacacaactg gtactgcaga gaccgtccgc gggtacggtg   10680
cacgtgccgt actctcaggc accatctggc ttcaagtatt ggctaaaaga acgaggggcg   10740
tcgctgcagc acacagcacc atttggctgt caaatagcaa caaacccggt aagagcgatg   10800
aactgcgccg tagggaacat gcctatctcc atcgacatac cggacgcggc cttcactagg   10860
gtcgtcgacg cgccatcttt aacgacacatg tcgtgtgagg taccagcctg cacccactcc   10920
tcagactttg ggggcgtagc catcattaaa tatgcagcca gcaagaaagg caagtgtgcg   10980
gtgcattcga tgactaacgc cgtcactatt cgggaagctg aaatagaagt agaagggaac   11040
tctcagttgc aaatctcttt ttcgacggcc ctagccagcg ccgaattccg cgtacaagtc   11100
tgttctacac aagtacactg tgcagccgag tgccatccac cgaaagacca tatagtcaat   11160
tacccggcgt cacacaccac cctcgggtc caagacattt ccgttacggc gatgtcatgg   11220
gtgcagaaga tcacgggagg tgtgggactg gttgtcgctg ttgcagcact gatcctaatc   11280
gtggtgctat gcgtgtcgtt tagcaggcac taacttgaca actaggtacg aaggtatatg   11340
tgtcccctaa gagacacacc acatatagct aagaatcaat agataagtat agatcaaagg   11400
gctgaacaac ccctgaatag taacaaaata taaaaatcaa caaaaatcat aaaatagaaa   11460
```

```
accagaaaca gaagtaggta agaaggtata tgtgtccect aagagacaca ccatatatag   11520
ctaagaatca atagataagt atagatcaaa gggctgaata acccctgaat aataacaaaa   11580
tataaaaatc aataaaaatc ataaaataga aaaccataaa cagaagtagt tcaaagggct   11640
ataaaacccc tgaaaagtaa caaaacataa aactaataaa aatcaaatga ataccataat   11700
tggcaatcgg aagagatgta ggtacttaag cttcctaaaa gcagccgaac tcgctttgag   11760
atgtaggcgt agcacaccga actcttccat aattctccga acccacaggg acgtaggaga   11820
tgttcaaagt ggctataaaa ccctgaacag taataaaaca taaaattaat aaggatcaaa   11880
tgagtaccat aattggcaaa cggaagagat gtaggtactt aagcttccta aaagcagccg   11940
aactcacttt gagatgtagg catagcatac cgaactcttc cacaattctc cgtacccata   12000
gggacgtagg agatgttatt ttgttttaa tatttcaaaa aaaaaaaaaa aaaaaaaaaa   12060
aaagcggccg cttaattaat cgaggggaat taattcttga agacgaaagg gccaggtggc   12120
acttttcggg gaaatgtgcg cggaaccect atttgtttat ttttctaaat acattcaaat   12180
atgtatccgc tcatgagaca ataaccctga taaatgcttc aataatattg aaaaaggaag   12240
agtatgagta ttcaacattt ccgtgtcgcc cttattccct tttttgcggc attttgcctt   12300
cctgtttttg ctcacccaga aacgctggtg aaagtaaaag atgctgaaga tcagttgggt   12360
gcacgagtgg gttacatcga actggatctc aacagcggta agatccttga gttttcgc    12420
cccgaagaac gttttccaat gatgagcact tttaaagttc tgctatgtgg cgcggtatta   12480
tcccgtgttg acgccgggca agagcaactc ggtcgccgca tacactattc tcagaatgac   12540
ttggttgagt actcaccagt cacagaaaag catcttacgg atggcatgac agtaagagaa   12600
ttatgcagtg ctgccataac catgagtgat aacactgcgg ccaacttact tctgacaacg   12660
atcggaggac cgaaggagct aaccgctttt ttgcacaaca tgggggatca tgtaactcgc   12720
cttgatcgtt gggaaccgga gctgaatgaa gccataccaa acgacgagcg tgacaccacg   12780
atgcctgtag caatggcaac aacgttgcgc aaactattaa ctggcgaact acttactcta   12840
gcttcccggc aacaattaat agactggatg gaggcggata agttgcagg accacttctg   12900
cgctcggccc ttccggctgg ctggtttatt gctgataaat ctggagccgg tgagcgtggg   12960
tctcgcggta tcattgcagc actggggcca gatggtaagc cctcccgtat cgtagttatc   13020
tacacgacgg ggagtcaggc aactatggat gaacgaaata gacagatcgc tgagataggt   13080
gcctcactga ttaagcattg gtaactgtca gaccaagttt actcatatat actttagatt   13140
gatttaaaac ttcattttta atttaaaagg atctaggtga agatccttt tgataatctc   13200
atgaccaaaa tcccttaacg tgagttttcg ttccactgag cgtcagaccc cgtagaaaag   13260
atcaaaggat cttcttgaga tcctttttt ctgcgcgtaa tctgctgctt gcaaacaaaa   13320
aaaccaccgc taccagcggt ggtttgtttg ccggatcaag agctaccaac tcttttccg   13380
aaggtaactg gcttcagcag agcgcagata ccaaatactg tccttctagt gtagccgtag   13440
ttaggccacc acttcaagaa ctctgtagca ccgcctacat acctcgctct gctaatcctg   13500
ttaccagtgg ctgctgccag tggcgataag tcgtgtctta ccgggttgga ctcaagacga   13560
tagttaccgg ataggcgca gcggtcgggc tgaacggggg gttcgtgcac acagcccagc   13620
ttggagcgaa cgacctacac cgaactgaga tacctacagc gtgagctatg agaaagcgcc   13680
acgcttcccg aagggagaaa ggcggacagg tatccggtaa gcggcagggt cggaacagga   13740
gagcgcacga gggagcttcc agggggaaac gcctggtatc tttatagtcc tgtcgggttt   13800
```

```
cgccacctct gacttgagcg tcgatttttg tgatgctcgt caggggggcg gagcctatgg    13860
aaaaacgcca gcaacgcgag ctcctggatt taggtgacac tatag                    13905

<210> SEQ ID NO 67
<211> LENGTH: 4006
<212> TYPE: DNA
<213> ORGANISM: Artificial Sequence
<220> FEATURE:
<223> OTHER INFORMATION: plasmid

<400> SEQUENCE: 67
tcaatattgg ccattagcca tattattcat tggttatata gcataaatca atattggcta      60
ttggccattg catacgttgt atctatatca taatatgtac atttatattg gctcatgtcc     120
aatatgaccg ccatgttggc attgattatt gactagttat taatagtaat caattacggg     180
gtcattagtt catagcccat atatggagtt ccgcgttaca taacttacgg taaatggccc     240
gcctggctga ccgcccaacg accccgccc attgacgtca ataatgacgt atgttcccat     300
agtaacgcca tagggacttt ccattgacg tcaatgggtg gagtatttac ggtaaactgc     360
ccacttggca gtacatcaag tgtatcatat gccaagtccg cccctattg acgtcaatga     420 cggtaaatgg cccgcctggc attatgccca gtacatgacc ttacgggact ttcctacttg     480
gcagtacatc tacgtattag tcatcgctat taccatggtg atgcggtttt ggcagtacac     540
caatgggcgt ggatagcggt ttgactcacg ggatttccaa gtctccaccc ccattgacgt     600
caatgggagt ttgttttggc accaaaatca acgggacttt ccaaaatgtc gtaataaccc     660
cgccccgttg acgcaaatgg gcggtaggcg tgtacggtgg gaggtctata taagcagagc     720
tcgtttagtg aaccgtcaga tcactagaag ctttattgcg gtagtttatc acagttaaat     780
tgctaacgca gtcagtgctt ctgacacaac agtctcgaac ttaagctgca gaagttggtc     840
gtgaggcact gggcaggtaa gtatcaaggt tacaagacag gtttaaggag accaatagaa     900
actgggcttg tcgagacaga gaagactctt gcgtttctga taggcaccta ttggtcttac     960
tgacatccac tttgcctttc tctccacagg tgtccactcc cagttcaatt acagctctta    1020
aggctagagt acttaatacg actcactata ggctagcctc gagaattcac gcgtggtacc    1080
tctagagtcg acccgggcgg ccgcttcgag cagacatgat aagatacatt gatgagtttg    1140
gacaaaccac aactagaatg cagtgaaaaa aatgctttat ttgtgaaatt tgtgatgcta    1200
ttgctttatt tgtaaccatt ataagctgca ataaacaagt taacaacaac aattgcattc    1260
attttatgtt tcaggttcag ggggagatgt gggaggtttt ttaaagcaag taaaacctct    1320
acaaatgtgg taaaatcgat aaggatccgg gctggcgtaa tagcgaagag gcccgcaccg    1380
atcgcccttc ccaacagttg cgcagcctga atggcgaatg gacgcgccct gtagcggcgc    1440
attaagcgcg gcgggtgtgg tggttacgcg cagcgtgacc gctacacttg ccagcgccct    1500
agcgcccgct cctttcgctt tcttcccttc ctttctcgcc acgttcgccg gctttccccg    1560
tcaagctcta atcggggggc tccctttagg gttccgattt agtgctttac ggcacctcga    1620
ccccaaaaaa cttgattagg gtgatggttc acgtagtggg ccatcgccct gatagacggt    1680
ttttcgccct ttgacgttgg agtccacgtt ctttaatagt ggactcttgt tccaaactgg    1740
aacaacactc aaccctatct cggtctattc ttttgattta agggatttt gccgatttc     1800 ggcctattgg ttaaaaaatg agctgattta acaaaaattt aacgcgaatt ttaacaaaat    1860
attaacgctt acaatttcct gatgcggtat tttctcctta cgcatctgtg cggtatttca    1920
caccgcatat ggtgcactct cagtacaatc tgctctgatg ccgcatagtt aagccagccc    1980
```

```
cgacacccgc caacacccgc tgacgcgccc tgacgggctt gtctgctccc ggcatccgct      2040
tacagacaag ctgtgaccgt ctccgggagc tgcatgtgtc agaggttttc accgtcatca      2100
ccgaaacgcg cgagacgaaa gggcctcgtg atacgcctat ttttataggt taatgtcatg      2160
ataataatgg tttcttagac gtcaggtggc acttttcggg gaaatgtgcg cggaacccct      2220
atttgtttat ttttctaaat acattcaaat atgtatccgc tcatgagaca ataaccctga      2280
taaatgcttc aataatattg aaaaaggaag agtatgagta ttcaacattt ccgtgtcgcc      2340
cttattccct tttttgcggc attttgcctt cctgtttttg ctcacccaga aacgctggtg      2400
aaagtaaaag atgctgaaga tcagttgggt gcacgagtgg gttacatcga actggatctc      2460
aacagcggta agatccttga gagttttcgc cccgaagaac gttttccaat gatgagcact      2520
tttaaagttc tgctatgtgg cgcggtatta tcccgtattg acgccgggca agagcaactc      2580
ggtcgccgca tacactattc tcagaatgac ttggttgagt actcaccagt cacagaaaag      2640
catcttacgg atggcatgac agtaagagaa ttatgcagtg ctgccataac catgagtgat      2700
aacactgcgg ccaacttact tctgacaacg atcggaggac cgaaggagct aaccgctttt      2760
ttgcacaaca tgggggatca tgtaactcgc cttgatcgtt gggaaccgga gctgaatgaa      2820
gccataccaa acgacgagcg tgacaccacg atgcctgtag caatggcaac aacgttgcgc      2880
aaactattaa ctggcgaact acttactcta gcttcccggc aacaattaat agactggatg      2940
gaggcggata agttgcagg accacttctg cgctcggccc ttccggctgg ctggtttatt       3000
gctgataaat ctggagccgg tgagcgtggg tctcgcggta tcattgcagc actggggcca      3060
gatggtaagc cctcccgtat cgtagttatc tacacgacgg ggagtcaggc aactatggat      3120
gaacgaaata gacagatcgc tgagataggt gcctcactga ttaagcattg gtaactgtca      3180
gaccaagttt actcatatat actttagatt gatttaaaac ttcatttta atttaaaagg       3240 atctaggtga agatcctttt tgataatctc atgaccaaaa tcccttaacg tgagttttcg      3300
ttccactgag cgtcagaccc cgtagaaaag atcaaaggat cttcttgaga tccttttttt      3360
ctgcgcgtaa tctgctgctt gcaaacaaaa aaaccaccgc taccagcggt ggtttgtttg      3420
ccggatcaag agctaccaac tcttttccg aaggtaactg gcttcagcag agcgcagata       3480
ccaaatactg ttcttctagt gtagccgtag ttaggccacc acttcaagaa ctctgtagca      3540
ccgcctacat acctcgctct gctaatcctg ttaccagtgg ctgctgccag tggcgataag      3600
tcgtgtctta ccgggttgga ctcaagacga tagttaccgg ataaggcgca gcggtcgggc      3660
tgaacggggg gttcgtgcac acagcccagc ttggagcgaa cgacctacac cgaactgaga      3720
tacctacagc gtgagctatg agaaagcgcc acgcttcccg aagggagaaa ggcggacagg      3780
tatccggtaa gcggcagggt cggaacagga gagcgcacga gggagcttcc agggggaaac      3840
gcctggtatc tttatagtcc tgtcgggttt cgccacctct gacttgagcg tcgatttttg      3900
tgatgctcgt caggggggcg gagcctatgg aaaaacgcca gcaacgcggc ctttttacgg      3960
ttcctggcct tttgctggcc ttttgctcac atggctcgac agatct                    4006
```

<210> SEQ ID NO 68
<211> LENGTH: 14011
<212> TYPE: DNA
<213> ORGANISM: Artificial Sequence
<220> FEATURE:
<223> OTHER INFORMATION: plasmid

<400> SEQUENCE: 68

```
tactcgtaaa gcgagttgaa ggatcatatt tagttgcgtt tatgagataa gattgaaagc    60
acgtgtaaaa tgtttcccgc gcgttggcac aactatttac aatgcggcca agttataaaa   120
gattctaatc tgatatgttt taaaacacct ttgcggcccg agttgtttgc gtacgtgact   180
agcgaagaag atgtgtggac cgcagaacag atagtaaaac aaaaccctag tattggagca   240
ataatcgatt taaccaacac gtctaaatat tatgatggtg tgcattttt gcgggcgggc   300 ctgttataca aaaaaattca agtacctggc cagactttgc cgcctgaaag catagttcaa   360
gaatttattg acacggtaaa agaatttaca gaaaagtgtc ccggcatgtt ggtgggcgtg   420
cactgcacac acggtattaa tcgcaccggt tacatggtgt gcagatattt aatgcacacc   480
ctgggtattg cgccgcagga agccatagat agattcgaaa aagccagagg tcacaaaatt   540
gaaagacaaa attacgttca agatttatta atttaattaa tattatttgc attctttaac   600
aaatacttta tcctattttc aaattgttgc gcttcttcca gcgaaccaaa actatgcttc   660
gcttgctccg tttagcttgt agccgatcag tggcgttgtt ccaatcgacg gtaggattag   720
gccggatatt ctccaccaca atgttggcaa cgttgatgtt acgtttatgc ttttggtttt   780
ccacgtacgt cttttggccg gtaatagccg taaacgtagt gccgtcgcgc gtcacgcaca   840
acaccggatg tttgcgcttg tccgcggggt attgaaccgc gcgatccgac aaatccacca   900
ctttggcaac taaatcggtg acctgcgcgt cttttttctg cattatttcg tctttctttt   960
gcatggtttc ctggaagccg gtgtacatgc ggtttagatc agtcatgacg cgcgtgacct  1020
gcaaatcttt ggcctcgatc tgcttgtcct tgatggcaac gatgcgttca ataaactctt  1080
gttttttaac aagttcctcg ttttttgcg ccaccaccgc ttgcagcgcg tttgtgtgct  1140
cggtgaatgt cgcaatcagc ttagtcacca actgtttgct ctcctcctcc cgttgtttga  1200
tcgcgggatc gtacttgccg gtgcagagca cttgaggaat tacttcttct aaaagccatt  1260
cttgtaattc tatggcgtaa ggcaatttgg acttcataat cagctgaatc acgccggatt  1320
tagtaatgag cactgtatgc ggctgcaaat acagcgggtc gccccttttc acgacgctgt  1380
tagaggtagg gccccccattt tggatggtct gctcaaataa cgatttgtat ttattgtcta  1440
catgaacacg tatagcttta tcacaaactg tatattttaa actgttagcg acgtccttgg  1500
ccacgaaccg gacctgttgg tcgcgctcta gcacgtaccg caggttgaac gtatcttctc  1560
caaatttaaa ttctccaatt ttaacgcgag ccatttgat acacgtgtgt cgattttgca  1620
acaactattg ttttttaacg caaactaaac ttattgtggt aagcaataat taaatatggg  1680
ggaacatgcg ccgctacaac actcgtcgtt atgaacgcag acggcgccgg tctcggcgca  1740
agcggctaaa acgtgttgcg cgttcaacgc ggcaaacatc gcaaaagcca atagtacagt  1800
tttgatttgc atattaacgg cgatttttta aattatctta tttaataaat agttatgacg  1860
cctacaactc cccgcccgcg ttgactcgct gcacctcgag cagttcgttg acgccttcct  1920
ccgtgtggcc gaaacacgtcg agcgggtggt cgatgaccag cggcgtgccg cacgcgacgc  1980
acaagtatct gtacaccgaa tgatcgtcgg gcgaaggcac gtcggcctcc aagtggcaat  2040
attggcaaat tcgaaaatat atacagttgg gttgtttgcg catatctatc gtggcgttgg  2100
gcatgtacgc ccgaacgttg atttgcatgc aagccgaaat taaatcattg cgattagtgc  2160
gattaaaacg ttgtacatcc tcgcttttaa tcatgccgtc gattaaatcg cgcaatcgag  2220
tcaagtgatc aaagtgtgga ataatgtttt ctttgtattc ccgagtcaag cgcagcgcgt  2280
attttaacaa actagccatc ttgtaagtta gtttcattta atgcaacttt atccaataat  2340
atattatgta tcgcacgtca agaattaaca atgcgcccgt tgtcgcatct caacacgact  2400
```

```
atgatagaga tcaaataaag cgcgaattaa atagcttgcg acgcaacgtg cacgatctgt    2460
gcacgcgttc cggcacgagc tttgattgta ataagttttt acgaagcgat gacatgaccc    2520
ccgtagtgac aacgatcacg cccaaaagaa ctgccgacta caaaattacc gagtatgtcg    2580
gtgacgttaa aactattaag ccatccaatc gaccgttagt cgaatcagga ccgctggtgc    2640
gagaagccgc gaagtatggc gaatgcatcg tataacgtgt ggagtccgct cattagagcg    2700
tcatgtttag acaagaaagc tacatattta attgatcccg atgatttat tgataaattg     2760 accctaactc catacacggt attctacaat ggcggggttt tggtcaaaat ttccggactg    2820
cgattgtaca tgctgttaac ggctccgccc actattaatg aaattaaaaa ttccaatttt    2880
aaaaaacgca gcaagagaaa catttgtatg aaagaatgcg tagaaggaaa gaaaaatgtc    2940
gtcgacatgc tgaacaacaa gattaatatg cctccgtgta taaaaaaat attgaacgat     3000 ttgaaagaaa acaatgtacc gcgcggcggt atgtacagga agaggtttat actaaactgt    3060
tacattgcaa acgtggtttc gtgtgccaag tgtgaaaacc gatgtttaat caaggctctg    3120
acgcatttct acaaccacga ctccaagtgt gtgggtgaag tcatgcatct tttaatcaaa    3180
tcccaagatg tgtataaacc accaaactgc caaaaaatga aaactgtcga caagctctgt    3240
ccgtttgctg gcaactgcaa gggtctcaat cctatttgta attattgaat aataaaacaa    3300
ttataaatgc taaatttgtt ttttattaac gatacaaacc aaacgcaaca gaacatttg     3360 tagtattatc tataattgaa aacgcgtagt tataatcgct gaggtaatat ttaaaatcat    3420
tttcaaatga ttcacagtta atttgcgaca atataatttt attttcacat aaactagacg    3480
ccttgtcgtc ttcttcttcg tattccttct ctttttcatt tttctcctca taaaaattaa    3540
catagttatt atcgtatcca tatatgtatc tatcgtatag agtaaatttt tgttgtcat     3600 aaatatatat gtcttttta atggggtgta tagtaccgct gcgcatagtt tttctgtaat    3660
ttacaacagt gctatttct ggtagttctt cggagtgtgt tgctttaatt attaaattta     3720
tataatcaat gaatttggga tcgtcggttt tgtacaatat gttgccggca tagtacgcag    3780
cttcttctag ttcaattaca ccattttta gcagcaccgg attaacataa ctttccaaaa     3840
tgttgtacga accgttaaac aaaaacagtt cacctccctt ttctatacta ttgtctgcga    3900
gcagttgttt gttgttaaaa ataacagcca ttgtaatgag acgcacaaac taatatcaca    3960
aactggaaat gtctatcaat atatagttgc tgatatcaga tccagacatg ataagataca    4020
ttgatgagtt tggacaaacc acaactagaa tgcagtgaaa aaaatgcttt atttgtgaaa    4080
tttgtgatgc tattgcttta tttgtaacca ttataagctg caataaacaa gttaacaaca    4140
acaattgcat tcattttatg tttcaggttc aggggggaggt gtgggaggtt ttttaaagca    4200
agtaaaacct ctacaaatgt ggtatggctg attatgatcc tctagagtcg agatcccct     4260 cgcccggtta ttattatttt tgacaccaga ccaactggta atggtagcga ccggcgctca    4320
gctggaattc cgccgatact gacgggctcc aggagtcgtc gccaccaatc cccatatgga    4380
aaccgtcgat attcagccat gtgccttctt ccgcgtgcag cagatggcga tggctggttt    4440
ccatcagttg ctgttgactg tagcggctga tgttgaactg gaagtcgccg cgccactggt    4500
gtgggccata attcaattcg cgcgtcccgc agcgcagacc gttttcgctc gggaagacgt    4560
acggggtata catgtctgac aatggcagat cccagcggtc aaaacaggcg gcagtaaggc    4620
ggtcgggata gttttcttgc ggccctaatc cgagccagtt tacccgctct gctacctgcg    4680
ccagctggca gttcaggcca atccgcgccg gatgcggtgt atcgctcgcc acttcaacat    4740
```

```
caacggtaat cgccatttga ccactaccat caatccggta ggttttccgg ctgataaata    4800
aggttttccc ctgatgctgc cacgcgtgag cggtcgtaat cagcaccgca tcagcaagtg    4860
tatctgccgt gcactgcaac aacgctgctt cggcctggta atggcccgcc gccttccagc    4920
gttcgaccca ggcgttaggg tcaatgcggg tcgcttcact tacgccaatg tcgttatcca    4980
gcggtgcacg ggtgaactga tcgcgcagcg gcgtcagcag ttgtttttta tcgccaatcc    5040
acatctgtga agaaagcct gactggcggt taaattgcca acgcttatta cccagctcga    5100
tgcaaaaatc catttcgctg gtggtcagat gcgggatggc gtgggacgcg gcggggagcg    5160
tcacactgag gttttccgcc agacgccact gctgccaggc gctgatgtgc ccggcttctg    5220
accatgcggt cgcgttcggt tgcactacgc gtactgtgag ccagagttgc ccggcgctct    5280
ccggctgcgg tagttcaggc agttcaatca actgtttacc ttgtggagcg acatccagag    5340
gcacttcacc gcttgccagc ggcttaccat ccagcgccac catccagtgc aggagctcgt    5400
tatcgctatg acggaacagg tattcgctgg tcacttcgat ggtttgcccg gataaacgga    5460
actgaaaaa ctgctgctgg tgttttgctt ccgtcagcgc tggatgcggc gtgcggtcgg    5520
caaagaccag accgttcata cagaactggc gatcgttcgg cgtatcgcca aaatcaccgc    5580
cgtaagccga ccacgggttg ccgttttcat catatttaat cagcgactga tccacccagt    5640
cccagacgaa gccgccctgt aaacggggat actgacgaaa cgcctgccag tatttagcga    5700
aaccgccaag actgttaccc atcgcgtggg cgtattcgca aaggatcagc gggcgcgtct    5760
ctccaggtag cgaaagccat tttttgatgg accatttcgg cacagccggg aagggctggt    5820
cttcatccac gcgcgcgtac atcgggcaaa taatatcggt ggccgtggtg tcggctccgc    5880
cgccttcata ctgcaccggg cgggaaggat cgacagattt gatccagcga tacagcgcgt    5940
cgtgattagc gccgtggcct gattcattcc ccagcgacca gatgatcaca ctcgggtgat    6000
tacgatcgcg ctgcaccatt cgcgttacgc gttcgctcat cgccggtagc cagcgcggat    6060
catcggtcag acgattcatt ggcaccatgc cgtgggtttc aatattggct tcatccacca    6120
catacaggcc gtagcggtcg cacagcgtgt accacagcgg atggttcgga taatgcgaac    6180
agcgcacggc gttaaagttg ttctgcttca tcagcaggat atcctgcacc atcgtctgct    6240
catccatgac ctgaccatgc agaggatgat gctcgtgacg gttaacgcct cgaatcagca    6300
acggcttgcc gttcagcagc agcagaccat tttcaatccg cacctcgcgg aaaccgacat    6360
cgcaggcttc tgcttcaatc agcgtgccgt cggcggtgtg cagttcaacc accgcacgat    6420
agagattcgg gatttcggcg ctccacagtt tcgggttttc gacgttcaga cgtagtgtga    6480
cgcgatcggc ataaccacca cgctcatcga taatttcacc gccgaaaggc gcggtgccgc    6540
tggcgacctg cgtttcaccc tgccataaag aaactgttac ccgtaggtag tcacgcaact    6600
cgccgcacat ctgaacttca gcctccagta cagcgcggct gaaatcatca ttaaagcgag    6660
tgcaacatg gaaatcgctg atttgtgtag tcggtttatg cagcaacgag acgtcacgga    6720
aaatgccgct catccgccac atatcctgat cttccagata actgccgtca ctccaacgca    6780
gcaccatcac cgcgaggcgg ttttctccgg cgcgtaaaaa tgcgctcagg tcaaattcag    6840
acggcaaacg actgtcctgg ccgtaaccga cccagcgccc gttgcaccac agatgaaacg    6900
ccgagttaac gccatcaaaa ataattcgcg tctggccttc ctgtagccag cttcatcaa    6960
cattaaatgt gagcgagtaa caacccgtcg gattctccgt gggaacaaac ggcggattga    7020
ccgtaatggg ataggttacg ttggtgtaga tgggcgcatc gtaaccgtgc atctgccagt    7080
ttgaggggac gacgacagta tcggcctcag gaagatcgca ctccagccag ctttccggca    7140
```

```
ccgcttctgg tgccggaaac caggcaaagc gccattcgcc attcaggctg cgcaactgtt     7200
gggaagggcg atcggtgcgg gcctcttcgc tattacgcca gctggcgaaa gggggatgtg     7260
ctgcaaggcg attaagttgg gtaacgccag ggttttccca gtcacgacgt tgtaaaacga     7320
cgggatctat catgattgta aataaaatgt aatttacagt atagtatttt aattaatata     7380
caaatgattt gataataatt cttatttaac tataatatat tgtgttgggt tgaattaaag     7440
gtcccggcat cctcaaatgc ataatttcat agtccccctt gttgtaagtg atgcgtattt     7500
ctgaatcttt gtaaaatagc acacaagact ccaacgcgtt tggcgtttta ttttcttgct     7560
cgaggatatc atggagataa ttaaaatgat aaccatctcg caaataaata agtattttac     7620
tgttttcgta acagttttgt aataaaaaaa cctataaata ttccggatta ttcataccgt     7680
cccaccatcg ggcgtgctag catcatgaaa ttcttagtca acgttgccct tgttttatg      7740 gtcgtgtaca tttcttacat ctatgcggac ccaagcccgg gcggccgcta ctaggatcct     7800
ttcctgggac ccggcaagaa ccaaaaactc actctcttca aggaaatccg taatgttaaa     7860
cccgacacga tgaagcttgt cgttggatgg aaaggaaaag agttctacag ggaaacttgg     7920
acccgcttca tggaagacag cttccccatt gttaacgacc aagaagtgat ggatgttttc     7980
cttgttgtca acatgcgtcc cactagaccc aaccgttgtt acaaattcct ggcccaacac     8040
gctctgcgtt gcgaccccga ctatgtacct catgacgtga ttaggatcgt cgagccttca     8100
tgggtgggca gcaacaacga gtaccgcatc agcctggcta agaagggcgg cggctgccca     8160
ataatgaacc ttcactctga gtacaccaac tcgttcgaac agttcatcga tcgtgtcatc     8220
tgggagaact tctacaagcc catcgtttac atcggtaccg actctgctga agaggaggaa     8280
attctccttg aagtttccct ggtgttcaaa gtaaaggagt ttgcaccaga cgcacctctg     8340
ttcactggtc cggcgtatta aaacacgata cattgttatt agtacattta ttaagcgcta     8400
gattctgtgc gttgttgatt tacagacaat tgttgtacgt attttaataa ttcattaaat     8460
ttataatctt tagggtggta tgttagagcg aaaatcaaat gattttcagc gtctttatat     8520
ctgaatttaa atattaaatc ctcaatagat ttgtaaaata ggtttcgatt agtttcaaac     8580
aagggttgtt tttccgaacc gatggctgga ctatctaatg gattttcgct caacgccaca     8640
aaacttgcca aatcttgtag cagcaatcta gctttgtcga tattcgtttg tgttttgttt     8700
tgtaataaag gttcgacgtc gttcaaaata ttatgcgctt ttgtatttct ttcatcactg     8760
tcgttagtgt acaattgact cgacgtaaac acgttaaata agcttggaca atatttaaca     8820
tcgggcgtgt tagctttatt aggccgatta tcgtcgtcgt cccaaccctc gtcgttagaa     8880
gttgcttccg aagacgattt tgccatagcc acacgacgcc tattaattgt gtcggctaac     8940
acgtccgcga tcaaatttgt agttgagctt tttggaatta tttctgattg cgggcgtttt     9000
tgggcgggtt tcaatctaac tgtgcccgat tttaattcag acaacacgtt agaaagcgat     9060
ggtgcaggcg gtggtaacat ttcagacggc aaatctacta atggcggcgg tggtggagct     9120
gatgataaat ctaccatcgg tggaggcgca ggcggggctg gcggcggagg cggaggcgga     9180
ggtggtggcg gtgatgcaga cggcggttta ggctcaaatg tctctttagg caacacagtc     9240
ggcacctcaa ctattgtact ggtttcgggc gccgttttg gtttgaccgg tctgagacga      9300
gtgcgatttt tttcgtttct aatagcttcc aacaattgtt gtctgtcgtc taaaggtgca     9360
gcgggttgag gttccgtcgg cattggtgga gcggcggca attcagacat cgatggtggt      9420
ggtggtggtg gaggcgctgg aatgttaggc acgggagaag gtggtggcgg cggtgccgcc     9480
```

```
ggtataattt gttctggttt agtttgttcg cgcacgattg tgggcaccgg cgcaggcgcc    9540
gctggctgca caacggaagg tcgtctgctt cgaggcagcg cttggggtgg tggcaattca    9600
atattataat tggaatacaa atcgtaaaaa tctgctataa gcattgtaat ttcgctatcg    9660
tttaccgtgc cgatatttaa caaccgctca atgtaagcaa ttgtattgta aagagattgt    9720
ctcaagctcc gcacgccgat aacaagcctt ttcatttta ctacagcatt gtagtggcga    9780
gacacttcgc tgtcgtcgac gtacatgtat gctttgttgt caaaaacgtc gttggcaagc    9840
tttaaaatat ttaaaagaac atctctgttc agcaccactg tgttgtcgta aatgttgttt    9900
ttgataattt gcgcttccgc agtatcgaca cgttcaaaaa attgatgcgc atcaattttg    9960
ttgttcctat tattgaataa ataagattgt acagattcat atctacgatt cgtcatggcc   10020
accacaaatg ctacgctgca aacgctggta caattttacg aaaactgcaa aaacgtcaaa   10080
actcggtata aataatcaa cgggcgcttt ggcaaaatat ctattttatc gcacaagccc   10140
actagcaaat tgtatttgca gaaaacaatt tcggcgcaca attttaacgc tgacgaaata   10200
aaagttcacc agtaatgag cgaccaccca aattttataa aaatctattt taatcacggt   10260
tccatcaaca accaagtgat cgtgatggac tacattgact gtcccgattt atttgaaaca   10320
ctacaaatta aaggcgagct ttcgtaccaa cttgttagca atattattag acagctgtgt   10380
gaagcgctca acgatttgca caagcacaat ttcatacaca acgacataaa actcgaaaat   10440
gtcttatatt tcgaagcact tgatcgcgtg tatgtttgcg attacggatt gtgcaaacac   10500
gaaaactcac ttagcgtgca cgacggcacg ttggagtatt ttagtccgga aaaaattcga   10560
cacacaacta tgcacgtttc gtttgactgg tacgcggcgt gttaacatac aagttgctaa   10620
ccggcggccg acacccattt gaaaaaagcg aagacgaaat gttggacttg aatagcatga   10680
agcgtcgtca gcaatacaat gacattggcg ttttaaaaca cgttcgtaac gttaacgctc   10740
gtgactttgt gtactgccta acaagataca acatagattg tagactcaca aattacaaac   10800
aaattataaa acatgagttt ttgtcgtaaa aatgccactt gttttacgag tagaattacg   10860
cgccctgtag cggcgcatta agcgcggcgg gtgtggtggt tacgcgcagc gtgaccgcta   10920
cacttgccag cgcccagcg cccgctcctt tcgctttctt cccttccttt ctcgccacgt   10980
tcgccggctt tccccgtcaa gctctaaatc ggggggctccc tttagggttc cgatttagtg   11040
ctttacggca cctcgacccc aaaaaacttg attagggtga tggttcacgt agtgggccat   11100
cgccctgata gacggttttt cgccctttga cgttggagtc cacgttcttt aatagtggac   11160
tcttgttcca aactgaaca acactcaacc ctatctcggt ctattctttt gatttataag   11220
ggattttgcc gatttcggcc tattggttaa aaaatgagct gatttaacaa aaatttaacg   11280
cgaattttaa caaatatta acgtttacaa tttaaatatt tgcttataca atcttcctgt   11340
ttttggggct tttctgatta tcaaccgggg taattcgtaa tcatggtcat agctgtttcc   11400
tgtgtgaaat tgttatccgc tcacaattcc acacaacata cgagccggaa gcataaagtg   11460
taaagcctgg ggtgcctaat gagtgagcta actcacatta attgcgttgc gctcactgcc   11520
cgctttccag tcgggaaacc tgtcgtgcca gctgcattaa tgaatcggcc aacgcgcggg   11580
gagaggcggt ttgcgtattg ggcgctcttc cgcttcctcg ctcactgact cgctgcgctc   11640
ggtcgttcgg ctgcggcgag cggtatcagc tcactcaaag gcggtaatac ggttatccac   11700
agaatcaggg gataacgcag gaaagaacat gtgagcaaaa ggccagcaaa aggccaggaa   11760
ccgtaaaaag gccgcgttgc tggcgttttt ccataggctc cgcccccctg acgagcatca   11820
caaaaatcga cgctcaagtc agaggtggcg aaacccgaca ggactataaa gataccaggc   11880
```

```
gtttccccct ggaagctccc tcgtgcgctc tcctgttccg accctgccgc ttaccggata   11940
cctgtccgcc tttctccctt cgggaagcgt ggcgctttct catagctcac gctgtaggta   12000
tctcagttcg gtgtaggtcg ttcgctccaa gctgggctgt gtgcacgaac cccccgttca   12060
gcccgaccgc tgcgccttat ccggtaacta tcgtcttgag tccaacccgg taagacacga   12120
cttatcgcca ctggcagcag ccactggtaa caggattagc agagcgaggt atgtaggcgg   12180
tgctacagag ttcttgaagt ggtggcctaa ctacggctac actagaagga cagtatttgg   12240
tatctgcgct ctgctgaagc cagttacctt cggaaaaaga gttggtagct cttgatccgg   12300
caaacaaacc accgctggta gcggtggttt ttttgtttgc aagcagcaga ttacgcgcag   12360
aaaaaaagga tctcaagaag atcctttgat cttttctacg gggtctgacg ctcagtggaa   12420
cgaaaactca cgttaaggga ttttggtcat gagattatca aaaaggatct tcacctagat   12480
ccttttaaat taaaaatgaa gttttaaatc aatctaaagt atatatgagt aaacttggtc   12540
tgacagttac caatgcttaa tcagtgaggc acctatctca gcgatctgtc tatttcgttc   12600
atccatagtt gcctgactcc ccgtcgtgta gataactacg atacgggagg gcttaccatc   12660
tggccccagt gctgcaatga taccgcgaga cccacgctca ccggctccag atttatcagc   12720
aataaaccag ccagccggaa gggccgagcg cagaagtggt cctgcaactt tatccgcctc   12780
catccagtct attaattgtt gccgggaagc tagagtaagt agttcgccag ttaatagttt   12840
gcgcaacgtt gttgccattg ctacaggcat cgtggtgtca cgctcgtcgt ttggtatggc   12900
ttcattcagc tccggttccc aacgatcaag gcgagttaca tgatccccca tgttgtgcaa   12960
aaaagcggtt agctccttcg gtcctccgat cgttgtcaga agtaagttgg ccgcagtgtt   13020
atcactcatg gttatggcag cactgcataa ttctcttact gtcatgccat ccgtaagatg   13080
cttttctgtg actggtgagt actcaaccaa gtcattctga gaatagtgta tgcggcgacc   13140
gagttgctct tgcccggcgt caatacggga taataccgcg ccacatagca gaactttaaa   13200
agtgctcatc attggaaaac gttcttcggg gcgaaaactc tcaaggatct taccgctgtt   13260
gagatccagt tcgatgtaac ccactcgtgc acccaactga tcttcagcat cttttacttt   13320
caccagcgtt tctgggtgag caaaaacagg aaggcaaaat gccgcaaaaa agggaataag   13380
ggcgacacgg aaatgttgaa tactcatact cttccttttt caatattatt gaagcattta   13440
tcagggttat tgtctcatga gcggatacat atttgaatgt atttagaaaa ataaacaaat   13500
aggggttccg cgcacatttc cccgaaaagt gccacctgac gtctaagaaa ccattattat   13560
catgacatta acctataaaa ataggcgtat cacgaggccc tttcgtctcg cgcgtttcgg   13620
tgatgacggt gaaaacctct gacacatgca gctcccggag acggtcacag cttgtctgta   13680
agcggatgcc gggagcagac aagcccgtca gggcgcgtca gcgggtgttg gcgggtgtcg   13740
gggctggctt aactatgcgg catcagagca gattgtactg agagtgcacc atatgcggtg   13800
tgaaataccg cacagatgcg taaggagaaa ataccgcatc aggcgccatt cgccattcag   13860
gctgcgcaac tgttgggaag ggcgatcggt gcgggcctct tcgctattac gccagctggc   13920
gaaaggggga tgtgctgcaa ggcgattaag ttgggtaacg ccagggtttt cccagtcacg   13980
acgttgtaaa acgacggcca gtgccaagct t                                 14011
```

<210> SEQ ID NO 69
<211> LENGTH: 14180
<212> TYPE: DNA
<213> ORGANISM: Artificial Sequence
<220> FEATURE:

<223> OTHER INFORMATION: plasmid

<400> SEQUENCE: 69

```
tactcgtaaa gcgagttgaa ggatcatatt tagttgcgtt tatgagataa gattgaaagc    60
acgtgtaaaa tgtttcccgc gcgttggcac aactatttac aatgcggcca agttataaaa   120
gattctaatc tgatatgttt taaaacacct ttgcggcccg agttgtttgc gtacgtgact   180
agcgaagaag atgtgtggac cgcagaacag atagtaaaac aaaaccctag tattggagca   240
ataatcgatt taaccaacac gtctaaatat tatgatggtg tgcattttt gcgggcgggc    300
ctgttataca aaaaaattca agtacctggc cagactttgc cgcctgaaag catagttcaa   360
gaatttattg acacggtaaa agaatttaca gaaaagtgtc ccggcatgtt ggtgggcgtg   420
cactgcacac acgtattaa tcgcaccggt tacatggtgt gcagatattt aatgcacacc    480
ctgggtattg cgccgcagga agccatagat agattcgaaa aagccagagg tcacaaaatt   540
gaaagacaaa attacgttca agatttatta atttaattaa tattatttgc attctttaac   600
aaatacttta tcctatttc aaattgttgc gcttcttcca gcgaaccaaa actatgcttc    660
gcttgctccg tttagcttgt agccgatcag tggcgttgtt ccaatcgacg gtaggattag   720
gccggatatt ctccaccaca atgttggcaa cgttgatgtt acgtttatgc ttttggtttt   780
ccacgtacgt cttttggccg gtaatagccg taaacgtagt gccgtcgcgc gtcacgcaca   840
acaccggatg tttgcgcttg tccgcggggt attgaaccgc gcgatccgac aaatccacca   900
ctttggcaac taaatcggtg acctgcgcgt ctttttctg cattatttcg tctttctttt    960
gcatggtttc ctggaagccg gtgtacatgc ggtttagatc agtcatgacg cgcgtgacct  1020
gcaaatcttt ggcctcgatc tgcttgtcct tgatggcaac gatgcgttca ataaactctt  1080
gttttttaac aagttcctcg gttttttgcg ccaccaccgc ttgcagcgcg tttgtgtgct  1140
cggtgaatgt cgcaatcagc ttagtcacca actgtttgct ctcctcctcc cgttgtttga  1200
tcgcgggatc gtacttgccg gtgcagagca cttgaggaat tacttcttct aaaagccatt  1260
cttgtaattc tatggcgtaa ggcaatttgg acttcataat cagctgaatc acgccggatt  1320
tagtaatgag cactgtatgc ggctgcaaat acagcgggtc gccccttttc acgacgctgt  1380
tagaggtagg gcccccattt tggatggtct gctcaaataa cgatttgtat ttattgtcta  1440
catgaacacg tatagcttta tcacaaactg tatattttaa actgttagcg acgtccttgg  1500
ccacgaaccg gacctgttgg tcgcgctcta gcacgtaccg caggttgaac gtatcttctc  1560
caaatttaaa ttctccaatt ttaacgcgag ccatttgat acacgtgtgt cgattttgca   1620
acaactattg ttttttaacg caaactaaac ttattgtggt aagcaataat taaatatggg  1680
ggaacatgcg ccgctacaac actcgtcgtt atgaacgcag acggcgccgg tctcggcgca  1740
agcggctaaa acgtgttgcg cgttcaacgc ggcaaacatc gcaaaagcca atagtacagt  1800
tttgatttgc atattaacgg cgattttta aattatctta tttaataaat agttatgacg  1860
cctacaactc cccgcccgcg ttgactcgct gcacctcgag cagttcgttg acgccttcct  1920
ccgtgtggcc gaacacgtcg agcgggtggt cgatgaccag cggcgtgccg cacgcgacgc  1980
acaagtatct gtacaccgaa tgatcgtcgg gcgaaggcac gtcggcctcc aagtggcaat  2040
attggcaaat tcgaaaatat atacagttgg gttgtttgcg catatctatc gtggcgttgg  2100
gcatgtacgt ccgaacgttg atttgcatgc aagccgaaat taaatcattg cgattagtgc  2160
gattaaaacg ttgtacatcc tcgcttttaa tcatgccgtc gattaaatcg cgcaatcgag  2220
tcaagtgatc aaagtgtgga ataatgtttt ctttgtattc ccgagtcaag cgcagcgcgt  2280
```

```
attttaacaa actagccatc ttgtaagtta gtttcattta atgcaacttt atccaataat    2340
atattatgta tcgcacgtca agaattaaca atgcgcccgt tgtcgcatct caacacgact    2400
atgatagaga tcaaataaag cgcgaattaa atagcttgcg acgcaacgtg cacgatctgt    2460
gcacgcgttc cggcacgagc tttgattgta ataagttttt acgaagcgat gacatgaccc    2520
ccgtagtgac aacgatcacg cccaaaagaa ctgccgacta caaaattacc gagtatgtcg    2580
gtgacgttaa aactattaag ccatccaatc gaccgttagt cgaatcagga ccgctggtgc    2640
gagaagccgc gaagtatggc gaatgcatcg tataacgtgt ggagtccgct cattagagcg    2700
tcatgtttag acaagaaagc tacatattta attgatcccg atgattttat tgataaattg    2760
accctaactc catacacggt attctacaat ggcggggttt tggtcaaaat ttccggactg    2820
cgattgtaca tgctgttaac ggctccgccc actattaatg aaattaaaaa ttccaattt    2880
aaaaaacgca gcaagagaaa catttgtatg aaagaatgcg tagaaggaaa gaaaaatgtc    2940
gtcgacatgc tgaacaacaa gattaatatg cctccgtgta taaaaaaaat attgaacgat    3000
ttgaaagaaa acaatgtacc gcgcggcggt atgtacagga agaggtttat actaaactgt    3060
tacattgcaa acgtggtttc gtgtgccaag tgtgaaaacc gatgtttaat caaggctctg    3120
acgcatttct acaaccacga ctccaagtgt gtgggtgaag tcatgcatct tttaatcaaa    3180
tcccaagatg tgtataaacc accaaactgc caaaaaatga aaactgtcga caagctctgt    3240
ccgtttgctg gcaactgcaa gggtctcaat cctatttgta attattgaat aataaaacaa    3300
ttataaatgc taaatttgtt ttttattaac gatacaaacc aaacgcaaca agaacatttg    3360
tagtattatc tataattgaa aacgcgtagt tataatcgct gaggtaatat ttaaaatcat    3420
tttcaaatga ttcacagtta atttgcgaca atataatttt attttcacat aaactagacg    3480
ccttgtcgtc ttcttcttcg tattccttct cttttttcatt tttctcctca taaaaattaa    3540
catagttatt atcgtatcca tatatgtatc tatcgtatag agtaaatttt tgttgtcat    3600
aaatatatat gtcttttta atggggtgta tagtaccgct gcgcatagtt tttctgtaat    3660
ttacaacagt gctatttct ggtagttctt cggagtgtgt tgctttaatt attaaattta    3720
tataatcaat gaatttggga tcgtcggttt tgtacaatat gttgccggca tagtacgcag    3780
cttcttctag ttcaattaca ccattttta gcagcaccgg attaacataa ctttccaaaa    3840
tgttgtacga accgttaaac aaaaacagtt cacctccctt ttctatacta ttgtctgcga    3900
gcagttgttt gttgttaaaa ataacagcca ttgtaatgag acgcacaaac taatatcaca    3960
aactggaaat gtctatcaat atatagttgc tgatatcaga tccagacatg ataagataca    4020
ttgatgagtt tggacaaacc acaactagaa tgcagtgaaa aaaatgcttt atttgtgaaa    4080
tttgtgatgc tattgcttta tttgtaacca ttataagctg caataaacaa gttaacaaca    4140
acaattgcat tcattttatg tttcaggttc aggggggaggt gtgggaggtt ttttaaagca    4200
agtaaaacct ctacaaatgt ggtatggctg attatgatcc tctagagtcg atccccct    4260
cgcccggtta ttattatttt tgacaccaga ccaactggta atggtagcga ccggcgctca    4320
gctggaattc cgccgatact gacgggctcc aggagtcgtc gccaccaatc cccatatgga    4380
aaccgtcgat attcagccat gtgccttctt ccgcgtgcag cagatggcga tggctggttt    4440
ccatcagttg ctgttgactg tagcggctga tgttgaactg gaagtcgccg cgccactggt    4500
gtgggccata attcaattcg cgcgtcccgc agcgcagacc gttttcgctc gggaagacgt    4560
acggggtata catgtctgac aatggcagat cccagcggtc aaaacaggcg gcagtaaggc    4620
```

```
ggtcgggata gttttcttgc ggccctaatc cgagccagtt tacccgctct gctacctgcg    4680
ccagctggca gttcaggcca atccgcgccg gatgcggtgt atcgctcgcc acttcaacat    4740
caacggtaat cgccatttga ccactaccat caatccggta ggttttccgg ctgataaata    4800
aggttttccc ctgatgctgc cacgcgtgag cggtcgtaat cagcaccgca tcagcaagtg    4860
tatctgccgt gcactgcaac aacgctgctt cggcctggta atggcccgcc gccttccagc    4920
gttcgaccca ggcgttaggg tcaatgcggg tcgcttcact tacgccaatg tcgttatcca    4980
gcggtgcacg ggtgaactga tcgcgcagcg gcgtcagcag ttgttttta tcgccaatcc    5040 acatctgtga aagaaagcct gactggcggt taaattgcca acgcttatta cccagctcga    5100
tgcaaaaatc catttcgctg gtggtcagat gcgggatggc gtgggacgcg gcggggagcg    5160
tcacactgag gttttccgcc agacgccact gctgccaggc gctgatgtgc ccggcttctg    5220
accatgcggt cgcgttcggt tgcactacgc gtactgtgag ccagagttgc ccggcgctct    5280
ccggctgcgg tagttcaggc agttcaatca actgtttacc ttgtggagcg acatccagag    5340
gcacttcacc gcttgccagc ggcttaccat ccagcgccac catccagtgc aggagctcgt    5400
tatcgctatg acggaacagg tattcgctgg tcacttcgat ggtttgcccg gataaacgga    5460
actggaaaaa ctgctgctgg tgttttgctt ccgtcagcgc tggatgcggc gtgcggtcgg    5520
caaagaccag accgttcata cagaactggc gatcgttcgg cgtatcgcca aaatcaccgc    5580
cgtaagccga ccacgggttg ccgttttcat catatttaat cagcgactga tccacccagt    5640
cccagacgaa gccgccctgt aaacggggat actgacgaaa cgcctgccag tatttagcga    5700
aaccgccaag actgttaccc atcgcgtggg cgtattcgca aaggatcagc gggcgcgtct    5760
ctccaggtag cgaaagccat tttttgatgg accatttcgg cacagccggg aagggctggt    5820
cttcatccac gcgcgcgtac atcgggcaaa taatatcggt ggccgtggtg tcggctccgc    5880
cgccttcata ctgcaccggg cgggaaggat cgacagattt gatccagcga tacagcgcgt    5940
cgtgattagc gccgtggcct gattcattcc ccagcgacca gatgatcaca ctcgggtgat    6000
tacgatcgcg ctgcaccatt cgcgttacgc gttcgctcat cgccggtagc cagcgcggat    6060
catcggtcag acgattcatt ggcaccatgc cgtgggtttc aatattggct tcatccacca    6120
catacaggcc gtagcggtcg cacagcgtgt accacagcgg atggttcgga taatgcgaac    6180
agcgcacggc gttaaagttg ttctgcttca tcagcaggat atcctgcacc atcgtctgct    6240
catccatgac ctgaccatgc agaggatgat gctcgtgacg gttaacgcct cgaatcagca    6300
acggcttgcc gttcagcagc agcagaccat tttcaatccg cacctcgcgg aaaccgacat    6360
cgcaggcttc tgcttcaatc agcgtgccgt cggcggtgtg cagttcaacc accgcacgat    6420
agagattcgg gatttcggcg ctccacagtt tcgggttttc gacgttcaga cgtagtgtga    6480
cgcgatcggc ataaccacca cgctcatcga taatttcacc gccgaaaggc gcggtgccgc    6540
tggcgacctg cgtttcaccc tgccataaag aaactgttac ccgtaggtag tcacgcaact    6600
cgccgcacat ctgaacttca gcctccagta cagcgcggct gaaatcatca ttaaagcgag    6660
tggcaacatg gaaatcgctg atttgtgtag tcggtttatg cagcaacgag acgtcacgga    6720
aaatgccgct catccgccac atatcctgat cttccagata actgccgtca ctccaacgca    6780
gcaccatcac cgcgaggcgg ttttctccgg cgcgtaaaaa tgcgctcagg tcaaattcag    6840
acggcaaacg actgtcctgg ccgtaaccga cccagcgccc gttgcaccac agatgaaacg    6900
ccgagttaac gccatcaaaa ataattcgcg tctggccttc ctgtagccag cttttcatcaa    6960 cattaaatgt gagcgagtaa caacccgtcg gattctccgt gggaacaaac ggcggattga    7020
```

```
ccgtaatggg ataggttacg ttggtgtaga tgggcgcatc gtaaccgtgc atctgccagt   7080
ttgaggggac gacgacagta tcggcctcag gaagatcgca ctccagccag ctttccggca   7140
ccgcttctgg tgccggaaac caggcaaagc gccattcgcc attcaggctg cgcaactgtt   7200
gggaagggcg atcggtgcgg gcctcttcgc tattacgcca gctggcgaaa gggggatgtg   7260
ctgcaaggcg attaagttgg gtaacgccag ggttttccca gtcacgacgt tgtaaaacga   7320
cgggatctat catgattgta aataaaatgt aatttacagt atagtatttt aattaatata   7380
caaatgattt gataataatt cttatttaac tataatatat tgtgttgggt tgaattaaag   7440
gtcccggcat cctcaaatgc ataatttcat agtccccctt gttgtaagtg atgcgtattt   7500
ctgaatcttt gtaaaatagc acacaagact ccaacgcgtt tggcgtttta ttttcttgct   7560
cgaggatatc atggagataa ttaaaatgat aaccatctcg caaataaata agtattttac   7620
tgttttcgta acagttttgt aataaaaaaa cctataaata ttccggatta ttcataccgt   7680
cccaccatcg ggcgtgctag catcatggtg gggccctgca tgctgctgct gctgctgctg   7740
ctgggcctga ggctacagct ctccctgggc atcatcccag ttgaggagga aacccggga   7800 aatagtgact ctgaatgtcc cctgtcccac gatgggtact gcctccatga tggtgtgtgc   7860
atgtatattg aagcattgga caagtatgca tgcaactgtg ttgttggtta catcggggag   7920
cgatgtcagt accgagacct gaagtggtgg gaactgcgct gaggatcctt tcctgggacc   7980
cggcaagaac caaaaactca ctctcttcaa ggaaatccgt aatgttaaac ccgacacgat   8040
gaagcttgtc gttggatgga aaggaaaaga gttctacagg gaaacttgga cccgcttcat   8100
ggaagacagc ttccccattg ttaacgacca agaagtgatg gatgttttcc ttgttgtcaa   8160
catgcgtccc actagaccca accgttgtta caaattcctg gcccaacacg ctctgcgttg   8220
cgaccccgac tatgtacctc atgacgtgat taggatcgtc gagccttcat gggtgggcag   8280
caacaacgag taccgcatca gcctggctaa aagggcggc ggctgcccaa taatgaacct   8340
tcactctgag tacaccaact cgttcgaaca gttcatcgat cgtgtcatct gggagaactt   8400
ctacaagccc atcgtttaca tcggtaccga ctctgctgaa gaggaggaaa ttctccttga   8460
agtttccctg gtgttcaaag taaggagtt tgcaccagac gcacctctgt tcactggtcc   8520
ggcgtattaa aacacgatac attgttatta gtacatttat taagcgctag attctgtgcg   8580
ttgttgattt acagacaatt gttgtacgta ttttaataat tcattaaatt tataatcttt   8640
agggtggtat gttagagcga aaatcaaatg attttcagcg tctttatatc tgaatttaaa   8700
tattaaatcc tcaatagatt tgtaaaatag gtttcgatta gtttcaaaca agggttgttt   8760
ttccgaaccg atggctggac tatctaatgg attttcgctc aacgccacaa aacttgccaa   8820
atcttgtagc agcaatctag ctttgtcgat attcgtttgt gttttgtttt gtaataaagg   8880
ttcgacgtcg ttcaaaatat tatgcgcttt tgtatttctt tcatcactgt cgttagtgta   8940
caattgactc gacgtaaaca cgttaaataa agcttggaca tatttaacat cgggcgtgtt   9000
agctttatta ggccgattat cgtcgtcgtc ccaaccctcg tcgttagaag ttgcttccga   9060
agacgatttt gccatagcca cacgacgcct attaattgtg tcggctaaca cgtccgcgat   9120
caaatttgta gttgagcttt ttggaattat ttctgattgc gggcgttttt gggcgggttt   9180
caatctaact gtgcccgatt ttaattcaga caacacgtta gaaagcgatg gtgcaggcgg   9240
tggtaacatt tcagacggca aatctactaa tggcggcggt ggtggagctg atgataaatc   9300
taccatcggt ggaggcgcag gcggggctgg cggcggaggc ggaggcggag gtggtggcgg   9360
```

```
tgatgcagac ggcggtttag gctcaaatgt ctctttaggc aacacagtcg gcacctcaac   9420
tattgtactg gtttcgggcg ccgttttttgg tttgaccggt ctgagacgag tgcgatttt    9480 ttcgtttcta atagcttcca acaattgttg tctgtcgtct aaaggtgcag cgggttgagg   9540
ttccgtcggc attggtggag cgggcggcaa ttcagacatc gatggtggtg gtggtggtgg   9600
aggcgctgga atgttaggca cgggagaagg tggtggcggc ggtgccgccg gtataatttg   9660
ttctggttta gtttgttcgc gcacgattgt gggcaccggc gcaggcgccg ctggctgcac   9720
aacggaaggt cgtctgcttc gaggcagcgc ttggggtggt ggcaattcaa tattataatt   9780
ggaatacaaa tcgtaaaaat ctgctataag cattgtaatt tcgctatcgt ttaccgtgcc   9840
gatatttaac aaccgctcaa tgtaagcaat tgtattgtaa agagattgtc tcaagctccg   9900
cacgccgata caagcctttt tcattttttac tacagcattg tagtggcgag acacttcgct   9960
gtcgtcgacg tacatgtatg ctttgttgtc aaaaacgtcg ttggcaagct ttaaaatatt  10020
taaaagaaca tctctgttca gcaccactgt gttgtcgtaa atgttgtttt tgataatttg  10080
cgcttccgca gtatcgacac gttcaaaaaa ttgatgcgca tcaattttgt tgttcctatt  10140
attgaataaa taagattgta cagattcata tctacgattc gtcatggcca ccacaaatgc  10200
tacgctgcaa acgctggtac aatttttacga aaactgcaaa aacgtcaaaa ctcggtataa  10260
aataatcaac gggcgctttg gcaaaatatc tattttatcg cacaagccca ctagcaaatt  10320
gtatttgcag aaaacaattt cggcgcacaa ttttaacgct gacgaaataa aagttcacca  10380
gttaatgagc gaccacccaa attttataaa aatctatttt aatcacggtt ccatcaacaa  10440
ccaagtgatc gtgatggact acattgactg tcccgattta tttgaaacac tacaaattaa  10500
aggcgagctt tcgtaccaac ttgttagcaa tattattaga cagctgtgtg aagcgctcaa  10560
cgatttgcac aagcacaatt tcatacacaa cgacataaaa ctcgaaaatg tcttatattt  10620
cgaagcactt gatcgcgtgt atgtttgcga ttacggattg tgcaaacacg aaaactcact  10680
tagcgtgcac gacggcacgt tggagtattt tagtccggaa aaaattcgac acacaactat  10740
gcacgtttcg tttgactggt acgcggcgtg ttaacataca agttgctaac cggcggccga  10800
cacccatttg aaaaaagcga agacgaaatg ttggacttga atagcatgaa gcgtcgtcag  10860
caatacaatg acattggcgt tttaaaacac gttcgtaacg ttaacgctcg tgactttgtg  10920
tactgcctaa caagatacaa catagattgt agactcacaa attacaaaca aattataaaa  10980
catgagtttt tgtcgtaaaa atgccacttg ttttacgagt agaattacgc gccctgtagc  11040
ggcgcattaa gcgcggcggg tgtggtggtt acgcgcagcg tgaccgctac acttgccagc  11100
gccctagcgc ccgctccttt cgctttcttc ccttcctttc tcgccacgtt cgccggcttt  11160
ccccgtcaag ctctaaatcg ggggctccct ttagggttcc gatttagtgc tttacggcac  11220
ctcgacccca aaaaacttga ttagggtgat ggttcacgta gtgggccatc gccctgatag  11280
acggtttttc gccctttgac gttggagtcc acgttcttta atagtggact cttgttccaa  11340
actggaacaa cactcaaccc tatctcggtc tattcttttg atttataagg gattttgccg  11400
atttcggcct attggttaaa aaatgagctg atttaacaaa aatttaacgc gaattttaac  11460
aaaatattaa cgtttacaat ttaaatattt gcttatacaa tcttcctgtt tttgggcttt  11520
ttctgattat caaccggggt aattcgtaat catggtcata gctgtttcct gtgtgaaatt  11580
gttatccgct cacaattcca cacaacatac gagccggaag cataaagtgt aaagcctggg  11640
gtgcctaatg agtgagctaa ctcacattaa ttgcgttgcg ctcactgccc gctttccagt  11700
cgggaaacct gtcgtgccag ctgcattaat gaatcggcca acgcgcgggg agaggcggtt  11760
```

```
tgcgtattgg gcgctcttcc gcttcctcgc tcactgactc gctgcgctcg gtcgttcggc   11820
tgcggcgagc ggtatcagct cactcaaagg cggtaatacg gttatccaca gaatcagggg   11880
ataacgcagg aaagaacatg tgagcaaaag gccagcaaaa ggccaggaac cgtaaaaagg   11940
ccgcgttgct ggcgtttttc cataggctcc gcccccctga cgagcatcac aaaaatcgac   12000
gctcaagtca gaggtggcga aacccgacag gactataaag ataccaggcg tttccccctg   12060
gaagctccct cgtgcgctct cctgttccga cccgccgct taccggatac ctgtccgcct   12120
ttctcccttc gggaagcgtg gcgctttctc atagctcacg ctgtaggtat ctcagttcgg   12180
tgtaggtcgt tcgctccaag ctgggctgtg tgcacgaacc ccccgttcag cccgaccgct   12240
gcgccttatc cggtaactat cgtcttgagt ccaacccggt aagacacgac ttatcgccac   12300
tggcagcagc cactggtaac aggattagca gagcgaggta tgtaggcggt gctacagagt   12360
tcttgaagtg gtggcctaac tacggctaca ctagaaggac agtatttggt atctgcgctc   12420
tgctgaagcc agttaccttc ggaaaaagag ttggtagctc ttgatccggc aaacaaacca   12480
ccgctggtag cggtggtttt tttgtttgca agcagcagat tacgcgcaga aaaaaggat   12540 ctcaagaaga tcctttgatc ttttctacgg ggtctgacgc tcagtggaac gaaaactcac   12600
gttaagggat tttggtcatg agattatcaa aaaggatctt cacctagatc cttttaaatt   12660
aaaaatgaag ttttaaatca atctaaagta tatatgagta aacttggtct gacagttacc   12720
aatgcttaat cagtgaggca cctatctcag cgatctgtct atttcgttca tccatagttg   12780
cctgactccc cgtcgtgtag ataactacga tacgggaggg cttaccatct ggccccagtg   12840
ctgcaatgat accgcgagac ccacgctcac cggctccaga tttatcagca ataaaccagc   12900
cagccggaag ggccgagcgc agaagtggtc ctgcaacttt atccgcctcc atccagtcta   12960
ttaattgttg ccgggaagct agagtaagta gttcgccagt taatagtttg cgcaacgttg   13020
ttgccattgc tacaggcatc gtggtgtcac gctcgtcgtt tggtatggct tcattcagct   13080
ccggttccca acgatcaagg cgagttacat gatcccccat gttgtgcaaa aaagcggtta   13140
gctccttcgg tcctccgatc gttgtcagaa gtaagttggc cgcagtgtta tcactcatgg   13200
ttatggcagc actgcataat tctcttactg tcatgccatc cgtaagatgc ttttctgtga   13260
ctggtgagta ctcaaccaag tcattctgag aatagtgtat gcggcgaccg agttgctctt   13320
gcccggcgtc aatacgggat aataccgcgc cacatagcag aactttaaaa gtgctcatca   13380
ttggaaaacg ttcttcgggg cgaaaactct caaggatctt accgctgttg agatccagtt   13440
cgatgtaacc cactcgtgca cccaactgat cttcagcatc ttttactttc accagcgttt   13500
ctgggtgagc aaaaacagga aggcaaaatg ccgcaaaaaa gggaataagg gcgacacgga   13560
aatgttgaat actcatactc ttcctttttc aatattattg aagcatttat cagggttatt   13620
gtctcatgag cggatacata tttgaatgta tttagaaaaa taaacaaata ggggttccgc   13680
gcacatttcc ccgaaaagtg ccacctgacg tctaagaaac cattattatc atgacattaa   13740
cctataaaaa taggcgtatc acgaggccct ttcgtctcgc gcgtttcggt gatgacggtg   13800
aaaacctctg acacatgcag ctcccggaga cggtcacagc ttgtctgtaa gcggatgccg   13860
ggagcagaca agcccgtcag ggcgcgtcag cgggtgttgg cgggtgtcgg gctggctta   13920 actatgcggc atcagagcag attgtactga gagtgcacca tatgcggtgt gaaataccgc   13980
acagatgcgt aaggagaaaa taccgcatca ggcgccattc gccattcagg ctgcgcaact   14040
gttgggaagg gcgatcggtg cgggcctctt cgctattacg ccagctggcg aaggggggat   14100
```

```
gtgctgcaag gcgattaagt tgggtaacgc cagggttttc ccagtcacga cgttgtaaaa    14160
cgacggccag tgccaagctt                                                14180

<210> SEQ ID NO 70
<211> LENGTH: 4452
<212> TYPE: DNA
<213> ORGANISM: Artificial Sequence
<220> FEATURE:
<223> OTHER INFORMATION: plasmid

<400> SEQUENCE: 70
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg gggctcccct ttagggttcc     180
gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttacgcgtta agatacattg     480
atgagtttgg acaaaccaca actagaatgc agtgaaaaaa atgctttatt tgtgaaattt     540
gtgatgctat tgctttattt gtaaccatta taagctgcaa taaacaagtt aacaacaaca     600
attgcattca ttttatgttt caggttcagg gggaggtgtg ggaggttttt taaagcaagt     660
aaaacctcta caaatgtggt atggctgatt atgatcatga acagactgtg aggactgagg     720
ggcctgaaat gagccttggg actgtgaatc taaaatacac aaacaattag aatcagtagt     780
ttaacacatt atacacttaa aaattggatc tccattcgcc attcaggctg cgcaactgtt     840
gggaagggcg atcggtgcgg gcctcttcgc tattacgcca gctggcgaaa gggggatgtg     900
ctgcaaggcg attaagttgg gtaacgccag gttttcccca gtcacgacgt tgtaaaacga     960
cggccagtga attgtaatac gactcactat agggcgaatt gggtacactt acctggtacc    1020
ccacccgggt ggaaaatcga tgggcccgcg gccgctctag aagtactctc gagaagcttt    1080
ttgaattctt tggatccact agtgtcgacc tgcaggcgcg cgagctccag cttttgttcc    1140
ctttagtgag ggttaatttc gagcttggcg taatcaaggt catagctgtt tcctgtgtga    1200
aattgttatc cgctcacaat tccacacaat atacgagccg aagtataaa gtgtaaagcc    1260 tggggtgcct aatgagtgag ctaactcaca gtaattgcgg ctagccaggt gcacaccaat    1320
gtggtgaatg gtcaaatggc gtttattgta tcgagctagg cacttaaata caattatctc    1380
tgcaatgcgg tattcagtgg ttcgtccaat ccatgtcaga cccgtctgtt gccttcctaa    1440
taaggcacga tcgtaccacc ttacttccac caatcggcat gcacggtgct ttttctctcc    1500
ttgtaaggca tgttgctaac tcatcgttac catgttgcaa gactacaaga gtattgcata    1560
agactacatt tcccctcccc tatgcaaaag cgaaactact atatcctgag gggactccta    1620
accgcgtaca accgaagccc cgcttttcgc ctaaacacac cctagtcccc tcagatacgc    1680
gtatatctgg cccgtacatc gcgaagcagc gcaaacgcc taaccctaag cagattcttc    1740
atgcaattgt cggtcaagcc ttgccttgtt gtagcttaaa ttttgctcgc gcactactca    1800
gcgacctcca acacacaagc agggagcaga tgcatggcgg taatacggtt atccacagaa    1860
tcaggggata acgcaggaaa gaacatgtga gcaaaaggcc agcaaaaggc caggaaccgt    1920
aaaaaggccg cgttgctggc gtttttccat aggctccgcc cccctgacga gcatcacaaa    1980
```

```
aatcgacgct caagtcagag gtggcgaaac ccgacaggac tataaagata ccaggcgttt    2040
ccccctggaa gctccctcgt gcgctctcct gttccgaccc tgccgcttac cggatacctg    2100
tccgcctttc tcccttcggg aagcgtggcg ctttctcata gctcacgctg taggtatctc    2160
agttcggtgt aggtcgttcg ctccaagctg ggctgtgtgc acgaaccccc cgttcagccc    2220
gaccgctgcg ccttatccgg taactatcgt cttgagtcca acccggtaag acacgactta    2280
tcgccactgg cagcagccac tggtaacagg attagcagag cgaggtatgt aggcggtgct    2340
acagagttct tgaagtggtg gcctaactac ggctacacta aaggacagt atttggtatc     2400 tgcgctctgc tgaagccagt taccttcgga aaaagagttg gtagctcttg atccggcaaa    2460
caaaccaccg ctggtagcgg tggttttttt gtttgcaagc agcagattac gcgcagaaaa    2520
aaaggatctc aagaagatcc tttgatcttt tctacggggt ctgacgctca gtggaacgaa    2580
aactcacgtt aagggatttt ggtcatgaga ttatcaaaaa ggatcttcac ctagatcctt    2640
ttaaattaaa aatgaagttt taaatcaatc taaagtatat atgagtaacc tgaggctatg    2700
gcagggcctg ccgccccgac gttggctgcg agccctgggc cttcacccga acttgggggg    2760
tggggtgggg aaaaggaaga aacgcgggcg tattggcccc aatggggtct cggtggggta    2820
tcgacagagt gccagccctg ggaccgaacc ccgcgtttat gaacaaacga cccaacaccg    2880
tgcgttttat tctgtctttt tattgccgtc atagcgcggg ttccttccgg tattgtctcc    2940
ttccgtgttt cagttagcct cccctaggg tgggcgaaga actccagcat gagatccccg      3000
cgctggagga tcatccagcc ggcgtccgg aaaacgattc cgaagcccaa cctttcatag      3060
aaggcggcgg tggaatcgaa atctcgtgat ggcaggttgg gcgtcgcttg gtcggtcatt    3120 tcgaaccca gagtcccgct cagaagaact cgtcaagaag gcgatagaag gcgatgcgct     3180
gcgaatcggg agcggcgata ccgtaaagca cgaggaagcg gtcagcccat cgccgccaa     3240 gctcttcagc aatatcacgg gtagccaacg ctatgtcctg atagcggtcc gccacaccca    3300
gccggccaca gtcgatgaat ccagaaaagc ggccattttc caccatgata ttcggcaagc    3360
aggcatcgcc atgggtcacg acgagatcct cgccgtcggg catgctcgcc ttgagcctgg    3420
cgaacagttc ggctggcgcg agcccctgat gctcttcgtc cagatcatcc tgatcgacaa    3480
gaccggcttc catccgagta cgtgctcgct cgatgcgatg tttcgcttgg tggtcgaatg    3540
ggcaggtagc cggatcaagc gtatgcagcc gccgcattgc atcagccatg atggatactt    3600
tctcggcagg agcaaggtga gatgacagga gatcctgccc cggcacttcg cccaatagca    3660
gccagtccct tcccgcttca gtgacaacgt cgagcacagc tgcgcaagga acgcccgtcg    3720
tggccagcca cgatagccgc gctgcctcgt cttgcagttc attcagggca ccggacaggt    3780
cggtcttgac aaaaagaacc gggcgcccct gcgctgacag ccggaacacg gcggcatcag    3840
agcagccgat tgtctgttgt gcccagtcat agccgaatag cctctccacc caagcggccg    3900
gagaacctgc gtgcaatcca tcttgttcaa tcatgcgaaa cgatcctcat cctgtctctt    3960
gatcgatctt tgcaaaagcc taggcctcca aaaaagcctc ctcactactt ctggaatagc    4020
tcagaggccg aggcggcctc ggcctctgca taaataaaaa aaattagtca gccatggggc    4080
ggagaatggg cggaactggg cggagttagg gcgggatgg gcggagttag gggcgggact     4140
atggttgctg actaattgag atgcatgctt tgcatacttc tgcctgctgg ggagcctggg    4200
gactttccac acctggttgc tgactaattg agatgcatgc tttgcatact tctgcctgct    4260
ggggagcctg gggactttcc acaccctaac tgacacacat tccacagctg gttctttccg    4320
```

```
cctcaggact cttccttttt caatattatt gaagcattta tcagggttat tgtctcatga    4380
gcggatacat atttgaatgt atttagaaaa ataaacaaat aggggttccg cgcacatttc    4440
cccgaaaagt gc                                                        4452

<210> SEQ ID NO 71
<211> LENGTH: 4518
<212> TYPE: DNA
<213> ORGANISM: Artificial Sequence
<220> FEATURE:
<223> OTHER INFORMATION: plasmid

<400> SEQUENCE: 71
cacctgacgc gccctgtagc ggcgcattaa gcgcggcggg tgtggtggtt acgcgcagcg      60
tgaccgctac acttgccagc gccctagcgc ccgctccttt cgctttcttc ccttcctttc     120
tcgccacgtt cgccggcttt ccccgtcaag ctctaaatcg gggctccct  ttagggttcc     180 gatttagtgc tttacggcac ctcgacccca aaaaacttga ttagggtgat ggttcacgta     240
gtgggccatc gccctgatag acggtttttc gccctttgac gttggagtcc acgttcttta     300
atagtggact cttgttccaa actggaacaa cactcaaccc tatctcggtc tattcttttg     360
atttataagg gattttgccg atttcggcct attggttaaa aaatgagctg atttaacaaa     420
aatttaacgc gaattttaac aaaatattaa cgcttacaat ttacgcgtta agatacattg     480
atgagtttgg acaaaccaca actagaatgc agtgaaaaaa atgctttatt tgtgaaattt     540
gtgatgctat tgctttattt gtaaccatta taagctgcaa taaacaagtt aacaacaaca     600
attgcattca tttatgtttc aggttcaggg ggaggtgtgg gaggttttt  taaagcaagt     660 aaaacctcta caaatgtggt atggctgatt atgatcatga acagactgtg aggactgagg     720
ggcctgaaat gagccttggg actgtgaatc taaaatacac aaacaattag aatcagtagt     780
ttaacacatt atacacttaa aaattggatc tccattcgcc attcaggctg cgcaactgtt     840
gggaagggcg atcggtgcgg gcctcttcgc tattacgcca gctggcgaaa ggggggatgtg     900 ctgcaaggcg attaagttgg gtaacgccag ggttttccca gtcacgacgt tgtaaaacga     960
cggccagtga attgtaatac gactcactat agggcgaatt gggtacactt acctggtacc    1020
ccacccgggt ggaaaatcga tgggcccgcg gccgctctag aagtactctc gagaagcttt    1080
ttgaattctt tggatccact agtgtcgacc tgcaggcgcg cgagctccag cttttgttcc    1140
ctttagtgag ggttaatttc gagcttggcg taatcaaggt catagctgtt tcctgtgtga    1200
aattgttatc cgctcacaat tccacacaat atacgagccg gaagtataaa gtgtaaagcc    1260
tggggtgcct aatgagtgag ctaactcaca gtaattgcgg ctagcggatc tgacggttca    1320
ctaaaccagc tctgcttata tagacctccc accgtacacg cctaccgccc atttgcgtca    1380
atggggcgga gttgttacga cattttggaa agtcccgttg attttggtgc caaaacaaac    1440
tcccattgac gtcaatgggg tggagacttg gaaatcccg  tgagtcaaac cgctatccac    1500
gcccattgat gtactgccaa aaccgcatca ccatggtaat agcgatgact aatacgtaga    1560
tgtactgcca agtaggaaag tcccataagg tcatgtactg gcataatgc  caggcgggcc    1620 atttaccgtc attgacgtca ataggggcg  tacttggcat atgatacact tgatgtactg    1680
ccaagtgggc agtttaccgt aaatactcca cccattgacg tcaatggaaa gtccctattg    1740
gcgttactat gggaacatac gtcattattg acgtcaatgg gcggggggtcg ttgggcggtc    1800 agccaggcgg gccatttacc gtaagttatg taacgcggaa ctccatatat gggctatgaa    1860
ctaatgaccc cgtaattgat tactattaat aactaatgca tggcggtaat acggttatcc    1920
```

```
acagaatcag gggataacgc aggaaagaac atgtgagcaa aaggccagca aaaggccagg    1980
aaccgtaaaa aggccgcgtt gctggcgttt ttccataggc tccgcccccc tgacgagcat    2040
cacaaaaatc gacgctcaag tcagaggtgg cgaaacccga caggactata aagataccag    2100
gcgtttcccc ctggaagctc cctcgtgcgc tctcctgttc cgaccctgcc gcttaccgga    2160
tacctgtccg cctttctccc ttcgggaagc gtggcgcttt ctcatagctc acgctgtagg    2220
tatctcagtt cggtgtaggt cgttcgctcc aagctgggct gtgtgcacga accccccgtt    2280
cagcccgacc gctgcgcctt atccggtaac tatcgtcttg agtccaaccc ggtaagacac    2340
gacttatcgc cactggcagc agccactggt aacaggatta gcagagcgag gtatgtaggc    2400
ggtgctacag agttcttgaa gtggtggcct aactacggct acactagaag gacagtattt    2460
ggtatctgcg ctctgctgaa gccagttacc ttcggaaaaa gagttggtag ctcttgatcc    2520
ggcaaacaaa ccaccgctgg tagcggtggt ttttttgttt gcaagcagca gattacgcgc    2580
agaaaaaaag gatctcaaga agatcctttg atcttttcta cggggtctga cgctcagtgg    2640
aacgaaaact cacgttaagg gattttggtc atgagattat caaaaaggat cttcacctag    2700
atccttttaa attaaaaatg aagttttaaa tcaatctaaa gtatatatga gtaacctgag    2760
gctatggcag ggcctgccgc cccgacgttg gctgcgagcc ctgggccttc acccgaactt    2820 gggggggtggg gtggggaaaa ggaagaaacg cgggcgtatt ggccccaatg gggtctcggt    2880
ggggtatcga cagagtgcca gccctgggac cgaacccgc gtttatgaac aaacgaccca    2940
acaccgtgcg ttttattctg tcttttattt gccgtcatag cgcgggttcc ttccggtatt    3000
gtctccttcc gtgtttcagt tagcctcccc ctagggtggg cgaagaactc cagcatgaga    3060
tccccgcgct ggaggatcat ccagccggcg tccggaaaaa cgattccgaa gcccaacctt    3120
tcatagaagg cggcggtgga atcgaaatct cgtgatggca ggttgggcgt cgcttggtcg    3180
gtcatttcga accccagagt cccgctcaga agaactcgtc aagaaggcga tagaaggcga    3240
tgcgctgcga atcgggagcg gcgataccgt aaagcacgag gaagcggtca gcccattcgc    3300
cgccaagctc ttcagcaata tcacgggtag ccaacgctat gtcctgatag cggtccgcca    3360
cacccagccg gccacagtcg atgaatccag aaaagcggcc attttccacc atgatattcg    3420
gcaagcaggc atcgccatgg gtcacgacga gatcctcgcc gtcgggcatg ctcgccttga    3480
gcctggcgaa cagttcggct ggcgcgagcc cctgatgctc ttcgtccaga tcatcctgat    3540
cgacaagacc ggcttccatc cgagtacgtg ctcgctcgat gcgatgtttc gcttggtggt    3600
cgaatgggca ggtagccgga tcaagcgtat gcagccgccg cattgcatca gccatgatgg    3660
atactttctc ggcaggagca aggtgagatg acaggagatc ctgccccggc acttcgccca    3720
atagcagcca gtcccttccc gcttcagtga acaacgtcga cacagctgcg caaggaacgc    3780
ccgtcgtggc cagccacgat agccgcgctg cctcgtcttg cagttcattc agggcaccgg    3840
acaggtcggt cttgacaaaa agaaccgggc gcccctgcgc tgacagccgg aacacgcgg    3900 catcagagca gccgattgtc tgttgtgccc agtcatagcc gaatagcctc tccacccaag    3960
cggccggaga acctgcgtgc aatccatctt gttcaatcat gcgaaacgat cctcatcctg    4020
tctcttgatc gatctttgca aaagcctagg cctccaaaaa agcctcctca ctacttctgg    4080
aatagctcag aggccgaggc ggcctcggcc tctgcataaa taaaaaaaat tagtcagcca    4140
tggggcggag aatgggcgga actgggcgga gttaggggcg ggatgggcgg agttaggggc    4200
gggactatgg ttgctgacta attgagatgc atgctttgca tacttctgcc tgctggggag    4260
```

| | |
|---|---:|
| cctggggact ttccacacct ggttgctgac taattgagat gcatgctttg catacttctg | 4320 |
| cctgctgggg agcctgggga cttttccacac cctaactgac acacattcca cagctggttc | 4380 |
| tttccgcctc aggactcttc cttttcaat attattgaag catttatcag ggttattgtc | 4440 |
| tcatgagcgg atacatattt gaatgtattt agaaaaataa acaaataggg gttccgcgca | 4500 |
| catttccccg aaaagtgc | 4518 |

<210> SEQ ID NO 72
<211> LENGTH: 4974
<212> TYPE: DNA
<213> ORGANISM: Artificial Sequence
<220> FEATURE:
<223> OTHER INFORMATION: plasmid

<400> SEQUENCE: 72

| | |
|---|---:|
| aagcttttg caaaagccta ggcctccaaa aaagcctcct cactacttct ggaatagctc | 60 |
| agaggccgag gcggcctcgg cctctgcata aataaaaaaa attagtcagc catggggcgg | 120 |
| agaatgggcg gaactgggcg gagttagggg cgggatgggc ggagttaggg gcgggactat | 180 |
| ggttgctgac taattgagat gcatgctttg catacttctg cctgctgggg agcctgggga | 240 |
| cttttccacac ctggttgctg actaattgag atgcatgctt tgcatacttc tgcctgctgg | 300 |
| ggagcctggg gactttccac accctaactg acacacattc cacaggatcc ggtcgcgcga | 360 |
| atttcgagcg gtgttccgcg gtcctcctcg tatagaaact cggaccactc tgagacgaag | 420 |
| gctcgcgtcc aggccagcac gaaggaggct aagtgggagg ggtagcggtc gttgtccact | 480 |
| agggggtcca ctcgctccag ggtgtgaaga cacatgtcgc cctcttcggc atcaaggaag | 540 |
| gtgattggtt tataggtgta ggccacgtga ccgggtgttc ctgaaggggg gctataaaag | 600 |
| gggggtgggg cgcgttcgtc ctcactctct tccgcatcgc tgtctgcgag ggccagctgt | 660 |
| tgggctcgcg gttgaggaca aactcttcgc ggtcttcca gtactcttgg atcggaaacc | 720 |
| cgtcggcctc cgaacggtac tccgccaccg agggacctga gcgagtccgc atcgaccgga | 780 |
| tcggaaaacc tctcgactgt tggggtgagt actccctctc aaaagcgggc atgacttctg | 840 |
| cgctaagatt gtcagttcc aaaaacgagg aggatttgat attcacctgg cccgcggtga | 900 |
| tgcctttgag ggtggccgcg tccatctggt cagaaaagac aatctttttg ttgtcaagct | 960 |
| tgaggtgtgg caggcttgag atctggccat acacttgagt gacaatgaca tccactttgc | 1020 |
| ctttctctcc acaggtgtcc actcccaggt ccaactgcag gcgagcctga attcgggggg | 1080 |
| ggggggggggg gggacagctc agggctgcga tttcgcgcca aacttgacgg caatcctagc | 1140 |
| gtgaaggctg gtaggatttt atccccgctg ccatcatggt tcgaccattg aactgcatcg | 1200 |
| tcgccgtgtc ccaaaatatg gggattggca agaacggaga cctaccctgg cctccgctca | 1260 |
| ggaacgagtt caagtacttc caaagaatga ccacaacctc ttcagtggaa ggtaaacaga | 1320 |
| atctggtgat tatgggtagg aaaacctggt tctccattcc tgagaagaat cgacctttaa | 1380 |
| aggacagaat taatatagtt ctcagtagag aactcaaaga accaccacga ggagctcatt | 1440 |
| ttcttgccaa aagtttggat gatgccttaa gacttattga caaccggaa ttggcaagta | 1500 |
| aagtagacat ggttggatag tcggaggcag ttctgtttac caggaagcca tgaatcaacc | 1560 |
| aggccacctc agactctttg tgacaaggat catgcaggaa tttgaaagtg acacgttttt | 1620 |
| cccagaaatt gatttgggga aatataaact tctcccagaa tacccaggcg tcctctctga | 1680 |
| ggtccaggag gaaaaggca tcaagtataa gtttgaagtc tacgagaaga agactaaca | 1740 |
| ggaagatgct ttcaagttct ctgctcccct cctaaagcta tgcattttta taagaccatg | 1800 |

```
ggacttttgc tggctttaga tcataatcag ccataccaca tttgtagagg ttttacttgc   1860
tttaaaaaac ctcccacacc tccccctgaa cctgaaacat aaaatgaatg caattgttgt   1920
tgttaacttg tttattgcag cttataatgg ttacaaataa agcaatagca tcacaaattt   1980
cacaaataaa gcattttttt cactgcattc tagttgtggt ttgtccaaac tcatcaatgt   2040
atcttatcat gtctggatcc ccggccaacg gtctggtgac ccggctgcga gagctcggtg   2100
tacctgagac gcgagtaagc ccttgagtca aagacgtagt cgttgcaagt ccgcaccagg   2160
tactgatatc ccaccaaaaa gtgcggcggc ggctggcggt agaggggcca gcgtagggtg   2220
gccggggctc cggggcgag  gtcttccaac ataaggcgat gatcatcgat gctagaccgt   2280
gcaaaggag  agcctgtaag cgggcactct tccgtggtct ggtggataaa ttcgcaaggg   2340
tatcatggcg gacgaccggg gttcgaaccc cggatccggc cgtccgccgt gatccatgcg   2400
gttaccgccc gcgtgtcgaa cccaggtgtg cgacgtcaga caacggggga gcgctccttt   2460
tggcttcctt ccaggcgcgg cggctgctgc gctagctttt ttggcgagct cgaattaatt   2520
ctgcattaat gaatcggcca acgcgcgggg agaggcggtt tgcgtattgg gcgctcttcc   2580
gcttcctcgc tcactgactc gctgcgctcg gtcgttcggc tgcggcgagc ggtatcagct   2640
cactcaaagg cggtaatacg gttatccaca gaatcagggg ataacgcagg aaagaacatg   2700
tgagcaaaag gccagcaaaa ggccaggaac cgtaaaaagg ccgcgttgct ggcgtttttc   2760
cataggctcc gcccccctga cgagcatcac aaaaatcgac gctcaagtca gaggtggcga   2820
aacccgacag gactataaag ataccaggcg tttccccctg gaagctccct cgtgcgctct   2880
cctgttccga ccctgccgct taccggatac ctgtccgcct ttctcccttc gggaagcgtg   2940
gcgctttctc atagctcacg ctgtaggtat ctcagttcgg tgtaggtcgt tcgctccaag   3000
ctgggctgtg tgcacgaacc ccccgttcag cccgaccgct gcgccttatc cggtaactat   3060
cgtcttgagt ccaacccggt aagacacgac ttatcgccac tggcagcagc cactggtaac   3120
aggattagca gagcgaggta tgtaggcggt gctacagagt tcttgaagtg gtggcctaac   3180
tacggctaca ctagaagaac agtatttggt atctgcgctc tgctgaagcc agttaccttc   3240
ggaaaaagag ttggtagctc ttgatccggc aaacaaacca ccgctggtag cggtggtttt   3300
tttgtttgca agcagcagat tacgcgcaga aaaaaaggat ctcaagaaga tcctttgatc   3360
ttttctacgg ggtctgacgc tcagtggaac gaaaactcac gttaagggat tttggtcatg   3420
agattatcaa aaaggatctt cacctagatc cttttaaatt aaaaatgaag ttttaaatca   3480
atctaaagta tatatgagta aacttggtct gacagttacc aatgcttaat cagtgaggca   3540
cctatctcag cgatctgtct atttcgttca tccatagttg cctgactccc cgtcgtgtag   3600
ataactacga tacgggaggg cttaccatct ggccccagtg ctgcaatgat accgcgagac   3660
ccacgctcac cggctccaga tttatcagca ataaaccagc cagccggaag ggccgagcgc   3720
agaagtggtc ctgcaacttt atccgcctcc atccagtcta ttaattgttg ccgggaagct   3780
agagtaagta gttcgccagt taatagtttg cgcaacgttg ttgccattgc tacaggcatc   3840
gtggtgtcac gctcgtcgtt tggtatggct tcattcagct ccggttccca acgatcaagg   3900
cgagttacat gatcccccat gttgtgcaaa aaagcggtta gctccttcgg tcctccgatc   3960
gttgtcagaa gtaagttggc cgcagtgtta tcactcatgg ttatggcagc actgcataat   4020
tctcttactg tcatgccatc cgtaagatgc ttttctgtga ctggtgagta ctcaaccaag   4080
tcattctgag aatagtgtat gcggcgaccg agttgctctt gcccggcgtc aatacgggat   4140
```

-continued

```
aataccgcgc cacatagcag aactttaaaa gtgctcatca ttggaaaacg ttcttcgggg    4200
cgaaaactct caaggatctt accgctgttg agatccagtt cgatgtaacc cactcgtgca    4260
cccaactgat cttcagcatc ttttactttc accagcgttt ctgggtgagc aaaaacagga    4320
aggcaaaatg ccgcaaaaaa gggaataagg gcgacacgga aatgttgaat actcatactc    4380 ttccttttc  aatattattg aagcatttat cagggttatt gtctcatgag cggatacata    4440
tttgaatgta tttagaaaaa taaacaaata ggggttccgc gcacatttcc ccgaaaagtg    4500
ccacctgacg tctaagaaac cattattatc atgacattaa cctataaaaa taggcgtatc    4560
acgaggccct ttcgtctcgc gcgtttcggt gatgacggtg aaaacctctg acacatgcag    4620
ctcccggaga cggtcacagc ttgtctgtaa gcggatgccg ggagcagaca agcccgtcag    4680
ggcgcgtcag cgggtgttgg cgggtgtcgg ggctggctta actatgcggc atcagagcag    4740
attgtactga gagtgcacca tatgcggtgt gaaataccgc acagatgcgt aaggagaaaa    4800
taccgcatca ggcgccattc gccattcagg ctgcgcaact gttgggaagg gcgatcggtg    4860
cgggcctctt cgctattacg ccagctgcg  aaagggggat gtgctgcaag gcgattaagt    4920
tgggtaacgc cagggttttc ccagtcacga cgttgtaaaa cgacggccag tgcc          4974
```

METHODS AND COMPOSITIONS RELATING TO LEPTIN ANTAGONISTS

RELATED APPLICATIONS

The instant application claims priority as a continuation in part under 35 U.S.C. 111(a) from International application No. PCT/IL2015/050866 filed on 27 Aug., 2015, which takes priority from U.S. provisional patent application 62/188,676 filed 5 Jul. 2015; U.S. Utility patent application Ser. No. 14/730,282 filed 4 Jun., 2015; and U.S. provisional patent application 62/120,966 filed 26 Feb., 2015, all four documents which are included by reference as if fully-set forth herein.

FIELD AND BACKGROUND OF THE INVENTION

The present invention relates to the field of medicine, and in some embodiments to devices and compositions comprising a leptin antagonist formulated for localized release of a leptin antagonist at the site of treatment as well as methods of using such compositions for treating disorders, including cardiovascular disorders.

Cardiovascular disease (CVD) is a class of diseases that involve the heart and/or the blood vessels. Several studies have related inflammatory markers to cardiovascular disease (CVD) and several assays for inflammatory markers are commercially available. For example, C-reactive protein (CRP), a common inflammatory marker, has been found to be present in increased levels in patients who are at risk for cardiovascular disease [Karakas and Koenig, 2009 Herz 34 (8); 607-13] while osteoprotegerin, which is involved with regulation of NF-κB, has been found to be a risk factor for cardiovascular disease and mortality [Venuraju et al., 2010 J. Am. Coll. Cardiol. 55 (19): 2049-61].

As a result of these findings, the number of inflammatory marker tests ordered by clinicians for CVD risk prediction has grown rapidly. However, to date there is no consensus among professionals as to how these markers of inflammation should be used as a basis for clinical treatment.

Although it has been shown that some cardiovascular disorders can benefit from suppression of inflammation-related processes and cellular proliferation as part of a remodeling response (e.g. use of locally released cytotoxic drugs such as paclitaxel or sirolimus in preventing restenosis or use of doxycycline in treatment of abdominal aortic aneurysm (AAA)), to date there is no evidence to suggest that cardiovascular disease can benefit from anti-inflammatory treatment.

Leptin is a naturally occurring pleiotropic molecule that regulates food intake as well as metabolic and endocrine functions. Leptin also plays a regulatory role in immunity, inflammation, and hematopoiesis.

The human leptin precursor is a linear polypeptide 167 amino acid residues long represented by NCBI Reference Sequence NP_000221.1 (SEQ ID NO 1) encoded by the mRNA having the nucleotide sequence NCBI Reference Sequence NM_000230. Residues 1-21 of the sequence constitute the signal peptide while residues 22-167 constitute the mature hormone.

Leptin antagonists are also known, see for example, U.S. Pat. Nos. 7,307,142 and 8,969,292.

SUMMARY OF THE INVENTION

The invention, in some embodiments, relates to the field of medicine, and more particularly to methods and devices that use leptin antagonists. In some embodiments, the invention relates to compositions comprising a leptin antagonist formulated for localized release of a leptin antagonist at the site of treatment as well as methods of using such compositions for treating disorders, including cardiovascular disorders.

According to an aspect of some embodiments of the invention, there is provided a method of treatment comprising: exposing in vivo tissue of a subject in need thereof to local administration of a pharmaceutically-effective amount of leptin antagonist, thereby providing a therapeutic effect to the tissue. In some embodiments, the tissue is substantially continuously exposed to a pharmaceutically-effective amount of leptin antagonist for a period of not less than three days, not less than 5 days, not less than 8 days and even not less than 14 days.

According to an aspect of some embodiments of the invention, there is also provided a method of treatment comprising implanting in contact with tissue in the body of a subject in need thereof a composition configured for in vivo local administration of leptin antagonist, thereby providing a therapeutic effect to the tissue. In some embodiments, the configuration for the in vivo release is such that when the composition is implanted in vivo, leptin antagonist is released from the composition in a pharmaceutically-effective amount for a period of not less than three days, not less than 5 days, not less than 8 days and even not less than 14 days.

In some embodiments of the methods, the need is that the subject suffers from at least one pathology selected from the group consisting of: cardiovascular disease; remodeling of stable athersclerotic plaque into an unstable lesion; ascending aortic aneurysm-associated hypertension, hypercholesterolemia or diabetes mellitus; bicuspid aortic valve; Takayasu disease; rheumatoid arteritis; Marfan's syndrome; ankylosing spondylitis; giant cell arteritis; inflammatory aortic aneurysm; pulmonary artery aneurysm in Marfan's syndrome; aortic dissection in an aortic or peripheral large artery; angiogenesis; cancer; local discrete lesion therapy; and arteriovenous malformation.

In some embodiments, the need is that the subject suffers from a cardiovascular disorder, wherein the therapeutic effect is down-regulation of an expression or activity of leptin in a cardiovascular tissue.

In some embodiments, the cardiovascular tissue is aortic and/or mitral heart valve leaflet tissue. In some embodiments, the local administration is effected by positioning a carrier capable of releasing the leptin antagonist on an outer wall (e.g., tunica externa) or the inner wall (e.g., tunica intima) of an aorta.

In some embodiments, the cardiovascular tissue is arterial or venous wall tissue. In some embodiments, the local administration is effected by positioning a carrier capable of releasing the leptin antagonist on an outer wall (e.g., tunica externa) or the inner wall (e.g., tunica intima) of the arterial or venous wall tissue.

In some embodiments, the cardiovascular disorder is a vascular aneurysm. In some embodiments, the cardiovascular disorder is an aortic vascular disorder. In some embodiments, the cardiovascular disorder is left ventricular remodeling.

In some embodiments, the local administration is effected via an intravascular catheter. In some embodiments, the local administration is effected via direct injection.

According to an aspect of some embodiments of the invention, there is also provided a method for treatment of atherscleotic plaque, comprising: administering a pharmaceutically-effective amount of a leptin antagonist to atherosclerotic plaque accumulated in the inner walls of an artery, thereby at least one of: (a) reducing the rate and (b) reducing the incidence, of conversion of a stable atherosclerotic plaque to an unstable lesion.

According to an aspect of some embodiments of the invention, there is also provided a composition comprising a leptin antagonist and a carrier, for use in treating a disorder selected from the group consisting of: cardiovascular disease; remodeling of stable atherosclerotic plaque into an unstable lesion; ascending aortic aneurysm-associated hypertension, hypercholesterolemia or diabetes mellitus; bicuspid aortic valve; Takayasu disease; rheumatoid arteritis; Marfan's syndrome; ankylosing spondylitis; giant cell arteritis; inflammatory aortic aneurysm; pulmonary artery aneurysm in Marfan's syndrome; aortic dissection in an aortic or peripheral large artery; site of arterial anastomosis, angiogenesis; cancer; local neoplastic discrete lesion therapy; and arteriovenous malformation, wherein the carrier is configured for localized administration of the leptin antagonist.

In some embodiments, the carrier is a biodegradable support. In some embodiments, the biodegradable support is composed of a polymer selected from the group consisting of a hydrogel, poly glycolic acid (PGA), poly lactic co-glycolic acid (PLGA), polylactide (PLA), and poly (L-lactide) (PLLA), and combinations thereof.

In some embodiments, the carrier is a hydrogel. In some embodiments, the carrier is configured as a film. In some embodiments, the carrier is a device selected from the group consisting of a mesh, a balloon and a vascular graft. In some embodiments, the carrier is a depot-forming injectable composition.

In some embodiments, the disorder is a cardiovascular disorder, wherein the leptin antagonist effects down-regulation of an expression or activity of leptin in a cardiovascular tissue. In some embodiments, the cardiovascular disorder is a vascular disorder. In some such embodiments, the vascular disorder is an aortic vascular disorder. In some embodiments, the cardiovascular disorder is left ventricular remodeling.

In some such embodiments, the cardiovascular tissue is aortic and/or mitral heart valve leaflet tissue. In some such embodiments, the cardiovascular tissue is arterial or venous wall tissue.

In some embodiments, the local administration is effected by positioning a carrier capable of releasing the leptin antagonist on a location selected from the group consisting of: an outer wall of an aorta, an outer wall of an artery, an outer wall of an vein, a luminal surface of an aorta, a luminal surface of an artery and a luminal surface of an vein. In some such embodiments, the local administration is effected by positioning a carrier capable of releasing the leptin antagonist on an outer wall (e.g., tunica externa) or the inner wall (e.g., tunica intima) of the arterial or venous wall tissue. In some embodiments, the localized administration is to be effected via an intravascular catheter. In some embodiments, the localized administration is to be effected via direct injection.

According to an aspect of some embodiments of the invention, there is also provided a method of treating a condition in a subject in need thereof, the method comprising administering intracavitarily to inner walls of a fluid-filled bodily cavity of the subject a composition comprising a leptin antagonist.

According to an aspect of some embodiments of the invention, there is also provided a composition comprising: a leptin antagonist for use in treating a condition, wherein the composition is configured for intracavitary administration to inner walls of a fluid-filled bodily cavity of a subject.

According to an aspect of some embodiments of the invention, there is also provided an intracavitarily-implantable medical device, comprising: at least one solid functional device part configured for deploying the device in a fluid-filled bodily cavity of a subject and functionally associated with at least one the device component, a leptin antagonist.

According to an aspect of some embodiments of the invention, there is also provided a surgical connecting device, comprising: a solid device body made of a material; and functionally associated with the device body, a pharmaceutically-effective amount of leptin antagonist. In some embodiments, the device body is in the form selected from the group consisting of surgical suture thread and a surgical staple.

Any suitable leptin antagonist may be used for implementing the teachings herein. Various types and specific suitable leptin antagonists are listed in the description herein. In some embodiments, the leptin antagonist is capable of binding a leptin receptor. In some embodiments, the leptin antagonist is incapable of dimerization. In some embodiments, the leptin antagonist comprises a polypeptide portion. In some embodiments, the leptin antagonist is selected from the group consisting of a polypeptide, a salt, and/or an ester thereof. In some embodiments, the leptin antagonist is a modified leptin polypeptide.

BRIEF DESCRIPTION OF THE FIGURES

Some embodiments of the invention are described herein with reference to the accompanying figures. The description, together with the figures, makes apparent to a person having ordinary skill in the an how some embodiments of the invention may be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures:

FIG. 2 illustrates a balloon catheter configured for local release of a leptin antagonist (drug release indicated by arrows).

FIG. 27 schematically depicts embodiments of surgical connecting devices according to the teachings herein:

FIG. 28 schematically depicts embodiments of the teachings herein suitable for intracavitary administration of leptin antagonist.

DESCRIPTION OF SOME EMBODIMENTS

Figure 1A:
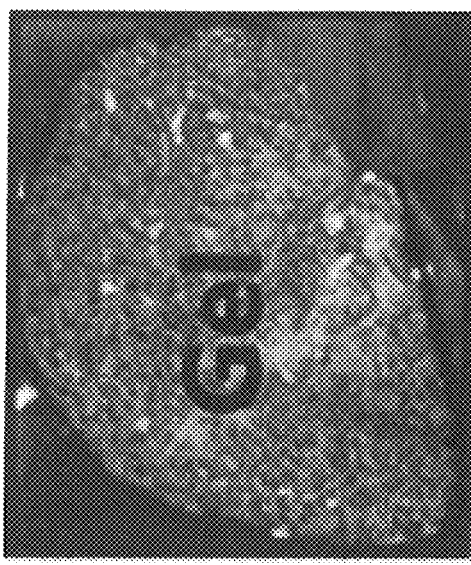
FIG. 1a-c illustrate a gel (FIG. 1a), film (FIG. 1b) and mesh (FIG. 1c) for local release of a leptin antagonist.

The invention, in some embodiments, relates to the field of medicine, and more particularly to methods and devices that use leptin antagonists. In some embodiments, the invention relates to compositions comprising a leptin antagonist formulated for localized release of a leptin antagonist at the site of treatment as well as methods of using such compositions for treating disorders, including cardiovascular disorders. In some embodiments, the compositions comprising a leptin antagonist can be used for localized suppression of leptin-related conditions, including tissue remodeling processes.

Although it has been proposed that leptin might play a role in vascular inflammation, oxidative stress, and vascular smooth muscle hypertrophy that may contribute to coronary heart disease among other pathologies, to date no one has conclusively shown that localized down-regulation of leptin activity can be used to treat cardiovascular disorders characterized by remodeling of cardiovascular tissue such as cardiac, arterial or valve tissue.

The present inventor set out to elucidate the role of leptin in disorders, such as cardiovascular disorders by employing a leptin antagonist in a localized manner. Experiments conducted by the present inventor (see Examples section hereinbelow) demonstrate that localized release of leptin in cardiovascular tissue can lead to cardiovascular tissue remodeling while localized down-regulation of leptin activity can lead to suppression and even reversal of cardiovascular tissue (arterial wall tissue, heart muscle tissue and valve leaflet tissue) remodeling induced by angiotensin II. Thus, the present inventor has shown for the first time that a locally administered leptin antagonist can be used to treat cardiovascular disorders characterized by tissue remodeling.

While reducing the present invention to practice, the present inventor has shown that down-regulation of leptin activity at specific sites in the cardiovascular system can lead to suppression and reversal of pathological tissue remodeling and thereby establishing localized leptin down-regulation as a suitable approach for treating various cardiovascular disorders, such as cardiovascular disorders characterized by pathological tissue remodeling.

The present inventor has discovered an unexpected pharmaceutical efficacy of locally administered leptin antagonists, especially leptin antagonists administered by sustained release.

Particularly, the present inventor has found that in vivo implantation of a composition configured for sustained-release of leptin antagonist can have a desirable pharmaceutical effect on tissue in proximity of the implanted composition with limited or no substantial side-effects, for example, no discernible hormonal or immunological effects.

The present inventor has also found that such in vivo administration (e.g., by implantation) inside a fluid-filled cavity of the body (for example of the cardiovascular system such as blood vessels or cardiac chambers) can have a desirable pharmaceutical effect on tissue in proximity of the implanted composition with limited or no substantial side-effects: leptin antagonist from the composition has not been found to be washed away by the fluid and, instead, has been found to interact with the tissue providing a desirable pharmaceutical effect. Presumably, leptin antagonist released from the composition passes into and through the cavity walls (e.g., tunica intima) in pharmaceutically-effective amounts. This is particularly surprising in cavities of the cardiovascular system (e.g., veins, arteries and cardiac chambers) where the large volumes of blood passing through such cavities are expected to wash away released leptin antagonist and where it is expected that the cardiovascular intima is relatively non-permeable to passage of compounds, especially proteins.

Without wishing to be held to any one theory, it is currently believed that the success of some embodiments of the teachings herein is at least partially attributable to the serendipitous increased permeability of cardiovascular intima during inflammation. It may be that the intima of healthy cardiovascular intima is relatively impermeable to leptin antagonist released from the composition, so that there is little or no passage of leptin antagonist into and through the endothelium and underlying tissue, thereby avoiding substantial negative side-effects. In contrast, it seems that the permeability of the cardiovascular intima during inflammation increases sufficiently to allow passage of a therapeutically-effective amount of leptin antagonist released from the composition into the tissue. It is currently believed that this effect is self-regulating. A higher degree of inflammation leads to a higher degree of intima permeability allowing passage of more leptin antagonist leading to a relatively high dose of leptin antagonist in the more pathological tissue. As inflammation decreases (inter alia, due to the pharmaceutical effect of the administered leptin antagonist), intima permeability decreases thereby decreasing the dose of leptin antagonist actually in the tissue that is still sufficient to exercise a desired pharmaceutical effect but with a reduced incidence of substantial negative side effects.

In some embodiments, the present invention includes local administration of leptin antagonist to treat and attenuate expansion of ascending aortic aneurysm, and corresponding cardiac sequelae (driven by the aorto-ventricular coupling), including left ventricular hypertrophy, as well as hyperplasia of left heart valve leaflets.

In some embodiments, the present invention includes treatment of peripheral vascular disorders such as the progression of arterial or venous aneurysms while minimizing systemic exposure to the administered leptin antagonist.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Thus, according to one aspect of the present invention there is provided a composition comprising a leptin antagonist and a carrier configured for localized administration, for treating disorders such as cardiovascular disorders. As used herein, "cardiovascular disorders" refer to disorders of the cardiovascular system, i.e. the heart and central, cranial and peripheral vasculature. Examples of such disorders include, but are not limited to valve stenosis, aneurysms, vessel response to vascular injury, cardiomyopathy and the like.

The carrier can be a solid, gel or liquid carrier, while the leptin antagonist can be any agent capable of down-regulating leptin activity in the target tissue. Examples of a leptin antagonist include agents capable of binding and/or degrading leptin or leptin receptors as well as agents capable of down-regulating leptin expression (at the DNA or RNA levels, i.e., agents capable of blocking transcription or translation). Specific preferred leptin antagonists are listed hereinbelow.

One example of a leptin antagonist that is an agent capable of down-regulating leptin is an antibody or antibody fragment capable of specifically binding leptin or a leptin receptor. Preferably, the antibody specifically binds at least one epitope of leptin, e.g., an epitope defined amino acids 26-59 of mammalian leptin (e.g. rat leptin—SEQ ID NO 48). As used herein, the term "epitope" refers to any antigenic determinant on an antigen to which the paratope of an antibody binds.

As used herein, the term "antibody" refers to a substantially intact antibody molecule.

As used herein, the phrase "antibody fragment" refers to a functional fragment of an antibody that is capable of binding to an antigen.

Suitable antibody fragments for practicing the present invention include, inter alia, a complementarity-determining region (CDR) of an immunoglobulin light chain (referred to herein as "light chain"), a CDR of an immunoglobulin heavy chain (referred to herein as "heavy chain"), a variable region of a light chain, a variable region of a heavy chain, a light chain, a heavy chain, an Fd fragment, and antibody fragments comprising essentially whole variable regions of both light and heavy chains such as an Fv, a single-chain Fv, an Fab, an Fab', and an F(ab')2.

Functional antibody fragments comprising whole or essentially whole variable regions of both light and heavy chains are defined as follows:

(i) Fv, defined as a genetically engineered fragment consisting of the variable region of the light chain and the variable region of the heavy chain expressed as two chains;

(ii) single-chain Fv ("scFv"), a genetically engineered single-chain molecule including the variable region of the light chain and the variable region of the heavy chain, linked by a suitable polypeptide linker.

(iii) Fab, a fragment of an antibody molecule containing a monovalent antigen-binding portion of an antibody molecule, obtained by treating whole antibody with the enzyme papain to yield the intact light chain and the Fd fragment of the heavy chain, which consists of the variable and CH1 domains thereof;

(iv) Fab', a fragment of an antibody molecule containing a monovalent antigen-binding portion of an antibody molecule, obtained by treating whole antibody with the enzyme pepsin, followed by reduction (two Fab' fragments are obtained per antibody molecule); and (v) F(ab')2, a fragment of an antibody molecule containing a monovalent antigen-binding portion of an antibody molecule, obtained by treating whole antibody with the enzyme pepsin (i.e., a dimer of Fab' fragments held together by two disulfide bonds).

Methods of generating monoclonal and polyclonal antibodies are well known in the art. Antibodies may be generated via any one of several known methods, which may employ induction of in vivo production of antibody molecules, screening of immunoglobulin libraries (Orlandi, R. et al. (1989). Cloning immunoglobulin variable domains for expression by the polymerase chain reaction. Proc Natl Acad Sci USA 86, 3833-3837; and Winter, G. and Milstein, C. (1991). Man-made antibodies. Nature 349, 293-299), or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler, G. and Milstein, C. (1975). Continuous cultures of fused cells secreting antibody of predefined specificity. Nature 256, 495-497; Kozbor, D. et al. (1985). Specific immunoglobulin production and enhanced tumorigenicity following ascites growth of human hybridomas. J Immunol Methods 81, 31-42; Cote R J. et al. (1983). Generation of human monoclonal antibodies reactive with cellular antigens. Proc Natl Acad Sci USA 80, 2026-2030; and Cole, S. P. et al. (1984). Human monoclonal antibodies. Mol Cell Biol 62, 109-120).

In cases where target antigens are too small to elicit an adequate immunogenic response, such antigens (referred to as "haptens") can be coupled to antigenically neutral carriers such as keyhole limpet hemocyanin (KLH) or serum albumin (e.g., bovine serum albumin (BSA)) carriers (see, for example, U.S. Pat. Nos. 5,189,178 and 5,239,078). Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill., USA. The resulting immunogenic complex can then be injected into suitable mammalian subjects such as mice, rabbits, and others. Suitable protocols involve repeated injection of the immunogen in the presence of adjuvants according to a schedule designed to boost production of antibodies in the serum. The titers of the immune serum can readily be measured using immunoassay procedures which are well known in the art.

The antisera obtained can be used directly or monoclonal antibodies may be obtained, as described hereinabove.

Antibody fragments may be obtained using methods well known in the art. (See, for example, Harlow, E. and Lane, D. (1988). Antibodies: A Laboratory Manual, Cold Spring Harbor Laboratory, New York.) For example, antibody fragments according to the present invention can be prepared by proteolytic hydrolysis of the antibody or by expression in *E. coli* or mammalian cells (e.g., Chinese hamster ovary (CHO) cell culture or other protein expression systems) of DNA encoding the fragment.

Alternatively, antibody fragments can be obtained by pepsin or papain digestion of whole antibodies by conventional methods. As described hereinabove, an (Fab')$_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages, to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: U.S. Pat. Nos. 4,036,945 and 4,331,647; and Porter, R. R. (1959). The hydrolysis of rabbit γ-globulin and antibodies with crystalline papain. Biochem J 73, 119-126). Other methods of cleaving antibodies, such as separation of heavy chains to form monovalent light-heavy chain fragments, further cleavage of fragments, or other enzymatic, chemical, or genetic techniques may also be used, so long as the fragments retain the ability to bind to the antigen that is recognized by the intact antibody.

As described hereinabove, an Fv is composed of paired heavy chain variable and light chain variable domains. This association may be noncovalent (see, for example, Inbar, D. et al. (1972). Localization of antibody-combining sites within the variable portions of heavy and light chains. Proc Natl Acad Sci USA 69, 2659-2662). Alternatively, as described hereinabove, the variable domains may be linked to generate a single-chain Fv by an intermolecular disulfide bond, or alternately such chains may be cross-linked by chemicals such as glutaraldehyde.

Preferably, the Fv is a single-chain Fv. Single-chain Fvs are prepared by constructing a structural gene comprising DNA sequences encoding the heavy chain variable and light chain variable domains connected by an oligonucleotide encoding a peptide linker. The structural gene is inserted into an expression vector, which is subsequently introduced into a host cell such as *E. coli*. The recombinant host cells synthesize a single polypeptide chain with a linker peptide bridging the two variable domains. Ample guidance for producing single-chain Fvs is provided in the literature of the art (see, e.g.: Whitlow, M. and Filpula, D. (1991). Single-chain Fv proteins and their fusion proteins. METHODS: A Companion to Methods in Enzymology 2(2), 97-105; Bird, R. E. et al. (1988). Single-chain antigen-binding proteins. Science 242, 423-426; Pack, P. et al. (1993). Improved bivalent miniantibodies, with identical avidity as whole antibodies, produced by high cell density fermentation of *Escherichia coli*. Biotechnology (N.Y.) 11(11), 1271-1277; and U.S. Pat. No. 4,946,778).

Isolated complementarity-determining region peptides can be obtained by constructing genes encoding the CDR of an antibody of interest. Such genes may be prepared, for example, by RT-PCR of the mRNA of an antibody-producing cell. Ample guidance for practicing such methods is provided in the literature of the art (e.g., Larrick, J. W. and Fry, K. E. (1991). PCR Amplification of Antibody Genes. METHODS: A Companion to Methods in Enzymology 2(2), 106-110).

It will be appreciated that for human therapy, humanized antibodies are preferred. Humanized forms of non-human (e.g., murine) antibodies are genetically engineered chimeric antibodies or antibody fragments having (preferably minimal) portions derived from non-human antibodies. Humanized antibodies include antibodies in which the CDRs of a human antibody (recipient antibody) are replaced by residues from a CDR of a non-human species (donor antibody), such as mouse, rat, or rabbit, having the desired functionality. In some instances, the Fv framework residues of the human antibody are replaced by corresponding non-human residues. Humanized antibodies may also comprise residues found neither in the recipient antibody nor in the imported CDR or framework sequences. In general, the humanized antibody will comprise substantially all of at least one, and typically two, variable domains, in which all or substantially all of the CDRs correspond to those of a non-human antibody and all or substantially all of the framework regions correspond to those of a relevant human consensus sequence. Humanized antibodies optimally also include at least a portion of an antibody constant region, such as an Fc region, typically derived from a human antibody (see, for example: Jones, P. T. et al. (1986). Replacing the complementarity-determining regions in a human antibody with those from a mouse. Nature 321, 522-525; Riechmann, L. et al. (1988). Reshaping human antibodies for therapy. Nature 332, 323-327; Presta, L. G. (1992b). Curr Opin Struct Biol 2, 593-596; and Presta, L. G. (1992a). Antibody engineering. Curr Opin Biotechnol 3(4), 394-398).

Methods for humanizing non-human antibodies are well known in the art. Generally, a humanized antibody has one or more amino acid residues introduced into it from a source which is non-human. These non-human amino acid residues are often referred to as imported residues, which are typically taken from an imported variable domain. Humanization can be performed essentially as described (see, for example: Jones et al. (1986); Riechmann et al. (1988); Verhoeyen, M. et al. (1988). Reshaping human antibodies: grafting an antilysozyme activity. Science 239, 1534-1536; and U.S. Pat. No. 4,816,567), by substituting human CDRs with corresponding rodent CDRs. Accordingly, humanized antibodies are chimeric antibodies, wherein substantially less than an intact human variable domain has been substituted by the corresponding sequence from a non-human species. In practice, humanized antibodies may be typically human antibodies in which some CDR residues and possibly some framework residues are substituted by residues from analogous sites in rodent antibodies.

Human antibodies can also be produced using various additional techniques known in the art, including phage-display libraries (Hoogenboom, H. R. and Winter, G. (1991). By-passing immunization. Human antibodies from synthetic repertoires of germline VH gene segments rearranged in vitro. J Mol Biol 227, 381-388; Marks, J. D. et al. (1991). By-passing immunization. Human antibodies from V-gene libraries displayed on phage. J Mol Biol 222, 581-597; Cole et al. (1985), Monoclonal Antibodies and Cancer Therapy, Alan R. Liss, Inc., pp. 77-96; and Boerner, P. et al. (1991). Production of antigen-specific human monoclonal antibodies from in vitro-primed human splenocytes. J Immunol 147, 86-95). Humanized antibodies can also be created by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807; 5,545,806; 5,569,825; 5,625,126; 5,633,425; and 5,661,016; Marks, J. D. et al. (1992). By-passing immunization: building high affinity human antibodies by chain shuffling. Biotechnology (N.Y.) 10(7), 779-783; Lonberg et al., 1994. Nature 368:856-859; Morrison, S. L. (1994). News and View: Success in Specification. Nature 368, 812-813; Fishwild, D. M. et al. (1996). High-avidity human IgG kappa monoclonal antibodies from a novel strain of minilocus transgenic mice. Nat Biotechnol 14, 845-851; Neuberger, M. (1996). Generating high-avidity human Mabs in mice. Nat Biotechnol 14, 826; and Lonberg, N. and Huszar, D. (1995). Human antibodies from transgenic mice. Int Rev Immunol 13, 65-93).

After antibodies have been obtained, they may be tested for activity, for example via enzyme-linked immunosorbent assay (ELISA).

Anti-leptin antibodies as well as epitope sequences suitable for generating antibodies and antibody fragments are described in US20070104708 (SEQ ID NOs 49-55) which is incorporated herein by reference as if fully set-forth herein.

Leptin peptide antagonists can also be used with the present invention. One leptin antagonist, a modified mammalian leptin polypeptide termed superactive leptin mutein is disclosed in U.S. Pat. No. 8,969,292 which is incorporated by reference as if fully set-forth herein.

The term "peptide" as used herein encompass native peptides (either degradation products, synthetically synthesized peptides, or recombinant peptides), peptidomimetics (typically, synthetically synthesized peptides), and the peptide analogues peptoids and semipeptoids, and may have, for example, modifications rendering the peptides more stable while in a body or more capable of penetrating into cells. Such modifications include, but are not limited to: N-terminus modifications; C-terminus modifications; peptide bond modifications, including but not limited to $CH_2$—NH, $CH_2$—S, $CH_2$—S=O, O=C—NH, $CH_2$—O, $CH_2$—$CH_2$, S=C—NH, CH=CH, and CF=CH; backbone modifications; and residue modifications. Methods for preparing peptidomimetic compounds are well known in the art and are specified, for example, in Ramsden, C. A., ed. (1992), Quantitative Drug Design, Chapter 17.2, F. Choplin Pergamon Press, which is incorporated by reference as if fully set forth herein. Further details in this respect are provided hereinbelow.

Peptide bonds (—CO—NH—) within the peptide may be substituted, for example, by N-methylated bonds (—N (CH3)-CO—); ester bonds (—C(R)H—C—O—O—C(R)—N—); ketomethylene bonds (—CO—CH2-); a_-aza bonds (—NH—N(R)—CO—), wherein R is any alkyl group, e.g., methyl; carba bonds (—CH2-NH—); hydroxyethylene bonds (—CH(OH)—CH2-); thioamide bonds (—CS—NH—); olefinic double bonds (—CH=CH—); retro amide bonds (—NH—CO—); and peptide derivatives (—N(R)—CH2-CO—), wherein R is the "normal" side chain, naturally presented on the carbon atom. These modifications can occur at any of the bonds along the peptide chain and even at several (2-3) at the same time.

Natural aromatic amino acids, Trp, Tyr, and Phe, may be substituted for synthetic non-natural acids such as, for instance, tetrahydroisoquinoline-3-carboxylic acid (TIC), naphthylelanine (Nol), ring-methylated derivatives of Phe, halogenated derivatives of Phe, and o-methyl-Tyr.

In addition to the above, the peptides of the present invention may also include one or more modified amino acids or one or more non-amino acid monomers (e.g., fatty acids, complex carbohydrates, etc.).

The term "amino acid" or "amino acids" is understood to include the 20 naturally occurring amino acids; those amino acids often modified post-translationally in vivo, including, for example, hydroxyproline, phosphoserine, and phosphothreonine; and other less common amino acids, including but not limited to 2-aminoadipic acid, hydroxylysine, isodesmosine, nor-valine, nor-leucine, and ornithine. Furthermore, the term "amino acid" includes both D- and L-amino acids.

Amino acids are referred to by the standard three letter code. Amino acids are L amino acids unless otherwise noted, for example, by addition of the prefix "D". For example, the code Trp refers to L-tryptophan, while the codes D-Trp and DTrp refers to D-tryptophan. The code Aib refers to 2-aminoisobutyric acid. The code Orn refers to ornithine. The code Lys-Ac refers to acetyllysine. The code HomoLys refers to homolysine. The code H-Cys refers to homocysteine.

In some embodiments, peptidic leptin antagonists used to implement the teachings herein are utilized in a linear form, although in some embodiments, cyclic forms thereof are used.

In some embodiments, peptidic leptin antagonists used to implement the teachings herein are synthesized by any techniques that are known to those skilled in the art of peptide synthesis. For solid phase peptide synthesis, a summary of the many techniques may be found in: Stewart, J. M. and Young, J. D. (1963), "Solid Phase Peptide Synthesis," W. H. Freeman Co. (San Francisco); and Meienhofer, J (1973). "Hormonal Proteins and Peptides," vol. 2, p. 46, Academic Press (New York). For a review of classical solution synthesis, see Schroder, G. and Lupke, K. (1965). The Peptides, vol. 1, Academic Press (New York).

In general, peptide synthesis methods comprise the sequential addition of one or more amino acids or suitably protected amino acids to a growing peptide chain. Normally, either the amino or the carboxyl group of the first amino acid is protected by a suitable protecting group. The protected or derivatized amino acid can then either be attached to an inert solid support or utilized in solution by adding the next amino acid in the sequence having the complimentary (amino or carboxyl) group suitably protected, under conditions suitable for forming the amide linkage. The protecting group is then removed from this newly added amino acid residue and the next amino acid (suitably protected) is then added, and so forth; traditionally this process is accompanied by wash steps as well. After all of the desired amino acids have been linked in the proper sequence, any remaining protecting groups (and any solid support) are removed sequentially or concurrently, to afford the final peptide compound. By simple modification of this general procedure, it is possible to add more than one amino acid at a time to a growing chain, for example, by coupling (under conditions which do not racemize chiral centers) a protected tripeptide with a properly protected dipeptide to form, after deprotection, a pentapeptide, and so forth.

Further description of peptide synthesis is disclosed in U.S. Pat. No. 6,472,505. A preferred method of preparing the peptide compounds of the present invention involves solid-phase peptide synthesis, utilizing a solid support.

In some embodiments, peptidic leptin antagonists used to implement the teachings herein are generated using cell expression approaches by utilizing expression vectors for prokaryotic or eukaryotic expression or alternatively, the peptide can be expressed in-situ by delivering a suitable expression construct to cardiovascular tissue.

To express the peptide sequence in cardiovascular cells, a polynucleotide sequence encoding the peptide (see, for example, US20130133089) is preferably ligated into a nucleic acid construct suitable for mammalian cell expression. Such a nucleic acid construct includes a promoter sequence for directing transcription of the polynucleotide sequence in the cell in a constitutive or inducible manner.

Constitutive promoters suitable for use with the present invention are promoter sequences that are active under most environmental conditions and most types of cells, such as the cytomegalovirus (CMV) and Rous sarcoma virus (RSV).

Polyadenylation sequences can also be added to the expression vector in order to increase the efficiency of mRNA translation. Two distinct sequence elements are required for accurate and efficient polyadenylation: GU- or U-rich sequences located downstream from the polyadenylation site and a highly conserved sequence of six nucleotides, namely AAUAAA, located 11-30 nucleotides upstream of the site. Termination and polyadenylation signals suitable for the present invention include those derived from SV40.

In addition to the embodiments already described, the expression vector of the present invention may typically contain other specialized elements intended to increase the level of expression of cloned nucleic acids or to facilitate the identification of cells that carry the recombinant DNA. For example, a number of animal viruses contain DNA sequences that promote extra-chromosomal replication of the viral genome in permissive cell types. Plasmids bearing these viral replicons are replicated episomally as long as the appropriate factors are provided by genes either carried on the plasmid or with the genome of the host cell.

The expression vector of the present invention may or may not include a eukaryotic replicon. If a eukaryotic replicon is present, the vector is capable of amplification in eukaryotic cells using the appropriate selectable marker. If the vector does not comprise a eukaryotic replicon, no episomal amplification is possible.

Examples for mammalian expression vectors include, but are not limited to, pcDNA3 (SEQ ID NO 56), pcDNA3.1 (+/−) (SEQ ID NO 57-58), pGL3 (SEQ ID NO 59), pZeoSV2(+/−) (SEQ ID NO 60), pSecTag2 (SEQ ID NO 61), pDisplay (SEQ ID NO 62), pEF/myc/cyto (SEQ ID NO 63), pCMV/myc/cyto (SEQ ID NO 64), pCR3.1 (SEQ ID NO 65), pSinRep5 (SEQ ID NO 66), DH26S, DHBB, pNMT1, pNMT41, and pNMT81, which are available from Invitrogen, pCI (SEQ ID NO 67) which is available from Promega, pMbac (SEQ ID NO 68), pPbac (SEQ ID NO 69), pBK-RSV (SEQ ID NO 70) and pBK-CMV (SEQ ID NO 71) which are available from Strategene, pTRES which is available from Clontech, and their derivatives.

Expression vectors containing regulatory elements from eukaryotic viruses such as retroviruses can be also used. SV40 vectors include pSVT7 and pMT2 (SEQ ID NO 72), for instance. Vectors derived from bovine papilloma virus include pBV-IMTHA, and vectors derived from Epstein-Barr virus include pHEBO and p2O5. Other exemplary vectors include pMSG, pAV009/A*, pMTO10/A*, pMAM-neo-5, baculovirus pDSVE, and any other vector allowing expression of proteins under the direction of the SV40 early promoter, SV40 later promoter, metallothionein promoter, murine mammary tumor virus promoter, Rous sarcoma virus promoter, polyhedrin promoter, or other promoters shown effective for expression in eukaryotic cells.

Viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by the present invention will depend on the cell type transformed. The ability to select suitable vectors according to the cell type transformed is well within the capabilities of the ordinarily skilled artisan and as such, no general description of selection considerations is provided herein. For example, bone marrow cells can be targeted using the human T-cell leukemia virus type I (HTLV-I) and kidney cells may be targeted using the heterologous promoter present in the baculovirus *Autographa californica* multiple nucleopolyhedrovirus (Ac-MNPV), as described by Liang, C. Y. et al. (2004). High efficiency gene transfer into mammalian kidney cells using baculovirus vectors. Arch Virol 149, 51-60.

Recombinant viral vectors are useful for in vivo expression of a leptin peptide since they offer advantages such as lateral infection and targeting specificity. Lateral infection is inherent in the life cycle of retrovirus, for example, and is the process by which a single infected cell produces many progeny virions that bud off and infect neighboring cells. The result is the rapid infection of a large area of cells, most of which were not initially infected by the original viral particles. This is in contrast to vertical-type infection in which the infectious agent spreads only through daughter progeny. Viral vectors can also be produced that are unable to spread laterally. This characteristic can be useful if the desired purpose is to introduce a specified gene into only a localized number of targeted cells.

Figure 1B:
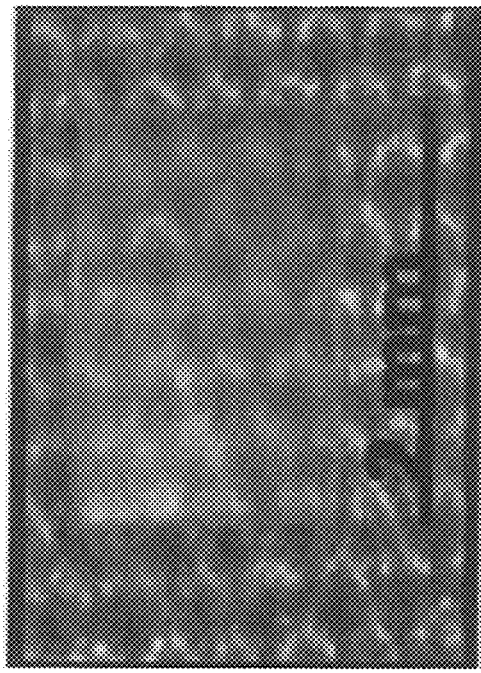
Figure 1C:
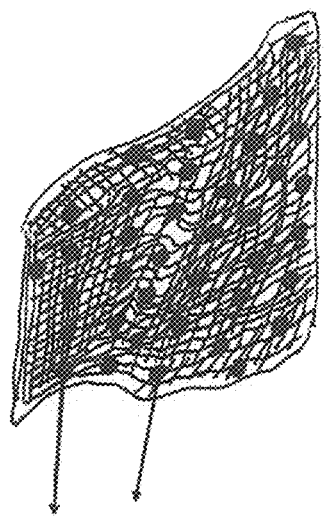
Figure 3:
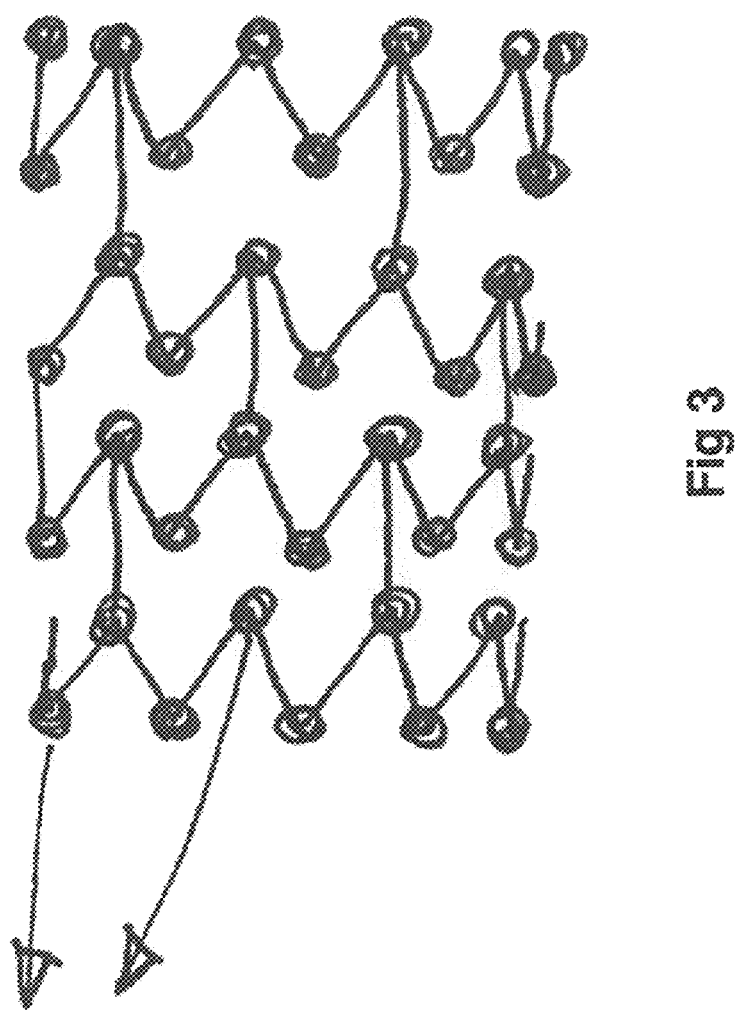
FIG. 3 illustrates a slow release leptin eluted from a scaffold.

As is mentioned hereinabove, compositions (also called, compositions-of-matter) according to the teachings herein also includes a carrier for local delivery of the leptin antagonist. Such a carrier can be a mesh (FIG. 1c) an injectable gel (e.g. in-situ forming depot) (FIG. 1a), a thin (preferably biodegradable) film (FIG. 1b), a scaffold (FIG. 3). In some embodiments, the composition is a coating on a medical device (FIG. 27A). In some embodiments, a medical device is impregnated with the composition (FIG. 27B). In some embodiments, the composition is in the form of a sheet (such as the film of FIG. 1b or the mesh of FIG. 1c) that constitutes a portion of a medical device such as a stent cover (FIG. 27C) or graft of a graft-stent assembly (FIG. 27D). In some embodiments, the composition constitutes a medical device (FIG. 27E).

In some embodiments a carrier of a composition is a balloon catheter, or a composition is delivered locally using a drug-eluting balloon catheter (FIG. 2). The manufacture and use of drug-eluting balloons for localized delivery of active-pharmaceutical ingredients are well known in the art (especially to the walls of fluid-filled bodily cavities, such as of the cardiovascular system), for example, the In.Pact Admiral® DCB drug-coated balloon by Medtronic (Dublin, Ireland) and Lutonix® 035 by C. R. Bard, Inc. (Murray Hill, N.J. USA).

Examples of in-situ formed depots (ISFD) include semi-solid polymers which can be injected as a melt and form a depot upon cooling to body temperature or two part systems which gel upon mixing (FIG. 3a). Depending on the embodiments, such compositions can be injected into or in contact with bodily tissue that is to be treated The requirements for a semi-solid ISFDs include low melting or glass transition temperatures in the range of 25-65° C. and an intrinsic viscosity in the range of 0.05-0.8 dl/g [12-14]. Below the viscosity threshold of 0.05 dl/g no delayed diffusion could be observed, whereas above 0.8 dl/g the ISFD was no longer injectable using a needle. At injection temperatures above 37° C. but below 65° C. these polymers behave like viscous fluids which solidify to highly viscous depots. Drugs are incorporated into the molten polymer by mixing without the application of solvents. In the art, it is known to use thermoplastic pastes (TP) can be used to generate a subcutaneous drug reservoir from which diffusion occurs into the systemic circulation. In contrast, in some embodiments of the teachings herein, a thermoplastic paste is used to generate a composition for the sustained release of leptin antagonist from which diffusion occurs into tissue in contact with the composition, thereby effecting sustained-release local administration of the leptin antagonist.

In situ cross-linked polymer systems utilize a cross-linked polymer network to control the diffusion of bioactive agents (e.g., leptin antagonists for implementing the teachings herein) over a prolonged period of time, thereby allowing implementation of sustained release compositions comprising leptin antagonists for use in local administration thereof. Use of in situ cross-linking implants necessitate protection of the bioactive agents during the cross-linking reaction. This could be achieved by encapsulation into fast degrading gelatin micro-particles.

An ISFD can also be based on polymer precipitation. A water-insoluble and biodegradable polymer is dissolved in a biocompatible organic solvent to which leptin antagonist is added forming a solution or suspension after mixing that constitutes a composition according to the teachings herein. When this composition is injected into the body of a subject in need thereof the water miscible organic solvent dissipates and water penetrates into the organic phase. This leads to phase separation and precipitation of the polymer forming a depot at the site of injection. One example of such a system is Atrigele™ (ARTIX Laboratories). The thus-formed depot is a composition for the sustained release of leptin antagonist from which diffusion occurs into tissue in contact with the composition, thereby effecting sustained-release local administration of the leptin antagonist.

Thermally induced gelling systems can also be used as ISFDs. Numerous polymers show abrupt changes in solubility as a function of environmental temperature. The prototypic thermosensitive polymer is poly(N-isopropyl acryl amide), poly-NIPAAM, which exhibits a rather sharp lower critical solution temperature.

Thermoplastic pastes such as the new generation of poly(ortho-esters) developed by AP Pharma can also be used for depot drug delivery. Such pastes include polymers that are semi-solid at room temperature, hence heating for drug incorporation and injection is no longer necessary. Injection is possible through needles no larger than 22 gauge. The leptin antagonist is mixed into the systems in a dry and, therefore, stabilized state. Shrinkage or swelling upon injection is thought to be marginal and, therefore, the initial drug burst is expected to be lower than in the other types of ISFD. An additional advantage is afforded by the self-catalyzed degradation by surface erosion. As noted above, IFSD compositions are suitable for effecting sustained-release local administration of the leptin antagonist. In some embodiments, an IFSD composition can be formulated for sustained-release (SR), extended-release (ER, XR, or XL), time-release or timed-release, controlled-release (CR), or continuous-release.

Examples of thin films (FIG. 3b) suitable for release of a leptin antagonist (or polynucleotide encoding same) include polymeric films (for a review of thin films, see Zelikin ACS Nano, 2010, 4 (5), pp 2494-2509; Venkat et al. 2010, Polymer Thin Films for Biomedical Applications, Wiley VCH Verlag GmbH & Co. KGaA, Weinheim). Such thin film carriers can be biodegradable or dissolvable over time.

Biodegradable microspheres fabricated from, for example, PGA, PLGA, PLA, or PLLA can also be used for local delivery of a leptin antagonist. Such microspheres can be produced as described by Kim and Park (J Control Release. 2004 Jul. 23; 98(1): 115-25).

A balloon such as an angioplasty balloon (FIG. 2) can also be used to deliver a leptin antagonist to a vascular wall or an inner wall of a heart chamber. Approach for coating/loading a balloon with a peptide are described in EP2643030; U.S. Pat. Nos. 8,617,136; 8,617,104; 8,617,114; WO1997017099; US20110166547 and US20120150142. As noted above, such drug-eluting balloons for use for localized delivery of active-pharmaceutical ingredients are well known in the art, for example, the In.Pact Admiral® drug-coated balloon by Medtronic (Dublin, Ireland) and Lutonix® 035 by C. R. Bard, Inc. (Murray Hill, N.J., USA). It is important to note that such drug-eluting balloons are known to administer extended release compositions of active pharmaceutical ingredients, e.g., In.Pact Admiral delivers a composition that provides extended release of a continuous therapeutic dose of Paclitaxel for over 180 days.

Although delivery of leptin or leptin receptor binding agents such as those described above (or expression thereof in cardiovascular cells), is presently preferred, downregulation of leptin activity at specific tissues can also be effected at the transcript level using a variety of molecules that interfere with transcription and/or translation (e.g., antisense, siRNA, Ribozyme, or DNAzyme).

RNA interference can be used to downregulate endogenous leptin via a small interfering RNA (siRNA) molecule. RNAi is a two-step process, in the first, the initiation step, input double-stranded (dsRNA) is digested into 21- to 23-nucleotide (nt) small interfering RNAs (siRNAs), probably by the action of Dicer, a member of the RNase III family of dsRNA-specific ribonucleases, which processes (cleaves) dsRNA (introduced directly or by means of a transgene or a virus) in an ATP-dependent manner. Successive cleavage events degrade the RNA to 19- to 21-bp duplexes (the siRNA), each with 2-nucleotide 3' overhangs (Hutvagner, G. and Zamore. P. D. (2002). RNAi: Nature abhors a double-strand. Curr Opin Gen Dev 12, 225-232; and Bernstein, E. (2001). Role for a bidentate ribonuclease in the initiation step of RNA interference. Nature 409, 363-366).

In the second step, termed the effector step, the siRNA duplexes bind to a nuclease complex to form the RNA-induced silencing complex (RISC). An ATP-dependent unwinding of the siRNA duplex is required for activation of the RISC. The active RISC then targets the homologous transcript by base-pairing interactions and cleaves the mRNA into 12-nucleotide fragments from the 3' terminus of the siRNA (Hutvagner and Zamore (2002); Hammond et al. (2001) Nat. Rev. Gen. 2:110-119 (2001); and Sharp, P. A. (2001). RNA interference. Genes Dev 15, 485-490). Although the mechanism of cleavage remains to be elucidated, research indicates that each RISC contains a single siRNA and an RNase (Hutvagner and Zamore (2002)).

Synthesis of RNAi molecules suitable for use with the present invention can be effected as follows. First, the leptin mRNA sequence (SEQ ID NO 2) is scanned downstream of the AUG start codon for AA-dinucleotide sequences. Occurrence of each AA and the 19 3'-adjacent nucleotides is recorded as a potential siRNA target site. Preferably, siRNA target sites are selected from the open reading frame (ORF), as untranslated regions (UTRs) are richer in regulatory protein binding sites. UTR-binding proteins and/or translation initiation complexes may interfere with binding of the siRNA endonuclease complex (Tuschl (2001)). It will be appreciated, however, that siRNAs directed at untranslated regions may also be effective, as demonstrated for GAPDH, wherein siRNA directed at the 5' UTR mediated about a 90% decrease in cellular GAPDH mRNA and completely abolished protein levels (wwwdotambiondotcom/techlib/tn/91/912dothtml).

Second, potential target sites are compared to an appropriate genomic database (e.g., human, mouse, rat, etc.) using any sequence alignment software, such as the BlastN software available from the NCBI server (wwwdotncbidotnlm-dotnihdotgov/BLAST/). Putative target sites that exhibit significant homology to other coding sequences are filtered out.

Qualifying target sequences are selected as templates for siRNA synthesis. Preferred sequences are those including low G/C content, as these have proven to be more effective in mediating gene silencing as compared with sequences including G/C content higher than 55%. Several target sites are preferably selected along the length of the target gene for evaluation. For better evaluation of the selected siRNAs, a negative control is preferably used in conjunction. Negative-control siRNAs preferably include the same nucleotide composition as the siRNAs but lack significant homology to the genome. Thus, a scrambled nucleotide sequence of the siRNA is preferably used, provided it does not display any significant homology to any other gene.

Another agent capable of downregulating leptin is a DNAzyme molecule, which is capable of specifically cleaving an mRNA transcript or a DNA sequence of the leptin. DNAzymes are single-stranded polynucleotides that are capable of cleaving both single- and double-stranded target sequences (Breaker, R. R. and Joyce, G. F. (1995). A DNA enzyme with $Mg^{2+}$-dependent RNA phosphoesterase activity. Curr Biol 2, 655-660; Santoro, S. W. and Joyce, G. F. (1997). A general purpose RNA-cleaving DNA enzyme. Proc Natl Acad Sci USA 94, 4262-4266). A general model (the "10-23" model) for the DNAzyme has been proposed. "10-23" DNAzymes have a catalytic domain of 15 deoxyribonucleotides, flanked by two substrate-recognition domains of seven to nine deoxyribonucleotides each. This type of DNAzyme can effectively cleave its substrate RNA at purine:pyrimidine junctions (Santoro and Joyce (1997)); for review of DNAzymes, see: Khachigian. L. M. (2002). DNAzymes: cutting a path to a new class of therapeutics. Curr Opin Mol Ther 4, 119-121.

Examples of construction and amplification of synthetic, engineered DNAzymes recognizing single- and double-stranded target cleavage sites are disclosed in U.S. Pat. No. 6,326,174 to Joyce et al. DNAzymes of similar design directed against the human Urokinase receptor were recently observed to inhibit Urokinase receptor expression, and successfully inhibit colon cancer cell metastasis in vivo (Itoh, T. et al., Abstract 409, American Society of Gene Therapy 5th Annual Meeting (wwwdotasgtdotorg), Jun. 5-9, 2002, Boston, Mass. USA.). In another application, DNAzymes complementary to bcr-abl oncogenes were successful in inhibiting the oncogene's expression in leukemia cells, and in reducing relapse rates in autologous bone marrow transplants in cases of Chronic Myelogenous Leukemia (CML) and Acute Lymphoblastic Leukemia (ALL).

Downregulation of leptin can also be effected by using an antisense polynucleotide capable of specifically hybridizing with an mRNA transcript encoding leptin.

Design of antisense molecules that can be used to efficiently downregulate a leptin must be effected while considering two aspects important to the antisense approach. The first aspect is delivery of the oligonucleotide into the cytoplasm of the appropriate cells, while the second aspect is design of an oligonucleotide that specifically binds the designated mRNA within cells in a manner inhibiting the translation thereof.

The prior art teaches of a number of delivery strategies which can be used to efficiently deliver oligonucleotides into a wide variety of cell types (see, for example: Lull, F. C. (1998). Making sense out of antisense oligodeoxynucleotide delivery: getting there is half the fun. J Mol Med 76(2), 75-76 (1998); Kronenwett et al. (1998). Oligodeoxyribonucleotide uptake in primary human hematopoietic cells is enhanced by cationic lipids and depends on the hematopoietic cell subset. Blood 91, 852-862; Rajur, S. B. et al. (1997). Covalent protein-oligonucleotide conjugates for efficient delivery of antisense molecules. Bioconjug Chem 8, 935-940; Lavigne et al. Biochem Biophys Res Commun 237: 566-71 (1997); and Aoki, M. et al. (1997). In vivo transfer efficiency of antisense oligonucleotides into the myocardium using HVJ-liposome method. Biochem Biophys Res Commun 231, 540-545).

In addition, also available are algorithms for identifying those sequences with the highest predicted binding affinity for their target mRNA based on a thermodynamic cycle that accounts for the energetics of structural alterations in both the target mRNA and the oligonucleotide (see, for example, Walton, S. P. et al. (1999). Prediction of antisense oligonucleotide binding affinity to a structured RNA target. Biotechnol Bioeng 65, 1-9).

Such algorithms have been successfully used to implement an antisense approach in cells. For example, the algorithm developed by Walton et al. enabled scientists to successfully design antisense oligonucleotides for rabbit beta-globin (RBG) and mouse tumor necrosis factor-alpha (TNF-alpha) transcripts. The same research group has more recently reported that the antisense activity of rationally selected oligonucleotides against three model target mRNAs (human lactate dehydrogenase A and B and rat gp130) in cell culture as evaluated by a kinetic PCR technique proved effective in almost all cases, including tests against three different targets in two cell types with phosphodiester and phosphorothioate oligonucleotide chemistries.

In addition, several approaches for designing and predicting efficiencies of specific oligonucleotides using an in vitro system were also published (Matveeva, O. et al. (1998). Prediction of antisense oligonucleotide efficacy by in vitro methods. Nature Biotechnology 16, 1374-1375).

Another agent capable of down-regulating leptin is a ribozyme molecule capable of specifically cleaving an mRNA transcript encoding leptin. Ribozymes increasingly are being used for the sequence-specific inhibition of gene expression by the cleavage of mRNAs encoding proteins of interest (Welch, P. J. et al. (1998). Expression of ribozymes in gene transfer systems to modulate target RNA levels. Curr Opin Biotechnol 9, 486-496).

An additional method of regulating the expression of leptin in cardiovascular cells is via triplex-forming oligonucleotides (TFOs). Recent studies show that TFOs can be designed to recognize and bind to polypurine or polypyrimidine regions in double-stranded helical DNA in a sequence-specific manner. These recognition rules are outlined in: Maher III, L. J., et al. (1989). Inhibition of DNA binding proteins by oligonucleotide-directed triple helix formation. Science 245, 725-730; Moser. H. E., et al. (1987). Sequence-specific cleavage of double helical DNA by triple helix formation. Science 238, 645-650; Beal, P. A. and Dervan, P. B. (1991). Second structural motif for recognition of DNA by oligonucleotide-directed triple-helix formation. Science 251, 1360-1363; Cooney, M., et al. (1988). Science 241, 456-459; and Hogan, M. E., et al., EP Publication 375408. Modifications of the oligonucleotides, such as the introduction of intercalators and backbone substitutions, and optimization of binding conditions (e.g., pH and cation concentration) have aided in overcoming inherent obstacles to TFO activity such as charge repulsion and instability, and it was recently shown that synthetic oligonucleotides can be targeted to specific sequences (for a recent review, see Seidman, M. M. and Glazer, P. M. (2003). The potential for gene repair via triple helix formation J Clin Invest 112, 487-494).

As is described hereinabove, the present invention can be used to treat cardiovascular disorders affecting heart or vascular tissue. The following describes several option for local delivery of a leptin antagonist to tissue, for example heart and other cardiovascular tissue, specifically muscle and valve tissue.

(i) Arterial catheterization can be used to deploy a medical device such as a mesh, a thin film, a biodegradable scaffold, a stent cover, a stent, a graft assembly, a coil, a stent, a ring or a prosthetic cardiac valve loaded with a leptin antagonist against a luminal wall of an ascending aorta distal to the orifice of the coronary arteries. In case of aneurysm at another location along the aorta, a visceral artery, or small tributary; the same intra-arterial approach can be used for local application.

(ii) An IFSD (for example, as described above, e.g., a gel) loaded with a leptin antagonist can be delivered via a balloon or needle to the aortic wall.

(iii) A composition such as a pliable non-degradable or biodegradable mesh or film loaded with the leptin antagonist that is placed in contact with an outer surface of tissue or an organ to be treated, e.g., by surgical delivery via open surgery or thorascopy, for example surgically delivered to the peri-aortic region (above the aortic root level). In case of small aneurysm in the abdominal aorta the leptin antagonist extended release film or mesh can be applied via open surgery or minimally invasive laparoscopy.

Method of Treatment

According to an aspect of some embodiments of the invention, there is also provided a method of treatment comprising: exposing in vivo tissue of a subject in need thereof to a pharmaceutically-effective amount of leptin antagonist thereby providing a therapeutic effect to the tissue. For example, in some such embodiments, a composition comprising leptin antagonist is administered (e.g., by injection) directly into the tissue. In some embodiments, the exposing of the in vivo tissue to the leptin antagonist is substantially continuously for a period of not less than three days. In some embodiments, the period is not less than five days, not less than 8 days and even not less than 14 days. For example, in some such embodiments, an extended release composition comprising leptin antagonist (e.g., a medical device impregnated with, coated with or made from a leptin antagonist is placed directly in contact with the tissue.

According to an aspect of some embodiments of the invention, there is also provided a method of treatment comprising implanting in contact with tissue in need thereof in the body of a subject a composition configured for the in vivo release of leptin antagonist, thereby providing a therapeutic effect to the tissue. In some embodiments, the composition is configured for sustained release of the leptin antagonist. In some embodiments, the implanting is intracavitary implanting within a fluid-filled bodily cavity of the subject. In some embodiments, by sustained release is meant that, when the composition is implanted in vivo, leptin antagonist is released from the composition in pharmaceutically effective amounts for a period of not less than three days, in some embodiments not less than five days, not less than 8 days and even not less than 14 days.

The subject in need thereof is any suitable mammalian subject. In some embodiments, the subject is a non-human animal. In some embodiments, the subject is a human.

The need is any suitable need. In some embodiments, the need is at least one need selected from the group consisting of: attenuating a pathology; reducing the chance of developing a pathology; reducing the rate of development a pathology; and mitigating the effect of a pathology.

The pathology is any pathology that can be treated by local administration of leptin antagonist, and in some embodiments, substantial continuous local exposure to leptin antagonist. In some embodiments, the pathology is at least one pathology selected from the group consisting of:

cardiovascular disease;

remodeling of stable atherosclerotic plaque into an unstable lesion (vulnerable plaque or rupture-prone plaque);

ascending aortic aneurysm, in some embodiments ascending aortic aneurysm associated with at least one member of the group consisting of hypertension, dyslipidemia, hypercholesterolemia, obesity, diabetes mellitus and bicuspid aortic valve (BAV);

thoracic aortic aneurysm (e.g., to prevent rupture or dissection thereof);

Takayasu disease (e.g., to attenuate cellular proliferative response, in some embodiments, by administration or implantation of a leptin antagonist composition to an inner or outer vessel wall in the vicinity of a vascular lesion);

Rheumatoid arteritis (e.g., to attenuate cellular proliferative response, in some embodiments, by administration or implantation of a leptin antagonist composition to an inner or outer vessel wall in the vicinity of a vascular lesion);

Marfan's syndrome (by mitigation or prevention of ascending aortic aneurysms or pulmonary artery aneurysms, in some embodiments, by perivascular administration or deployment of a leptin antagonist composition to the outer or inner wall of the ascending aorta); giant cell arteritis; ankylosing spondylitis; inflammatory aortic aneurysm; peripheral arterial or venous aneurysms; prevention of arterial dilatation at site of anchorage of bridging stent grafts ("landing zone") applied for EVAR (in the abdominal or thoracic aorta), visceral or peripheral arteries; prevention of myointimal hyperplasia at sites of vascular injury; prevention of restenosis following PTA or PTCA (peripheral or cardiac balloon angioplasty); angiogenesis; cancer; and arteriovenous malformation (e.g., administration of leptin antagonist composition directly into a malformation or into the feeding artery).

Depending on the embodiment, any pathology, including any pathology listed above, may be treated in accordance with the teachings herein by local administration of leptin antagonist. For example, in some embodiments, administration is local administration of a dose (optionally repeated) of leptin antagonist, for example by direct injection into the affected tissue or tissue proximal to the affected tissue or with the use of a drug-eluting balloon. For example, in some embodiments, administration is local administration by a sustained release composition (that releases a pharmaceutically-effective amount of leptin antagonist for a period of not less than three days) placed in contact with an outer surface of tissue (e.g., with tunica externa), inside the tissue (e.g., injection of a IFSD as described above into the tissue) or with a composition placed in contact with an inner surface of a tissue (e.g. with tunica intima).

The tissue is any suitable tissue. In some embodiments the tissue is part of the cardiovascular system. In some such embodiments, the tissue is selected from the group consisting of arteries, coronary arteries, ascending aorta, abdominal aorta, mitral valve, aortic valve and pulmonary valve. In some embodiments, the tissue is cardiovascular tissue with accumulated plaque, for example, an artery with accumulated plaque. In some embodiments, the tissue is a tumor, especially a cancerous tumor that grows or spreads in a process that includes angiogenesis. In some embodiments, the tissue is an arteriovenous malformation.

In some embodiments, the leptin antagonist composition is locally administered during or post surgery, e.g., following carotid thrombendartrectomy or after ablation of atherosclerotic occlusion from a vessel.

In some embodiments, the leptin antagonist is locally administered by contact to the outside of tissue to be treated, e.g., in contact with tunica externa.

In some embodiments, the leptin antagonist is locally administered inside tissue, for example, is injected or implanted inside tissue such as a tumor or the site of arteriovenous malformation.

In some embodiments, the leptin antagonist is locally administered intraluminally, e.g., a leptin antagonist composition is deployed in contact with a tunica intima, inside a fluid-filled bodily cavity such as inside the lumen of a blood vessel e.g., using an intraluminal catheter, for example, in conjunction with a stent or prosthetic cardiac valve.

It should be noted that in some embodiments, local administration of a leptin antagonist in accordance with the teachings herein at the ascending aorta may be effective in attenuating ascending aortic aneurysms, as well as moderating left ventricular hypertrophy, and left heart valve thickness (aortic and mitral). Administration of leptin antagonist at arterial aneurysms in other locations is anticipated to achieve a similar outcome, attenuating aneurysm expansion.

Accordingly, embodiments of the teachings herein are used to treat cardiovascular disorders such as heart valve stenosis, arterial or venous aneurysms, or left ventricular remodeling by enabling localized release of a leptin antagonist at the site of treatment.

Pharmaceutical Composition and Method of Making Pharmaceutical Composition

According to an aspect of some embodiments of the teachings herein, there is also provided a pharmaceutical composition, comprising: as an active ingredient a leptin antagonist; and a pharmaceutically acceptable carrier configured for in vivo sustained release of the leptin antagonist.

According to an aspect of some embodiments of the teachings herein, there is also provided a method of making a pharmaceutical composition, comprising: combining a leptin antagonist; and a pharmaceutically acceptable carrier configured for in vivo sustained release of the leptin antagonist.

In some embodiments, by sustained release is meant that, when the composition is implanted in vivo, leptin antagonist is released from the composition in pharmaceutically effective amounts for a period of not less than three days, in some embodiments not less than five days, not less than 8 days and even not less than 14 days.

In some embodiments, the in vivo implantation is in a human subject. The in vivo implantation is in any suitable location. In some embodiments, the in vivo implantation is contacting an organ through a serous tissue layer or adventitia (tunica externa) layer covering the organ, e.g., is placed contacting a blood vessel such as the aorta from the outside of the blood vessel. In some embodiments, the in vivo implantation is outside an organ directly contacting tissue of the organ (for organs covered with serous tissue, the composition is implanted underneath the serous tissue). In some embodiments, the in vivo implantation is into an organ. In some embodiments, the implantation is from inside a hollow defined by the organ, for example, inside a blood vessel lumen contacting the endothelium thereof.

In some embodiments, the composition is in the form of a leptin antagonist containing sheet, in some such embodiments configured to be contacted with in vivo tissue, for example, by suturing, with the use of biological adhesive, or pressed against the tissue, for example with the help of a stent or such component, e.g., the sheet is used as a stent cover for a balloon-expandable or self-expanding stent.

In some embodiments, the composition is configured to coat or be supported by an implantable medical device, e.g., is used as a coating for, is adsorbed or absorbed into or onto a stent (thereby constituting a drug-eluting balloon expandable or self-expanding stent), prosthetic valve (e.g., cardiac valve), implantable spike or rod.

In some embodiments, the composition is formed into the shape of an implantable medical device, e.g., a bioresorbable stent, a bioresorbable spike or rod.

In some embodiments, the composition is injectable, e.g., is a viscous fluid or a fluid that subsequent to injection solidifies or gels, e.g., a hydrogel.

Any suitable pharmaceutically-acceptable carrier that can be configured for in vivo sustained release of the leptin antagonist can be used. In some embodiments the carrier comprises a biodegradable polymer. In some such embodiments, the carrier comprises a polymer selected from the group consisting of a hydrogel, poly glycolic acid (PGA), poly lactic co-glycolic acid (PLGA), polylactide (PLA), and poly (L-lactide) (PLLA), and combinations thereof.

The pharmaceutical composition and methods of making such a composition are in accordance with those known in the art of pharmacology, using any suitable method or combination of methods as known in the art such as described in "Remington's Pharmaceutical Sciences." Mack Publishing Co., Easton, Pa., latest edition, which is incorporated herein by reference. Such methods include conventional mixing, curing, polymerizing, dissolving, granulating, dragee-making, levigating, emulsifying, encapsulating, entrapping or lyophilizing. Pharmaceutical compositions may be formulated in conventional manner using one or more physiologically acceptable carriers, diluents, excipients or auxiliaries which facilitate processing of the leptin antagonist into a pharmaceutical composition.

Use of Leptin Antagonist

According to an aspect of some embodiments of the teachings herein, there is also provided a use of a leptin antagonist according to the teachings herein for the localized treatment of tissue of a living organism, comprising, implanting a composition comprising a leptin antagonist in vivo to contact tissue in need thereof so that the tissue is exposed to a pharmaceutically effective amount of leptin antagonist, thereby providing a therapeutic effect to the tissue. In some embodiments, the composition and the implanting is such that the tissue is exposed to a pharmaceutically effective amount of leptin antagonist substantially continuously for a period of at least three days. In some embodiments, the period is not less than five days, not less than 8 days and even not less than 14 days.

In some embodiments, an above administration is periodically repeated. For example, in some embodiments, administration of leptin antagonist is repeated. For example, in some embodiments, administration of leptin antagonist is repeated after at least a period, the period selected from the group consisting of 1 week, 2 weeks, 3 weeks, 4 weeks, 1 month, 2 months and 3 months.

Treatment of Athersclerotic Plaque

It is known that stable athersclerotic plaque accumulates in the inner walls of mammalian arteries. In some instances, the stable plaque transforms into an unstable lesion such as vulnerable plaque or rupture-prone plaque. The unstable lesion may disintegrate, forming emboli.

An aspect of the teachings herein is based on the Inventor's discovery that locally synthesized leptin within the carotid atherosclerotic plaque, which characterize unstable plaques (rupture prone), correlates with brain emboli. Therefore, the Inventor believes that a leptin antagonist administered to a stable athersclerotic plaque should reduce the rate and/or incidence of the conversion of a stable athersclerotic plaque to an unstable lesion.

According to an aspect of some embodiments of the teachings herein, there is provided a method for treatment of athersclerotic plaque, comprising: administering a pharmaceutically-effective amount of a leptin antagonist to athersclerotic plaque accumulated in the inner walls of an artery, thereby at least one of: (a) reducing the rate and (b) reducing the incidence, of conversion of a stable athersclerotic plaque to an unstable lesion.

Administration of the leptin antagonist is any suitable administration. In some embodiments, the administration is by sustained-release of the leptin antagonist directly to an inner wall in which plaque is accumulated, from a leptin antagonist containing composition. In some embodiments, such sustained release is substantial continuous release of a pharmaceutically-effective amount of leptin antagonist for a period of not less than three days, not less than 5 days, not less than 8 days and even not less than 14 days. In some such embodiments, the composition is in direct contact with the surface of the plaque to be treated. In some embodiments, the composition is in contact with the inner walls of a blood vessel with accumulated plaque.

Surgical Connecting Devices

It is know that trauma to a blood vessel may lead to myointimal hyperplasia (MIH), One type of trauma that may cause MIH is caused by surgical connecting devices such as surgical staples and suture threads that are applied to blood vessels, for example, during surgery for example surgical anastomosis. It has been found that in some instances, local administration of leptin antagonist to such wounds may be able to mitigate or prevent MIH.

Thus, according to an aspect of some embodiments of the invention, there is also provided a surgical connecting device, comprising: a solid device body made of a material; and functionally associated with the device body, a pharmaceutically-effective amount of leptin antagonist. In some embodiments, the device body is in the form selected from the group consisting of surgical suture thread and a surgical staple.

An embodiment of a suture thread 10 and of a surgical staple 12 in accordance with the teachings herein are schematically depicted in FIG. 27.

In some embodiments, the device body, e.g., of thread 10 or staple 12, is absorbable (i.e., bioresorbable).

The device body, e.g., of thread 10 or staple 12, is made of any suitable material. In some embodiments, the device body is made of a material comprises a polymer selected from the group consisting of poly glycolic acid (PGA), poly lactic co-glycolic acid (PLGA), polylactide (PLA), and poly (L-lactide) (PLLA), and combinations thereof.

The leptin antagonist is functionally associated with the device body, e.g., of thread 10 or staple 12, in any suitable manner.

In some embodiments, the functional association of the leptin antagonist with the device body is that a composition comprising the leptin antagonist coats the device body. For example, in some such embodiments thread 10 or staple 12 are made of PGA, and coated with a coating of PLGA that includes a pharmaceutically effective amount of leptin antagonist.

In some embodiments, the functional association of the leptin antagonist with the device body is that a composition comprising the leptin antagonist impregnates the device body. For example, in some such embodiments thread 10 is made of silk and impregnated with a composition that includes a pharmaceutically effective amount of leptin antagonist.

In some embodiments, the functional association of the leptin antagonist with the device body is that the material from which the device body is made is a composition comprising the leptin antagonist. For example, in some such embodiments thread 10 or staple 12 are made of PGA that includes a pharmaceutically effective amount of leptin antagonist.

Administration of Leptin Antagonist in Fluid-filled Cavities

As noted above, the present inventor has found that in vivo implantation inside a fluid-filled cavity of the body (for example of the cardiovascular system such as blood vessels or cardiac chambers) can have a desirable pharmaceutical effect on tissue in proximity of the implanted composition with limited or no substantial side-effects:

Method of Treatment in a Fluid-filled Bodily Cavity

Thus, according to an aspect of some embodiments of the invention, there is also provided a method of treating a condition in a subject in need thereof, the method comprising administering intracavitarily to inner walls of a fluid-filled bodily cavity of the subject a composition comprising a leptin antagonist. In some embodiments of the method, the subject is human. In some embodiments of the method, the subject is a non-human animal.

In some embodiments of the method, the intracavitary administration exposes in vivo tissue to a pharmaceutically-effective amount of the leptin antagonist and thereby provides a therapeutic effect to the in vivo tissue.

In some embodiments of the method, the in vivo tissue comprises tissue of the inner walls of the cavity (e.g., tunica intima).

In some embodiments of the method, the administration is local administration. In some such embodiments, the in vivo tissue exposed to the pharmaceutically-effective amount of the leptin antagonist is exclusively tissue in physical proximity to the administered composition. In some such embodiments, the in vivo tissue exposed to the pharmaceutically-effective amount of the leptin antagonist is exclusively tissue in physical contact with the administered composition.

In some embodiments of the method, exposing of the in vivo tissue to a pharmaceutically-effective amount of the leptin antagonist is substantially continuously for a period of at least three days, at least five days, at least eight days and in some embodiments, even at least fourteen days.

In some embodiments of the method, the composition is a sustained-release composition, configured for sustained release of a pharmaceutically-effective amount of the leptin antagonist when located inside a bodily cavity. In some embodiments, the sustained release comprises release of a pharmaceutically-effective amount of the leptin antagonist over a period of at least three days, at least five days, at least eight days and in some embodiments, even at least fourteen days.

In some embodiments of the method, the intracavitary administering comprises implantation of the composition within the cavity in contact with the inner walls of the cavity.

In some embodiments of the method, the intracavitary administering comprises deploying an intracavitarily-implantable medical device in the cavity. In some such embodiments, the medical device is deployed in contact with the inner walls of the cavity. In some such embodiments, the leptin antagonist is functionally associated with the deployed intracavitarily-implantable medical device. In some preferred such embodiments, the leptin antagonist is functionally associated with a portion of the deployed intracavitarily-implantable medical device that contacts bodily tissue when the medical device is deployed. In some such embodiments, the intracavitarily implantable medical device is selected from the group consisting of: a stent cover, a graft assembly, a coil (e.g., aneurysm coil), a stent (e.g., expandable stent, self-expanding stent, covered stent, partially covered stent, not covered stent), a ring (e.g, a graft anchor), a suture, a staple and a prosthetic cardiac valve. Although the teachings herein are applicable to any prosthetic cardiac valve, the teachings are particularly advantageous for implementing with catheter-deployed prosthetic cardiac valves (e.g., TAMVI, TAVI); since these valves are typically held in place without sutures so that myointimal hyperplasia that potentially develops as a result of trauma caused during deployment may lead to leakage.

Composition for Treatment in a Fluid-filled Bodily Cavity

According to an aspect of some embodiments of the invention, there is also provided a composition comprising: a leptin antagonist for use in treating a condition, wherein the composition is configured for intracavitary administration to inner walls of a fluid-filled bodily cavity of a subject.

In some embodiments of the composition, the subject is human. In some embodiments of the composition, the subject is a non-human animal.

In some embodiments, the intracavitary administration of the composition exposes in vivo tissue to a pharmaceutically-effective amount of the leptin antagonist, thereby providing a therapeutic effect to the in vivo tissue. In some embodiments, such in vivo tissue comprises tissue of inner walls of a the cavity.

In some embodiments, the administration is local administration. In some such embodiments, the in vivo tissue exposed to the pharmaceutically-effective amount of the leptin antagonist is exclusively tissue in physical proximity to the administered composition. In some such embodiments, the in vivo tissue exposed to the pharmaceutically-effective amount of the leptin antagonist is exclusively tissue in physical contact with the administered composition.

In some embodiments of the composition, exposing of the in vivo tissue to a pharmaceutically-effective amount of the leptin antagonist is substantially continuously for a period of at least three days, at least five days, at least eight days and in some embodiments, even at least fourteen days.

In some embodiments, the composition is a sustained-release composition, configured for sustained release of a pharmaceutically-effective amount of the leptin antagonist when located inside a bodily cavity. In some embodiments, the sustained release comprises release of a pharmaceutically-effective amount of the leptin antagonist over a period of at least three days, at least five days, at least eight days and in some embodiments, even at least fourteen days.

In some embodiments of the composition, the configuration for intracavitary administration comprises configuration for implantation of the composition within the cavity in contact with the inner walls of the cavity.

In some embodiments of the composition, the configuration for intracavitary administration comprises configuration for deploying with an intracavitarily-implantable medical device in the cavity. In some such embodiments, the medical device is configured for deployment in contact with the inner walls of the cavity. In some such embodiments, the leptin antagonist is functionally associated with the intracavitarily-implantable medical device. In some preferred such embodiments, the leptin antagonist is functionally associated with a portion of the intracavitarily-implantable medical device that contacts bodily tissue when the medical device is deployed. In some such embodiments, the intracavitarily implantable medical device is selected from the group consisting of: a stent cover, a graft assembly, a coil (e.g., aneurysm coil), a stent (e.g., expandable stent, self-expanding stent, covered stent, partially covered stent, not covered stent), a ring (e.g, a graft anchor), a suture, a staple and a prosthetic cardiac valve. As noted above, although the teachings herein are applicable to any prosthetic cardiac valve, the teachings are particularly advantageous for implementing with catheter-deployed prosthetic cardiac valves (e.g., TAMVI, TAVI).

In some embodiments of the method or composition, the condition is a pathological cardiovascular condition. In some embodiments of the method or composition, the condition is a cardiovascular condition selected from the group consisting of atherosclerosis, valve stenosis, aneurysms, vessel response to vascular injury, and cardiomyopathy. In some embodiments of the method or composition, the administration of the leptin antagonist is to atherosclerotic plaque accumulated in the inner walls of an artery, thereby at least one of: (a) reducing the rate and (b) reducing the incidence, of conversion of a stable athersclerotic plaque to an unstable lesion. In some embodiments of the method or composition, the administration of the leptin antagonist is to bodily tissue in order to prevent or mitigate the development of myointimal hyperplasia, for example, myointimal hyperplasia that potentially develops as a result of trauma caused during deployment of a medical device in a the body of a living subject.

In some embodiments of the method or composition, the composition constitutes a coating of an intracavitarily implantable medical device. In some embodiments of the method or composition, the composition is impregnated in an intracavitarily implantable medical device. In some such embodiments of the method or composition, the composition comprises, in addition to the leptin antagonist, a polymer selected from the group consisting of a hydrogel, poly glycolic acid (PGA), poly lactic co-glycolic acid (PLGA), polylactide (PLA), and poly (L-lactide) (PLLA), and combinations thereof.

In some embodiments of the method or composition, the composition is in the form selected from the group consisting of a sheet and a tube constituting a portion of an intracavitarily implantable medical device comprising the leptin antagonist. In some such embodiments of the method or composition, the composition comprises, in addition to the leptin antagonist, a polymer selected from the group consisting of a hydrogel, poly glycolic acid (PGA), poly lactic co-glycolic acid (PLGA), polylactide (PLA), and poly (L-lactide) (PLLA), and combinations thereof. In some such embodiments of the method or composition, the intracavitarily implantable medical device comprises a stent and the composition constitutes a stent cover (e.g., a partial or complete stent cover, a balloon-expandable or a self-expanding stent). In some such embodiments of the method or composition, the intracavitarily implantable medical device comprises a graft-assembly (e.g., a stent-graft or ring-graft assembly) and the composition constitutes a graft portion thereof. For example, some embodiments are configured to function as a stent-graft assembly for treatment of AAA, like the Endurant® II by Medtronic (Dublin, Ireland).

In some embodiments of the method or composition, the composition constitutes at least a portion of an intracavitarily implantable medical device, and in some embodiments, the composition constitutes substantially an entire intracavitarily implantable medical device. As noted above, in some such embodiments of the method or composition, the intracavitarily implantable medical device is selected from the group consisting of a stent cover, a graft assembly, a coil (e.g., aneurysm coil), a stent (e.g., expandable stent, self-expanding stent, covered stent, partially covered stent, not covered stent), a ring (e.g, a graft anchor), a suture, a staple and a prosthetic cardiac valve. In some such embodiments of the method or composition, the composition comprises, in addition to the leptin antagonist, a polymer selected from the group consisting of a hydrogel, poly glycolic acid (PGA), poly lactic co-glycolic acid (PLGA), polylactide (PLA), and poly (L-lactide) (PLLA), and combinations thereof.

Medical Device for Treatment in a Fluid-filled Bodily Cavity

According to an aspect of some embodiments of the invention, there is also provided an intracavitarily-implantable medical device, comprising:

at least one solid functional device part configured for deploying the device in a fluid-filled bodily cavity of a subject; and functionally associated with at least one the device component, a leptin antagonist.

In some embodiments of the medical device, the leptin antagonist is functionally associated with the at least one the device part as a component of a pharmaceutical composition comprising the leptin antagonist.

In some embodiments of the medical device, the pharmaceutical composition is a sustained-release composition, configured for sustained release of a pharmaceutically-effective amount of the leptin antagonist when located inside a bodily cavity.

In some embodiments of the medical device, sustained release comprises release of a pharmaceutically-effective amount of the leptin antagonist over a period of at least three days, at least five days, at least eight days and in some embodiments, even at least fourteen days.

In some embodiments of the medical device, the pharmaceutically-acceptable carrier further comprises a polymer selected from the group consisting of a hydrogel, poly glycolic acid (PGA), poly lactic co-glycolic acid (PLGA), polylactide (PLA), and poly (L-lactide) (PLLA), and combinations thereof.

In some embodiments of the medical device, the functional association is at least one device component having a coating comprising the pharmaceutical composition. In some embodiments of the medical device, the functional association is at least one device component being impregnated with the pharmaceutical composition. In some embodiments of the medical device, the functional association is at least one device component being fashioned of the pharmaceutical composition.

In some embodiments of the medical device, the medical device is selected from the group consisting of a stent cover, a graft assembly, a coil (e.g., aneurysm coil), a stent (e.g., expandable stent, self-expanding stent, covered stent, partially covered stent, not covered stem), a ring (e.g, a graft anchor), a suture, a staple and a prosthetic cardiac valve (as noted above, preferably catheter-deployed prosthetic cardiac valves.

In some embodiments of the method, composition and device, the fluid-filled bodily cavity is a bodily cavity of the cardiovascular system. In some such embodiments, the cavity is selected from the group consisting of a cardiac chamber, an artery and a vein. In some such embodiments, the cardiac chamber is selected from the group consisting of left ventricle, right ventricle, left atrium and right atrium. In some such embodiments, the artery is selected from the group consisting of a systemic artery, a cardiac artery and a pulmonary artery. In some such embodiments, the systemic artery is an aorta, for example selected from the group consisting of an ascending aorta, aortic arch, descending aorta and an abdominal aorta.

In FIG. 28, an aneurysm coil 14 according to the teachings herein is schematically depicted. Aneurysm coil 14 is substantially similar to known aneurysm coils except by being functionally associated with a pharmaceutically-effective amount of leptin antagonist, is made in substantially the same way, and is used in substantially the same way. Depending on the embodiment, a given aneurysm coil 14 may include one or more of the additional features detailed hereinabove. For example, in some embodiments, coil 14 is made of platinum, and coated with a coating of a hydrogel that includes a pharmaceutically effective amount of leptin antagonist. For example, in some embodiments, coil 14 is made of a material such as platinum or a polymer textured with micrometer dimension features such as valleys and pores, where inside the features is held a composition (e.g., a gel such as of Example 11) that comprises leptin antagonist. For example, in some embodiments, coil 14 is made of a composition comprising the leptin antagonist, e.g., is made of PGA that includes a pharmaceutically effective amount of leptin antagonist.

In FIG. 28, a prosthetic cardiac valve 16 according to the teachings herein is schematically depicted. Prosthetic cardiac valve 16 is substantially similar to known prosthetic cardiac valves except by being functionally associated with a pharmaceutically-effective amount of leptin antagonist, is made in substantially the same way, and is used in substantially the same way. Specifically, prosthetic cardiac valve 16 has at least one component that is functionally associated with a pharmaceutically-effective amount of leptin antagonist. Depending on the embodiment, a given prosthetic cardiac valve 16 according to the teachings herein may include one or more components, each having one or more of the additional features detailed hereinabove. For example, in some embodiments, the retainer ring of prosthetic cardiac valve 16 is made of a cobalt chromium ring with a polyester cloth cover, the ring and cloth cover both coated with a coating of a hydrogel that includes a pharmaceutically effective amount of leptin antagonist. For example, in some embodiments, the leaflets of prosthetic cardiac valve 16 are made of a material such as porcine or bovine tissue (e.g., cardiac leaflets, pericardium) that has been soaked in and is therefore impregnated with a composition (e.g., a gel such as of Example 11) that comprises leptin antagonist.

In FIG. 28, a graft assembly 18 according to the teachings herein is schematically depicted. Graft assembly 18 is a ring-graft assembly suitable for treatment of abdominal aorta aneurysms and includes a flexible graft 20 that defines a conduit for blood flow and three expandable anchoring rings 22 as graft anchors. Each anchoring ring 22 is a radially expandable device that is substantially a single 360° ring of material. As known in the art, some embodiments of graft assemblies are stent-graft assemblies where one or more of the anchors are radially expandable stents, that are longer in the axial direction and/or describe more than a 360° degree rotation and/or comprise more than a single ring of material. Stents are preferred as anchors as these typically also provide support for the vessel in which deployed and provide greater anchoring of the graft to a vessel in which deployed. Graft assembly 18 is substantially similar to known graft assemblies except by being functionally associated with a pharmaceutically-effective amount of leptin antagonist, is made in substantially the same way, and is used in substantially the same way. Specifically, graft assembly 18 has at least one component that is functionally associated with a pharmaceutically-effective amount of leptin antagonist. Depending on the embodiment, a given graft assembly 18 according to the teachings herein may include one or more components, each having one or more of the additional features detailed hereinabove.

For example, in some embodiments, graft 20 is substantially a tube made of a high-density multifilament polyester cloth coated with a coating of a hydrogel that includes a pharmaceutically effective amount of leptin antagonist. In some embodiments, the coating is on the entire outer surface of graft 20. In some embodiments, the coating is on the outer surface of the termini of the three legs of graft 20 (e.g., a 5 cm length from each terminus.

For example, in some embodiments, graft 20 is made of a high-density multifilament polyester cloth coat that has been soaked in and is therefore impregnated with a composition (e.g., a gel such as of Example 11) that comprises leptin antagonist. In some embodiments, the entire graft 20 is impregnated with leptin antagonist composition. In some embodiments, only the termini of the three legs of graft 20 (e.g., a 5 cm length from each terminus) is impregnated with leptin antagonist composition.

For example, in some embodiments, rings 22 are made of nitinol, and coated with a coating of a hydrogel that includes a pharmaceutically effective amount of leptin antagonist. For example, in some embodiments, rings 22 are made of a material such as nitinol textured with micrometer dimension features such as valleys and pores, where inside the features is held a composition (e.g., a gel such as of Example 11) that comprises leptin antagonist.

Figure 29:
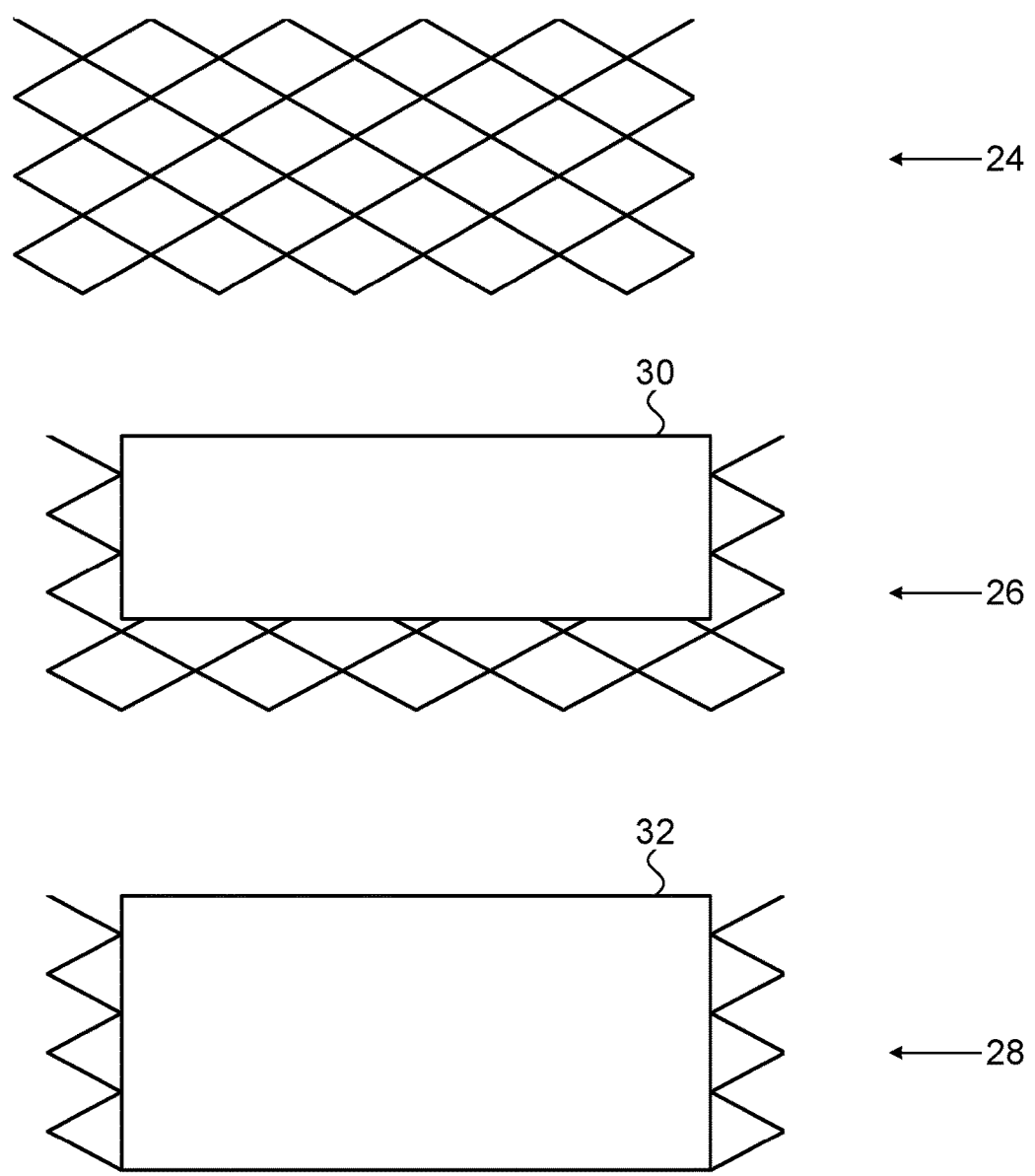
FIG. 29 schematically depicts further embodiments of the teachings herein suitable for intracavitary administration of leptin antagonist.

In FIG. 29, stents 24, 26 and 28 according to the teachings herein are schematically depicted. Stents 24, 26 and 28 are all elongated, tubular, outwardly radially-expandable frameworks that are known in the art. Stent 24 is a coverless stent without a cover. Stent 26 is a partially-covered stent with a partial cover 30. Partial cover 30 is a sheet secured to the framework of stent 26 in the usual way, e.g., with sutures. Stent 28 is a covered stent with a full cover 32. Full cover 30 is a tube secured to the framework of stent 28 in the usual way, e.g., with sutures or by tension.

Stents 24, 26 and 28 are substantially similar to known stents except by being functionally associated with a pharmaceutically-effective amount of leptin antagonist, are made in substantially the same way, and are used in substantially the same way. Specifically, each one of stents 24, 26 and 28 has at least one component that is functionally associated with a pharmaceutically-effective amount of leptin antagonist. Depending on the embodiment, a given stent 24, 26 and 28 according to the teachings herein may include one or more components, each having one or more of the additional features detailed hereinabove. Embodiments of any one of stents 24, 26 and 28 are self-expanding stents. Embodiments of any one of stents 24, 26 and 28 are balloon-expandable stents.

For example, in some embodiments, a cover 30 or a cover 32 is made of a high-density multifilament polyester cloth coated with a coating of a hydrogel that includes a pharmaceutically effective amount of leptin antagonist, typically on the outer surface of the cover.

For example, in some embodiments, a cover 30 or a cover 32 is made of a high-density multifilament polyester cloth coated that has been soaked in and is therefore impregnated with a composition (e.g., a gel such as of Example 11) that comprises leptin antagonist.

For example, in some embodiments, a cover 30 or a cover 32 is made of a material that is a composition comprising leptin antagonist, e.g., a PLGA sheet of example 4.

For example, in some embodiments, a framework of any one of stents 24, 26 and 28 is made of cobalt chromium coated with a coating of a hydrogel that includes a pharmaceutically effective amount of leptin antagonist.

For example, in some embodiments, a framework of any one of stents 24, 26 and 28 is made of a material such as nitinol or a polymer textured with micrometer dimension features such as valleys and pores, where inside the features is held a composition (e.g., a gel such as of Example 11) that comprises leptin antagonist.

For example, in some embodiments, a framework of any one of stents 24, 26 and 28 is made of a material that is a composition comprising leptin antagonist, e.g., PLA or PLLA comprising a pharmaceutically-effective amount of leptin antagonist.

Suitable Leptin Antagonists

Any suitable leptin antagonist may be used in implementing any specific aspect or embodiment of the teachings herein. In some embodiments, a single leptin antagonist is used. In some embodiments, two or more leptin antagonists are used simultaneously or concurrently.

Various leptin antagonists suitable for implementing the teachings herein have been described in detail hereinabove.

In some embodiments, the leptin antagonist comprises a polypeptide portion.

In some embodiments, the leptin antagonist is a polypeptide.

Preferred leptin antagonists include all of the leptin antagonists listed and taught in U.S. Pat. No. 7,307,142 (SEQ ID NOs 3-35) and U.S. Pat. No. 8,969,292 (SEQ ID NOs 36-47), which are both included by reference as if fully set-forth herein. In some embodiments, the leptin antagonist is selected from the group consisting of:

a leptin antagonist consisting of: (a) a mammalian leptin polypeptide in which the LDFI (SEQ ID NO:33 in U.S. Pat. No. 7,307,142 or SEQ ID NO 35 in the preset application) hydrophobic binding site at the positions corresponding to positions 39-42 of the wild-type human leptin, is modified such that from two to four amino acid residues of the hydrophobic binding site are substituted with different amino acid residues such that the site becomes less hydrophobic, the modified, mammalian leptin polypeptide being a leptin antagonist (b) a fragment of the modified mammalian leptin polypeptide of (a) comprising the altered hydrophobic binding site, wherein the fragment is itself a leptin antagonist; (c) a fragment of (b)

a synthetic leptin antagonist comprising: (d) a full length modified mammalian leptin polypeptide in which: (i) the LDFI hydrophobic binding site at the position corresponding to positions 39-42 of the wild-type human leptin is modified such that from two to four amino acid residues of the hydrophobic binding site are substituted with different amino acid residues such that the site becomes less hydrophobic; and (ii) the aspartic acid at the position corresponding to position 23 of the wild-type human leptin (D23) is substituted with an amino acid residue selected from the group consisting of glycine, alanine, leucine, lysine, arginine, phenylalanine, tryptophan and histidine, or the threonine at the position corresponding to position 12 of the wild-type human leptin (T12) is substituted with a different amino acid residue that is hydrophobic; (e) a synthetic leptin antagonist consisting of a polypeptide having the amino acid sequence of SEQ ID NO: 1 of U.S. Pat. No. 8,969,292 or SEQ ID NO 36 of the present application;

(f) a modified mammalian leptin polypeptide in which: (i) the LDFI hydrophobic binding site at the position corresponding to 5 positions 39-42 of the wild-type human leptin is modified such that from two to four amino acid residues of the hydrophobic binding site are substituted with different amino acid residues such that the site becomes less hydrophobic, the modified mammalian leptin polypeptide being a leptin antagonist; and (ii) the aspartic acid at the position corresponding to position 23 of the wild-0 type human leptin (D23) is substituted with a different amino acid residue that is not negatively charged or the threonine at the position corresponding to position 12 of the wild-type human leptin (T12) is substituted with a different amino acid residue that is hydrophobic;

(g) a fragment of the modified mammalian leptin polypeptide of (f), in which D235 is substituted with a different amino acid residue that is not negatively charged or T12 is substituted with a different amino acid residue that is hydrophobic, wherein the fragment is itself a leptin antagonist;

a synthetic leptin agonist comprising: (h) a modified mammalian leptin polypeptide in which D23 is substituted with a different amino acid residue that is not negatively charged or T12 is substituted with a different amino acid residue that is hydrophobic;

(j) a fragment of the modified mammalian leptin polypeptide of (h), in which D23 is substituted with a different amino acid residue that is not negatively charged or T12 is substituted with a different amino acid residue that is hydrophobic, wherein the fragment is itself a leptin agonist;

(k) any one of the above wherein the mammalian leptin is selected from the group consisting of human, ovine and murine;

(l) any one of (a), (b), (c), (d), (e), (f), (g), (h), (j) and (k) in pegylated form; and a pharmaceutically acceptable salt of any one of (a)-(l).

Unless otherwise defined, all technical and scientific terms used herein have the same meaning as commonly understood by one of ordinary skill in the art to which the invention pertains. In case of conflict, the specification, including definitions, will take precedence.

As used herein, intracavitary relates to within an organ or body cavity.

Art that provides enabling support for the teachings herein, and that may also be useful in understanding the background and the inventive aspects of the teachings herein includes U.S. Pat. Nos. 7,307,142; 8,969,292; "leptin Locally Synthesized in Carotid Atherosclerotic Plaques Could Be Associated With Lesion Instability and Cerebral Emboli" by Schneiderman J et al in J Am Heart Assoc. 2012, 1:e001727 doi: 10.1161/JAHA.112.001727 and "Locally Applied leptin Induces Regional Aortic Wall Degeneration Preceding Aneurysm Formation in Apolipoprotein E-Deficient Mice" by Tao M et al in Arterioscler Thromb Vase Biol. 2013; 33:311-320, all four which are included by reference (together with any published supplemental materials) as if fully set-forth herein.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein, when a numerical value is preceded by the term "about", the term "about" is intended to indicate +/−10%.

Additional objects, advantages, and novel features of the present invention will become apparent to one ordinarily skilled in the art upon examination of the following examples, which are not intended to be limiting.

EXAMPLES

Reference is now made to the following examples, which together with the above descriptions, illustrate the invention in a non limiting fashion.

Example 1

Localized Leptin Synthesis in a Mouse Model

A novel mouse model was used to simulate local leptin synthesis in the ascending aorta in order to assess the effect of leptin on aortic remodeling and heart structure and function.

Materials and Methods

Figure 4:
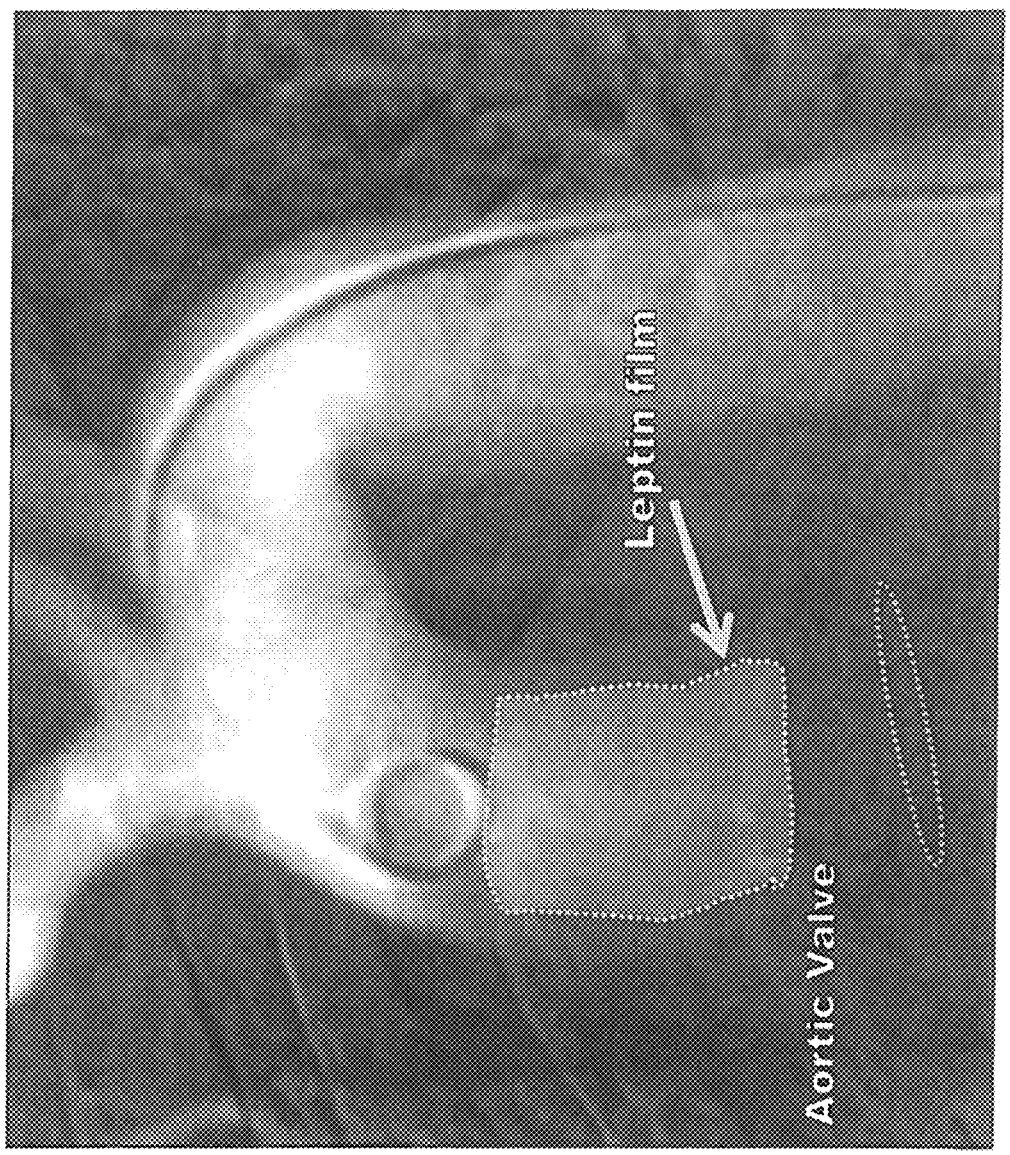
FIG. 4 illustrates the location of leptin film application on the anterior outer surface of the ascending aorta. Human arch angiogram depicts mouse anatomy.
Figure 5:
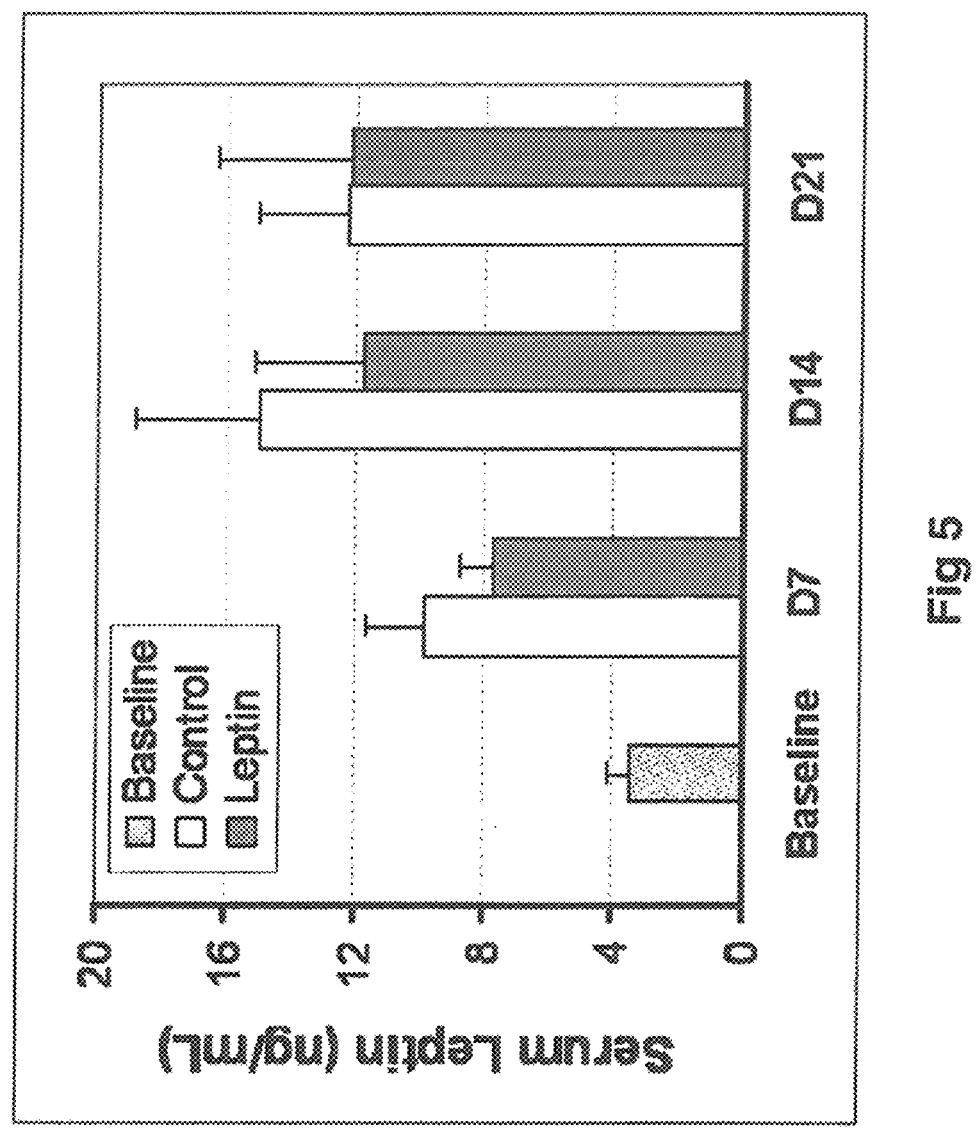
FIG. 5 illustrates a time course analysis of serum leptin level in ApoE$^{-/-}$ mice that underwent peri-aortic application of leptin film (20 µg).

A slow release leptin film (FIG. 1b) made of polylactic co-glycolic acid (PLGA) matrix (1×1.5 mm), and containing either 2 µg leptin or no protein (control) was applied to the anterior surface of the proximal ascending aorta (FIG. 4).

The leptin slow-release film was manufactured by impregnating a poly lactic-co-glycolic acid (PLGA) film with leptin. One gram of PLGA 6535 polymer (D,L-lactide:glycolide: 65:35, Mw=45,000-75,000 Da; Lakeshore. Biomaterials, Birmingham, Ala., USA) was dissolved in 10 mL $MgCl_2$ (Fisher Scientific, Loughborough, UK). Sodium chloride (10 mg in 0.2 mL distilled water) and 25 µL ethylene glycol (Sigma-Aldrich, St. Louis, Mo., USA) were added to the polymeric solution and sonicated for 20 seconds. Mouse leptin powder (1 mg; #L3772; Sigma-Aldrich, St. Louis, Mo., USA) was suspended in 2 mL of the polymeric solution, followed by casting on a flat surface of Teflon molds to create a flat film. Films were dried in a hood for 48 hours, and then subjected to high vacuum for 12 hours to extract any residual solvent. Control (placebo) films were fabricated in the same way without the addition of leptin. The calculated amount of leptin per 1×1.5-mm film used currently for implantation in each mouse was 2 µg.

Another option of leptin application for local slow-release has been a gel composed of two liquid materials which gel (solidify) upon mixing at the time of injection. These are a modified carboxymethyl cellulose with adipic dihydrazide (CMC-ADH) and an oxidized dextrane in DDW (DX-COH). Methylene blue dye (0.5%) was also added to the DX-COH solution to make the resulting gel more visible. Leptin (Sigma, L3772, St. Louis, Mo., USA) was added to the gel by an emulsion technique.

Figure 6:
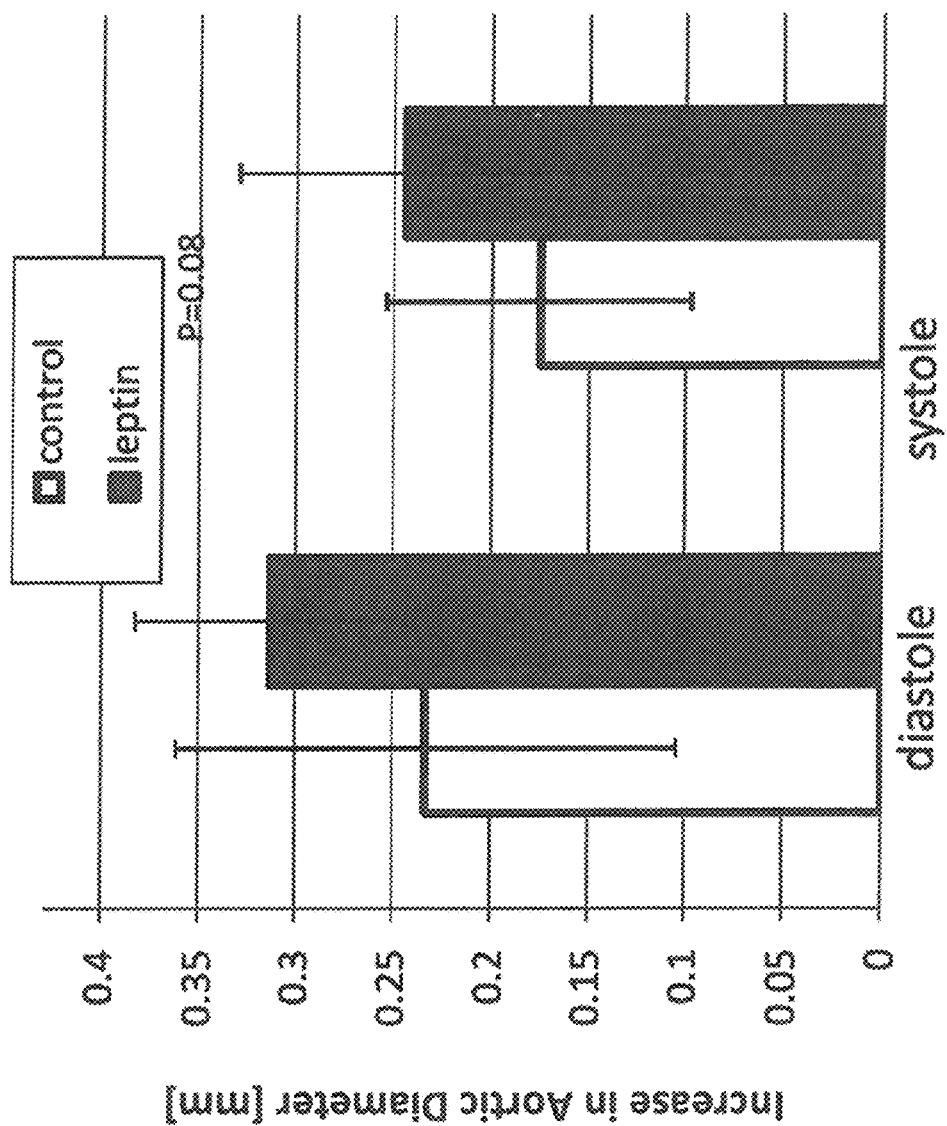
FIG. 6 illustrates increased ascending aortic diameter at the location of leptin film application versus controls.

Serum leptin levels were determined in ApoE$^{-/-}$ mice after receiving 20 µg mouse leptin via peri-aortic application (in another experiment, Tao et al. ATVB 2013). Blood was samples on days 0, 7, 14, and 21, and leptin analyzeded by ELISA assay (Quantikine Mouse Lep Kit, R&D Systems, Minneapolis, Minn., USA): Day 0—3.5 ng/mL; day 7—leptin 8.0 ng/mL, placebo 9.2 ng/mL; day 14—leptin 12.0 ng/mL, placebo 14.5 ng/mL; and day 21-leptin 12.25 ng/mL, placebo 12.5 ng/mL (FIG. 6). Notably, these values fell within the normal range of plasma leptin in ApoE-/- mice receiving Western diet (mean 5.1±1.4 to 17±3.4 ng/mL). It should also be emphasized that circulating leptin levels are known to increase with age, as also observed in our series.

This unique mouse model was utilized to perform two experiments: Mice in experiment 1 were fed postoperatively with high fat diet (HFD), and were followed up for 45 days. In experiment 2 mice received normal chow for 30 or 60 days. Mouse weight and blood pressure (BP) were assessed weekly. All mice recovered from surgery uneventfully.

Results

In both mouse model experiments, leptin or control treated mice gained weight equally during the follow up period, suggesting no systemic leptin effect. Systolic BP measured weekly in mice of experiment 2 was 100 mmHg throughout the first 4 weeks, and increased to 120 mmHg by week 6 in both leptin treated and control mice. Based on two separate experiments, both HFD and normal chow feeding yielded in general similar results.

The following data report the results of experiment 2 (normal chow feeding).

Figure 7:
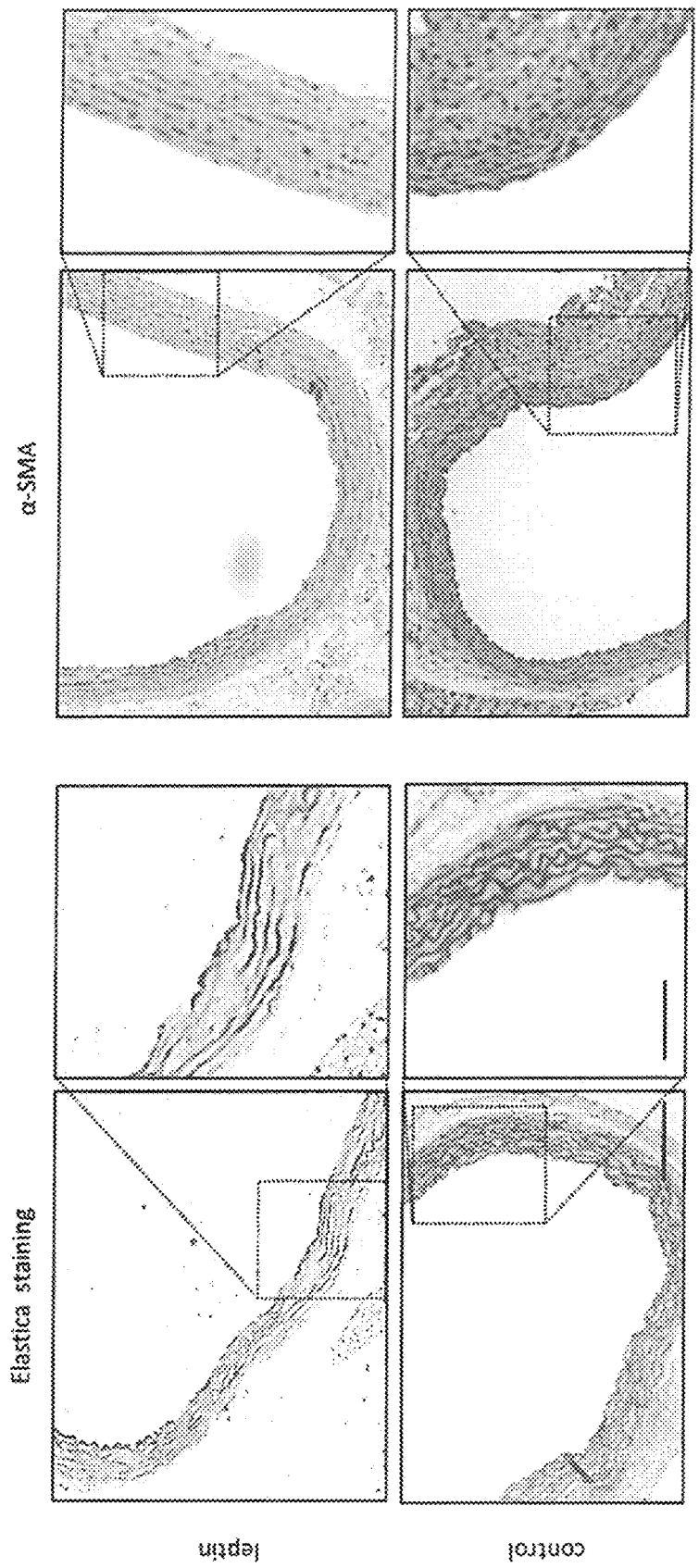
FIG. 7 illustrates elastica staining and αSMA 1HC analysis of ascending aortic cross sections of mice locally treated with leptin versus controls.

Echocardiography of the ascending aorta at 2 mm distal to the aortic valve level revealed an increase in aortic diameter at peak systole in leptin treated mice vs controls (p=0.08, FIG. 6; Exp. 1 using HFD yielded P<0.003). That same aortic location exhibited decreased elasticity, which was defined as the percent increase in aortic diameter in systole vs. diastole, in leptin compared to control treated mice. There was no significant difference in diameter further distally on the ascending aorta. Notably, the aortic valve annulus did not dilate in response to local leptin application. Histological analysis of the ascending aorta revealed features of medial degeneration at the site of leptin application, including fragmentation of the elastic lamellas, as demonstrated by elastica van Giesen staining, and depletion of αSMA in the media (FIG. 7). These structural changes likely underlie local stiffening and dilatation in the proximal ascending aorta.

Figure 8:
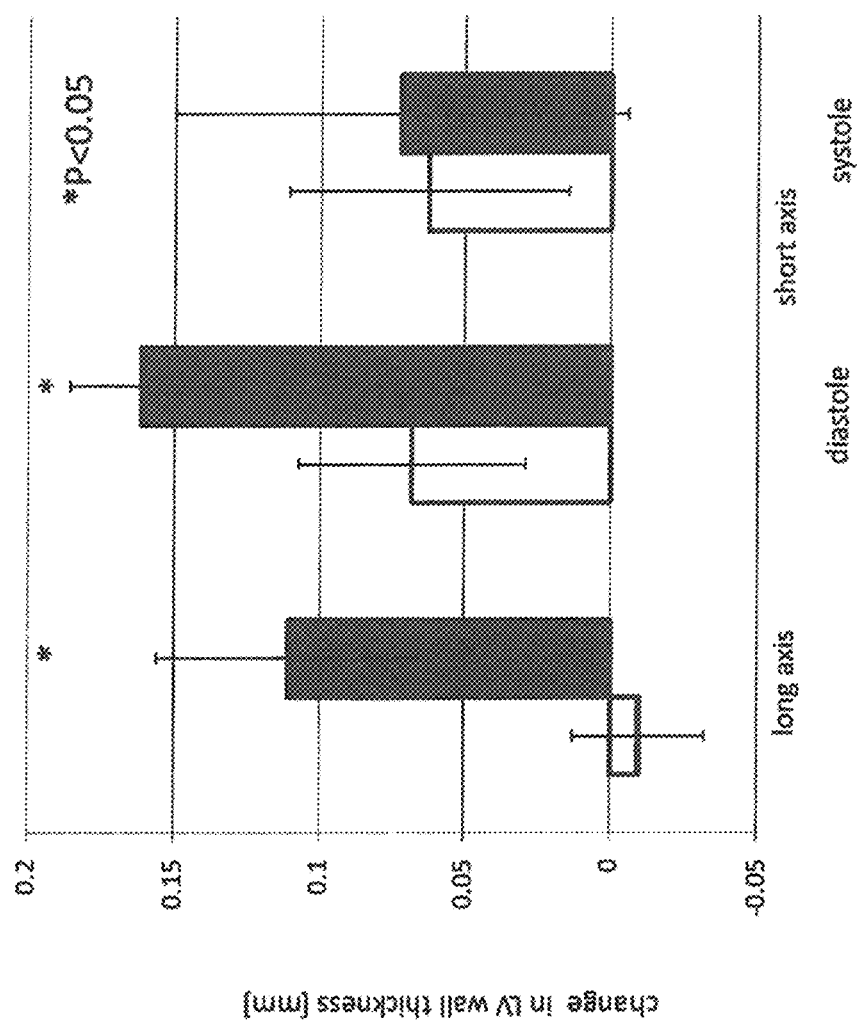
FIG. 8 illustrates change in left ventricle (LV) wall thickness in leptin-treated (filled columns) versus control (open columns) mice.
Figure 9:
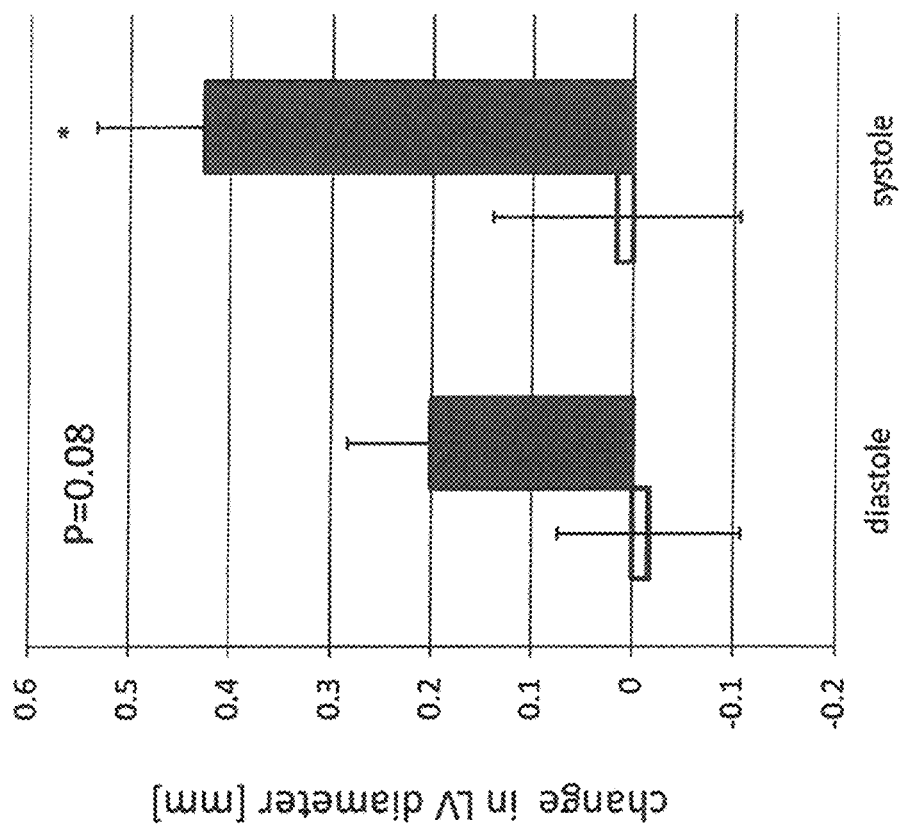
FIG. 9 illustrates LV diameter in systole and diastole in leptin-treated (filled columns) and control (open columns) mice.
Figure 10:
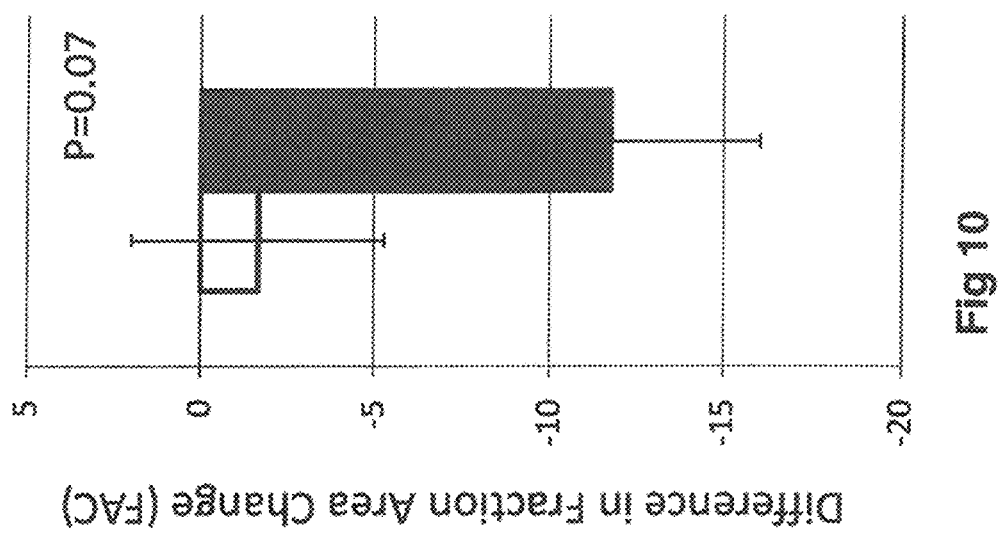
FIG. 10 illustrates LV fractional area change in leptin-treated (filled columns) versus control (open columns) mice.

Echocardiography (final vs. pre-operative) revealed a concentric remodeling of the left ventricle, with hypertrophy of all LV walls (p<0.001). Wall thickening was most pronounced in diastole (p=0.002, FIG. 8). Left ventricular diameter was increased in both systole and diastole (p=4.08, p=0.02, respectively, FIG. 9), leading to a reduction in the LV fractional area change (FAC, p=0.07, FIG. 10).

Figure 11:
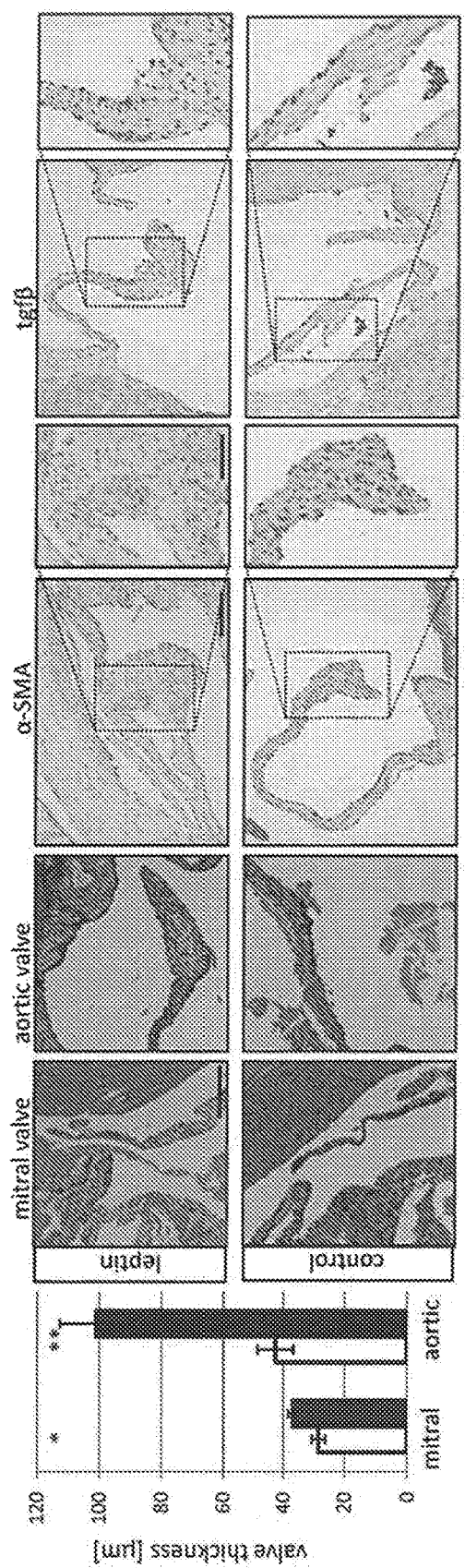
FIG. 11 illustrates aortic and mitral valve leaflet thickness in leptin-treated and control mice.

Local leptin application at the proximal ascending aorta promoted thickening of the mitral and aortic valve leaflets (p=0.01, p<0.001 accordingly, FIG. 11). Mitral leaflets were diffusely thickened, while aortic valve leaflets displayed thickening in their free edge, composed mostly of ECM and stromal cells. These proliferating cells are assumed analogous to human valvular interstitial cells (VICs). A few stromal cells within these lesions were positive for αSMA and TGFβ as shown by IHC staining (in analyzed aortic valve leaflets), suggesting VICs activation (FIG. 11). A trend was observed for increased VIC proliferation through Ki67 IHC in leptin treated mice. However, the lack of statistical significance implies that most leaflet hyperplasia took place at an earlier time.

Increased peak systolic velocity (PSV), as measured at the aortic valve in leptin treated vs control mice was short of statistical significance. However, PSV was significantly augmented in postoperative HFD fed animals.

These experiments reveal that available leptin in the proximal ascending aorta induces local aortic stiffening and dilatation. The resulting changes in local hemodynamics likely drive remodeling of the left ventricle, including LV wall hypertrophy and valve thickening through the aorto-ventricular coupling axis.

Example 2

Local Leptin Antagonism in an Ang II Mouse Model

Angiotensin II (AngII) is the key hormone of the renin-angiotensin system, underlying hypertension and cardiovascular remodeling (Renna et al. Pathophysiology of vascular remodeling in hypertension. Int J Hypertens. 2013; 2013: 808353). The phenotypes induced by local leptin application described in Example 1 are reminiscent of AngII induced aortic-ventricular (coupling) remodeling, suggesting that leptin mediates these processes. As such, a leptin antagonist was delivered locally to the ascending aorta in order to assess the effects of leptin down-regulation on AngII induced local aortic remodeling, and aortic-ventricular remodeling in mice.

Materials and Methods

Figure 12:
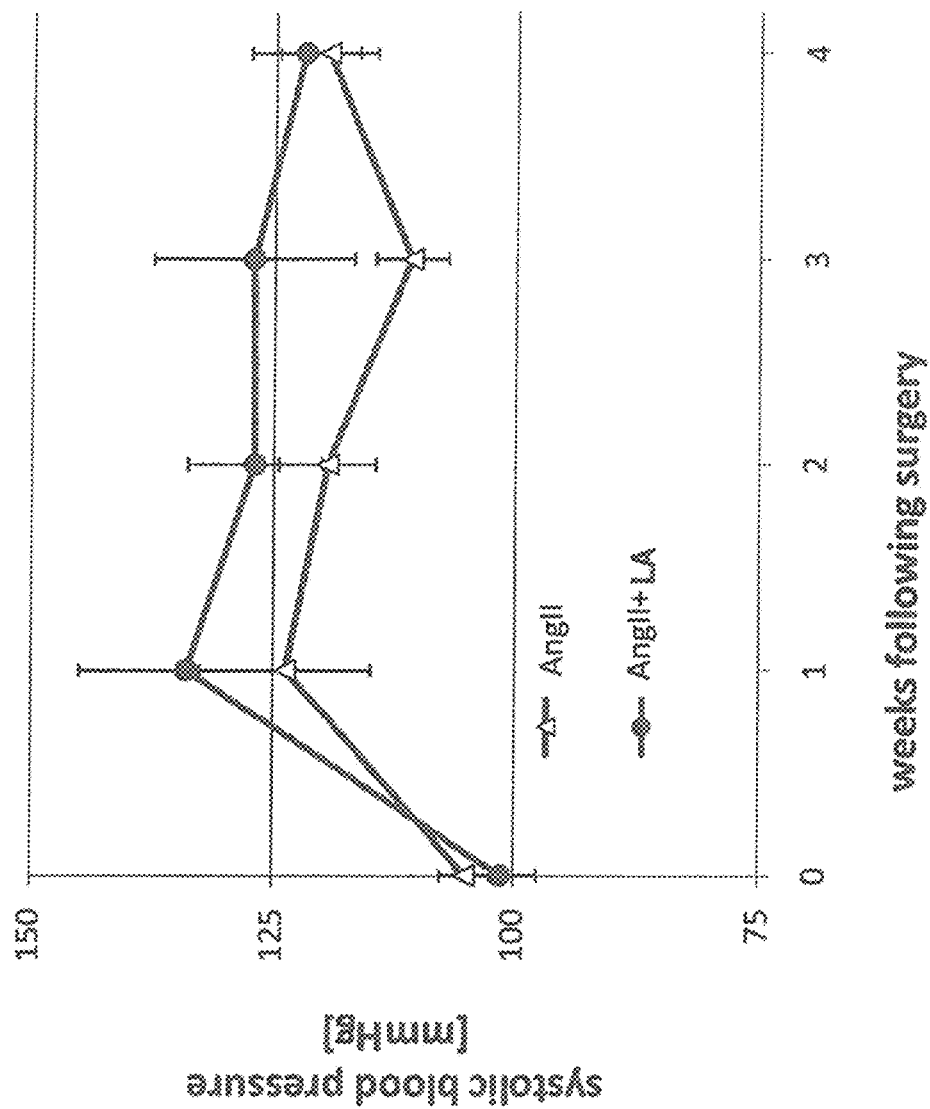
FIG. 12 illustrates mean systolic blood pressure in angiotensin II treated mice.
Figure 13:
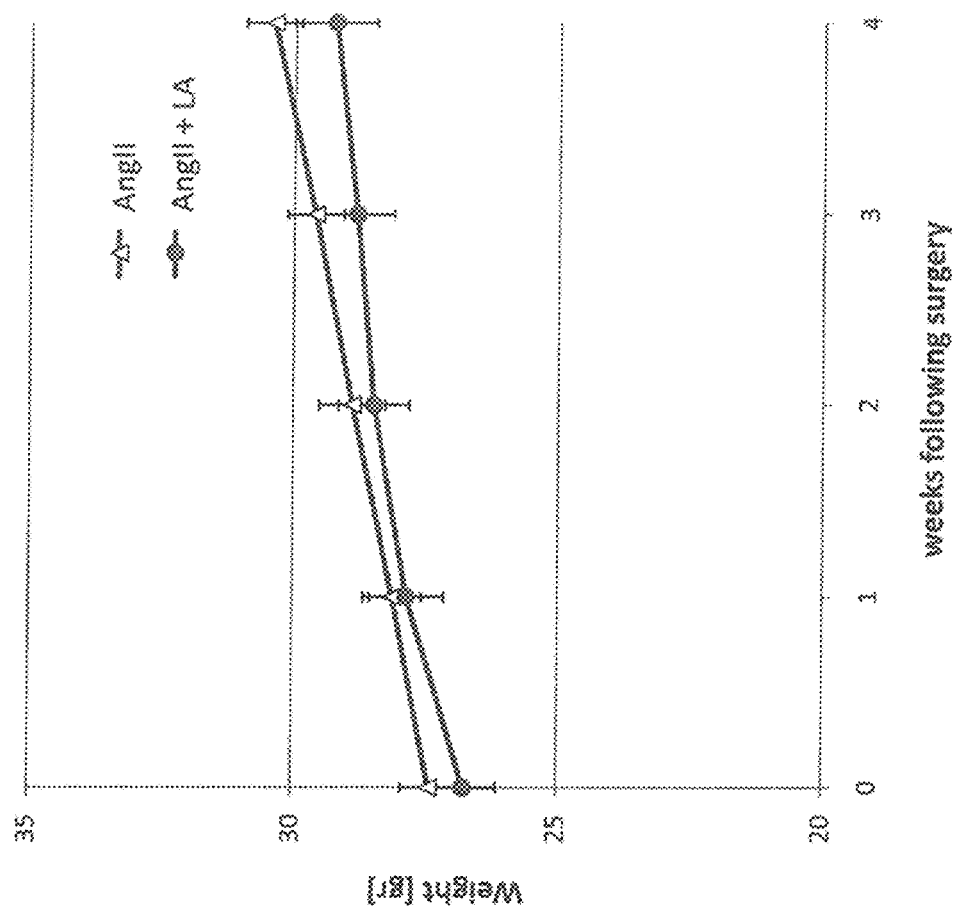
FIG. 13 illustrates a time course analysis presenting weight of angiotensin II treated mice (open triangles), and mice receiving both, angiotensin II and leptin antagonist (LA).

An osmotic mini-pump, delivering AngII at a rate of 1000 ng/kg/min was implanted subcutaneously in the back of the neck of 14 week old ApoE$^{-/-}$ mice. Each mouse also underwent left mini-thoracotomy for application of a slow release miniature PLGA film (1×1.5 mm) containing either 5 µg leptin antagonist (LA), or PLGA matrix devoid of protein (control). The slow release film was deployed on the surface of the proximal ascending aorta at the position described in Experiment 1. Mice were euthanized 4 weeks following surgery. As expected, blood pressure assessed in both Ang II treated groups after one week was increased by approximately 20% (125 mmHg mean systolic), and was sustained throughout the follow up (FIG. 12). Weight gain pattern was similar in both groups, indicating no systemic effects related to the leptin antagonist (FIG. 13).

Results

Figure 14:
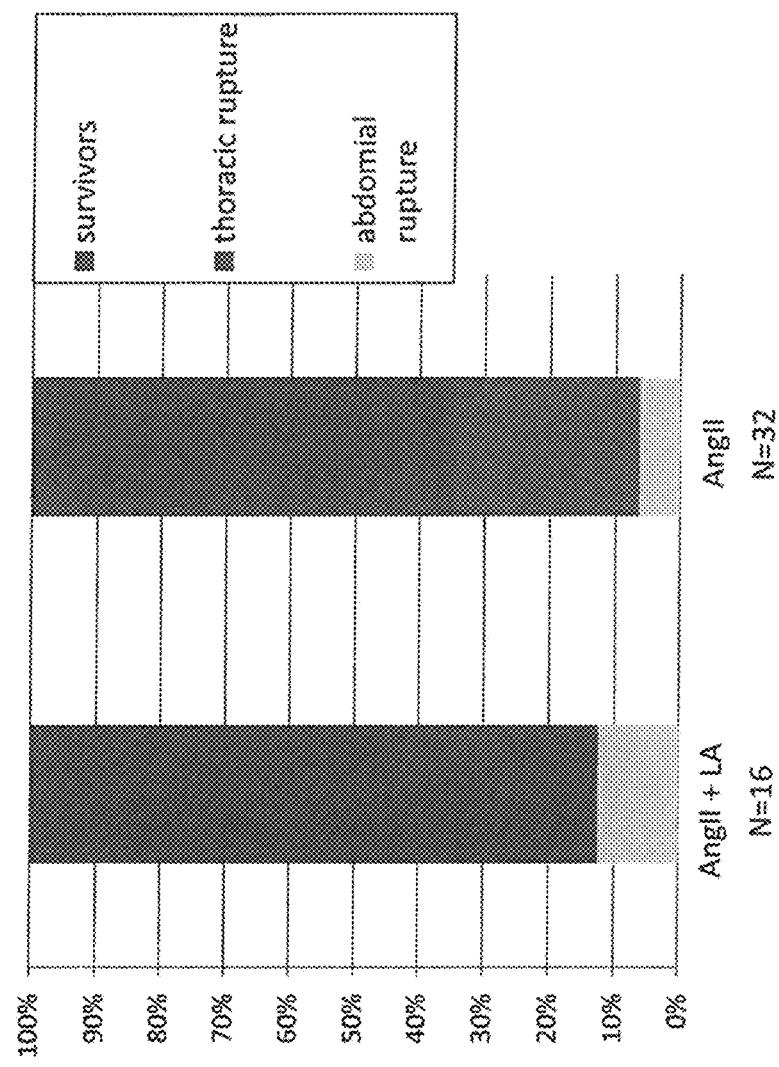
FIG. 14 illustrates number of mice that succumbed due to ruptured abdominal and thoracic aneurysms in angiotensin II treated mice versus mice receiving angiotensin II and leptin antagonist (LA).

To assess the impact of AngII alone versus AngII plus leptin antagonist on mouse longevity, mortality data from the present experiment were combined with data from a previous experiment, which included a similar cohort of ApoE$^{-/-}$ mice exposed to AngII, in same dose and duration (Tao M, et al. ATVB 2013). Collectively, a 34% mortality (referred to premature death, prior to the completion of the experiment) was observed in mice treated with AngII (either Ang II alone or Ang 11 with control film applied on the ascending aorta). Death was related to thoracic (28%) or abdominal (6%) aortic aneurysm rupture. Notably, mice treated with AngII that received also LA were protected from thoracic aneurysm rupture (p=0.04, FIG. 14). Death rate in mice receiving LA was only 13%, related exclusively to 2) rupture of abdominal aortic aneurysms.

Figure 15:
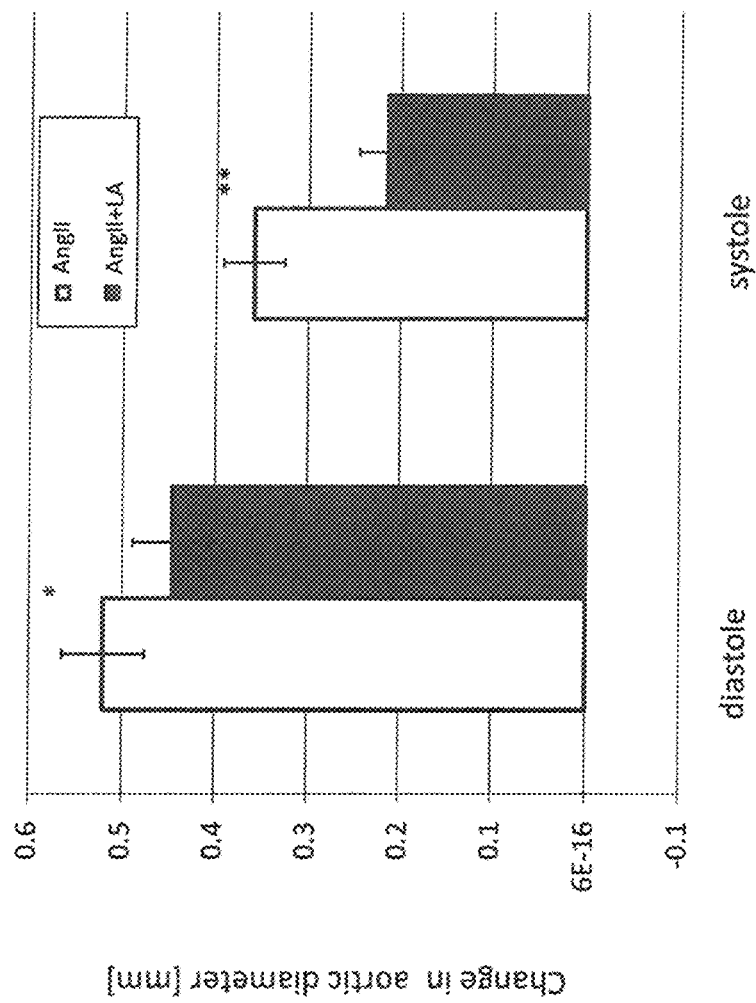
FIG. 15 illustrates ascending aortic dilatation in angiotensin II treated mice versus mice receiving angiotensin II and leptin antagonist (LA).

Echocardiograpic imaging of the ascending aorta demonstrated that local LA application in AngII treated mice significantly attenuated dilatation of the ascending aorta compared to AngII alone when measured 2 mm from the valve, at both diastole and systole (p=0.03, p=0.005, respectively, FIG. 15). However, these data did not suggest moderation of increased aortic stiffness by LA application.

Figure 16:
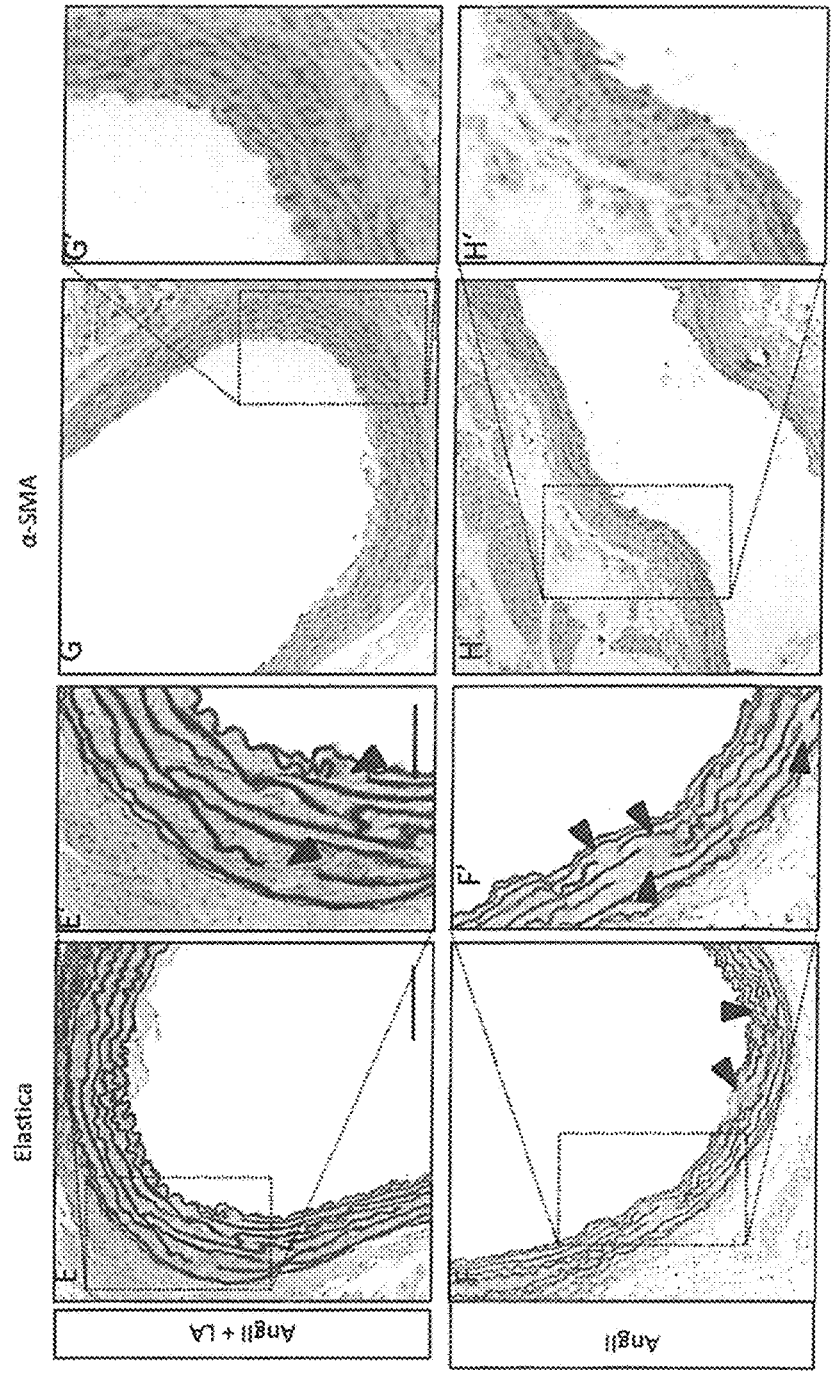
FIG. 16 illustrates elastic lamella fragmentation and αSMA depletion in angiotensin II treated mice versus mice receiving angiotensin II and leptin antagonist (LA).

Histological analysis revealed medial degeneration in both groups that were treated with AngII. Nevertheless, additional LA application resulted in less fragmentation of the elastic lamellas and fewer sites of αSMA depletion in the aortic media (FIG. 16). Notably, amongst mice receiving AngII, medial degeneration was rather diffused throughout the aorta. This was in sharp contrast to the effects of local leptin application, which exhibited medial degeneration within the segment in contact with the leptin film alone.

Figure 17:
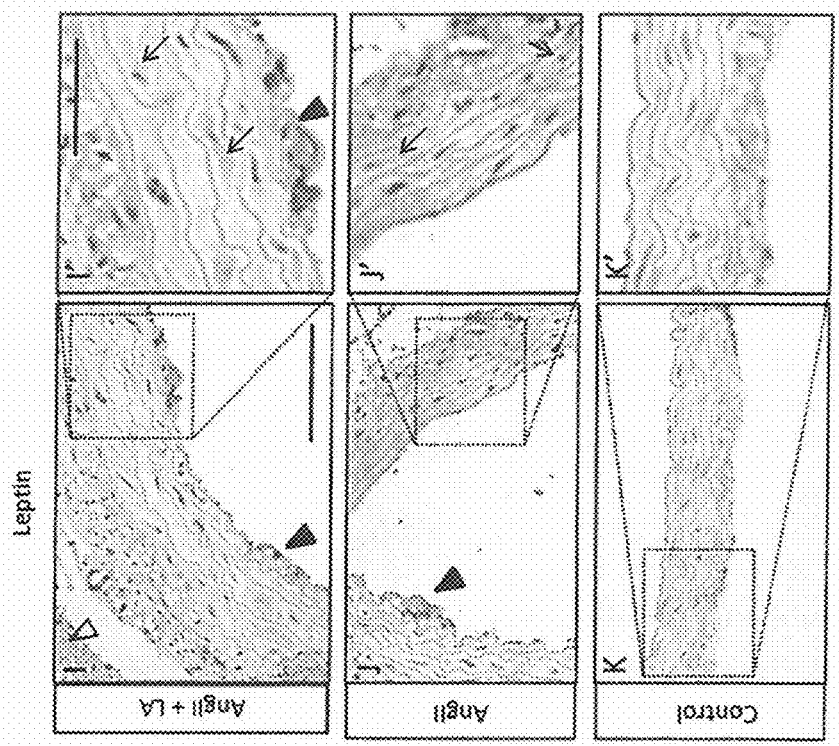
FIG. 17 illustrates leptin expression in medial SMCs (arrows) and macrophages of atherosclerotic lesions (filled arrowheads) in angiotensin II treated, angiotensin II and leptin antagonist (LA) treated, and control mice.

Immunohistochemical analysis for leptin antigen revealed a weak expression in medial SMCs, and a strong signal within foam cells of aortic luminal atherosclerotic plaques (FIG. 17).

Figure 18:
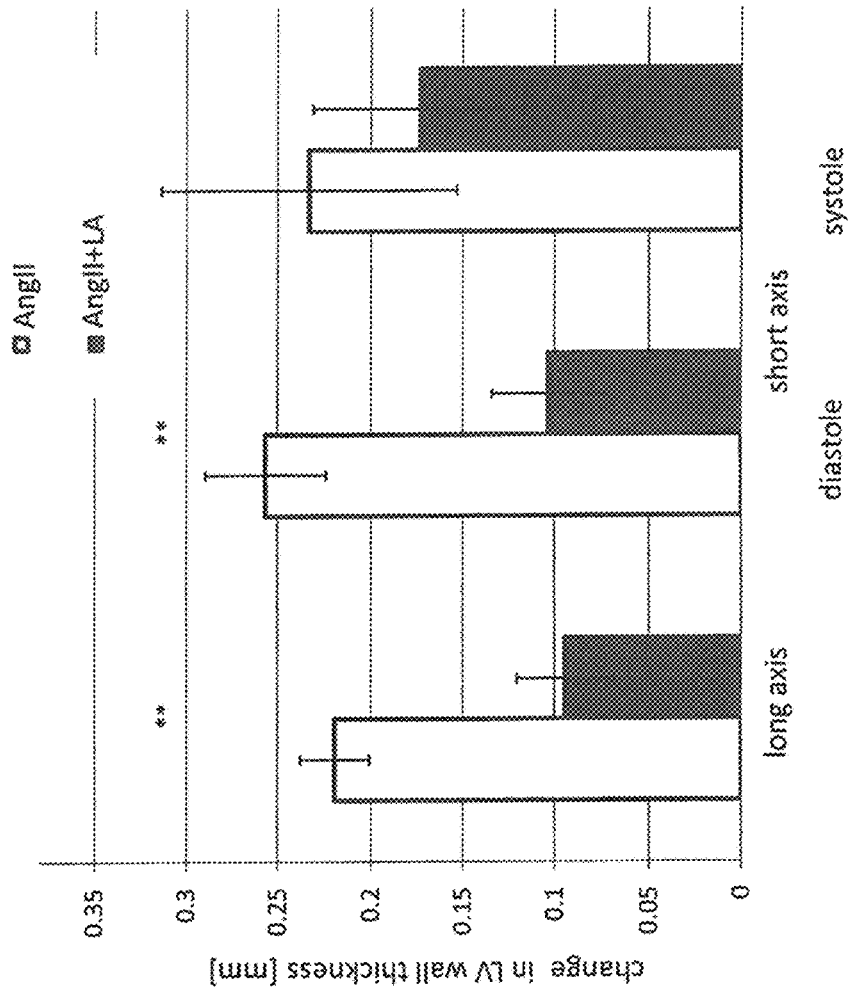
FIG. 18 illustrates LV hypertrophy in angiotensin II treated mice versus mice receiving angiotensin II and leptin antagonist (LA).
Figure 19:
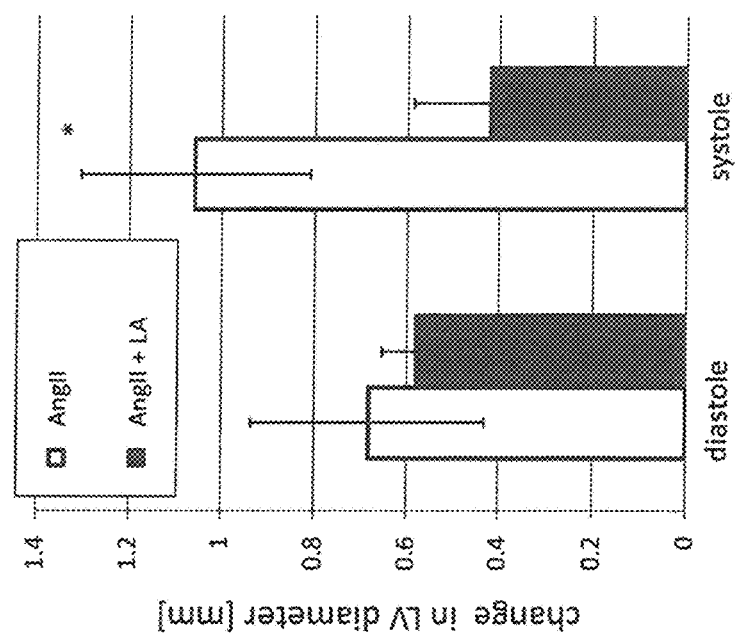
FIG. 19 illustrates changes in LV diameter in angiotensin II treated mice versus mice receiving angiotensin II and leptin antagonist (LA).
Figure 20:
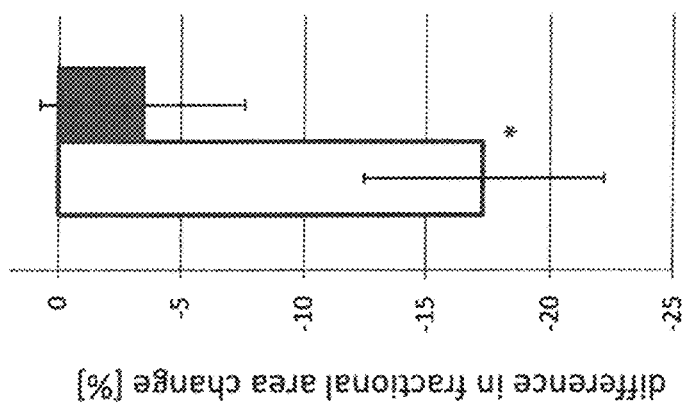
FIG. 20 illustrates LV fractional area change in angiotensin II treated mice (open column) versus mice receiving angiotensin II and leptin antagonist (LA) (filled column).

Mice treated with LA presented less thickening of the left ventricular wall, particularly in diastole (p<0.01, FIG. 18). Left ventricular diameter increased similarly in both groups in diastole however, LA treatment attenuated the increase in LV diameter during systole (p=0.05, FIG. 19). As anticipated, and corresponding to these results, a decrease in FAC in mice co-treated with AngII and LA, was observed, while mice treated by AngII alone exhibited a decrease in fractional area change by over 15% (p=0.03, FIG. 20). Moreover, LV diameter which increased in response to AngII treatment, was preserved within the baseline (pre-AngII treatment) range in the LA treated mice (P<0.05).

Figure 21:
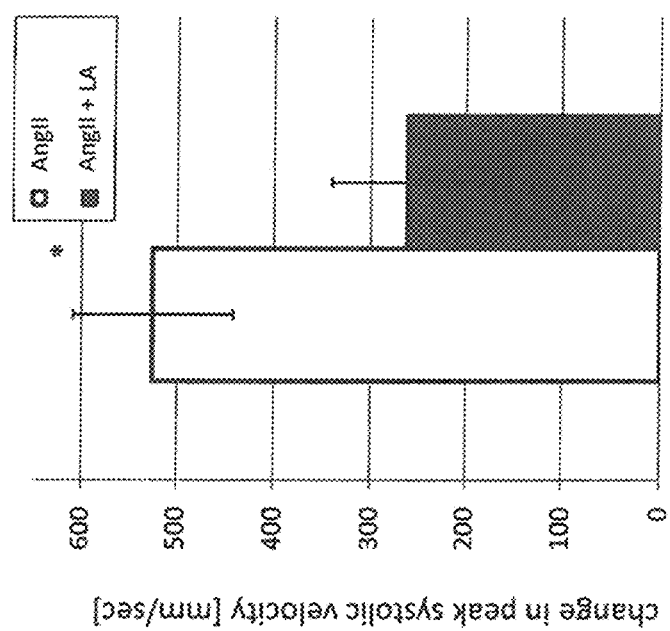
FIG. 21 illustrates peak systolic velocity at the aortic valve in angiotensin II treated mice versus mice receiving angiotensin II and leptin antagonist (LA).

Peak systolic velocity was decreased in AngII treated mice that also received LA application, vs. AngII alone (p=0.03, FIG. 21). Notably, since no aortic valve obstruction or changes in its annulus diameter were detected, the PSV parameter is likely reflecting the interaction between proximal aortic hemodynamics, and left ventricular systolic contraction. Thus, PSV moderation by LA may represent attenuation of both aortic and LV remodeling.

Figure 22:
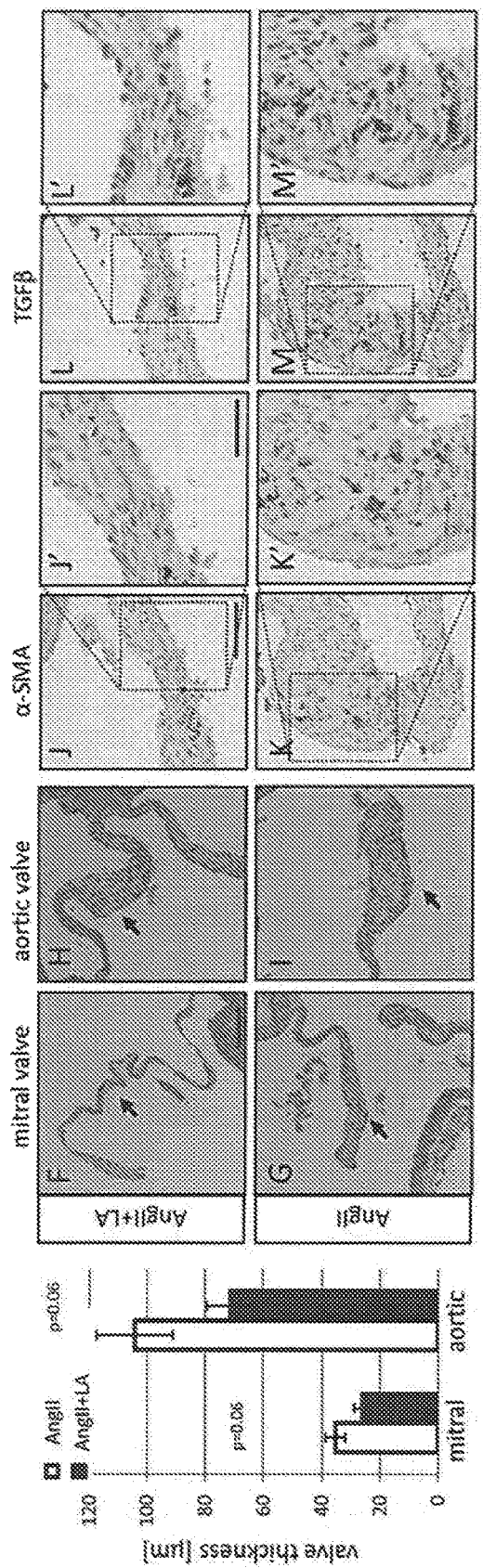
FIG. 22 illustrates aortic and mitral valve thickness (graph on left), and staining of valve leaflets with H&E (panels F-I). αSMA and TGFβ (panels J-M', staining for aortic valves) in mice receiving angiotensin II versus mice treated with angiotensin II and leptin antagonist (LA).

LA also attenuated remodeling of the LV valve. AngII-induced thickening of aortic and mitral valve leaflets was reduced by LA application in both valves (p=0.06 in both valves, FIG. 22 left panels F-I).

The αSMA and TGFβ antigens were observed in aortic valve leaflet stromal cells in all AngII treated mice (FIG. 22 panels J-M'); decreased proliferation of stromal cells in LA treated mice was demonstrated through Ki67 staining (p=0.26).

Thus, the present findings show that application of a leptin antagonist at the pivotal location on the proximal ascending aortic surface prevents rupture of thoracic aneurysms induced by systemic infusion of Ang II. Local inhibition of leptin activity reduces the degenerative effects of Ang II on the proximal aorta, which underlie aortic wall destabilization. Thus, moderation of Ang II induced aortic dilatation and attenuates left heart remodeling, presumably via the aorto-ventricular coupling.

These results highlight the role of leptin as a key mediator of Ang II signaling and indicate that leptin which underlie left ventricular hypertrophy also drives the formation of early aortic valve hyperplastic lesions, which may progress to aortic valve stenosis (AVS).

Example 3

The Role of Leptin in AVS

Materials and Methods

Human AVS and normal arterial valve (AV) samples were collected for analysis, including autopsy samples, freshly collected AVS specimens from patients undergoing aortic valve replacement surgery, and normal aortic valves from explanted hearts. Formalin fixed valve samples were analyzed by immunohistochemistry for leptin, leptin receptor, CD68 and αSMA. Fresh samples of AVS valves and normal aortic valves underwent total RNA extraction and analyzed by qPCR and Nanostring technique to assess leptin and leptin receptor mRNA levels. Retroperitoneal fat was used as a positive control in both assays.

Results

Figure 23:
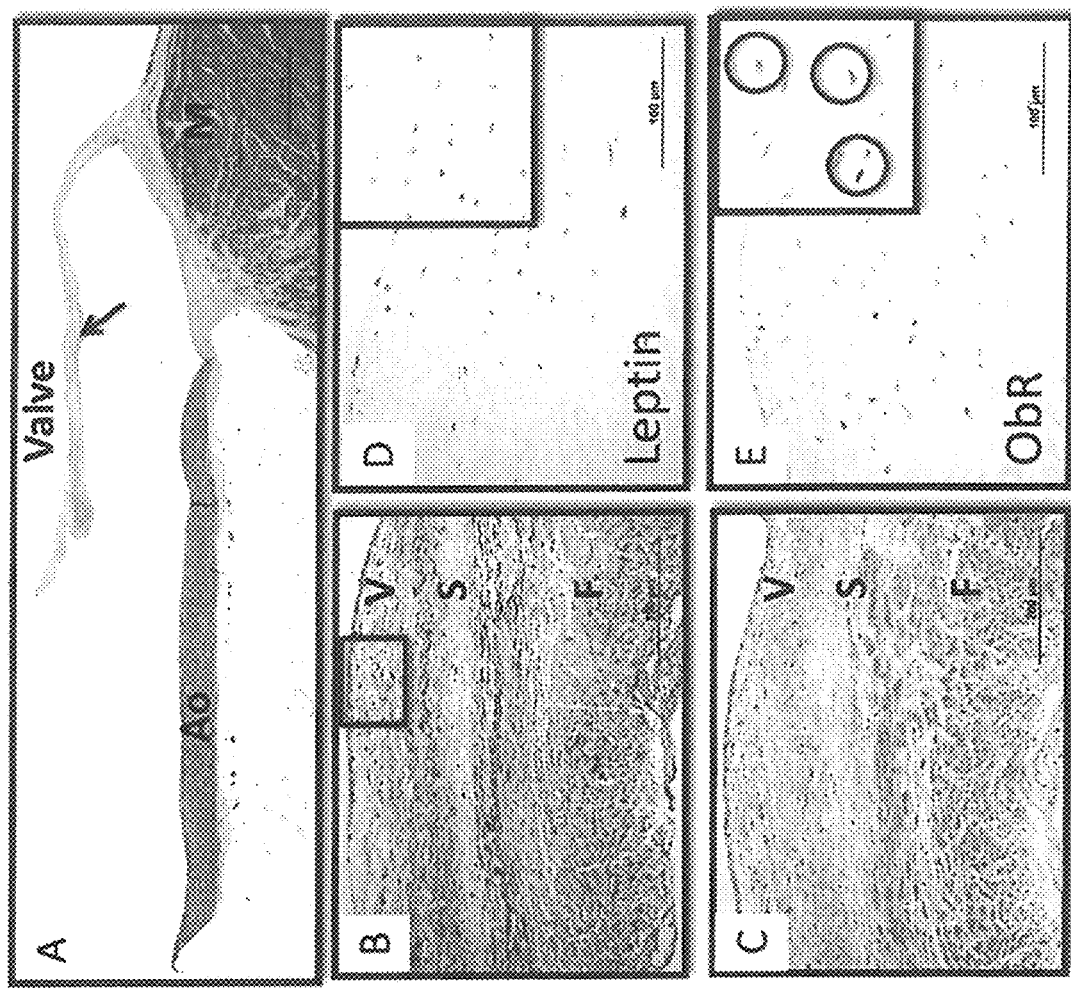
FIG. 23 illustrates expression of leptin (D), and leptin receptor (E) in normal human aortic valve leaflet tissue.
Figure 24:
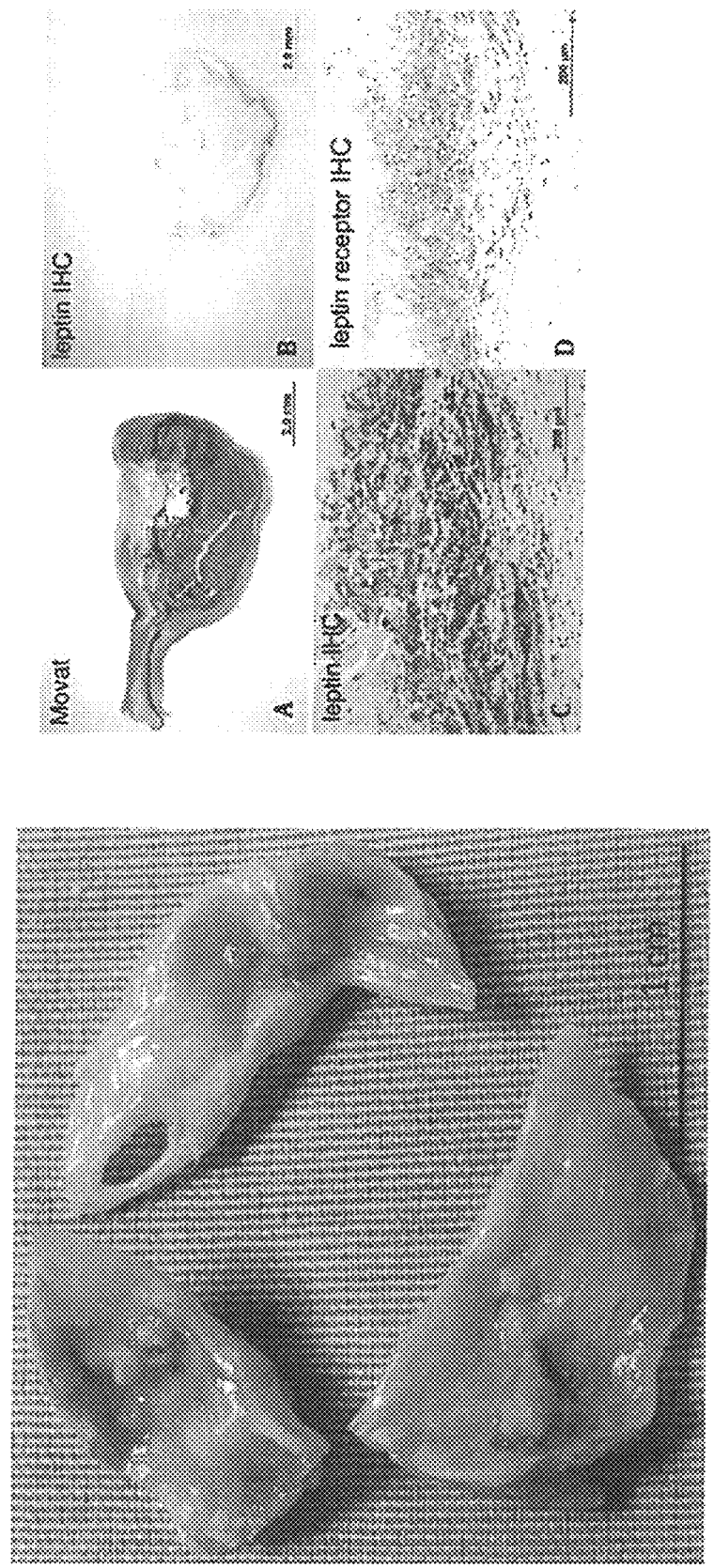
FIG. 24 illustrates leptin and leptin receptor antigen prevalent in severe aortic valve stenosis, evident in SMC-like cells, and infiltrating macrophages.
Figure 25:
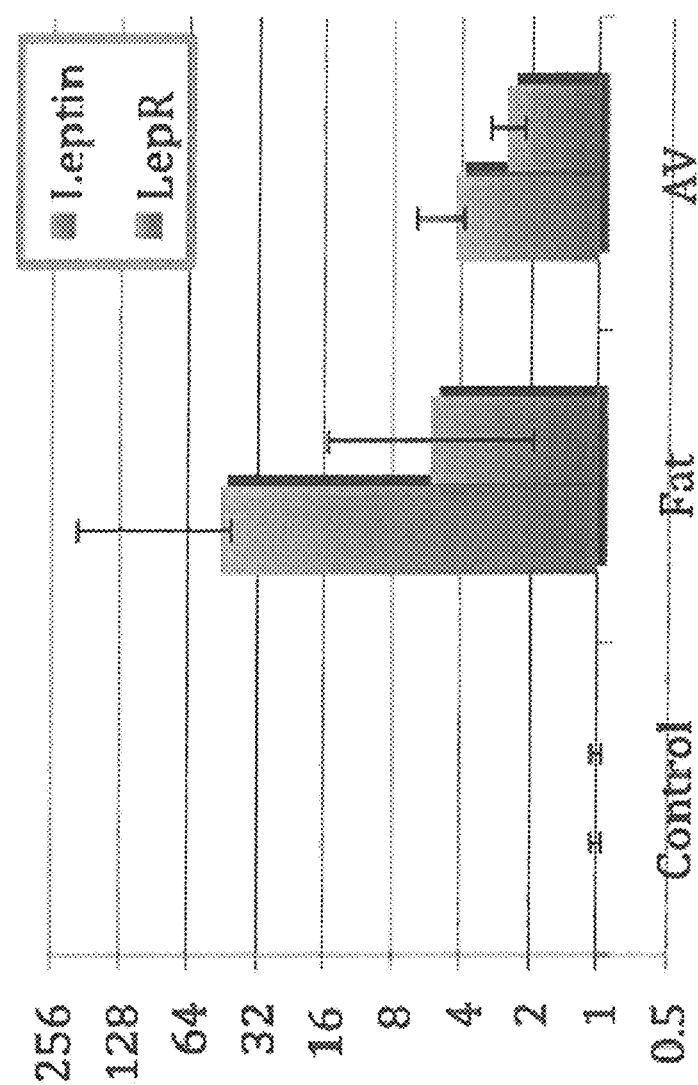
FIG. 25 illustrates leptin and leptin receptor mRNA levels in leaflets of stenosed aortic valve versus normal aortic valve controls, and fat tissue (as positive control)

Normal aortic valve leaflets lack leptin (Ob) antigen, and show very few leptin receptor (ObR) positive cells (FIG. 23). Advanced AVS disease was characterized by extensive ossification and infiltration of inflammatory macrophages in the non-calcified rim of cellular tissue (FIG. 24). Leptin was demonstrated mostly in two cell types, SMC-like elongated cells, and macrophage-like round cells, and its prevalence was proportional to the severity of AVS disease. In situ hybridization analysis performed on AVS samples demonstrated leptin mRNA expression, suggesting de novo synthesis (not shown) leptin and leptin receptor mRNA levels were assessed by qPCR and Nanostrings hybridization, using total RNA extracted from freshly collected AVS. AVS were compared to normal AV leaflets (FIG. 25), revealing increased leptin and leptin receptor mRNA in AVS samples.

Figure 26:
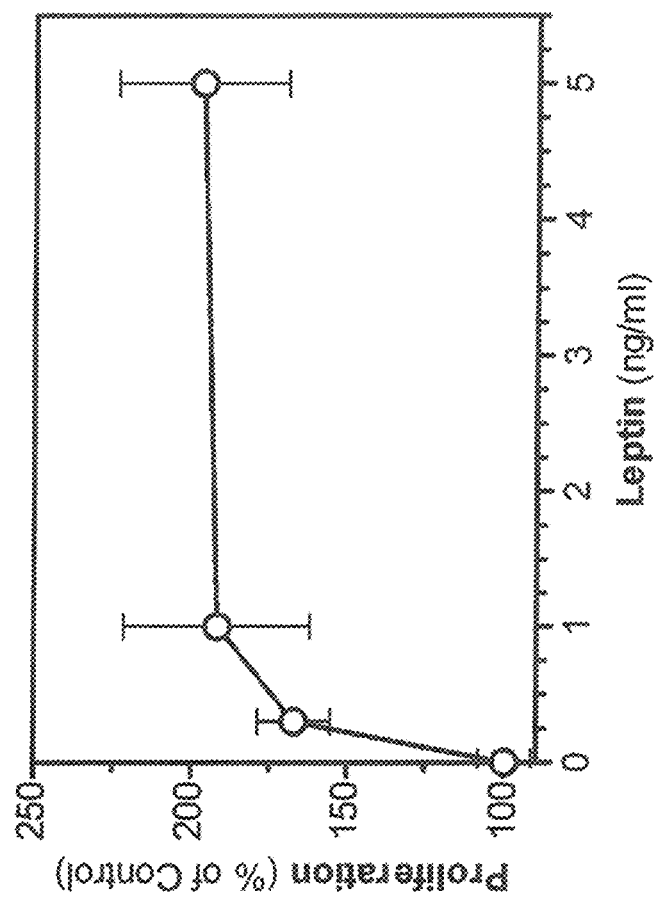
FIG. 26 illustrates proliferation of valve interstitial cells (VICs) in response to leptin stimulation.

To investigate the potential impact of AngII and leptin on human valve cells, in vitro analysis revealed that AngII-mediated proliferation of human valve interstitial cells (VICs) is leptin mediated (leptin-induced proliferation of VICs in FIG. 26). This suggests that leptin synthesized in aortic valve leaflets by VICs and inflammatory macrophages may elicit VIC proliferation and subsequent ossification via a paracrine/autocrine pathways.

Example 4

Preparation of Sustained-Release Film

Poly lactic-co-glycolic acid (PLGA) films containing a leptin antagonist (e.g., a leptin antagonist described in U.S. Pat. No. 8,969,292) is produced in a manner analogous to the described in Webber W L et al "Characterization of soluble, salt-loaded degradable PLGA films and their release of tetracycline" J Biomed Mater Res 1998, 41, 18-29.

Specifically, 1 g PLGA 6535 polymer (D,L-lactide:glycolide: 65:35, Mw=45,000-75,000 Da, Lakeshore. Biomaterials, Birmingham, Ala., USA) is dissolved in 10 mL $MeCl_2$ (Fisher Scientific, Loughborough, UK). Sodium chloride (10 mg in 0.2 ml distilled water) and 25 μL ethylene glycol (Sigma-Aldrich, St. Louis. Mo., USA) are added to the PLGA solution and sonicated for 20 seconds. 1 mg of the leptin antagonist is suspended in 2 mL of the PLGA solution, followed by casting on the flat surface of a Teflon mold to create a film comprising a leptin antagonist.

Example 5

Evaluation of Sustained-Release Properties of Film

A 2×2.5-mm patch of PLGA film of Example 4 is maintained in 5 mL sterile PBS at 37° C. for 28 days. Every 7 days the PBS medium is sampled before being aspirated and replaced by 5 mL of fresh PBS. The medium samples are analyzed by ELISA (RayBiotech, Norcross, Ga., USA) for leptin antagonist levels. The in vitro measurement of leptin discharged from the slow-release PLGA film yields substantial release of leptin antagonist for at least two weeks.

Example 6

Preparation of Two-Component Gelling Sustained-Release Gel Composition

A first component of the composition is an aqueous solution of modified carboxymethyl cellulose with adipic dihydrazide (CMC-ADH). Dried and finely ground sustained-release gel with leptin antagonist as described in Example 1 is added to the CMC-ADH solution and vortexed to yield a suspension.

A second component of the composition is oxidized dextrane in DDW (DX-COH). A dye such as methylene blue (0.5%) is optionally added to the DX-COH solution to make the resulting gel more visible.

For use the two components are mixed together to form a viscous fluid that is immediately administered by injection. In a short time, the viscous fluid gels.

Example 7

Covered Stents

A stent cover is fashioned from the PLGA film of Example 4,

The stent cover is used to cover the balloon expandable stents of a MULTI-LINK 8 LL coronary stent system, a MULTI-LINK ULTRA coronary stent system and a MULTI-LINK MINI VISION coronary stent system (all of Abbot Laboratories, Abbot Park, Ill., USA).

The graft (stent cover) portion of an Endurant II AAA Stent Graft System (Medtronic, Dublin, Ireland) is impregnated with a leptin antagonist. In one example, impregnation is by immersion in a first component of the composition of Example 3, followed by contact with contact with the second component thereof.

The stent cover is used as an external cover for a self-expanding WallFlex Stent (Boston Scientific Corporation, Natick, Mass., USA).

The covered stents are deployed in the usual way inside the lumen of a blood vessel of a living subject in need thereof. Once implanted, the leptin antagonist elutes from the stent cover through the blood vessel endothelium into the blood vessel to exert a desired pharmaceutical effect.

Example 8

Drug-eluting Stent

An XIENCE Alpine coronary stent system (Abbot Laboratories, Abbot Park, Ill., USA) is prepared in the usual way, but impregnated with a leptin antagonist as an active pharmaceutical ingredient instead of Everolimus.

The resulting drug-eluting stent is deployed in the usual way inside the lumen of a blood vessel of a living subject in need thereof. Once implanted, the leptin antagonist elutes from the stent through the blood vessel endothelium into the blood vessel to exert a desired pharmaceutical effect.

Example 9

Bioresorbable Stent

A bioresorbable balloon-expandable stent is fashioned of bioresorbable polylactide (PLA) comprising a leptin antagonist, substantially as done to fashion a bioresorbable stent by Arterial Remodeling Technologies (Paris, France).

A bioresorbable balloon-expandable stent is fashioned of bioresorbable poly (L-lactide) (PLLA) comprising a leptin antagonist and also comprises a bioresorbable coating of PLLA including a leptin antagonist, substantially as done to fashion an Absorb GT1 vascular scaffold stent.

The resulting bioresorbable stents are deployed in the usual way inside the lumen of a blood vessel of a living subject in need thereof. Once implanted, the leptin antagonist elutes from the stents as these resorb, to pass through the blood vessel endothelium into the blood vessel to exert a desired pharmaceutical effect.

Example 10

Spike or Rod

An implantable spike or rod (bioresorbable or not) is made as known in the art, for example as described above with reference to the stents and includes leptin antagonist integrated into the material of the spike or rod, or adsorbed, absorbed or coated onto the spike or rod.

The resulting spike or rod is implanted in the usual way inside an organ, for example by piercing the organ. Once implanted, the leptin antagonist elutes from the spike or rod, to exert a desired pharmaceutical effect on the organ.

Example 11

Injectable Gel

The two components of the composition of Example 3 are provided. The components are mixed together and implanted in the body of the subject by injection into or onto an organ to form a gelled mass in or on the organ.

Once implanted, the leptin antagonist elutes from the gelled mass, to exert a desired pharmaceutical effect on the organ.

Example 12

Sheet

A sheet of the film of Example 1 is provided. The sheet is placed against the outer surface of an organ (e.g., aorta, for example, ascending aorta, aortic arch, descending aorta, abdominal aorta) and optionally held in place by sutures and/or biological glue (e.g., Evicel® by Ethicon of Johnson and Johnson).

Once implanted, the leptin antagonist elutes from the film, to exert a desired pharmaceutical effect on the organ.

Example 13

Treatment of AAA

A human subject is diagnosed with an abdominal aortic aneurysm (AAA).

A composition according to the teachings herein in the form of a long sheet such as described in Example 12 (a ribbon) comprising leptin antagonist is provided. The abdominal aorta of the subject is surgically accessed from the outside (e.g., using keyhole surgery) and the composition administered by winding the long sheet around the abdominal aorta to wrap the entire aneurysm as well as a portion of the aorta above and below the aneurysm, and held in place with a biological glue and/or sutures. Optionally, a stent graft (e.g., an Endurant® II AAA Stent Graft System (Medtronic, Dublin, Ireland)) is deployed in the aneurysm in the usual way, before or after administration of the composition. Subsequently, leptin antagonist from the composition passes through the tunica externa to provide a beneficial effect to the subject.

Alternatively or additionally, an AAA stent graft is provided that is similar to known AAA stent grafts (e.g., similar to an Endurant® II AAA Stent Graft System (Medtronic, Dublin, Ireland)) where at least one of: the graft and/or anchoring stents are a composition of the teachings herein and comprises a leptin antagonist; at least the anchoring portions of the graft and/or anchoring stents are impregnated with a composition of the teachings herein that comprises a leptin antagonist; and at least the anchoring portions of the graft and/or anchoring stents are coated with a composition of the teachings herein that comprises a leptin antagonist. The stent-graft is deployed in the usual way in the abdominal aneurysm, that is to say, where the anchoring stents are expanded against healthy portions of tunica intima above and below the aneurysm. Subsequently, leptin antagonist from the composition passes through the tunica intima to provide a beneficial effect to the subject, for example, preventing or reducing the extent that the aneurysm spreads to portions of tissue in proximity of the anchoring stents, thereby preventing loosening of the anchoring stents.

Alternatively or additionally, a drug-eluting balloon similar to the In.Pact Admiral® DCB drug-coated balloon by Medtronic (Dublin, Ireland) that is coated with a composition comprising leptin antagonist according to the teachings herein is introduced through the femoral arteries and advanced to areas of the abdominal and iliac arteries that are just above and just below the aneurysm (for example, "landing zones" where anchoring stents of a stent-graft would be deployed. The balloon is expanded to contact the aorta and iliac walls, thereby administering composition to the healthy tissue and preventing advancement of the aneurysm. In some such embodiments, the administration of leptin antagonist is repeated periodically, e.g., with a frequency that is less than once a month, less than once every two months and even less than once every 3 months. In some such embodiments, the administration of the leptin antagonist leads to stabilization of the wall tissue, halting the processes of aneurysm formation at the portions of the blood vessels above and below the aneurysm and at the portions of the blood vessel in contact with the deployed stent graft.

Example 14

Treatment of Thoracic Aortic Aneurysm

A human subject is diagnosed with an aneurysm in the thoracic aorta, including one or more of the ascending aorta, aortic arch and descending aorta. It is known that segmental increased stiffness and aortic dilatation cause local aneurysm formation. These structural changes underlie hemodynamic perturbation, which increases left ventricular afterload. This results in left ventricular remodeling, including left ventricular hypertrophy, and thickening of the aortic and mitral valve leaflets. Left ventricular hypertrophy may lead to heart failure, and aortic valve remodeling may progress to the full clinical presentation of aortic valve stenosis.

A composition according to the teachings herein in the form of a patch such as described in Example 12 comprising leptin antagonist is provided. The thoracic aorta of the subject is surgically accessed from the outside (e.g., using thorascopy) and the composition administered by contacting the outer surface of the affected portions of the aorta with the patch, and optionally holding the patch in place with a biological glue and/or sutures. Optionally, in cases of dilated ascending aorta beyond the sinuses of valsalva (preserved aortic valve annulus diameter) a drug eluting stent graft impregnated with leptin antagonist is deployed in the aneurysm in the usual way, without oversizing.

Another shape of intra-vascular device that may be deployed within an aortic aneurysm is a tubular self-expandable biodegradable (or non-degradable, like bare metal) leptin antagonist slow release mesh or stent. Such a device may self-expand upon deployment, and gently adhere to the luminal surface of the aortic aneurysm (applying minimal radial force to the luminal surface). Leptin antagonist that is associated with, e.g., incorporated within the biodegradable or non-degradable struts of the mesh or stent or covered or coated onto the mesh or stent, will access the aortic wall at the aneurysm by local diffusion. Yet another shape of a device for proximity and local slow release of leptin antagonist at the luminal surface of aortic or peripheral aneurysm will be a single wire (biodegradable or bare metal) possessing the memory of spiral expansion within the aneurysm cavity. The leptin antagonist incorporated within this wire will diffuse into the arterial wall. Subsequently, leptin antagonist from the composition passes into the tissue to provide a beneficial effect to the subject, in some embodiments one or more of attenuate aneurysm progression, stabilize the vessel wall and prevent rupture or dissection of the aneurysm. In some embodiments of treatment of the ascending aorta, the administration of the leptin antagonist also leads to reducing the rate of development, or stopping the development and in some embodiments, reversing the remodeling of parts of the heart.

Example 15

Angioplasty

A human subject is diagnosed with arterial stenosis that is treatable by angioplasty.

A drug-eluting balloon similar to the In.Pact Admiral® DCB drug-coated balloon by Medtronic (Dublin, Ireland) that is coated with a composition comprising leptin antagonist according to the teachings herein is used in the usual way to perform the angioplasty procedure, for example, at sites of arterial bifurcations and in-stent stenoses. At least some of the composition according to the teachings herein that coats the balloon is administered to the surface of the treated blood vessel, thereby administering a composition according to the teachings herein. In some such embodiments, the administration of leptin antagonist is repeated periodically, e.g., with a frequency that is less than once a month, less than once every two months and even less than once every 3 months, even when there is no express need for repeated angioplasty. Subsequently, leptin antagonist from the composition passes into and/or through the lesion and/or tunica intima to provide a beneficial effect to the subject.

Alternatively or additionally, at least one of:

a composition according to the teachings herein in the form of a stent;

a stent impregnated with a composition according to the teachings herein;

a stent coated with a composition according to the teachings herein;

a composition according to the teachings herein in the form of a stent cover;

a stent cover impregnated with a composition according to the teachings herein; and a stent cover coated with a composition according to the teachings herein;

is deployed in the usual way, e.g., during performance of an angioplasty procedure, thereby administering a composition according to the teachings herein. Subsequently, leptin antagonist from the administered composition passes into and/or through the lesion and/or tunica intima to provide a beneficial effect to the subject.

Example 16

Myocardial Infarction

Myocardial infarction causes left ventricular remodeling, leading to progressive impairment of cardiac function. A human subject is diagnosed with an acute myocardial infarction and is treated in the usual way, for example coronary catheterization for primary revascularization and myocardial salvage. A treating health-care professional identifies that the subject has an elevated risk of developing cardiac dysfunction.

A composition comprising leptin antagonist is administered to the ascending aorta as described in the preceding examples using one or more of a drug-eluting balloon, a stent, a covered stent and a stent graft. Subsequently, leptin antagonist from the administered composition passes into and/or through the tunica intima of the aorta to provide a beneficial effect to the subject. In some embodiments, the beneficial effect is prophylactic, preventing development of or reducing the rate of development of an thoracic aortic aneurysm, and/or remodeling of the heart (in particular the left ventricle and associated valves) and/or a recurring infarction. Without wishing to be held to any one theory, it is currently believed that such administration of a leptin antagonist in the ascending aorta reduces angiotensin II synthesis in the left ventricle, thereby moderating the hypertrophy response to the ischemic insult associated with the acute myocardial infarction suffered by the subject.

Example 16-A

Post Myocardial Ischemia (MI) Therapy

In order to minimize the extent of post MI left ventricular remodeling, a bolus of leptin antagonist in aqueous solution may be administered into the involved coronary artery. The following strategy may be exercised for acute MI patients: Patients who sustain acute MI are most frequently admitted through the catheterization lab, to undergo coronary catheterization and primary PTCA (Percutaneous Transarterial Coronary Angioplasty) for primary revascularization. Once blood-flow is re-established in the coronary artery involved, a bolus of leptin antagonist in an aqueous solution is to be injected into the coronary artery through the catheter, after which the catheter will be withdrawn. This new strategy should achieve local distribution of leptin antagonist within the left ventricular heart muscle cells (cardiomyocytes) that were exposed to the ischemic as well as reperfusion insult. Inhibition of cardiomyocyte leptin activity is anticipated to mitigate left ventricular remodeling, and reduce the damage to left ventricular function.

Experimentally induced controlled myocardial ischemia may be achieved by temporary balloon inflation within the proximal left anterior descending (LAD) coronary artery. Leptin antagonist aqueous solution may be injected into the LAD after balloon deflation. Control group may receive intracoronary bolus of saline injection.

An intravascular injection of leptin antagonist may be provided into the treated coronary artery after it has been reopened and blood flow to the ischemic myocardium is restored, in order to prevent post MI left ventricular remodeling. Leptin antagonist may be administered by intravascular injection into a vascular territory that sustained ischemia and reperfusion injury. This injection is a localized injection to a specific section of the left ventricle and does not constitute a systemic treatment.

Example 17

Myointimal Hyperplasia (MIH)

It is know that trauma to a blood vessel may lead to myointimal hyperplasia (MIH), where medial smooth muscle cells undergo uncontrolled proliferation that may lead to stenosis or restenosis of the blood vessel in the area of the trauma. Such trauma include vascular injury caused by expansion of a blood vessel during angioplasty, stent deployment, stent-graft deployment, as a result of surgical anastomosis and associated suturing, clamping of blood vessels, and as a result of blunt and/or penetrating vascular injury.

A health-care professional identifies that a subject has an elevated risk of developing myointimal hyperplasia due to some vascular trauma, administers a composition comprising leptin antagonist according to the teachings herein to the site of the trauma. The administered leptin antagonist reduces the rate or stops the uncontrolled proliferation of cells, reducing the rate of development or preventing MIH. Administration includes the use of any of the compositions according to the teachings herein, including localized administration of a leptin antagonist composition on the outer surface of the blood vessel at the site of injury during surgery (e.g., application of a film of Example 4 as a patch), intravascular administration using a drug eluting balloon, or by administration of a composition that impregnates or coats a medical device, or a composition that is in the shape of a medical device by deploying the medical device. In some embodiments, specific suitable medical devices include intracavitary devices such as a stent cover, a stent, a graft assembly, a ring, a suture and a prosthetic cardiac valve as well as extraluminal devices such as sheets, all such comprising leptin antagonist according to the teachings herein.

Example 18

Treatment of Aneurysm

A human subject is diagnosed with a peripheral or venous aneurysm, e.g., a visceral artery aneurysm, a cerebral aneurysm, especially a saccular or pseudo-fusiform aneurysm.

A composition according to the teachings herein associated with a covered stent is provided, e.g., one or more of coating the stent, coating the stent cover, impregnating the stent, impregnating the stent cover, constituting the stent and constituting the stent cover. The covered stent is deployed in the usual way, where the stent cover covers the mouth of the stent. Subsequently, leptin antagonist from the composition passes into and/or through the tissue in proximity to the aneurysm to provide a beneficial effect to the subject.

Alternatively or additionally, a composition according to the teachings herein is placed inside the cavity of the aneurysm through the mouth thereof, e.g., as a fluid composition (e.g., Example 6) or as an aneurysm coil that is impregnated with leptin antagonist, coated with leptin antagonist or is made of a composition according to the teachings herein. A person having ordinary skill in the art is able to implement coating an aneurysm coil with an active pharmaceutical ingredient with reference to, for example, Cerecyte® (Codman Neuro, a division of DePuySynthes, part of Johnson & Johnson, New Brunswick, N.J., USA), Nexus® (Micro Therapeutics, Inc., Irvine, Calif., USA), and HydroCoil®, HydroSoft® (Terumo Corporation, Tokyo, Japan). Subsequently, leptin antagonist from the composition passes into the cavity of the aneurysm, and subsequently to affected tissue to provide a beneficial effect to the subject.

Example 19

Treatment of Aneurysm

A human subject is diagnosed with an aneurysm, e.g., aortic aneurysms, which are typically related to a variety of diseases associated with angiotensin II hormonal activity. Also peripheral arterial aneurysms, which affect visceral, carotid, peripheral, and cerebral arteries, as well as venous aneurysms, including pulmonary artery (which carries venous blood) may be diagnosed.

A leptin antagonist eluting stem or scaffold may be provided, e.g., intravascular stent or scaffold device (which may or may not be biodegradable) covered or coated with leptin antagonist, available for slow release into the vessel wall locally, thereby attenuating aortic aneurysm progression. A stent-graft destined for treatment of aortic aneurysm may be provided, covered or coated with leptin antagonist available for slow release into the vessel wall at the specific sites of stent-graft attachment to non-dilated (normal) proximal and distal vessel (landing zones). In some embodiments, a stent-like prosthetic heart valve for intravascular application, covered with leptin antagonist may be provided, to prevent local dilation of the hosting tissue ring.

Example 20

Treatment of Vascular Injury

A human subject may be exposed to localized vascular injury which may occur as a result of vascular surgery, local balloon angioplasty. This may cause local arterial narrowing due to smooth muscle cell proliferation, namely myointimal hyperplasia (MIH). This proliferative response may also occur at arterio-venous anastomosis or graft-arterial anastomosis, and in leptin-induced inflammatory and cellular proliferative arterial disease (e.g., Takayasu disease). In order to prevent local arterial narrowing due to cellular proliferation at the sites of vascular injury, and circumstances as described above, an intravascular stent or scaffold device may be provided, (which may or may not be biodegradable) which may be associated with, e.g., covered or coated with leptin antagonist that is available for slow release into the vessel wall.

Example 21

Treatment of Athersclerotic Plaques

A human subject is diagnosed with atherosclerotic plaques. These lesions frequently undergo transformation from a stable plaque into an unstable rupture-prone lesion. An intravascular stent or scaffold device (which may or may not be biodegradable) covered with leptin antagonist that is available for slow release into the vessel wall may be provided, in order to provide vessel stabilization. Deployment of such a stent or scaffold device may apply to any arterial site.

Example 22

Treatment of Left Heart Failure and Aortic Valve Disease

Patients who are diagnosed as hypertensive and hypercholesterolemic and exhibit initial dilation of the ascending aorta may be treated by positioning an intravascular stent or scaffold device at the ascending aorta. The stent or scaffold device may or may not be biodegradable. The device, may be associated with, e.g., covered or coated with leptin antagonist that is available for slow release into the vessel wall, may control left heart failure and attenuate the progression of aortic and mitral valve disease.

The intravascular stent or scaffold device carrying or covered with leptin antagonist, may be positioned intraluminally at the ascending aorta. Such a stent or scaffold device may attenuate local dilation and stiffening thereby prevent local hemodynamic perturbation, which activate the aorto-ventricular coupling. This coupling, when turned on promotes the production and release of angiotensin II from left ventricular cells (cardiomyocytes). Angiotensin II drives intracellular synthesis of leptin in cardiomyocytes and in aortic valve interstitial cells (VICs). Leptin synthesis in cardiomyocytes and VICs contributes to left ventricular hypertrophy, and aortic/mitral valve thickening, respectively. Therefore, de-activation of the aorto-ventricular coupling will control both left ventricular hypertrophy (heart failure) and also attenuate the progression of aortic/mitral valve disease.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. Section headings are used herein to ease understanding of the specification and should not be construed as necessarily limiting.

TABLE I

| SEQ ID NOs | Name | Organism |
|---|---|---|
| 1 | leptin precursor | Homo sapiens |
| 2 | leptin mRNA | Homo sapiens |
| 3 | U.S. Pat. No. 7,307,142 seq1 | Artificial Sequence |
| 4 | U.S. Pat. No. 7,307,142 seq2 | Artificial Sequence |
| 5 | U.S. Pat. No. 7,307,142 seq3 | Artificial Sequence |
| 6 | U.S. Pat. No. 7,307,142 seq4 | Artificial Sequence |
| 7 | U.S. Pat. No. 7,307,142 seq5 | Artificial Sequence |
| 8 | U.S. Pat. No. 7,307,142 seq6 | Artificial Sequence |
| 9 | U.S. Pat. No. 7,307,142 seq7 | Artificial Sequence |

TABLE I-continued

| SEQ ID NOs | Name | Organism |
|---|---|---|
| 10 | U.S. Pat. No. 7,307,142 seq8 | Artificial Sequence |
| 11 | U.S. Pat. No. 7,307,142 seq9 | Artificial Sequence |
| 12 | U.S. Pat. No. 7,307,142 seq10 | Artificial Sequence |
| 13 | U.S. Pat. No. 7,307,142 seq11 | Artificial Sequence |
| 14 | U.S. Pat. No. 7,307,142 seq12 | Artificial Sequence |
| 15 | U.S. Pat. No. 7,307,142 seq13 | Artificial Sequence |
| 16 | U.S. Pat. No. 7,307,142 seq14 | Artificial Sequence |
| 17 | U.S. Pat. No. 7,307,142 seq15 | Artificial Sequence |
| 18 | U.S. Pat. No. 7,307,142 seq16 | Artificial Sequence |
| 19 | U.S. Pat. No. 7,307,142 seq17 | Artificial Sequence |
| 20 | U.S. Pat. No. 7,307,142 seq18 | Artificial Sequence |
| 21 | U.S. Pat. No. 7,307,142 seq19 | Artificial Sequence |
| 22 | U.S. Pat. No. 7,307,142 seq20 | Artificial Sequence |
| 23 | U.S. Pat. No. 7,307,142 seq21 | Artificial Sequence |
| 24 | U.S. Pat. No. 7,307,142 seq22 | Artificial Sequence |
| 25 | U.S. Pat. No. 7,307,142 seq23 | Artificial Sequence |
| 26 | U.S. Pat. No. 7,307,142 seq24 | Artificial Sequence |
| 27 | U.S. Pat. No. 7,307,142 seq25 | Artificial Sequence |
| 28 | U.S. Pat. No. 7,307,142 seq26 | Artificial Sequence |
| 29 | U.S. Pat. No. 7,307,142 seq27 | Artificial Sequence |
| 30 | U.S. Pat. No. 7,307,142 seq28 | Artificial Sequence |
| 31 | U.S. Pat. No. 7,307,142 seq29 | Artificial Sequence |
| 32 | U.S. Pat. No. 7,307,142 seq30 | Artificial Sequence |
| 33 | U.S. Pat. No. 7,307,142 seq31 | Artificial Sequence |
| 34 | U.S. Pat. No. 7,307,142 seq32 | Artificial Sequence |
| 35 | U.S. Pat. No. 7,307,142 seq33 | Artificial Sequence |
| 36 | U.S. Pat. No. 8,969,292 seq1 | Artificial Sequence |
| 37 | U.S. Pat. No. 8,969,292 seq2 | Homo Sapiens |
| 38 | U.S. Pat. No. 8,969,292 seq3 | Artificial Sequence |
| 39 | U.S. Pat. No. 8,969,292 seq4 | Artificial Sequence |
| 40 | U.S. Pat. No. 8,969,292 seq5 | Artificial Sequence |
| 41 | U.S. Pat. No. 8,969,292 seq6 | Artificial Sequence |
| 42 | U.S. Pat. No. 8,969,292 seq7 | Artificial Sequence |
| 43 | U.S. Pat. No. 8,969,292 seq8 | Artificial Sequence |
| 44 | U.S. Pat. No. 8,969,292 seq9 | Artificial Sequence |
| 45 | U.S. Pat. No. 8,969,292 seq10 | Artificial Sequence |
| 46 | U.S. Pat. No. 8,969,292 seq11 | Artificial Sequence |
| 47 | U.S. Pat. No. 8,969,292 seq12 | Artificial Sequence |
| 48 | leptin precursor Rat | Rattus norvegicus |
| 49 | US20070104708 seq1 | Mus musculus |
| 50 | US20070104708 seq2 | Mus musculus |
| 51 | US20070104708 seq3 | Homo sapiens |
| 52 | US20070104708 seq4 | Homo sapiens |
| 53 | US20070104708 seq5 | Homo sapiens |
| 54 | US20070104708 seq6 | Homo sapiens |
| 55 | US20070104708 seq7 | Artificial Sequence |
| 56 | pcDNA3 | Artificial Sequence |
| 57 | pcDNA3.1(+) | Artificial Sequence |
| 58 | pcDNA3.1(−) | Artificial Sequence |
| 59 | pGL3 | Artificial Sequence |
| 60 | pZeoSV2(+) | Artificial Sequence |
| 61 | pSecTag2 | Artificial Sequence |
| 62 | pDisplay | Artificial Sequence |

What is claimed is:

1. An intracavitarily implantable device for treating a cardiovascular disorder, said device comprising:
   a non-biodegradable solid body configured for deploying the device in a fluid-filled bodily cavity in proximity to, or in contact with, a cardiovascular tissue affected by said disorder; and
   a leptin antagonist associated with said solid body,
   wherein said leptin antagonist is a modified mammalian leptin peptide having an amino acid sequence selected from SEQ ID NOs: 3-10, 36 and 38; and
   wherein said device is configured for sustained-release of said leptin antagonist from said device into said cardiovascular tissue.

2. The device according to claim 1, wherein said device is an intravascular stent configured to be deployed into a blood vessel.

3. The device according to claim 1, wherein said solid body is at least partially covered by or at least partially coated with a composition comprising said leptin antagonist.

4. The device according to claim 1, wherein said leptin antagonist is incorporated within said solid body.

5. The device according to claim 2, wherein said stent comprises struts.

6. The device according to claim 5, wherein said leptin antagonist is incorporated within said struts.

7. The device according to claim 1, wherein said device is configured to self-expand upon deployment of said device into a blood vessel.

8. The device according to claim 2, wherein said leptin antagonist is in contact with inner walls of the blood vessel upon its release from the stent.

9. The device according to claim 2, wherein said blood vessel is an aorta.

10. The device according to claim 1, wherein said cardiovascular disorder is selected from a group consisting of: aneurysm, aortic aneurysm, atherosclerotic plaques, left ventricular remodeling, myocardial infarction, myointimal hyperplasia, vascular injury, left heart failure and aortic valve disease.

11. A method for treating a cardiovascular disorder, said method comprising: administering into a fluid-filled bodily cavity of a subject in need thereof the device of claim 1.

12. The method according to claim 11, wherein said solid body is covered with said leptin antagonist.

13. The method according to claim 11, wherein said solid body is coated with said leptin antagonist.

14. The method according to claim 11, wherein said leptin antagonist is incorporated within said solid body.

15. The method according to claim 11, wherein said sustained-release is continuous for a period of not less than three days.

16. The method according to claim 11, wherein said administering comprises administering said device such that the leptin antagonist is in contact with inner walls of said bodily cavity.

17. The method according to claim 11, further comprising providing a therapeutic effect to the bodily cavity tissue.

18. The method according to claim 11, wherein said device is a stent and said bodily cavity is an aorta.

19. The method according to claim 11, wherein said cardiovascular disorder is selected from a group consisting of: aneurysm, aortic aneurysm, atherosclerotic plaques, left ventricular remodeling, myocardial infarction, myointimal hyperplasia, vascular injury, left heart failure and aortic valve disease.

20. The device according to claim 1, wherein said leptin antagonist is the leptin antagonist peptide having the amino acid sequence of SEQ ID NO:36.

21. The device according to claim 1, said device is a graft assembly comprising a non-biodegradable flexible tube and one or more non-biodegradable anchoring rings or non-biodegradable anchoring stents and wherein said device is configured to be positioned in an ascending aorta of a patient in need thereof.

22. The device according to claim 3, wherein said composition comprises, in addition to the leptin antagonist, a polymer selected from the group consisting of a hydrogel, poly glycolic acid (PGA), poly lactic co-glycolic acid (PLGA), polylactide (PLA), and poly (L-lactide) (PLLA), and combinations thereof.

23. The device according to claim 3, wherein said composition is in the form of a leptin antagonist containing sheet.

24. An implantable device for treating a cardiovascular disorder, said device comprising:
   an intravascular non-biodegradable stent configured to be deployed into a blood vessel; and
   a leptin antagonist associated with the stent;
   wherein said leptin antagonist is a modified mammalian leptin peptide having an amino acid sequence selected from SEQ ID NOs: 3-10, 36 and 38; and
   wherein said device is configured for sustained-release of said leptin antagonist from said device into tissue of the blood vessel.

25. The device according to claim 1, wherein said cardiovascular tissue is a cardiac or valve tissue.

26. The device according to claim 1, wherein said cardiovascular tissue is a cardiovascular tissue with accumulated plaque.

27. The device according to claim 1, wherein said device is a prosthetic cardiac valve.

28. An intracavitarily implantable device for treating a cardiovascular disorder, said device comprising:
   a non-biodegradable solid body configured for deploying the device in a fluid-filled bodily cavity in proximity to, or in contact with, a cardiovascular tissue affected by said disorder;
   and
   a leptin antagonist associated with said solid body;
   wherein said device is configured for sustained-release of said leptin antagonist from said device into said cardiovascular tissue; and
   wherein said leptin antagonist is selected from the group consisting of (a) a modified mammalian leptin polypeptide consisting of a mammalian leptin polypeptide in which the LDFI hydrophobic binding site at the positions corresponding to positions 39-42 of the wild-type human leptin (SEQ ID NO:1) is modified such that from two to four amino acid residues of said hydrophobic binding site are substituted with different amino acid residues such that the site becomes less hydrophobic; and
(b) the modified mammalian leptin polypeptide according to (a) in which the aspartic acid at the position corresponding to position 23 of the wild-type human leptin (D23) is substituted with an amino acid residue selected from the group consisting of glycine, alanine, leucine, lysine, arginine, phenylalanine, tryptophan and histidine, or in which the threonine at the position corresponding to position 12 of the wild- type human leptin (T12) is substituted with a different amino acid residue that is hydrophobic.

* * * * *